(12) United States Patent
Kim et al.

(10) Patent No.: US 9,601,700 B2
(45) Date of Patent: Mar. 21, 2017

(54) CONDENSED CYCLIC COMPOUND AND ORGANIC LIGHT-EMITTING DEVICE INCLUDING THE SAME

(71) Applicant: SAMSUNG DISPLAY CO., LTD., Yongin, Gyeonggi-Do (KR)

(72) Inventors: Jong-Woo Kim, Yongin (KR); Seok-Hwan Hwang, Yongin (KR); Young-Kook Kim, Yongin (KR); Hye-Jin Jung, Yongin (KR); Jun-Ha Park, Yongin (KR); Eun-Young Lee, Yongin (KR); Jin-O Lim, Yongin (KR); Sang-Hyun Han, Yongin (KR); Kwang-Hyun Kim, Yongin (KR); Eun-Jae Jeong, Yongin (KR); Soo-Yon Kim, Yongin (KR)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 397 days.

(21) Appl. No.: 14/277,946

(22) Filed: May 15, 2014

(65) Prior Publication Data

US 2015/0069344 A1 Mar. 12, 2015

(30) Foreign Application Priority Data

Sep. 10, 2013 (KR) ........................ 10-2013-0108623

(51) Int. Cl.

| | |
|---|---|
| *H01L 51/00* | (2006.01) |
| *H01L 51/50* | (2006.01) |
| *C07D 311/78* | (2006.01) |
| *C07C 335/04* | (2006.01) |
| *C07F 7/08* | (2006.01) |

(52) U.S. Cl.
CPC ........ *H01L 51/0054* (2013.01); *C07C 335/04* (2013.01); *C07D 311/78* (2013.01); *C07F 7/0812* (2013.01); *C07F 7/0814* (2013.01); *H01L 51/0052* (2013.01); *H01L 51/0073* (2013.01); *H01L 51/006* (2013.01); *H01L 51/0059* (2013.01); *H01L 51/0081* (2013.01)

(58) Field of Classification Search
None
See application file for complete search history.

(56) References Cited

U.S. PATENT DOCUMENTS

| | | | |
|---|---|---|---|
| 5,635,308 | A | 6/1997 | Inoue et al. |
| 5,972,247 | A | 10/1999 | Shi et al. |
| 6,465,115 | B2 | 10/2002 | Shi et al. |
| 6,596,415 | B2 | 7/2003 | Shi et al. |
| 7,053,255 | B2 | 5/2006 | Ikeda et al. |
| 7,233,019 | B2 | 6/2007 | Ionkin et al. |
| 2005/0156164 | A1 | 7/2005 | Sotoyama |
| 2009/0026930 | A1 | 1/2009 | Shin et al. |

FOREIGN PATENT DOCUMENTS

| | | |
|---|---|---|
| JP | 08-12600 A | 1/1996 |
| JP | 11-003782 A | 1/1999 |
| JP | 2006-151930 A | 6/2006 |
| KR | 10-2006-0006760 A | 1/2006 |
| KR | 10-2009-0010763 A | 1/2009 |

*Primary Examiner* — J. L. Yang

(74) *Attorney, Agent, or Firm* — Lee & Morse, P.C.

(57) ABSTRACT

A condensed cyclic compound and an organic light-emitting device including the same, the compound being represented by Formula 1, below:

$$Ar_1-(L_{11})_{b1}-(L_1)_{a1}-(L_{12})_{b2}-Ar_2 \quad <\text{Formula 1}>$$

20 Claims, 1 Drawing Sheet

10

| 190 |
|-----|
| 150 |
| 110 |

CONDENSED CYCLIC COMPOUND AND ORGANIC LIGHT-EMITTING DEVICE INCLUDING THE SAME

CROSS-REFERENCE TO RELATED APPLICATION

Korean Patent Application No. 10-2013-0108623, filed on Sep. 10, 2013, in the Korean Intellectual Property Office, and entitled: "Condensed Cyclic Compound and Organic Light-Emitting Device Including The Same," is incorporated by reference herein in its entirety.

BACKGROUND

1. Field

Embodiments relate to a condensed cyclic compound and an organic light-emitting device including the same.

2. Description of the Related Art

Organic light emitting devices are self-emitting devices that have wide viewing angles, high contrast ratios, short response time, and excellent brightness, driving voltage, and response speed characteristics, and produce full-color images.

The organic light-emitting device may include a first electrode on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, e.g., holes and electrons, may be recombined in the emission layer to produce excitons. These excitons may change from an excited state to a ground state, thereby generating light.

SUMMARY

Embodiments are directed to a condensed cyclic compound and an organic light-emitting device including the same.

According to one or more embodiments, a condensed cyclic compound may be represented by Formula 1 below:

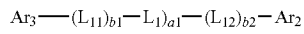

<Formula 1>

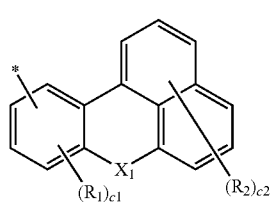

<Formula 2A>

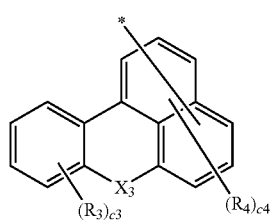

<Formula 2B>

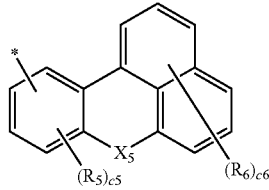

<Formula 2C>

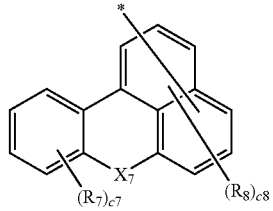

<Formula 2D> wherein, in Formulae 2A to 2D and Formula 1, $X_1$, $X_3$, $X_5$, and $X_7$ are each independently O or S;

$L_1$, $L_{11}$ and $L_{12}$ are each independently selected from a substituted or unsubstituted $C_3$-$C_{10}$ cycloalkylene group, a substituted or unsubstituted $C_3$-$C_{10}$ heterocycloalkylene group, a substituted or substituted $C_3$-$C_{10}$ cycloalkenylene group, a substituted or unsubstituted $C_3$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic hetero-condensed polycyclic group;

a1 is an integer selected from 1 to 5;

b1 and b2 are each independently an integer selected from 0 to 5;

$Ar_1$ is represented by Formulas 2A or 2B;

$Ar_2$ is represented by Formulas 2C or 2D;

$R_1$ to $R_8$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a substituted or unsubstituted $C_1$-$C_{60}$ alkyl group, is substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic hetero-condensed polycyclic group, —N($Q_1$)($Q_2$), —Si($Q_3$)($Q_4$)($Q_5$), and —B($Q_6$)($Q_7$)

c1 and c5 are each independently an integer selected from 0 to 3;

c2 and c6 are each independently an integer selected from 0 to 6;

c3 and c7 are each independently an integer selected from 0 to 4;

c4 and c8 are each independently an integer selected from 0 to 5;

in Formulae 2A and 2B, * indicates a binding site to $L_1$ in Formula 1 or a binding site to $L_{11}$ in Formula 1;

in Formulae 2C and 2D, * indicates a binding site to $L_1$ in Formula 1 or a binding site to $L_{12}$ in Formula 1;

at least one substituent of the substituted $C_3$-$C_{10}$ cycloalkylene group, the substituted $C_3$-$C_{10}$ heterocycloalkylene group, the substituted $C_3$-$C_{10}$ cycloalkenylene group, the substituted $C_3$-$C_{10}$ heterocycloalkenylene group, the substituted $C_6$-$C_{60}$ arylene group, the substituted $C_2$-$C_{60}$ heteroarylene group, the substituted divalent non-aromatic aromatic condensed polycyclic group, the substituted divalent non-aromatic hetero-condensed polycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy, the substituted $C_3$-$C_{10}$ cycloalkyl group, the substituted $C_3$-$C_{10}$ heterocycloalkyl group, the substituted $C_3$-$C_{10}$ cycloalkenyl group, the substituted $C_3$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic hetero-condensed polycyclic group is selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_3$-$C_{10}$ heterocycloalkyl group, a $C_6$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic hetero-condensed polycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_3$-$C_{10}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic hetero-condensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, —$N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$; and $Q_1$ to $Q_7$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic hetero-condensed polycyclic group.

According to one or more embodiments, an organic light-emitting device includes: a first electrode; a second electrode facing the first electrode; and an organic layer that is disposed between the first electrode and the second electrode and includes an emission layer, wherein the organic layer includes at least one of the condensed cyclic compound described above.

BRIEF DESCRIPTION OF THE DRAWING

Features will be apparent to those of skill in the art by describing in detail exemplary embodiments with reference to the attached drawing in which:

FIG. 1 illustrates a schematic view of an organic light-emitting device according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figure, the dimensions of layers and regions may be exaggerated for clarity of illustration. Like reference numerals refer to like elements throughout.

A condensed cyclic compound according to an embodiment may be represented by Formula 1 below:

$$Ar_1\text{-}(L_{11})_{b1}\text{-}(L_1)_{a1}\text{-}(L_{12})_{b2}\text{-}Ar_2 \qquad \text{<Formula 1>}$$

In Formula 1, $Ar_1$ may be represented by Formulae 2A or 2B, and $Ar_2$ may be represented by Formulae 2C or 2D.

<Formula 2A>

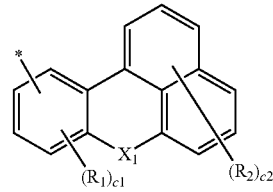

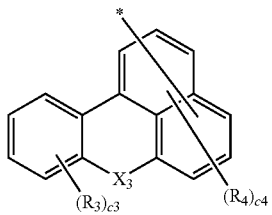
<Formula 2B>

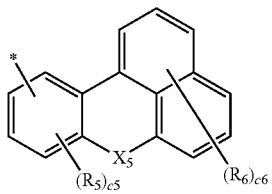
<Formula 2C>

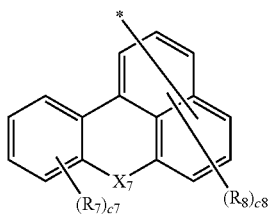
<Formula 2D>

In an implementation, $L_1$, $L_{11}$, and $L_{12}$ in Formula 1 may be each independently selected from substituted or unsubstituted $C_6$-$C_{20}$ arylene groups.

In an implementation, $L_1$, $L_{11}$, and $L_{12}$ Formula 1 may be each independently selected from;

a phenylene group, a pentalenylene group, an indeylene group, a naphthylene group, an azulenylene group, a heptalenylene group, a indacenylene group, an acenaphthylene group, a fluorenylene group, a spiro-fluorenylene group, a benzofluorenylene group, a dibenzofluorenylene group, a phenalenylene group, a phenanthrenylene group, a anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coroneylene group, a ovalenylene group, a pyrrolylene group, a thiophenylene group, a furanylene group, a imidazolylene group, a pyrazolylene group, a thiazolylene group, an isothiazolylene group, a oxazolylene group, an isooxazolylene group, a pyridinylene group, a pyrazinylene group, a pyrimidinylene group, a pyridazinylene group, an isoindolylene group, a indolylene group, a indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, a oxadiazolylene group, a triazinylene group, a dibenzofuranylene group, a dibenzothiophenylene group, a benzocarbazolylene group, a dibenzocarbazolylene group, a thiadiazolylene group, and an imidazopyridinylene group; and a phenylene group, a pentalenylene group, an indeylene group, a naphthylene group, an azulenylene group, a heptalenylene group, a indacenylene group, an acenaphthylene group, a fluorenylene group, a spiro-fluorenylene group, a benzofluorenylene group, a dibenzofluorenylene group, a phenalenylene group, a phenanthrenylene group, a anthracenylene group, a fluorathenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, a ovalenylene group, a pyrrolylene group, a thiophenylene group, a furanylene group, a imidazolylene group, a pyrazolylene group, a thiazolylene group, an isothiazolylene group, a oxazolylene group, an isooxazolylene group, a pyridinylene group, a pyrazinylene group, a pyrimdinylene group, a pyridazinylene group, an isoindolylene group, a indolylene group, a indazolylene group, a pyridazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, a acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, a oxadiazolylene group, a triazinylene group, a dibenzofuranylene group, a dibenzothiophenylene group, is benzocarbazolylene group, a dibenzocarbazolylene and imidazopyridinylene group, each substituted with at least one selected from a deuterium, , —O, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a cyclopentyl group, is cyclohexyl group, a cycloheptyl group, a cyclopentenyl group, a cyclohexenyl group, a phenyl group, a pentalenyl group, an indeyl group, a naphthyl group, an azulenyl group, a heptalenyl group, a indacenyl group, an acenaphthyl group, a fluorenyl group, a spiro-fluorenyl group, a benzofluorenyl group, a dibenzofluorenyl group, a phenalenyl group, a phenanthrenyl group, a anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, a imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, a indolyl group, a indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, a acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and —Si($Q_{33}$)($Q_{34}$)($Q_{35}$).

$Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a pyridinyl group, a pyrimidinyl group, and a triazinyl group, but are not limited thereto.

According to another embodiment, $L_1$, $L_{11}$, and $L_{12}$ may be each independently selected from Formulae 3-1 to 3-24 below, but are not limited thereto:

Formula 3-1
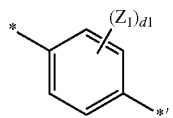

Formula 3-2
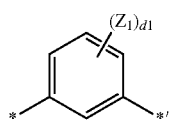

Formula 3-3
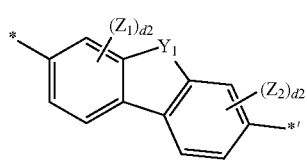

Formula 3-4
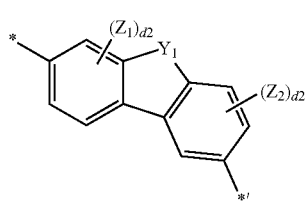

Formula 3-5
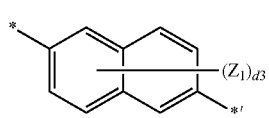

Formula 3-6
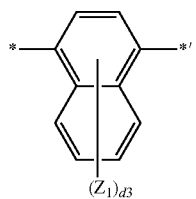

Formula 3-7
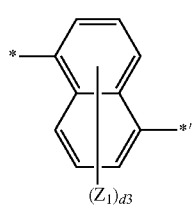

Formula 3-8
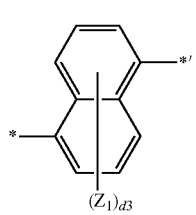

-continued

Formula 3-9
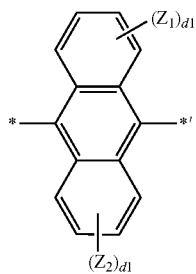

Formula 3-10
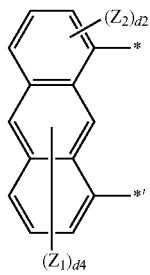

Formula 3-11
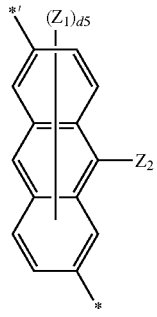

Formula 3-12
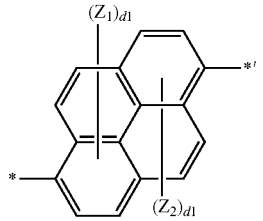

Formula 3-13
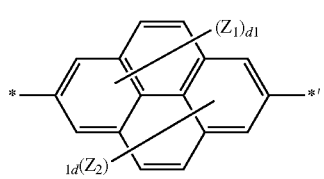

Formula 3-14
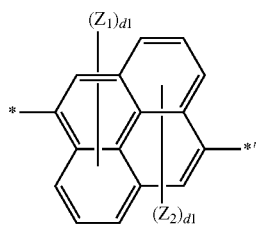

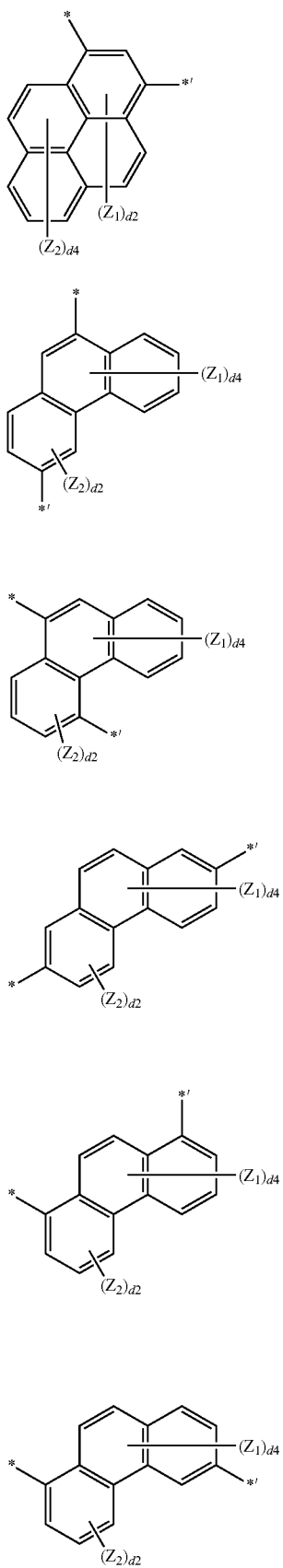

In Formulae 3-1 to 3-24, $Y_1$ may be O, S, $C(Z_3)(Z_4)$, $N(Z_5)$, or $Si(Z_6)(Z_7)$;

$Z_1$ to $Z_7$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a pentalenyl group, an indeyl group, a naphthyl group, an azulenyl group, a heptalenyl group, a indacenyl group, an acenaphthyl group, a fluorenyl group, a spiro-fluorenyl group a benzo-fluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, a imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, a indolyl group, a indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazoyl group, a phenanthridinyl group, a acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and $-Si(Q_{33})(Q_{34})(Q_{35})$;

$Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a pyridinyl group, a pyrimidinyl group, and a triazinyl group;

d1 may be an integer selected from 1 to 4;
d2 may be an integer selected from 1 to 3;
d3 may be an integer selected from 1 to 6;
d4 may be an integer selected from 1 to 5; and
d5 may be an integer selected from 1 to 7.

For example, $Z_1$ to $Z_7$ in Formulae 3-1 to 3-24 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, to sulfonic acid and a salt thereof, a phosphoric acid and a salt thereof a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a quinoxalinyl group, a quinazolinyl group, a cinnolinyl group, a quinazolinyl group, and $-Si(Q_{33})(Q_{34})(Q_{35})$, in which $Q_{33}$ to $Q_{35}$ are each independently selected from hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a pyridinyl group, a pyrimidinyl group, and a triazinyl group, but are not limited thereto.

a1 in Formula 1 may be an integer selected from 1 to 5. For example, a1 in Formula 1 may be 1, 2, or 3. As another example, a1 in Formula 1 may be 1, or 2. When a1 is 2 or more, a plurality of $L_1$ may be identical or different.

b1 in Formula 1 may be an integer selected from 0 to 5. For example, b1 in Formula 1 may be 0, 1, or 2. As another example, b1 in Formula 1 may be 0 or 1. When b1 is 0, $Ar_1$ in Formula 1 may be directly linked to $L_1$. When b1 is 2 or more, a plurality of $L_{11}$ may be identical or different.

b2 in Formula 1 may be an integer selected from 0 to 5. For example, b2 in Formula 1 may be 0, 1, or 2. As another example, b2 in Formula 1 may be 0 or 1. When b2 is 0, $Ar_2$ in Formula 1 may be directly linked to $L_2$. When b2 is 2 or more, a plurality of $L_{12}$ may be identical or different.

According to an embodiment, a moiety represented by- $(L_1)_{a1}$- in Formula 1 may be represented by, e.g., one of Formulae 4-1 to 4-17 below:

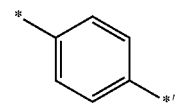

Formula 4-1

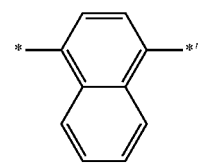

Formula 4-2

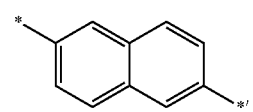

Formula 4-3

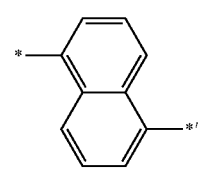

Formula 4-4

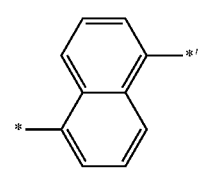

Formula 4-5

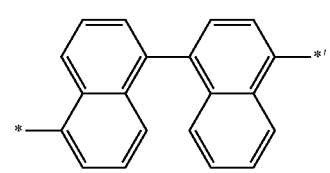

Formula 4-6

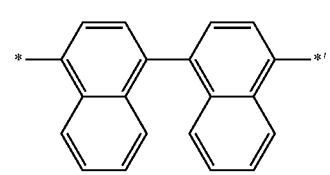

Formula 4-7

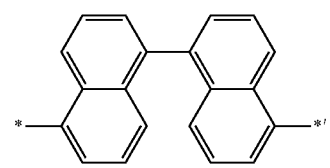

Formula 4-8

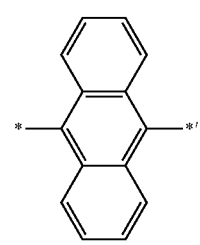

Formula 4-9

Formula 4-10

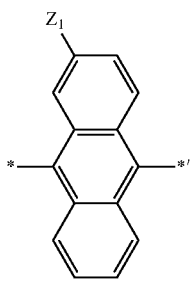

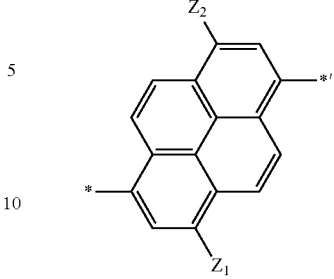

Formula 4-15

Formula 4-11

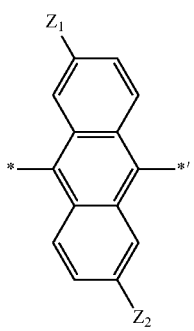

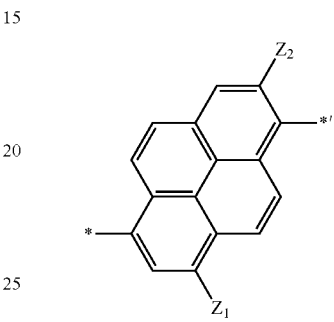

Formula 4-16

Formula 4-12

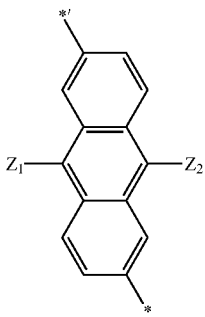

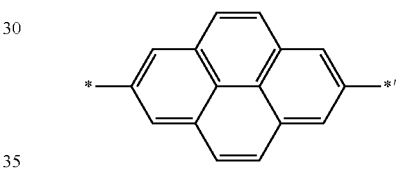

Formula 4-17

Formula 4-13

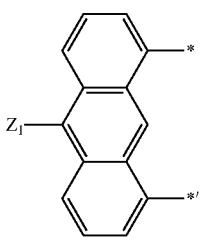

Formula 4-14

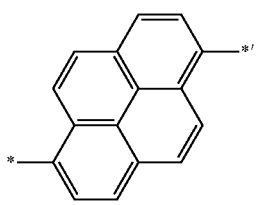

For example, $Z_1$ and $Z_2$ in Formulae 4-1 to 4-17 may be each independently selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof a phosphoric acid and a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a quinoxalinyl group, a quinazolinyl group, a cinnolinyl group, a quinazolinyl group, and —Si($Q_{33}$)($Q_{34}$)($Q_{35}$), wherein $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a pyridinyl group, a pyrimidinyl group, and a triazinyl group, but are not limited thereto.

In Formula 1, i) b1=0 and b2=0; ii) b1=0 and b2=1; iii) b1=1 and b2=0, or iv) b1=1 and b2=1.

In an implementation, at least one of b1 or b2 may be an integer of 1 or greater, and $L_{11}$ and $L_{12}$ in Formula 1 may be each independently represented by one of Formulae 3-1, 3-2, and 3-5 to 3-8, but are not limited thereto.

In Formula 1, $Ar_1$ may be represented by one of Formulae 2A-1, 2B-1, 2B-2, and 2B-3 below; and $Ar_2$ may be represented by one of Formulae 2C-1, 2D-1, 2D-2, and 2D-3.

<Formula 2A-1>

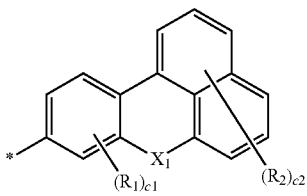

<Formula 2B-1>

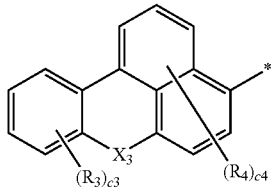

<Formula 2B-2>

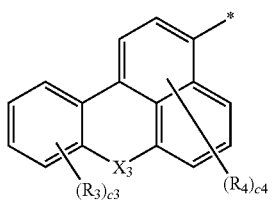

<Formula 2B-3>

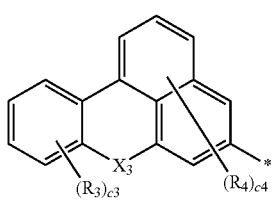

<Formula 2C-1>

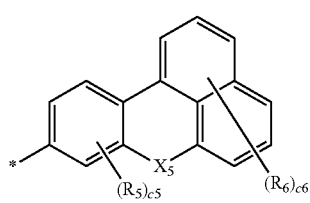

<Formula 2D-1>

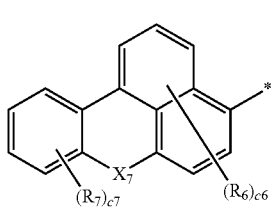

<Formula 2D-2>

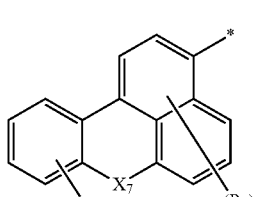

-continued

<Formula 2D-3>

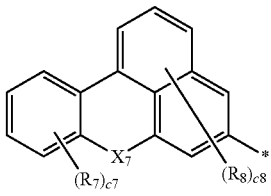

In Formulae 2A to 2D, 2A-1, 2B-1 2B-2, 2B-3, 2C-1, 2D-1, 2D-2, and 2D-3, $X_1$, $X_3$, $X_5$, and $X_7$ may be each independently O or S; and $R_1$ to $R_8$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a substituted or unsubstituted $C_1$-$C_{60}$ alkyl group, a substituted or unsubstituted $C_2$-$C_{60}$ alkenyl group, a substituted or unsubstituted $C_1$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic heterocondensed polycyclic group, —N($Q_1$)($Q_2$), —Si($Q_3$)($Q_4$)($Q_5$), and —B($Q_6$)($Q_7$). Herein, $Q_1$ to $Q_7$ may be understood by referring to the description presented above.

For example, $R_1$ to $R_8$ or $R_1$ and to $R_8$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, and a $C_1$-$C_{20}$ alkoxy group;

a phenyl group, a pentalenyl group, an indeyl group, a naphthyl group, an azulenyl group, a heptalenyl group, a indacenyl group, an acenaphthyl group, a fluorenyl group, a spiro-fluorenyl group, a benzofluorenyl group, a dibenzofluorenyl group, a phenalenyl group, a phenanthrenyl group, a anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl, group, a ovalenyl group, a pyrrolyl group, a thiophenyl group, a furanyl group, a imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, a indolyl group, a indazolyl group, a purinyl group, a quinolinyl group, an isoquinolinyl group, a benzoquinolinyl group, a phthalazinyl group, a naphthyridinyl group, a quinoxalinyl group, a quinzolinyl group, a cinnolinyl group, a carbazolyl group, a phenanthridinyl group, a acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, a thiadiazolyl group, and an imidazopyridinyl group; and a phenyl group, a pentalenyl group, an indeyl group, a naphthyl group, an azulenyl group, a heptalenyl group, a indacenyl group, an acenaphthyl group, a fluorenyl group, a spiro-fluorenyl group, a benzofluorenyl group, a dibenzofluorenyl group, a phenalenyl group, a phenanthrenyl group, a anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, a imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, a indolyl group, a indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, a acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and an imidazopyridinyl group, each substituted with at least one selected from a deuterium —F, —Cl, —Br, —I, a hydroxyl group, a cyano group, a nitro group, an amino group, an amidino group, a hydrazine group, a hydrazone group, a carboxylic add and a salt thereof, a sulfonic acid and a salt thereof, a phosphoric acid and a salt thereof, a $C_1$-$C_{20}$ alkyl group, a $C_1$-$C_{20}$ alkoxy group, —Si($Q_{33}$),($Q_{34}$)($Q_{35}$), a phenyl group, a pentalenyl group, an indeyl group, a naphthyl group, an azulenyl group, heptalenyl group a indacenyl group, an acenaphthyl group, a fluorenyl group, a spiro-fluorenyl group, a benzofluorenyl group, a dibenzofluorenyl group, a phenalenyl group, phenanthrenyl group, a anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, a imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, a indolyl group, a indazolyl group, a purinyl group, a quinolinyl group, an isoquinolinyl group, a benzoquinolinyl group, a phthalazinyl group, a naphthyridinyl group, a quinoxalinyl group, a quinazolinyl group, is cinnolinyl group, a carbazolyl group, a phenanthridinyl group, a acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, a thiadiazolyl group, and an imidazopyridinyl group; and —Si($Q_3$)($Q_4$)($Q_5$);

$Q_3$ to $Q_5$ and $Q_{33}$ to $Q_{35}$ may be each independently selected from a hydrogen, as $C_1$-$C_{20}$ alkyl group, a $C_1$-$C_{20}$ alkoxy group, a phenyl group, a naphthyl group, an anthracenyl group, a pyrenyl group, a phenanthrenyl group, a pyridinyl group, a pyrimidinyl group, and a triazinyl group, but are not limited thereto.

c1 and c5 may be each independently an integer selected from 0 to 3; c2 and c6 may be each independently an integer selected from 0 to 6; c3 and c7 may be each independently an integer selected from 0 to 4; and c4 and c8 may be each independently an integer selected from 0 to 5.

In Formulae 2A, 2B, 2A-1, 2B-1 , 2B-2, and 2B-3, * indicates a binding site to $L_1$ or $L_{11}$ in Formula 1, and * in Formulae 2C, 2D, 2C-1 2D-1, 2D-2, and 2D-3 indicates a binding site to $L_1$ or $L_{12}$ in Formula 1.

According to an embodiment, $R_1$ to $R_8$ in Formulae 2A to 2D, 2B-1, 2B-2, 2B-3, 2C-1, 2D-1, 2D-2, and 2D-3 may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, and a $C_1$-$C_{20}$ alkoxy group;

a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a quinoxalinyl group, a quinazolinyl group, a cinnolinyl group, and a quinazolinyl group;

a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a quinoxalinyl group, a quinazolinyl group, a cinnolinyl group, and a quinazolinyl group, each substituted with a least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, —Si($Q_{33}$)($Q_{34}$)($Q_{35}$), a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a quinoxalinyl group, a quinazolinyl group, a cinnolinyl group, and quinazolinyl group; and —Si($Q_3$)($Q_4$)($Q_5$);

$Q_3$ to $Q_5$ and $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a pyridinyl group, a pyrimidinyl group, and a triazinyl group;

c1 to c8 may be each independently 0, 1 or 2, but are not limited thereto.

According to another embodiment, $R_1$ to $R_8$ Formulae 2A to 2D, 2A-1, 2B-1, 2B-2, 2B-3, 2C-1, 2D-1, 2D-2, and 2D-3 may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, and a $C_1$-$C_{20}$ alkoxy group;

a phenyl group, a naphthyl group, an anthracenyl group, a pyrenyl group, a phenanthrenyl group, and a fluorenyl group;

a phenyl group, a naphthyl group, an anthrancenyl group, a pyrenyl group, a phenanthrenyl group, and a fluorenyl group, each substituted with at least one selected from a deuterium, —F, —Cl, —Br, —I, a hydroxyl group, a cyano group, a nitro group, an amino group, an amidino group, a hydrazine group, a hydrozone group, a carboxylic, acid and a salt thereof, a sulfonic acid and a salt thereof, a phosphoric acid and a salt thereof, a $C_1$-$C_{20}$ alkyl group, a $C_1$-$C_{20}$ alkoxy group, —Si($Q_{33}$)($Q_{34}$)($Q_{35}$), a phenyl group, a naphthyl group, an anthracenyl group, a pyrenyl group, a phenanthrenyl group, and a fluorenyl group; and —Si($Q_3$)($Q_4$)($Q_5$); and $Q_3$ to $Q_5$ and $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a pyridinyl group, a pyrimidinyl group, and a triazinyl group, but are not limited thereto.

c1 to c8 in Formulae 2A to 2D, 2A-1, 2B-1, 2B-2, 2B-3, 2C-1, 2D-1, 2D-2, and 2D-3 may be each independently 0, 1, or 2. For example, c1 to c8 may be 0 or 1, but are not limited thereto. When c1 is 2 or more, a plurality of $R_1$ may be identical or different. This is also the same for $R_2$ to $R_8$.

According to an embodiment, the condensed cyclic compound represented by Formula 1 may be represented by Formula 1A to 1G below.

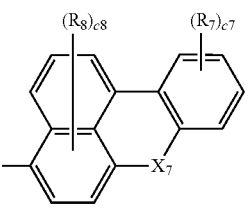

<Formula 1A>

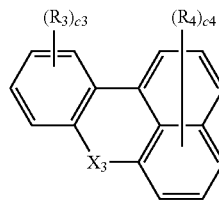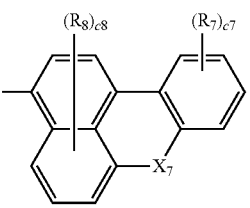

<Formula 1B>

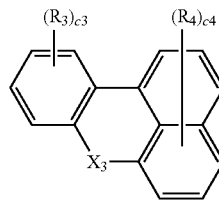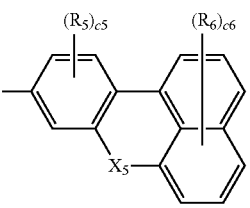

<Formula 1C>

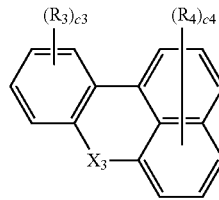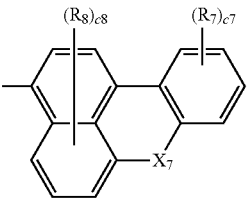

<Formula 1D>

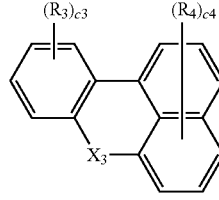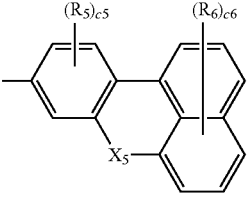

<Formula 1E>

<Formula 1F>

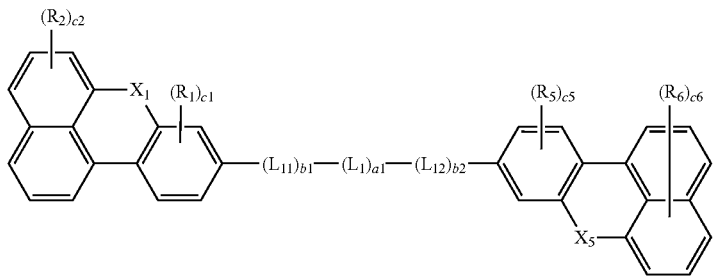

<Formula 1G>

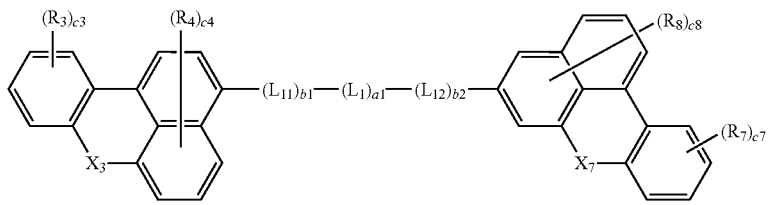

$X_1$, $X_3$, $X_5$, $X_7$, $L_1$, $L_{11}$, $L_{12}$, a1, b1, b2, $R_1$ to $R_8$ and c1 to c8 in Formulae 1A to 1G may be understood by referring to the description presented above with respect to Formulae 1 and 2A to 2D.

For example, the condensed cyclic compound may be represented by one of Formulae 1A to 1G above. In an implementation, in Formulae 1A to 1G, $X_1$, $X_3$, $X_5$, and $X_7$ and may be each independently O or S;

$L_1$, $L_{11}$, and $L_{12}$ may be each independently represented by one of Formulae 3-1 to 3-24 below:

a1 may be 1 or 2; and b1 and b2 may be each independently 0, 1, or 2;

$R_1$ to $R_8$ or $R_1$ and $R_8$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, and a $C_1$-$C_{20}$ alkoxy group;

a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl, group, a triazinyl group, a quinolinyl group, an isoquinolinyl group, a quinoxalinyl group, a quinazolinyl group, a cinnolinyl group, and a quinazolinyl group;

a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a quinoxalinyl group, a quinazolinyl group, a cinnolinyl group, and a quinazolinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, —Si$(Q_{33})(Q_{34})(Q_{35})$, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a quinoxalinyl group, a quinazolinyl group, a cinnolinyl group, and a quinazolinyl group; and —Si$(Q_3)(Q_4)(Q_5)$; and $Q_3$ to $Q_5$ and $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a pyridinyl group, a pyrimidinyl group, and a triazinyl group; and c1 and c8 may be each independently 0, 1, or 2.

According to another embodiment, the condensed cyclic compound may be represented by one of Formulae 1A to 1G above. In an implementation, in Formulae 1A to 1G.

$X_1$, $X_3$, $X_5$, and $X_7$ and may be each independently O or S;

a moiety represented by -$(L_1)_{a1}$- may be represented by any one of Formulae 4-1 to 4-17;

$L_{11}$ and $L_{12}$ may be each independently represented by one of Formulae 3-1, 3-2, and 3-5 to 3-8;

i) b1=0 and b2=0; ii) b1=0 and b2=1; iii) b1=1 and b2=0, or iv) b1=1 and b2=1;

$R_1$ to $R_8$ or $R_1$ and $R_8$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, and a $C_1$-$C_{20}$ alkoxy group;

a phenyl group, a naphthyl group, an anthracenyl group, a pyrenyl group, a phenanthrenyl group, and a fluorenyl group;

a phenyl group, a naphthyl group, an anthracenyl group, a pyrenyl group, a phenanthrenyl group, and a fluorenyl group, each substituted with at least one selected from a deuterium, —F, —Cl, —Br, —I, a hydroxyl group, a cyano group, a nitro group, an amino group, an amidino group, a hydrazine group, is hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, —Si($Q_{33}$)($Q_{34}$)($Q_{35}$), a phenyl group, a naphthyl group, an anthracenyl group, a pyrenyl group, a phenanthrenyl group, and a fluorenyl group; and —Si($Q_3$)($Q_4$)($Q_5$); and $Q_3$ to $Q_5$ and $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a pyridinyl group, a pyrimidinyl group, and a triazinyl group; and c1 and c8 may be each independently 0, 1, or 2;

According to an embodiment, in the present specification, at least one substituent of the substituted $C_3$-$C_{10}$ cycloalkylene group, the substituted $C_3$-$C_{10}$ heterocycloalkylene group, the substituted $C_3$-$C_{10}$ cycloalkenylene group, the substituted $C_3$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic hetero-condensed polycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy, the substituted $C_3$-$C_{10}$ cycloalkyl group, the substituted $C_3$-$C_{10}$ heterocycloalkyl group, the substituted $C_3$-$C_{10}$ cycloalkenyl group, the substituted $C_3$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic hetero-condensed polycyclic group may be selected from:

a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkenyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a cyclopentyl group, a cyclohexyl group, a cycloheptyl group, a cyclopentenyl group, a cycloheptenyl group, a phenyl group, a pentalenyl group, an indeyl group, a naphthyl group, an azulenyl group, a heptalenyl group, a indacenyl group, an acenaphthyl group, a fluorenyl group, a spiro-fluorenyl group, a benzofluorenyl group, a dibenzofluorenyl group, a phenalenyl group, a phenanthrenyl group, a anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, a imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, a indolyl group, a indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, a acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, a imidazopyridinyl group, —N($Q_{11}$)($Q_{12}$), —Si($Q_{13}$)($Q_{14}$)($Q_{15}$), and —B($Q_{16}$)($Q_{17}$);

a cyclopentyl group, a cyclohexyl group, a cycloheptyl group, a cyclopentenyl group, a cycloheptenyl group, a phenyl group, a pentalenyl group, an indeyl group, a naphthyl group, an azulenyl group, a heptalenyl group, a indacenyl group, an acenaphthyl group, a fluorenyl group, a spiro-fluorenyl group, a benzofluorenyl group, a dibenzofluorenyl group, a phenalenyl group, a phenanthrenyl group, a anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, a imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, a indolyl group, a indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, a acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and an imidazopyridinyl group;

a cyclopentyl group, a cyclohexyl group, a cycloheptyl group, a cyclopentenyl group, a cycloheptenyl group, a phenyl group, a pentalenyl group, an indeyl group, a naphthyl group, an azulenyl group, a heptalenyl group, a indacenyl group, an acenaphthyl group, a fluorenyl group, a spiro-fluorenyl group, a benzofluorenyl group, a dibenzofluorenyl group, a phenalenyl group, a phenanthrenyl group, a anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, a imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, a indolyl group, a indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, a acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and imidazopyridinyl group, a each substituted with at least one selected from of deuterium, —F, —Cl, —Br, —I, a hydroxyl group, a cyano group, a nitro group, an amino group, an amidino group, a hydrazine group, a hydrazone group, a carboxylic acid and a salt thereof; a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cycloheptenyl group, a phenyl, group, a pentalenyl group, an indeyl group, a naphthyl group, an azulenyl group, a heptalenyl group, a indacenyl group, an acenaphthyl group, a fluorenyl group, a spiro-fluorenyl group, a benzofluorenyl group, a dibenzofluorenyl group, a phenalenyl group, a phenanthrenyl group, a anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, coronenyl group, a ovalenyl group, a pyrrolyl group, a thiophenyl group, a furanyl group, a imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, a indolyl group, a indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, a acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, an imidazopyridinyl group, —N($Q_{21}$)($Q_{22}$), —Si($Q_{23}$)($Q_{24}$)($Q_{25}$) and —B($Q_{26}$)($Q_{27}$), and —N($Q_{31}$)($Q_{32}$), —Si($Q_{33}$)($Q_{34}$)($Q_{35}$), and —B($Q_{36}$)($Q_{37}$); and $Q_1$ to $Q_7$, $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cycloheptenyl group, a phenyl group, a pentalenyl group, an indeyl group, a naphthyl group, an azulenyl group, a heptalenyl group, a indacenyl group, an acenaphthyl group, a fluorenyl group, a spiro-fluorenyl group, is benzofluorenyl group, a dibenzofluorenyl group, a phenalenyl group, a phenanthrenyl group, a anthracenyl group, a fluorantenyl, group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, a imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, a indolyl group, a indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, a acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and an imidazopyridinyl.

According to an embodiment, the condensed cyclic compound represented by Formula 1 may be one of Compounds 1 to 219 below, but is not limited thereto.

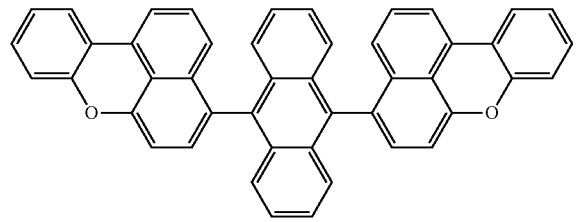

1

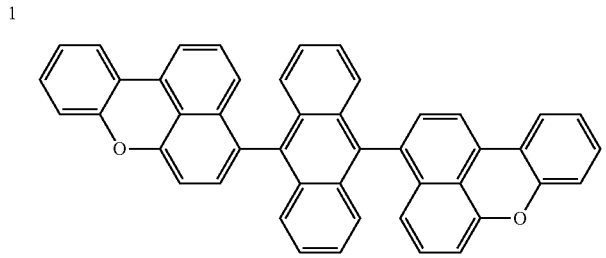

2

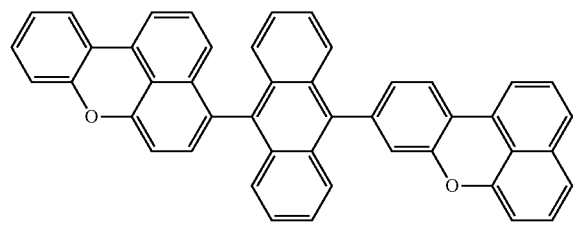

3

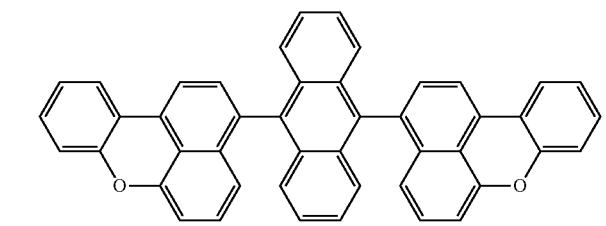

4

-continued
5
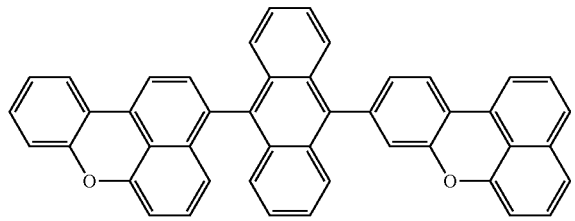
6
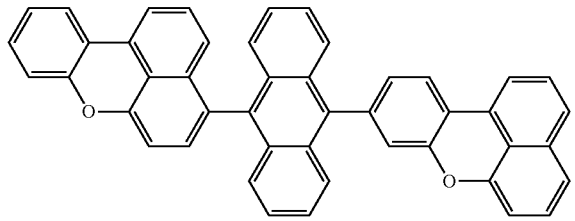
7
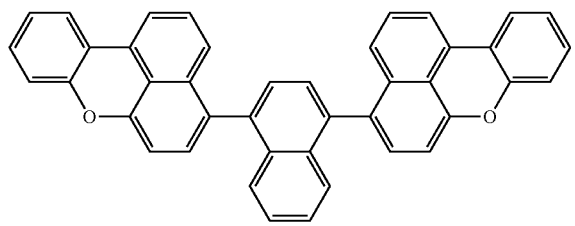
8
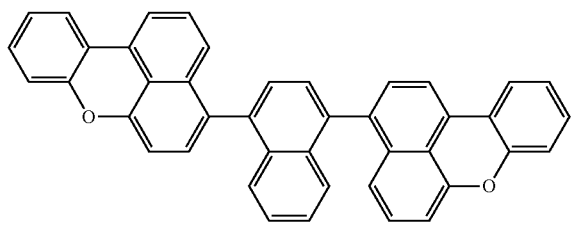
9
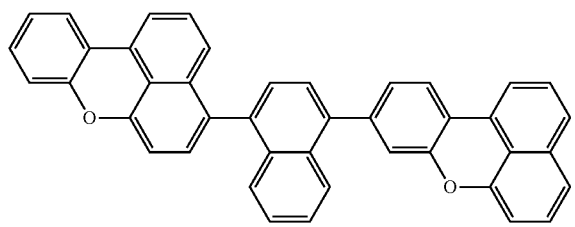
10
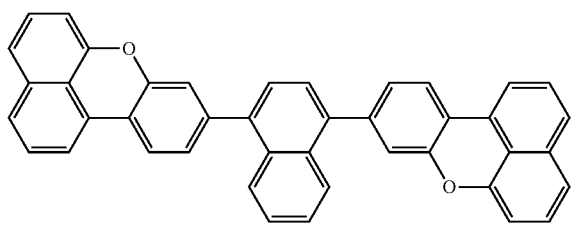
11
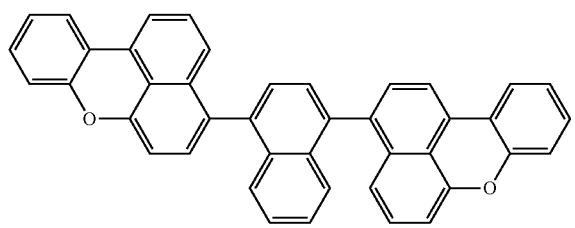
12
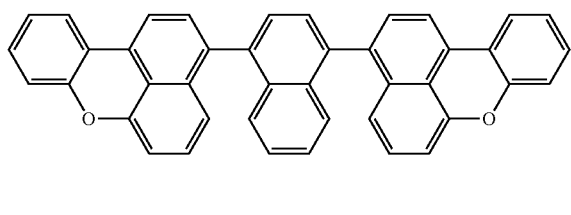
13
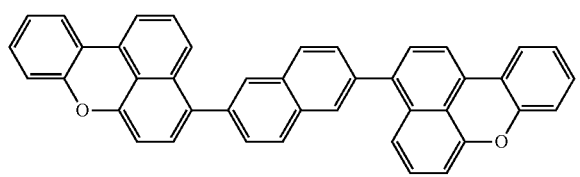
14
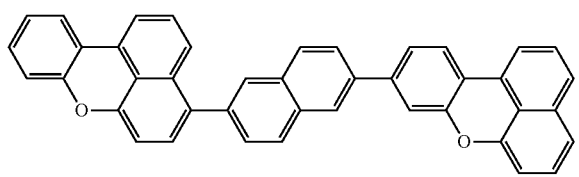
15
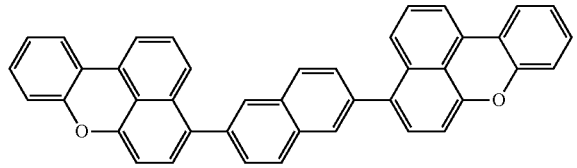
16
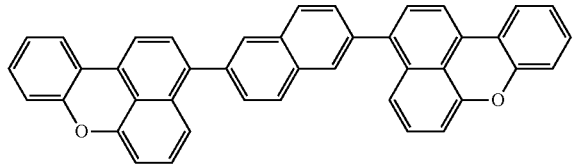
17
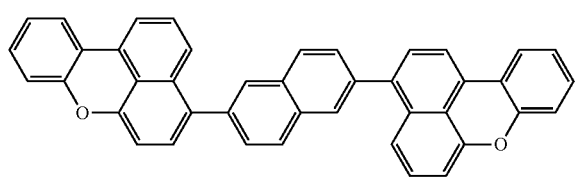

-continued
19
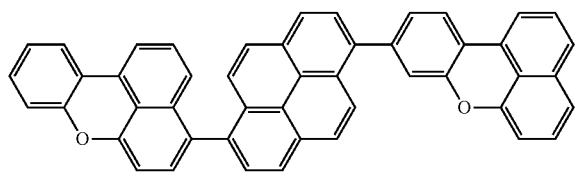
20
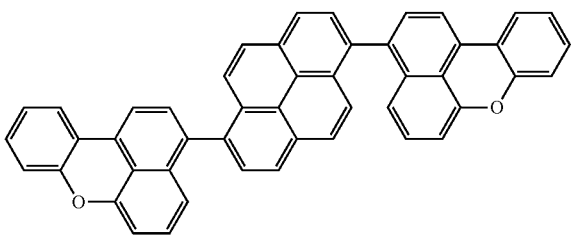
21
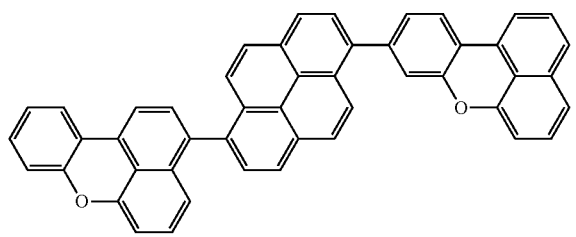
22
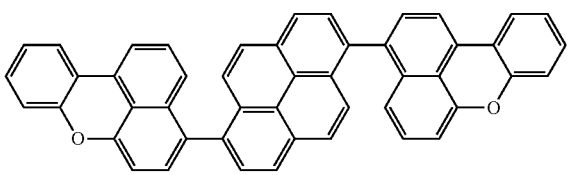
23
24
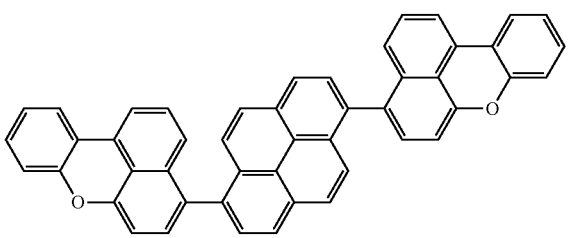
25
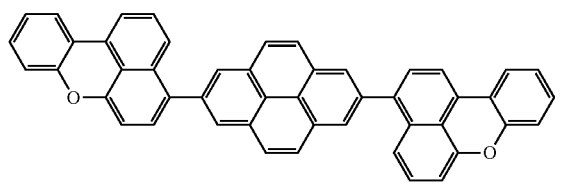
26
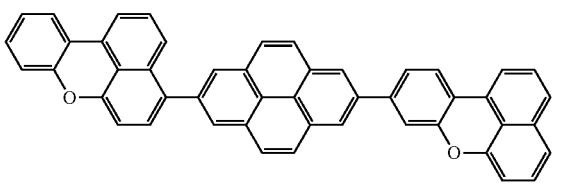
27
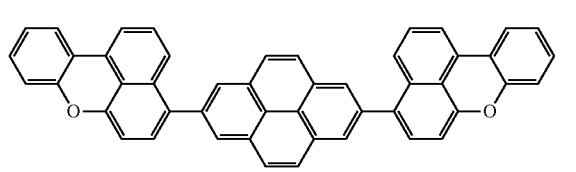
28
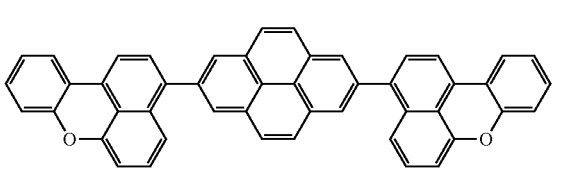
29
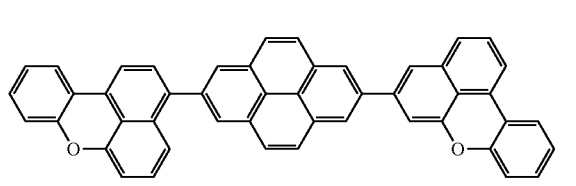
30
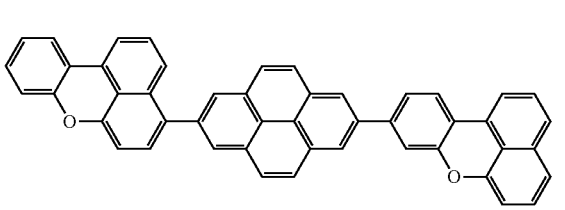
31
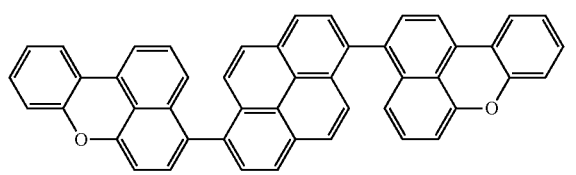
32
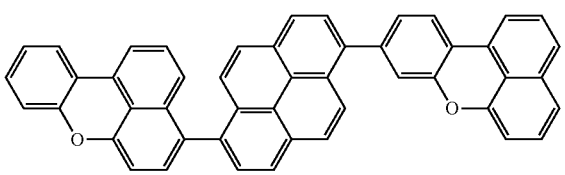

-continued
33
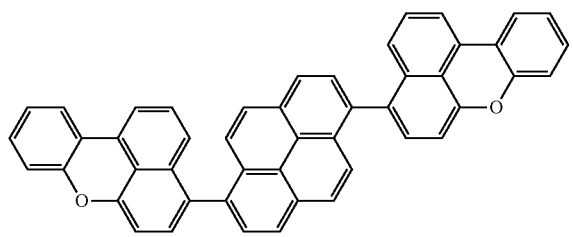
34
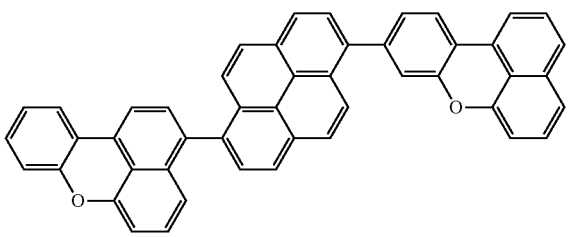
35
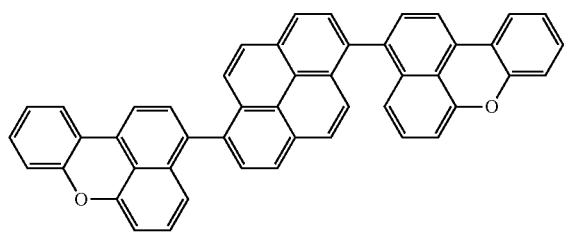
36
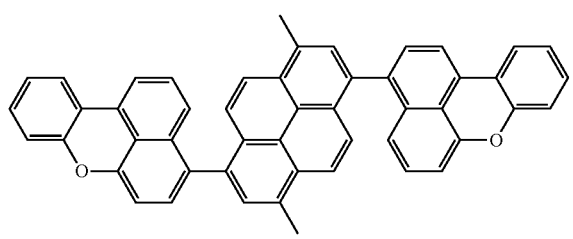
37
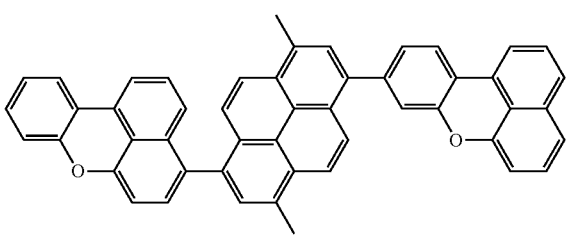
38
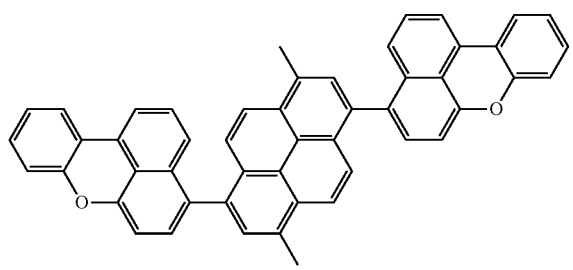
39
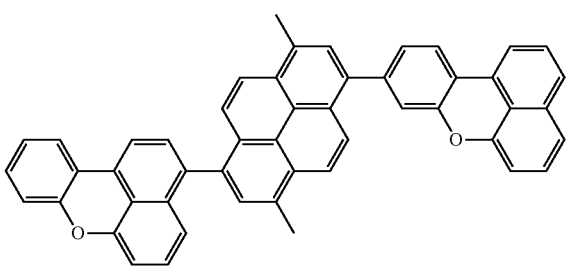
40
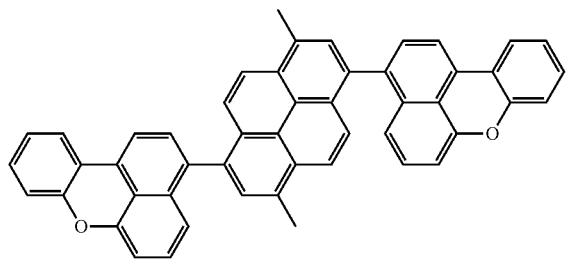
41
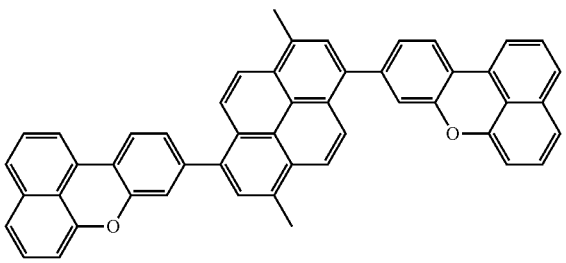
42

-continued
43
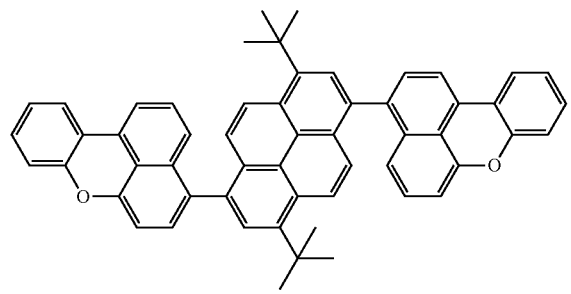
44
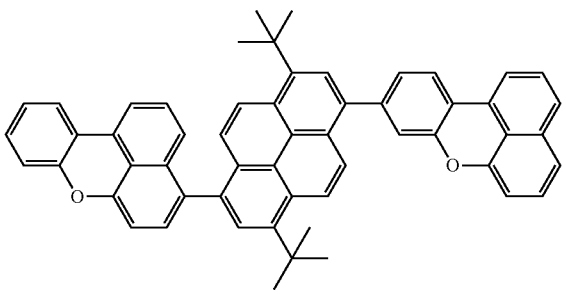
45
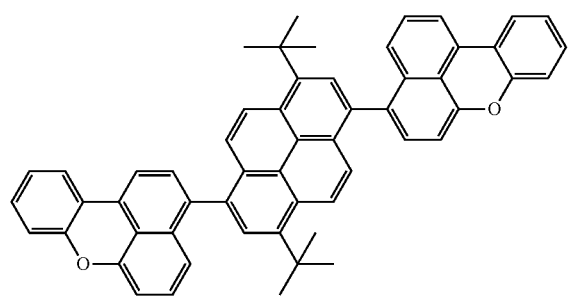
46
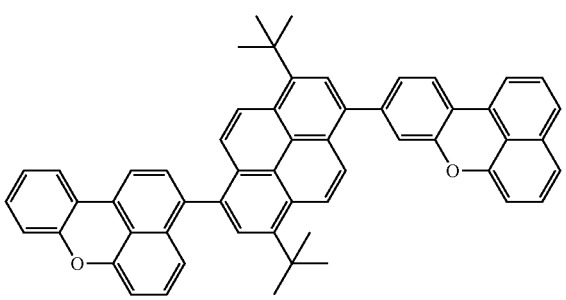
47
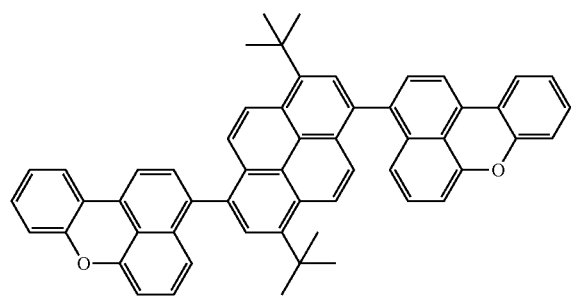
48
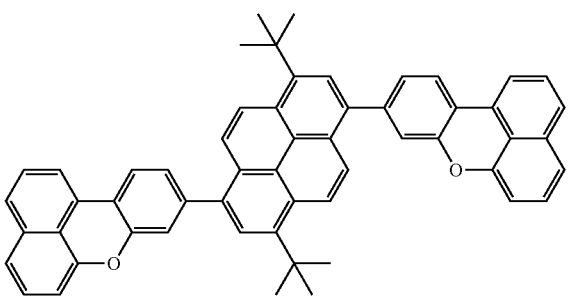
49
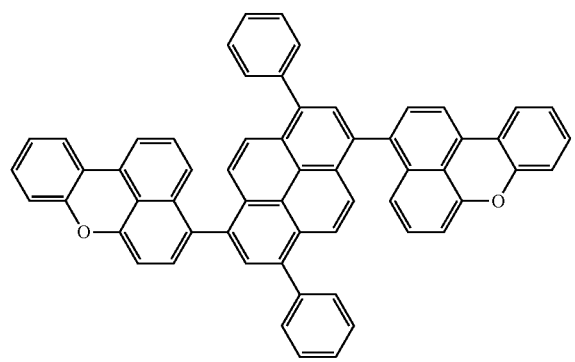
50
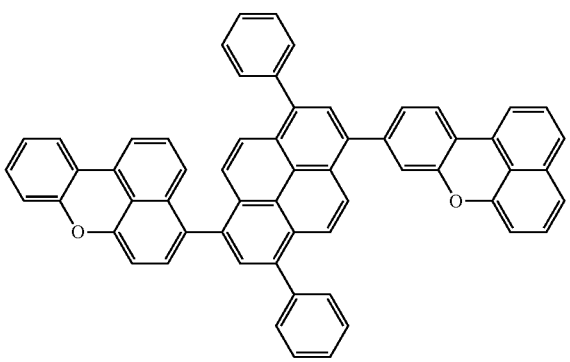

-continued
51
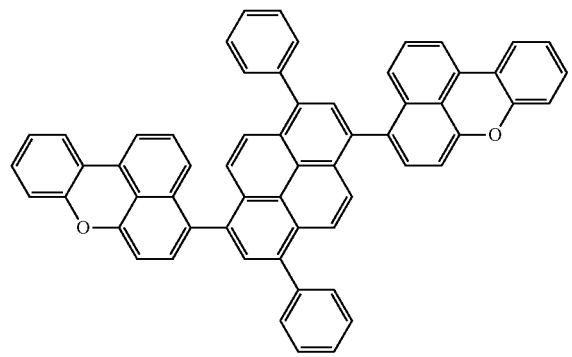
52
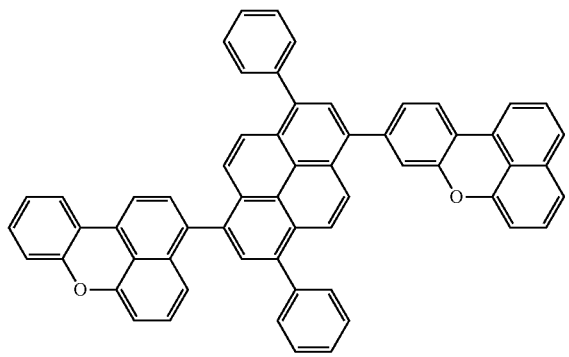
53
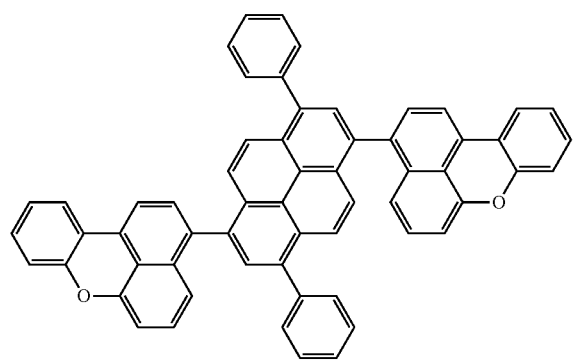
54
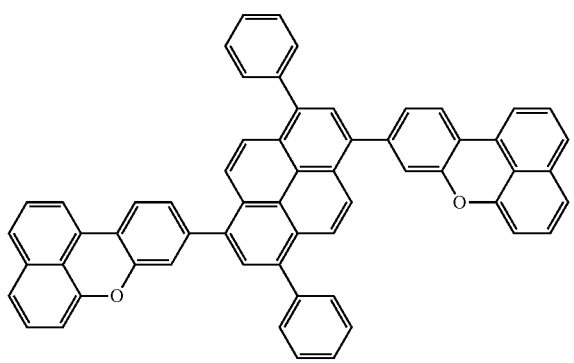
55
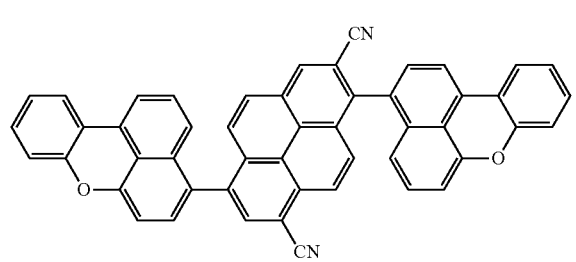
56
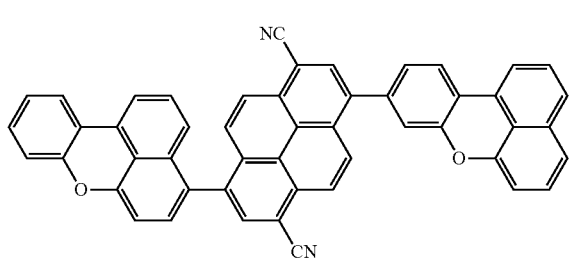
57
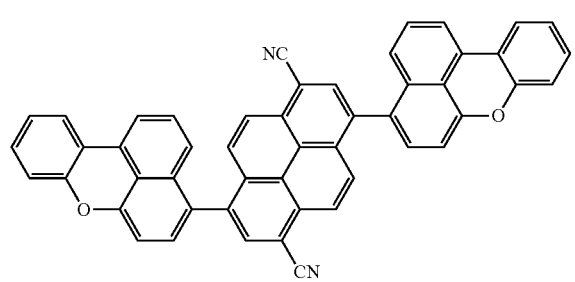
58
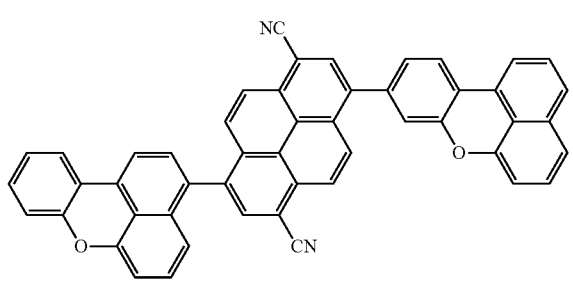
59
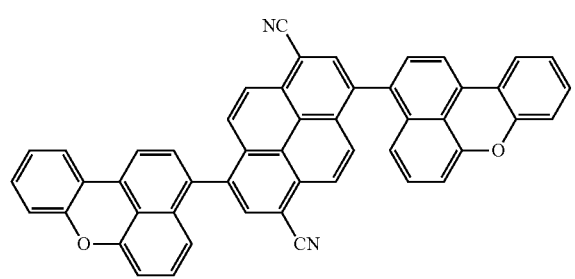
60
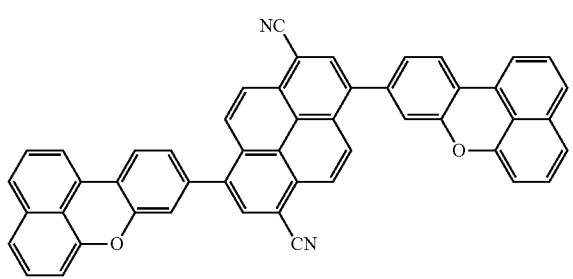

-continued
61
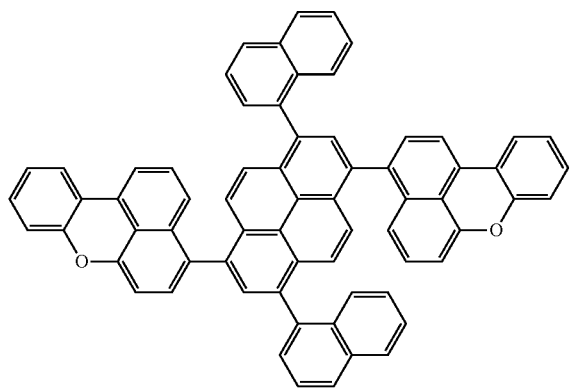
62
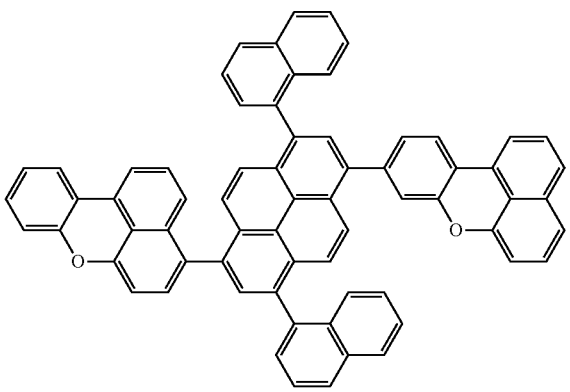
63
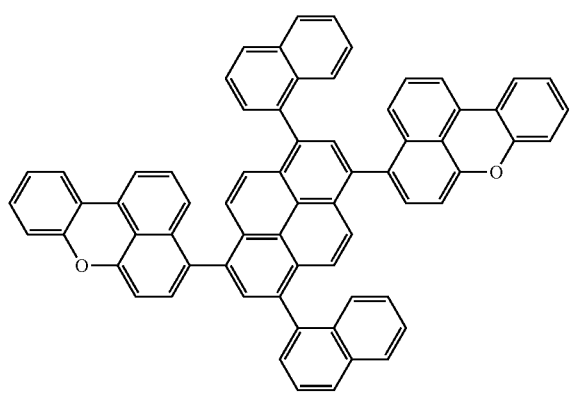
64
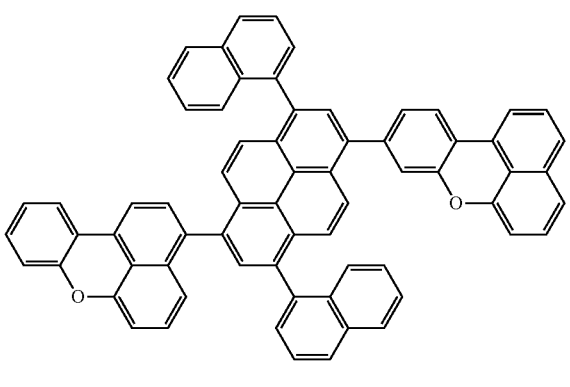
65
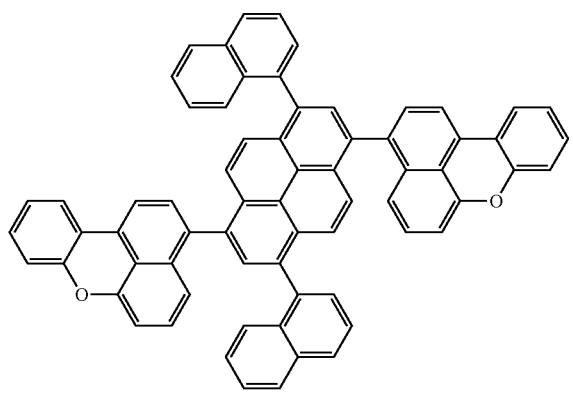
66
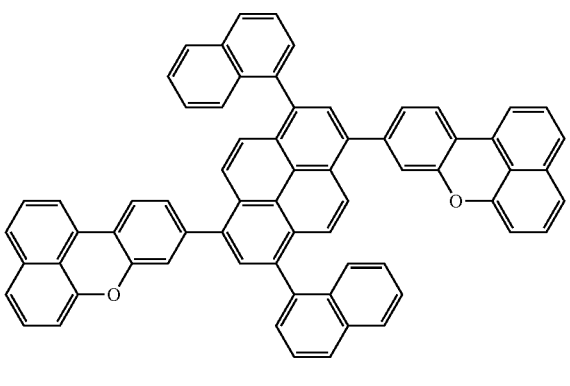

67
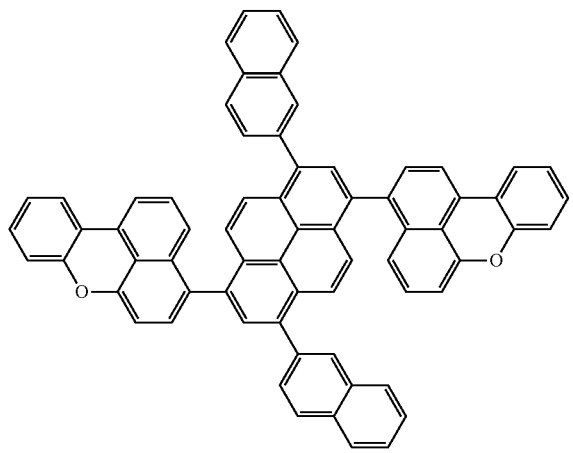
68
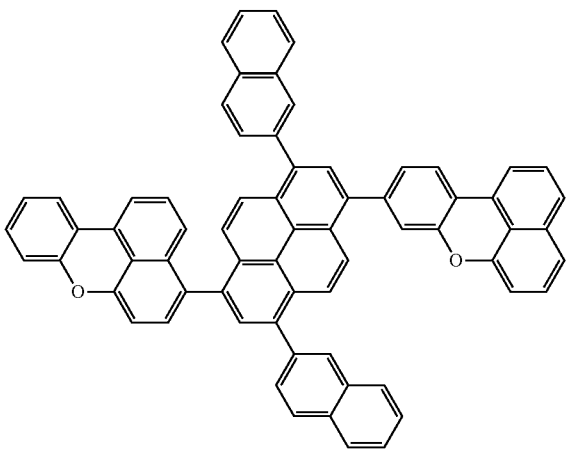
69
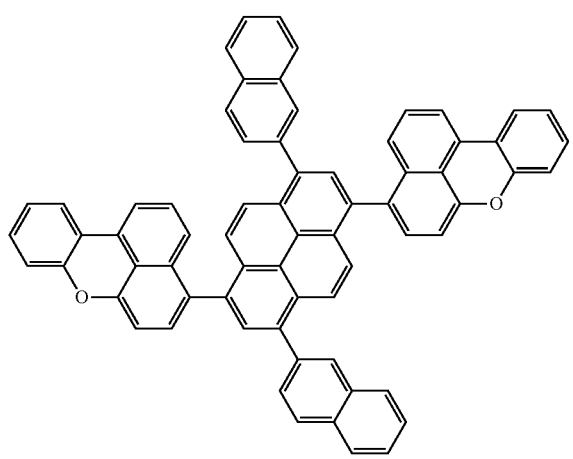
70
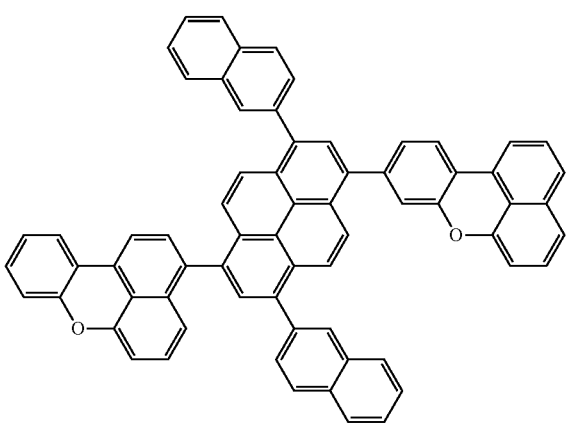
71
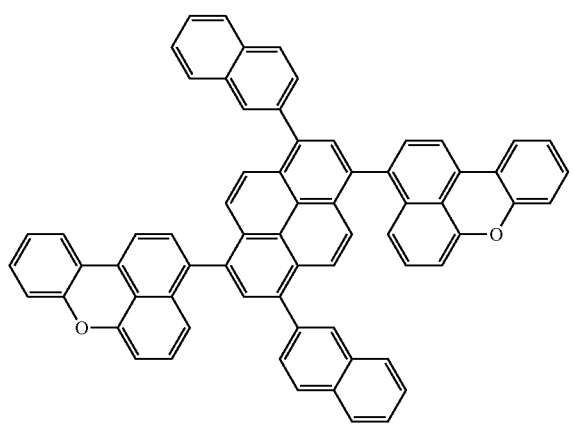
72
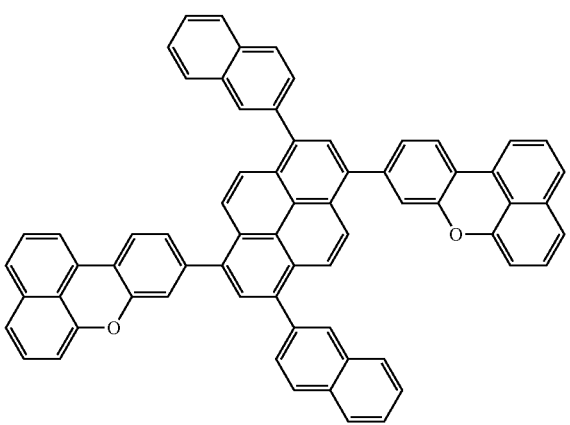
73
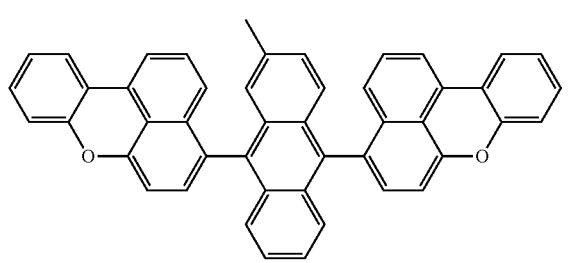
74
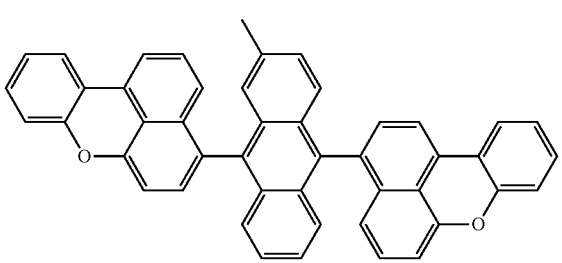

75
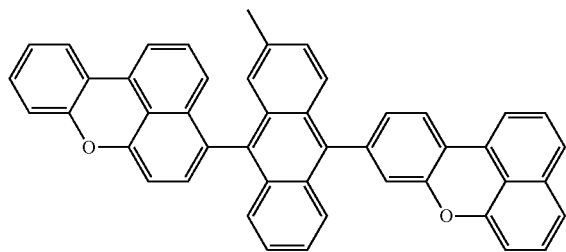
76
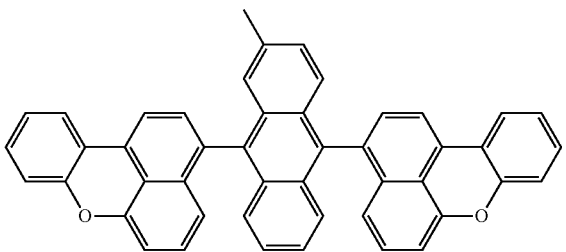
77
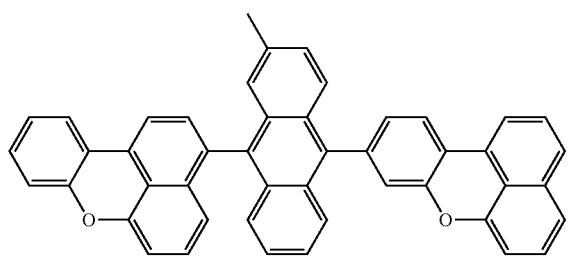
78
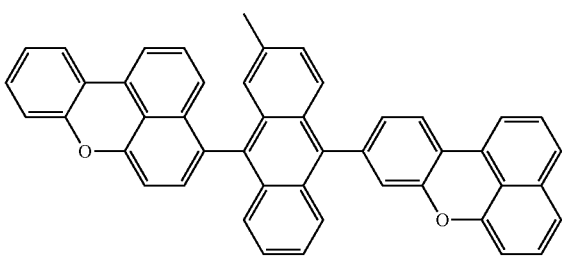
79
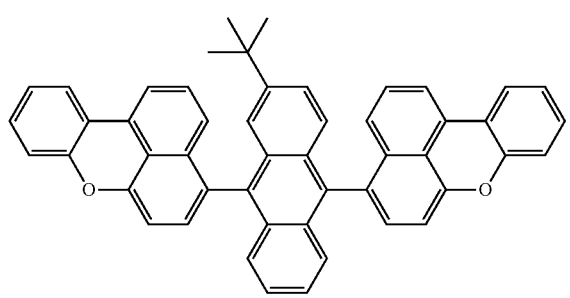
80
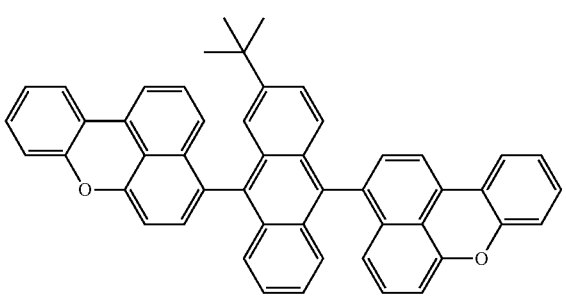
81
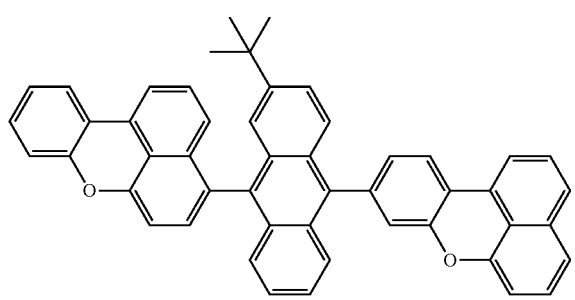
82
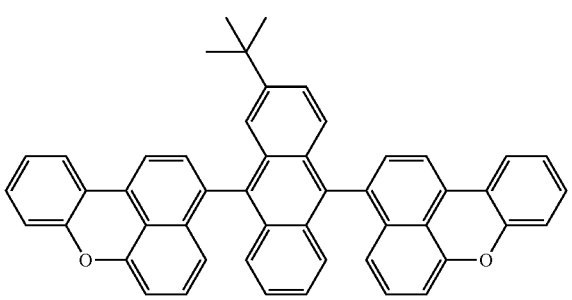
83
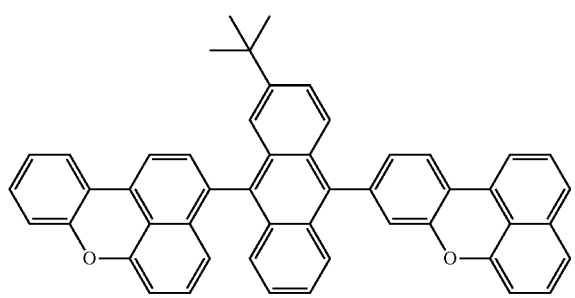
84
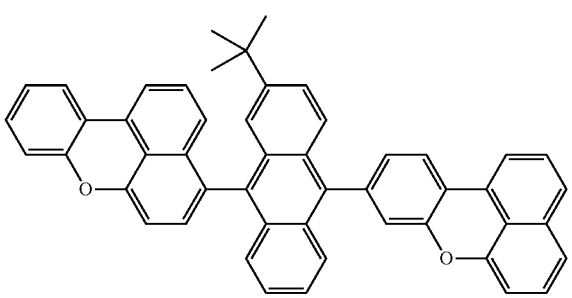

-continued
85
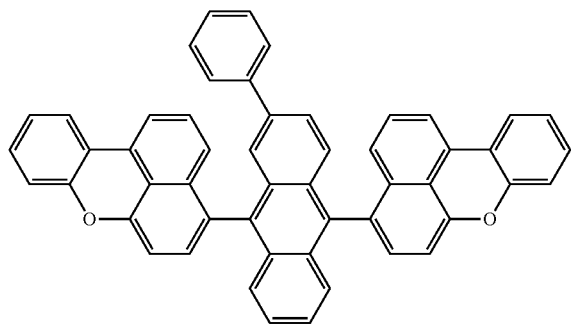
86
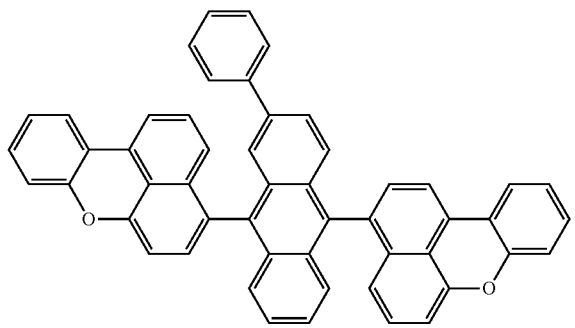
87
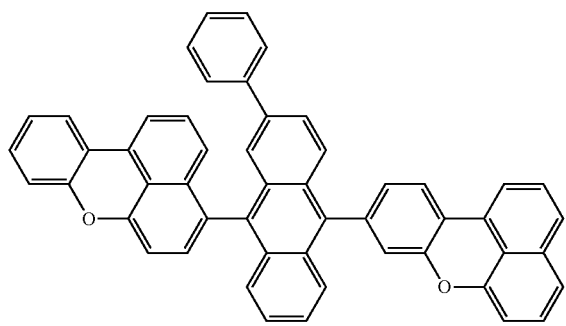
88
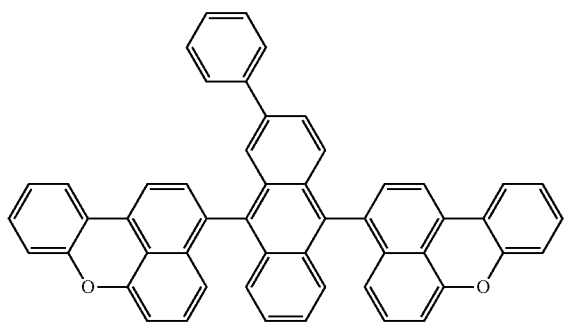
89
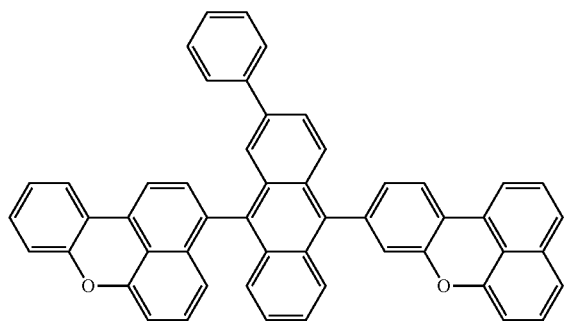
90
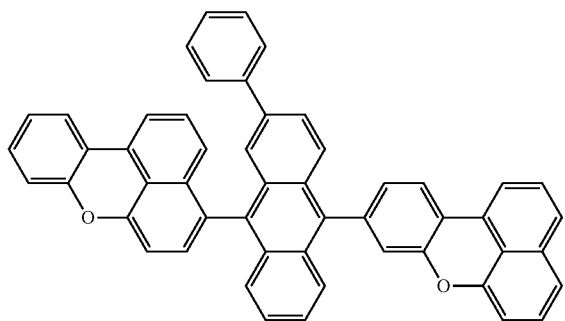
91
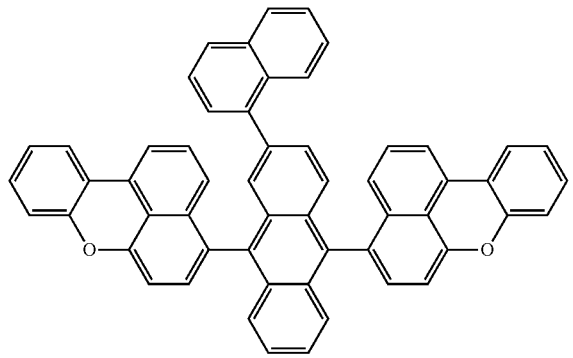
92
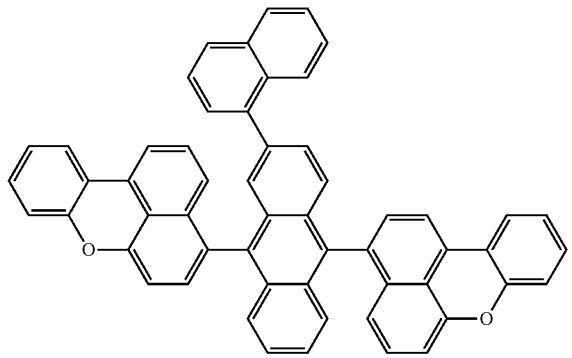

93
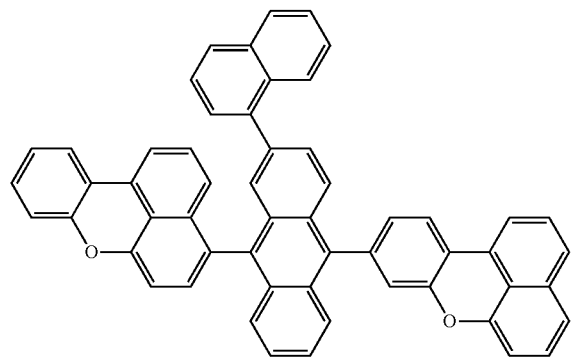
94
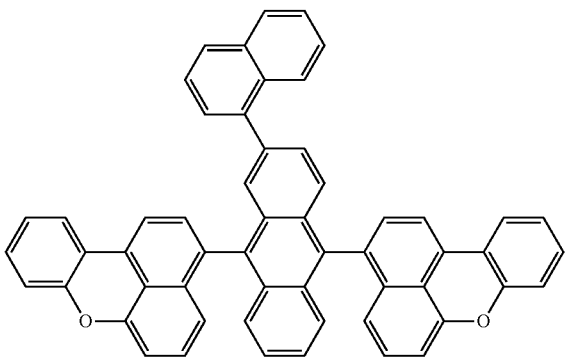
95
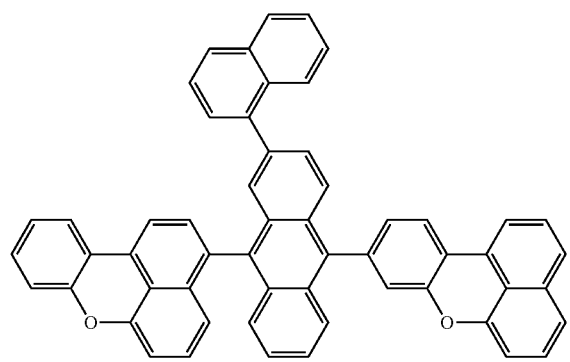
96
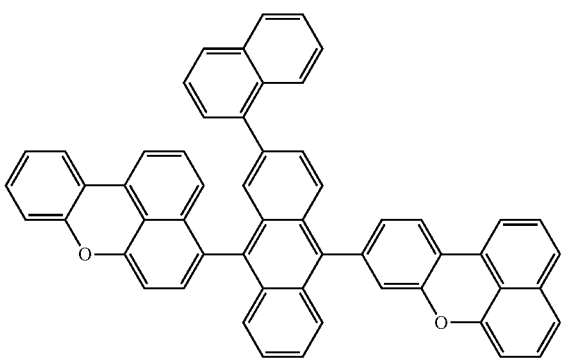
97
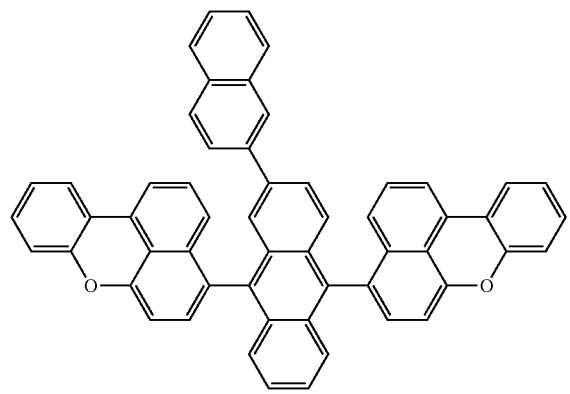
98
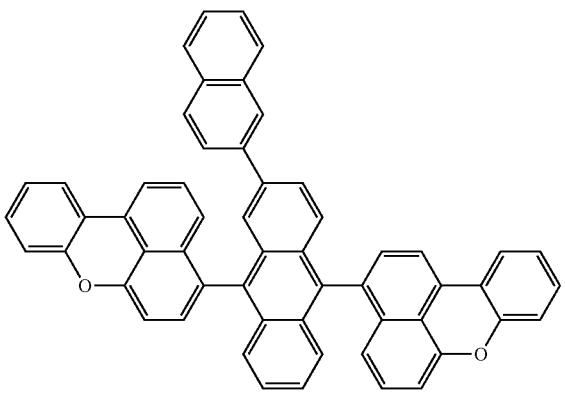
99
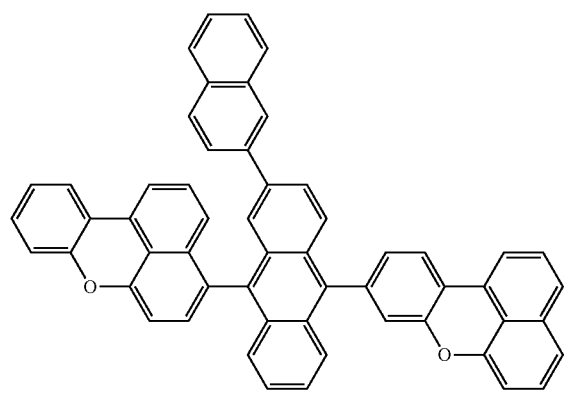
100
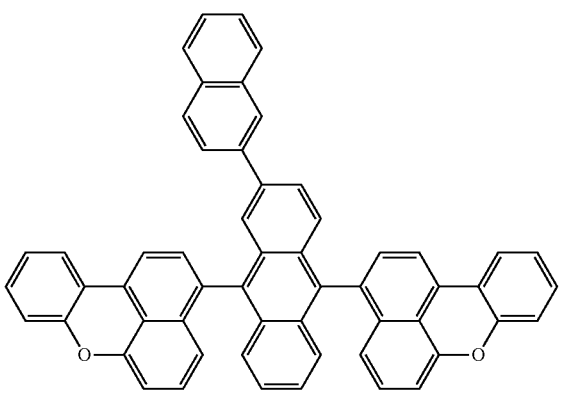

-continued
101
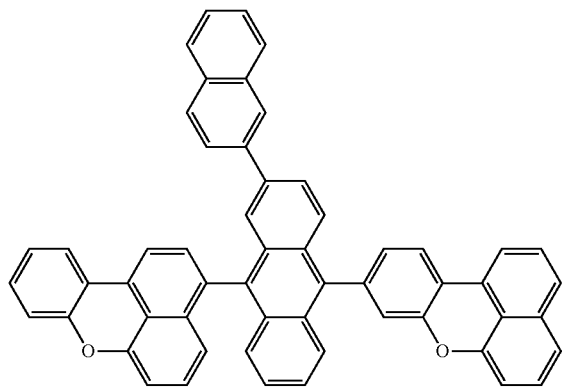
102
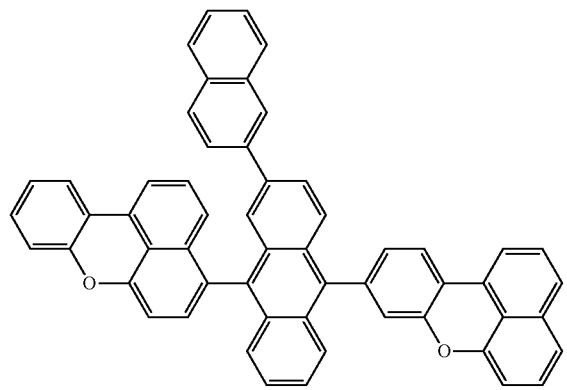
103
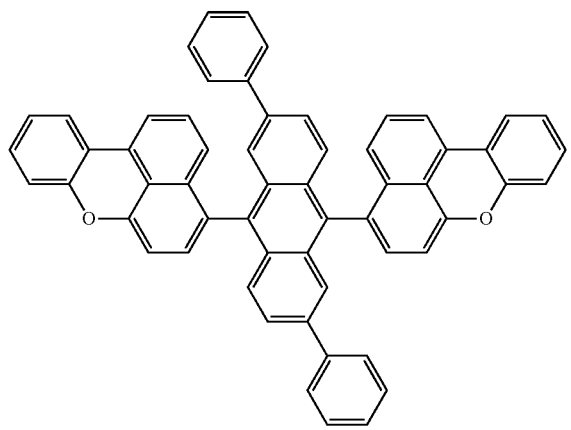
104
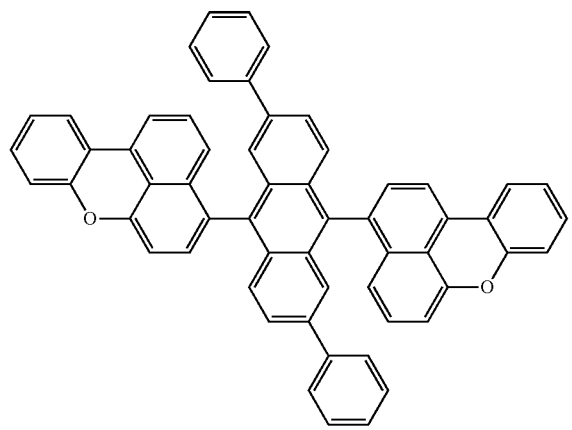
105
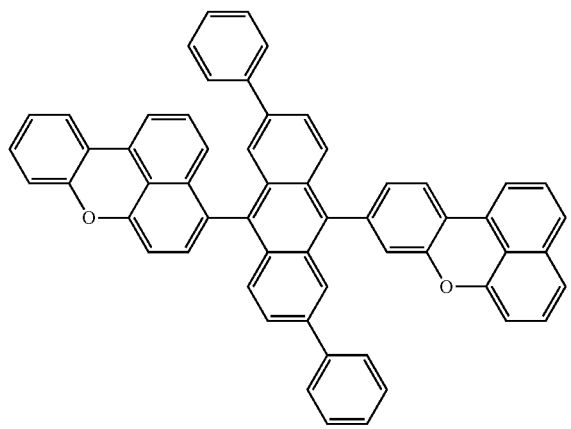
106
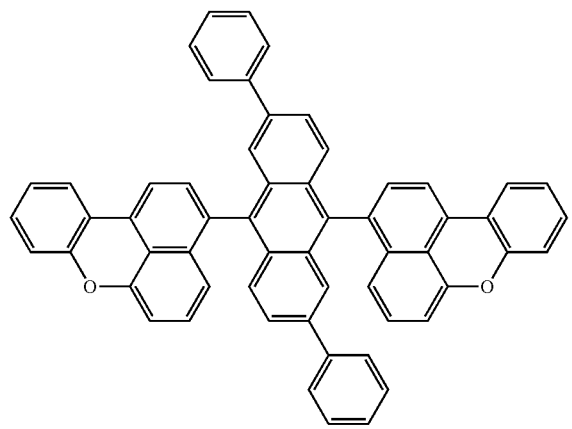

-continued
107
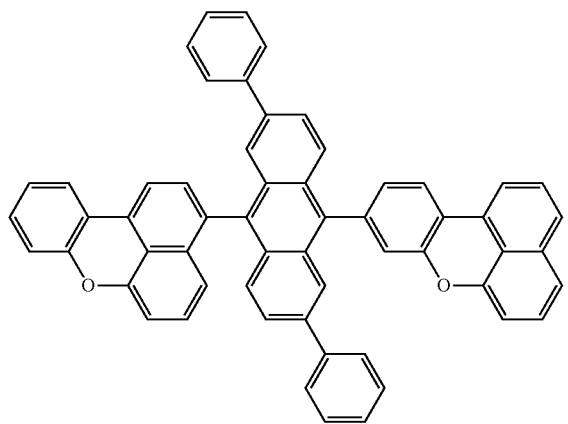
108
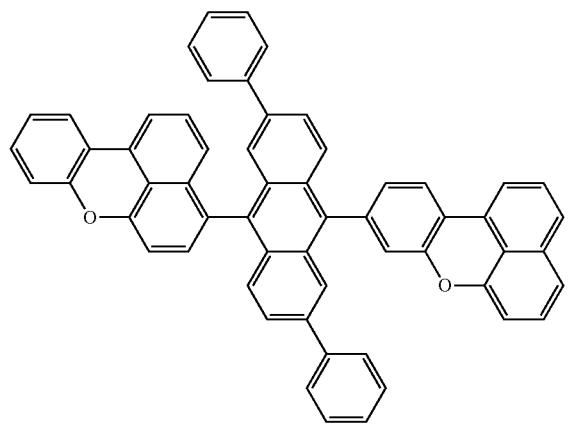
109
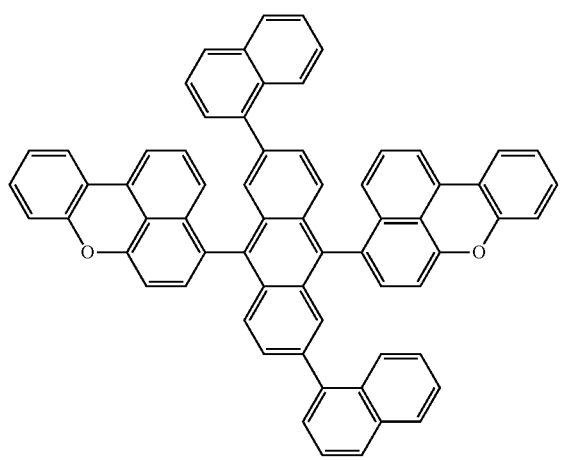
110
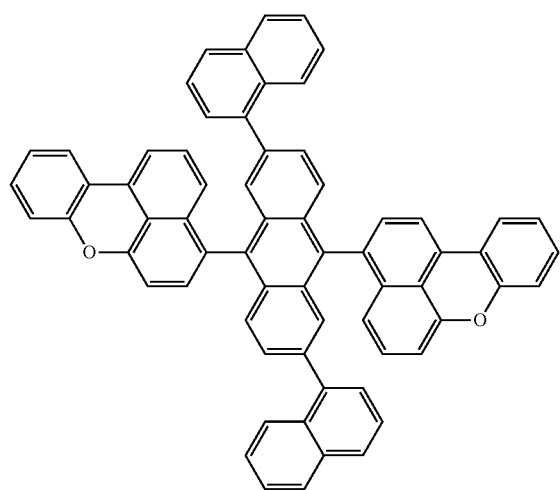
111
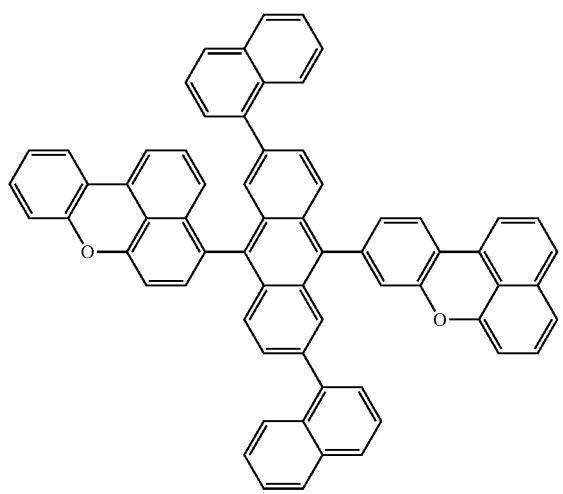
112
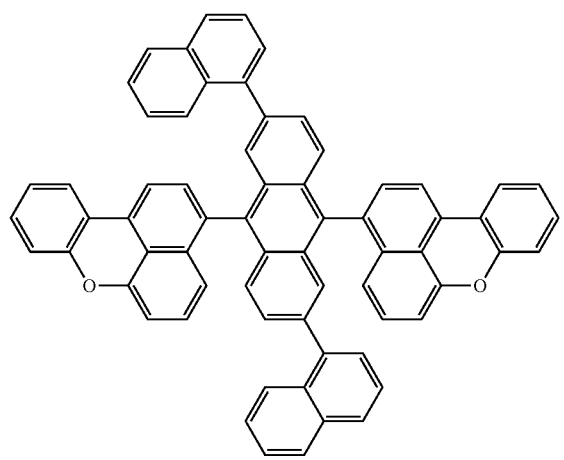

-continued
113
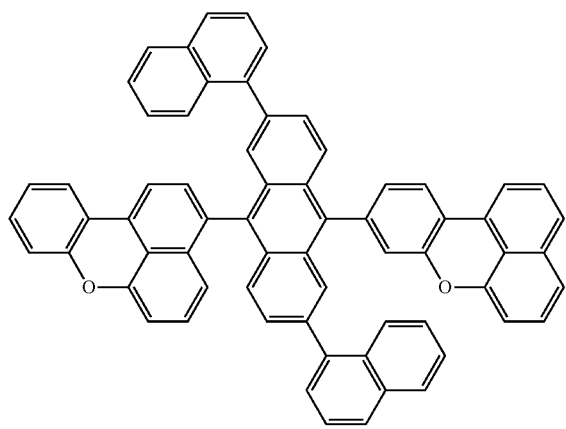
114
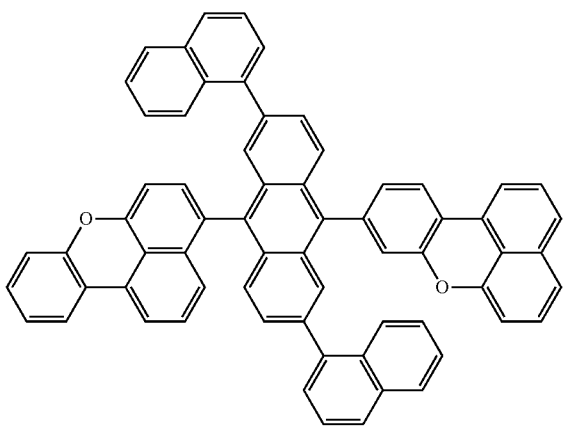
115
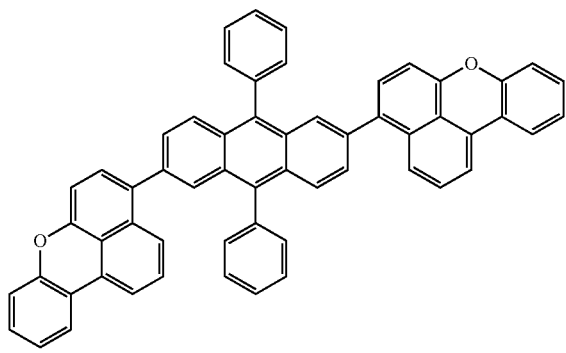
116
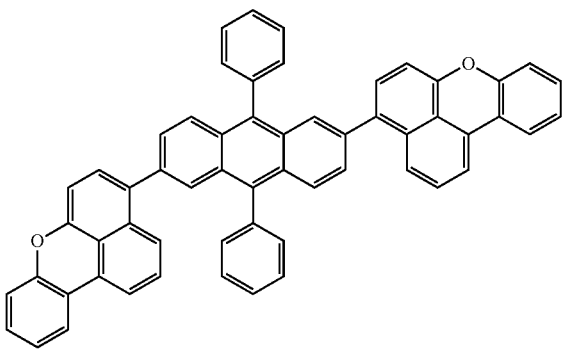
117
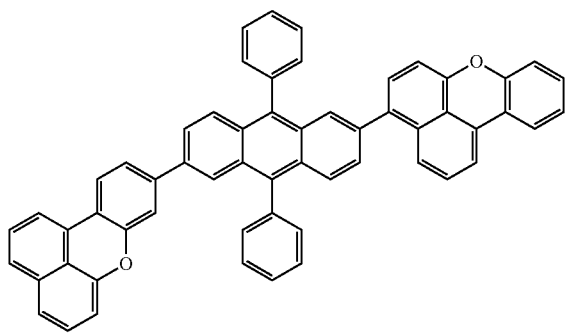
118
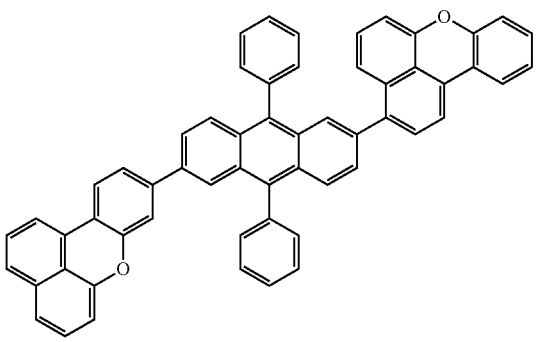
119
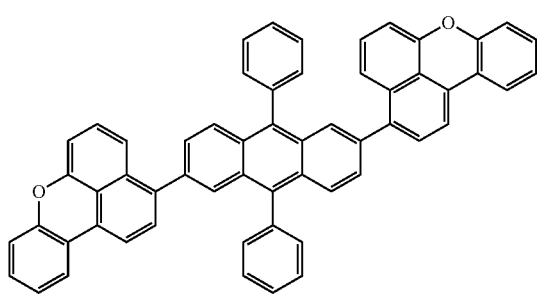
120
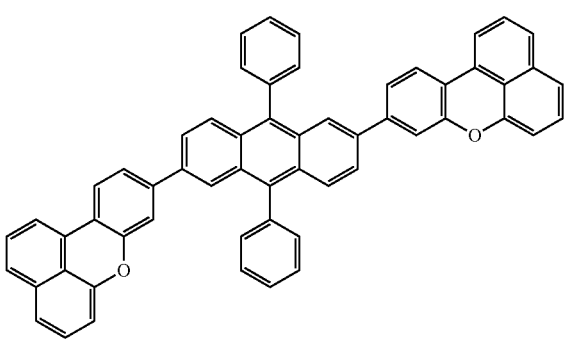

-continued
121 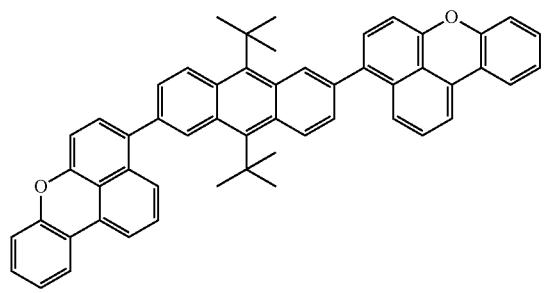
122 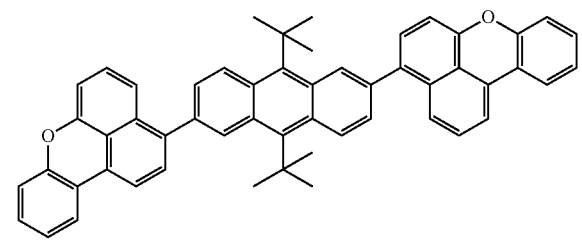
123 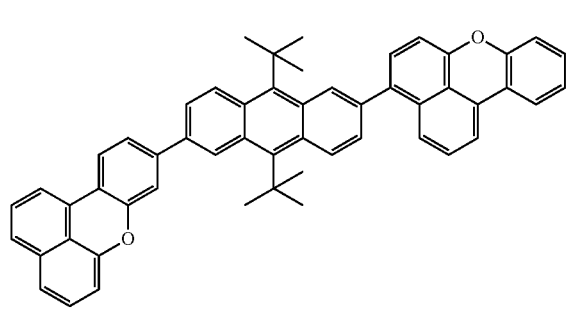
124 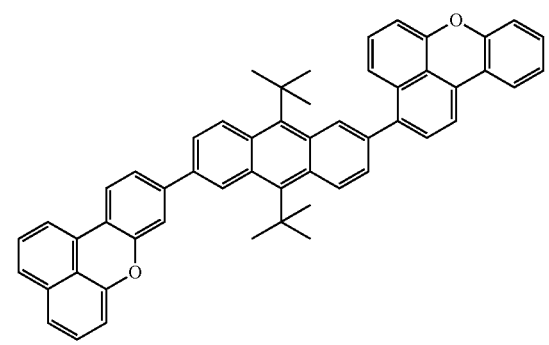
125 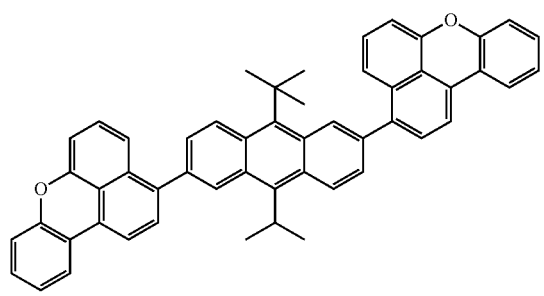
126 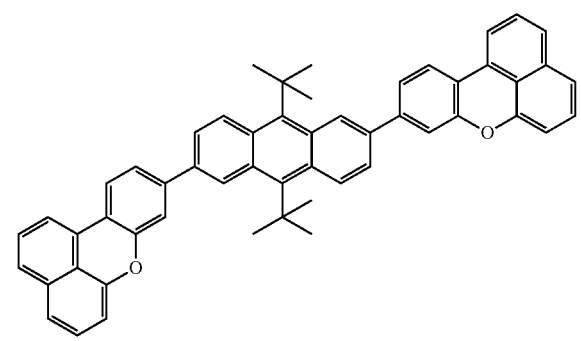
127 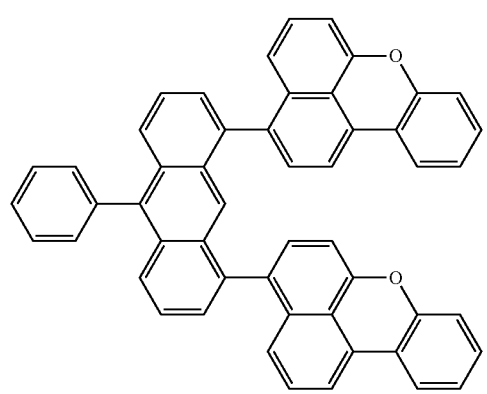
128 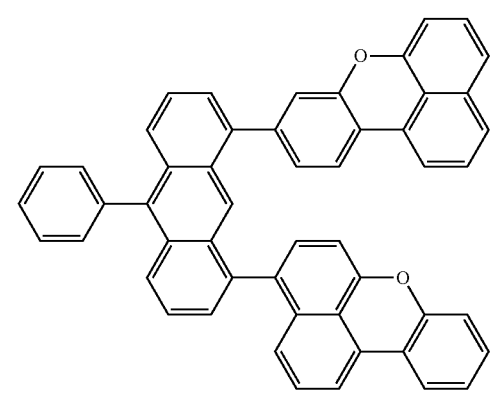

-continued
129
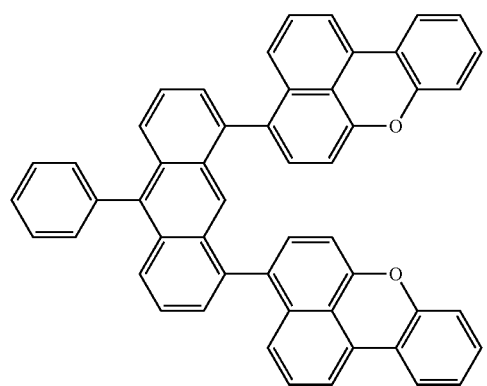
130
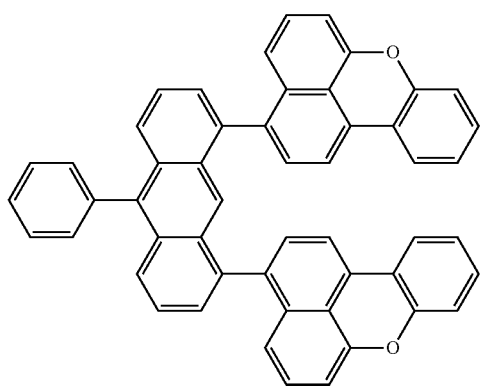
131
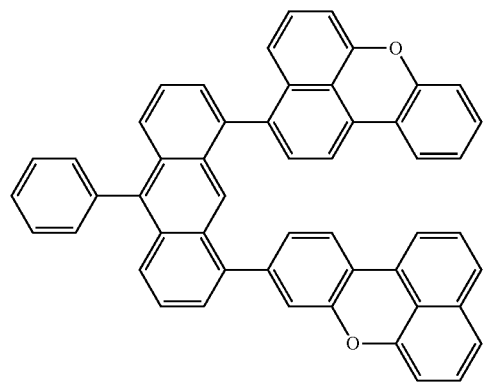
132
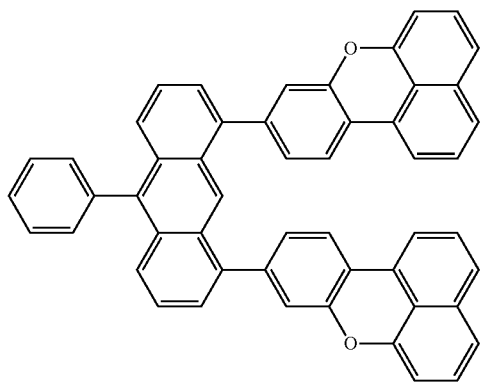
133
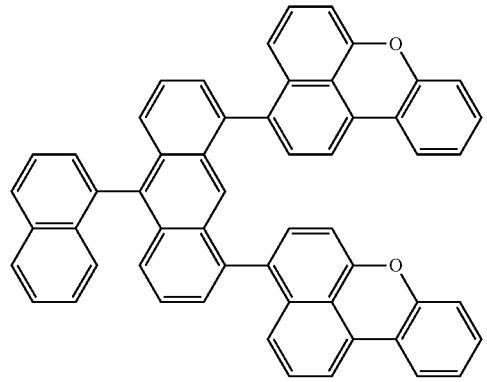
134
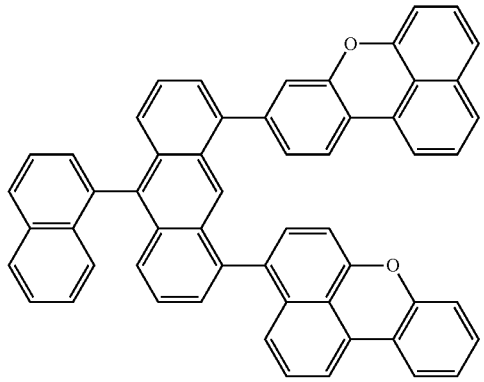
135
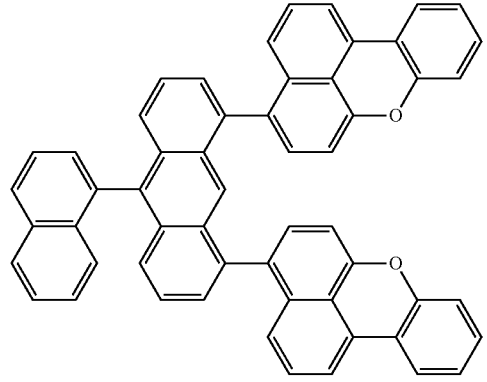
136
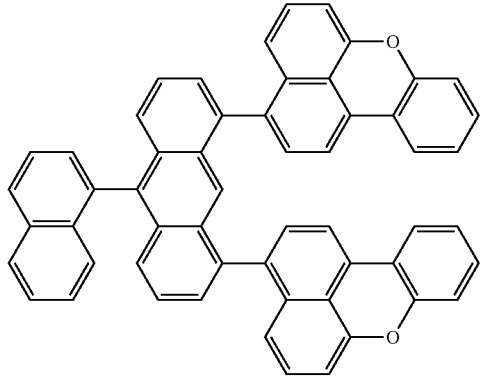

-continued
137
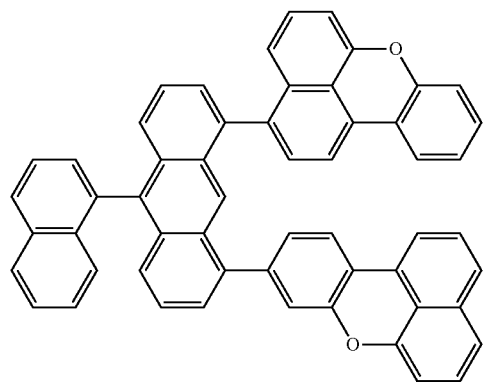
138
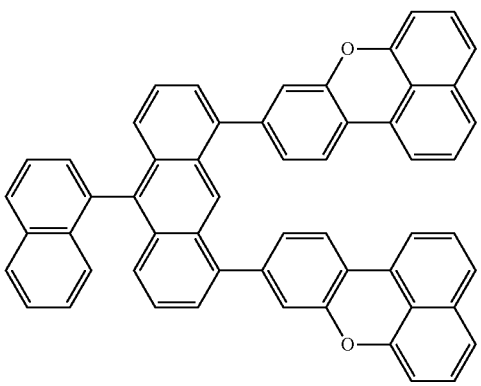
139
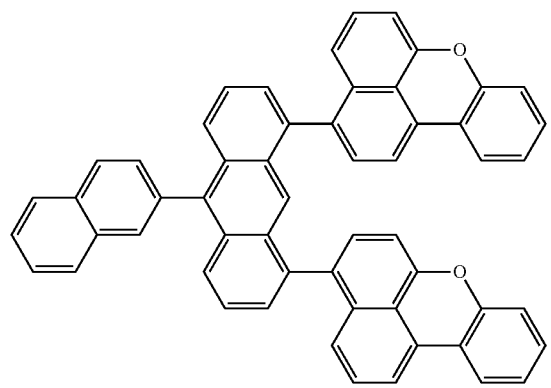
140
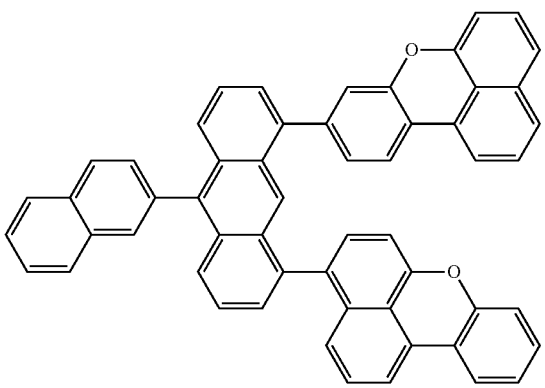
141
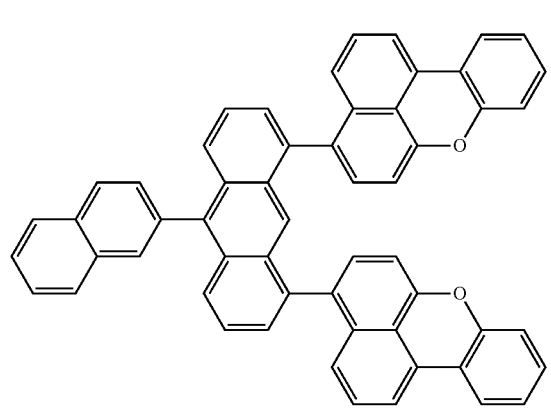
142
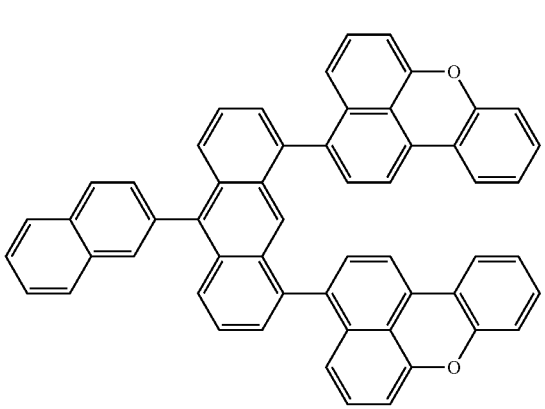
143
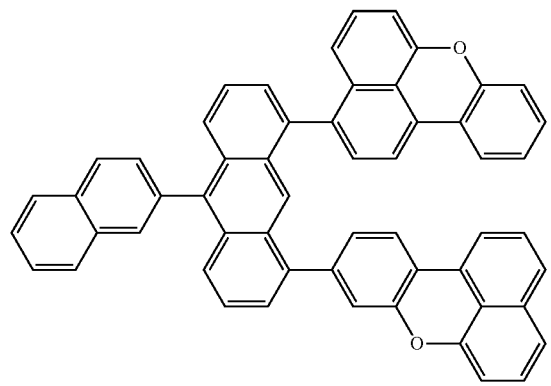
144
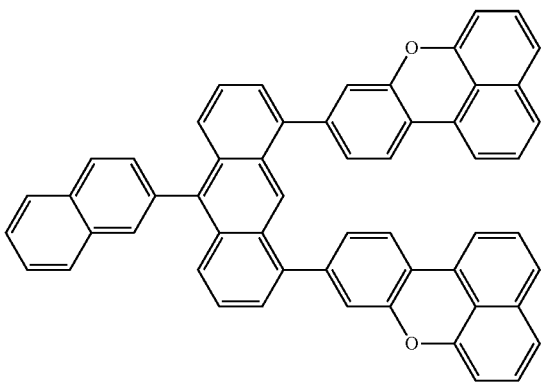

-continued
145
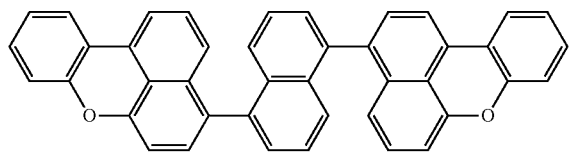
146
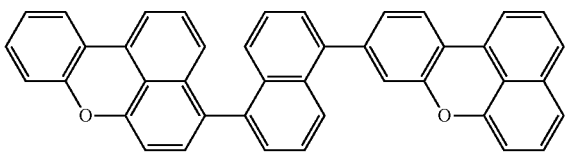
147
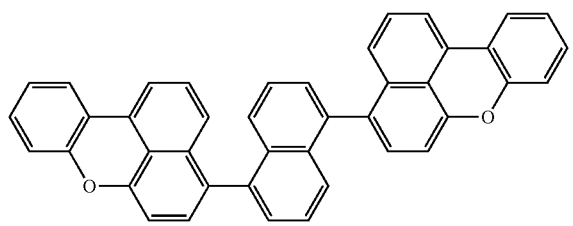
148
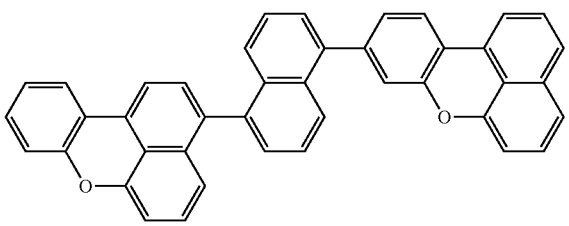
149
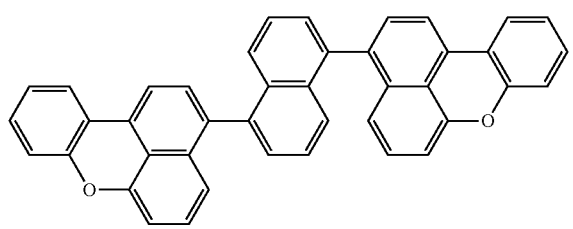
150
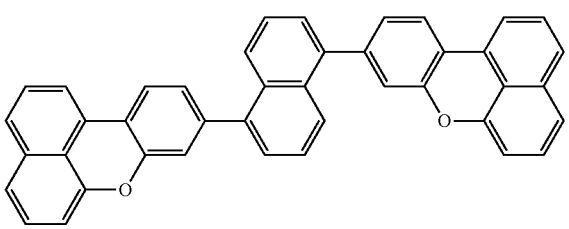
151
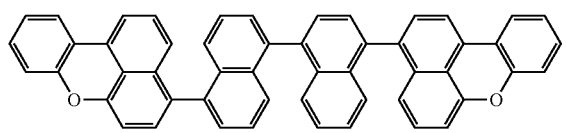
152
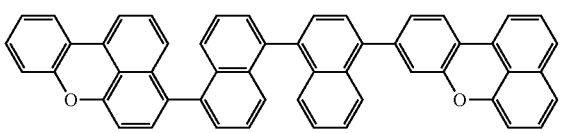
153
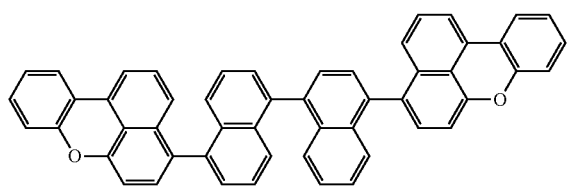
154
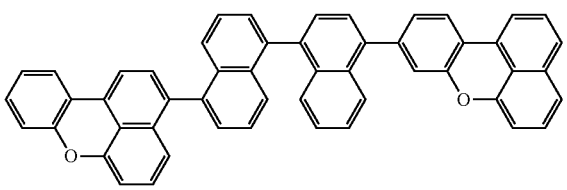
155
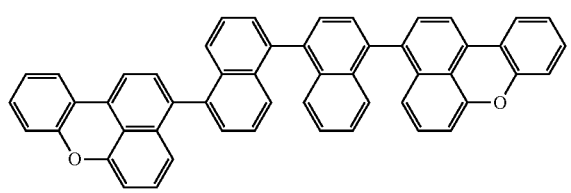
156
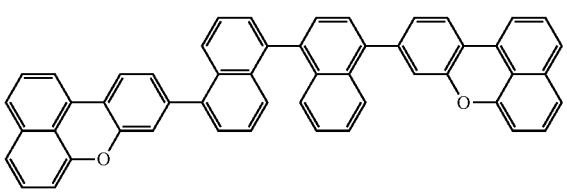
157
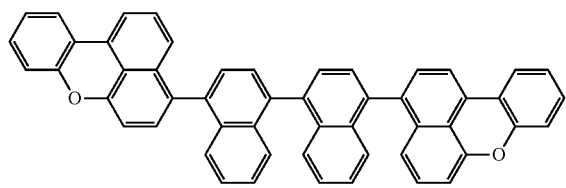
158
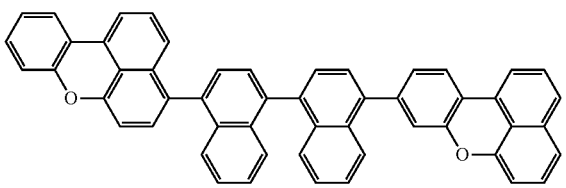

159
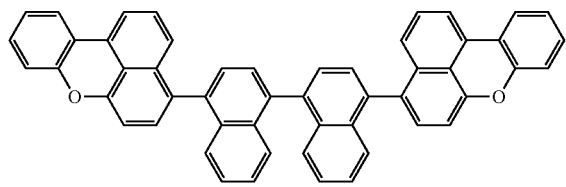
160
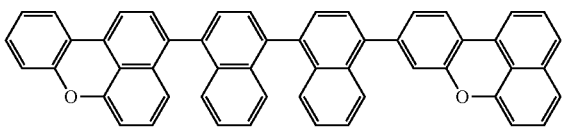
161
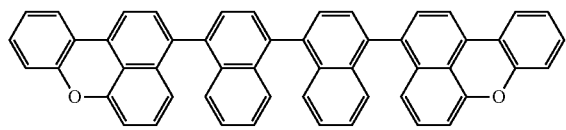
162
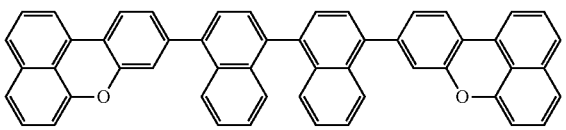
163
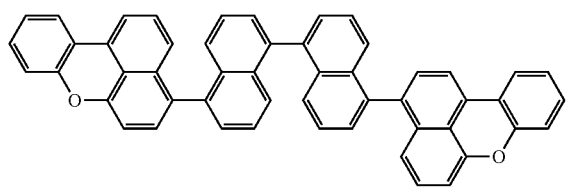
164
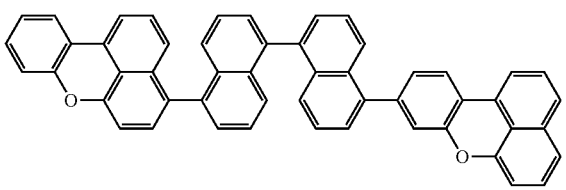
165
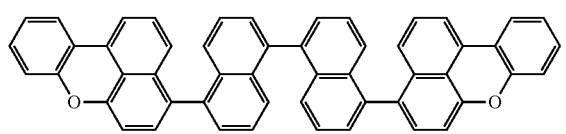
166
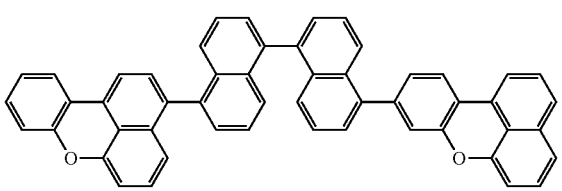
167
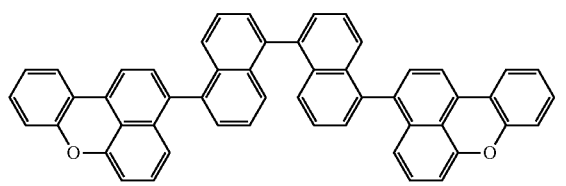
168
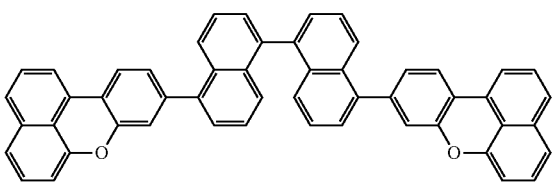
169
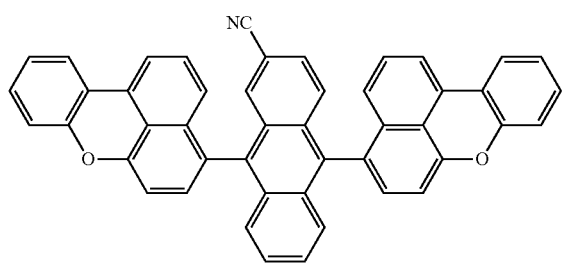
170
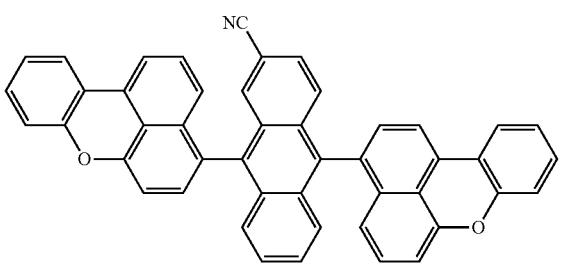
171
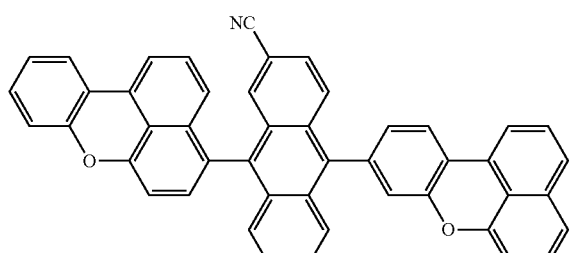
172
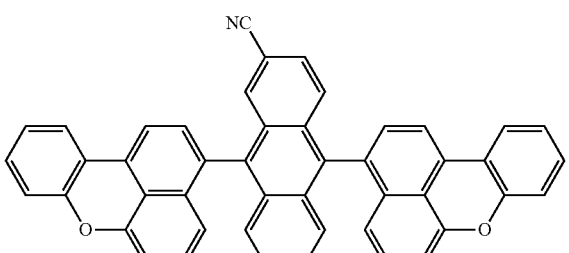

-continued
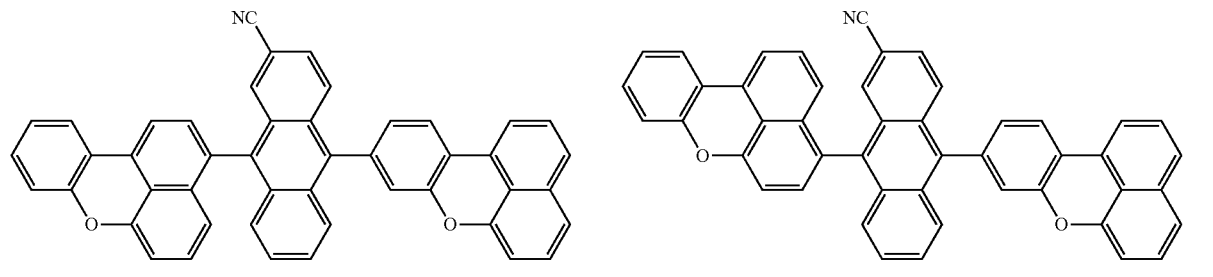
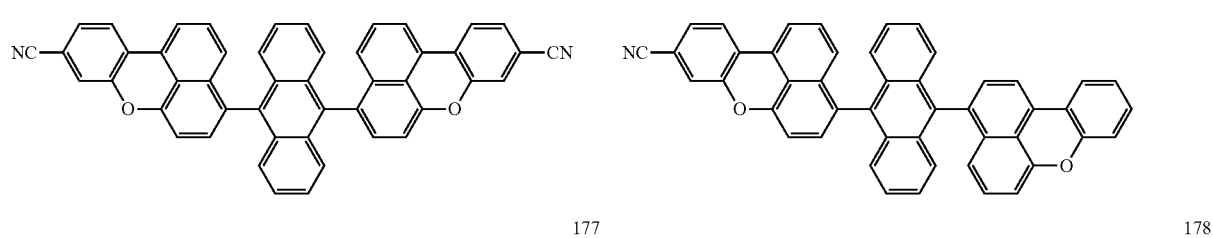
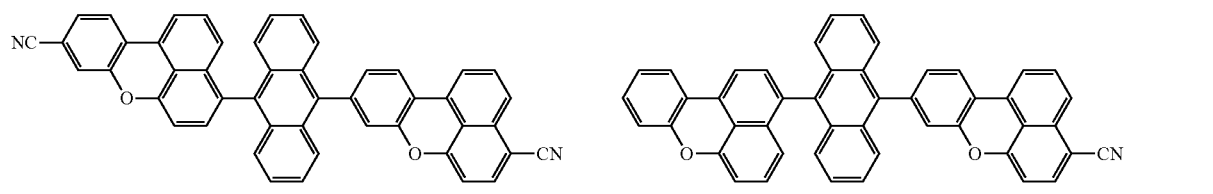
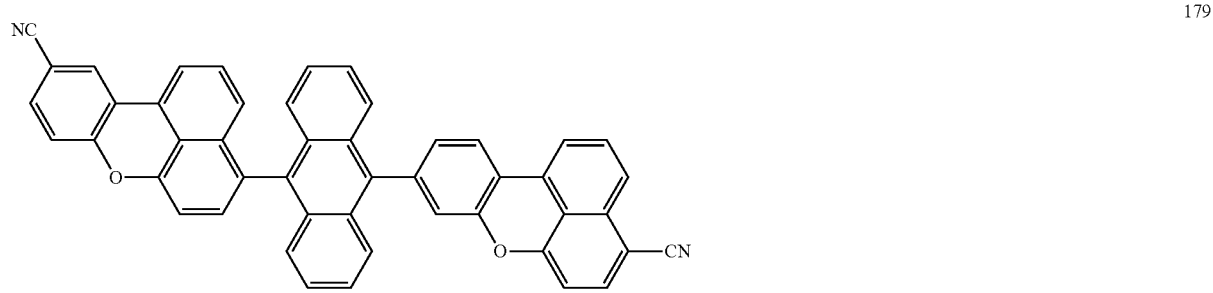
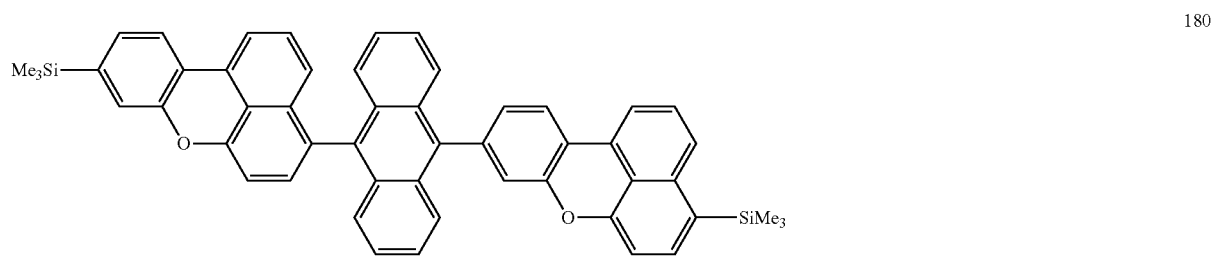
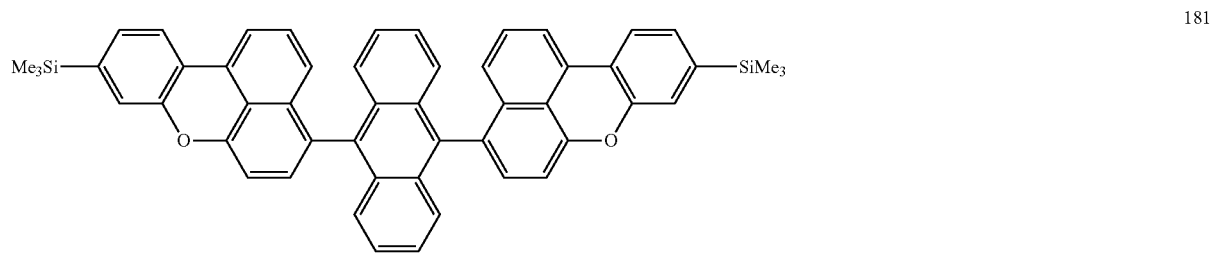

-continued
182
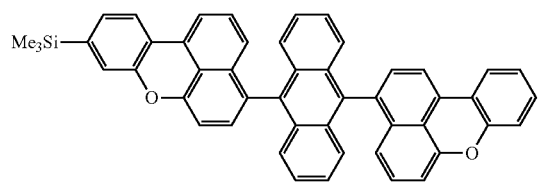
183
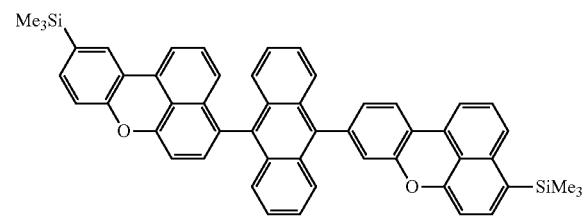
184
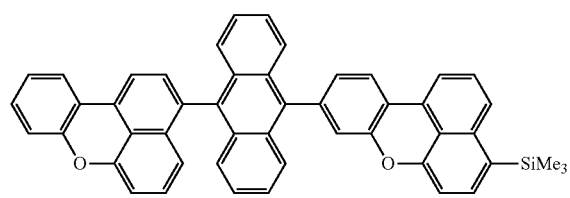
185
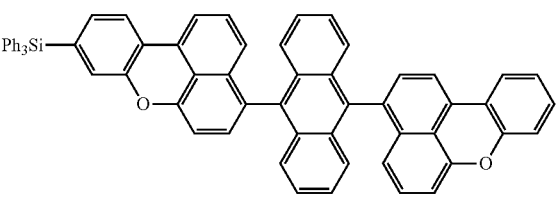
186
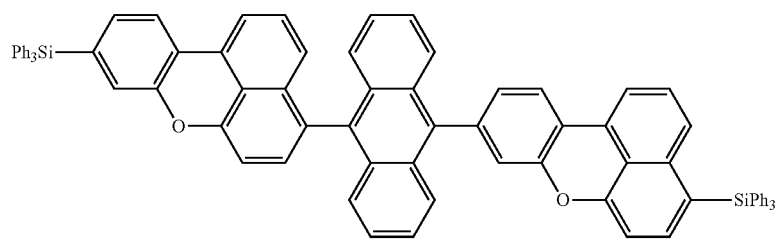
187
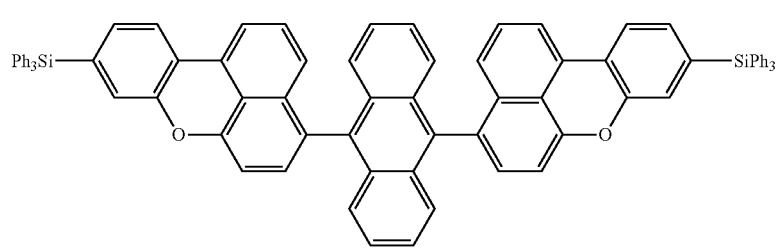
188
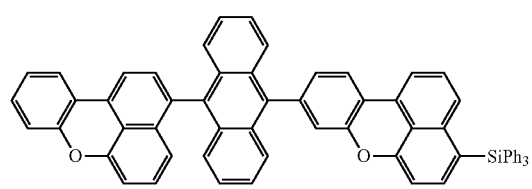
189
190
191

-continued
192
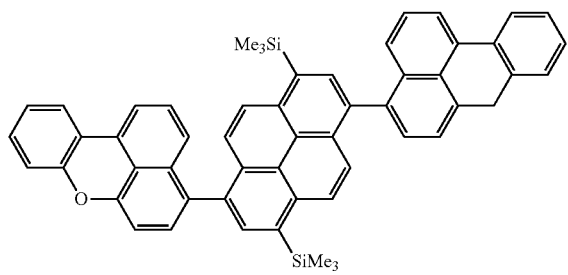
193
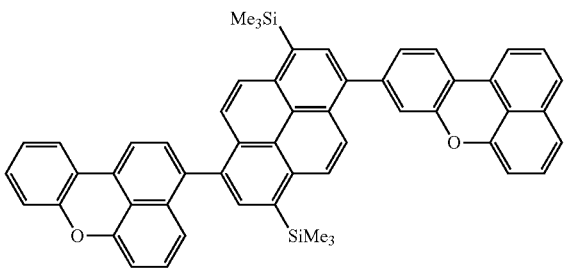
194
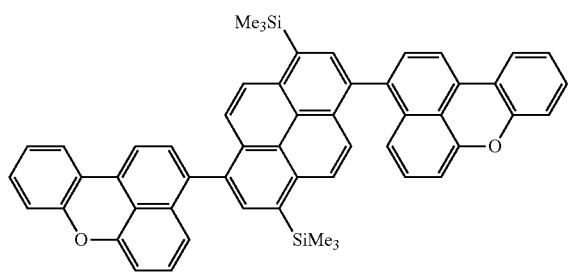
195
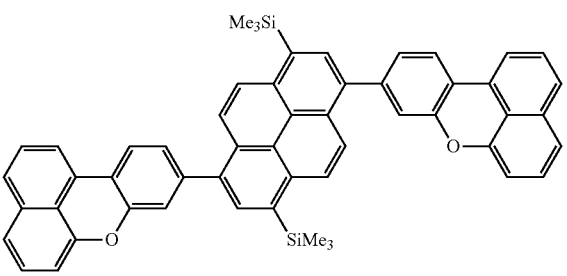
196
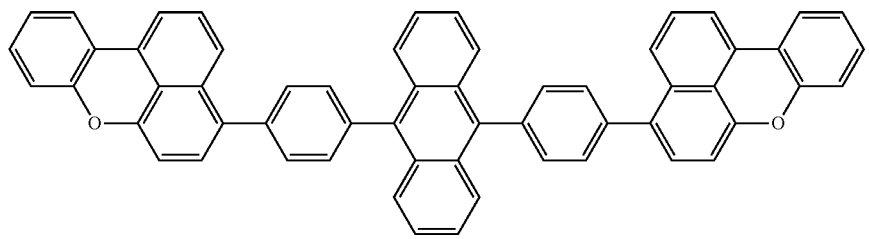
197
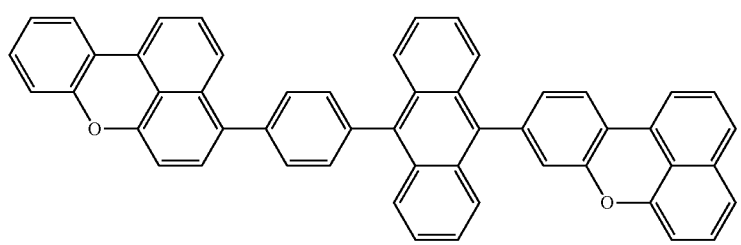
198
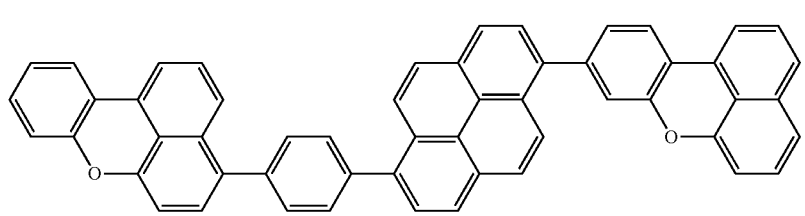
199
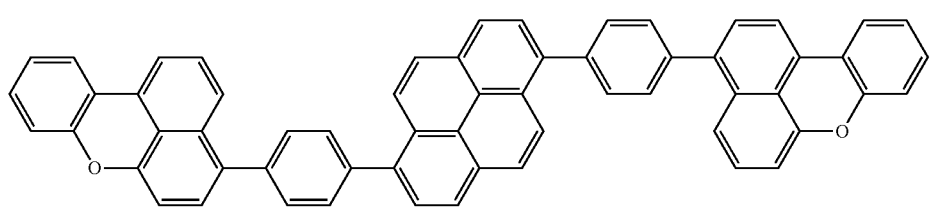

-continued
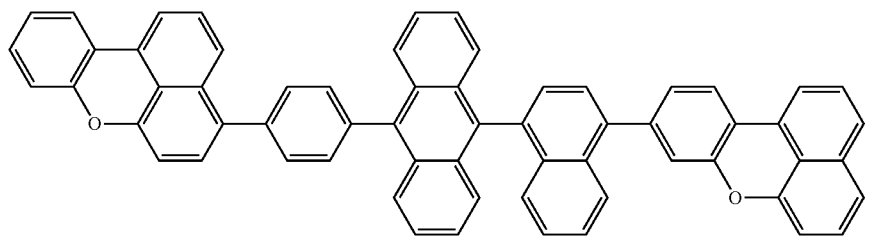
200
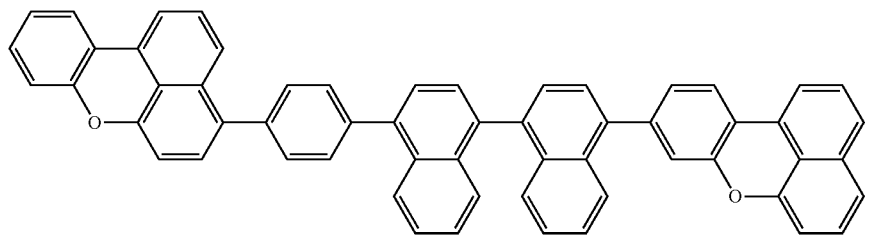
201
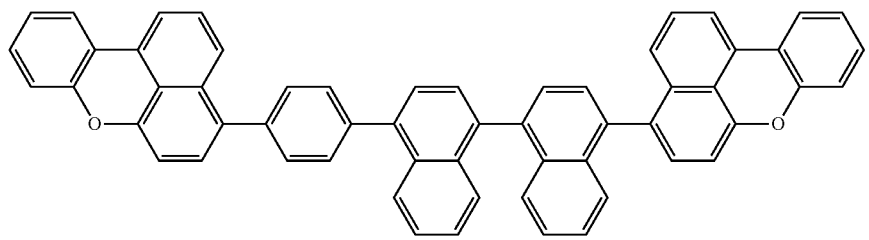
202
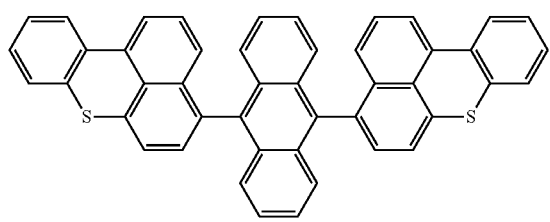
203
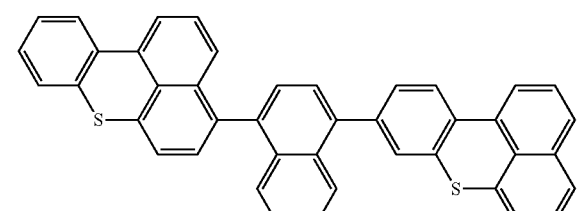
204
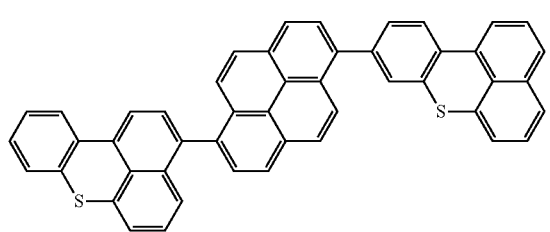
205
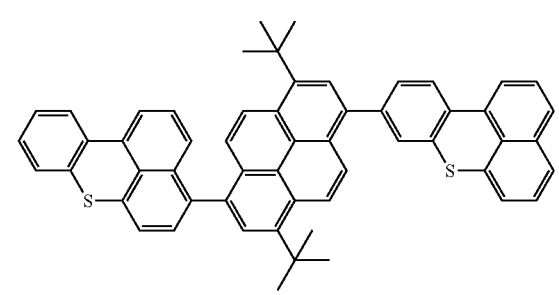
206
207
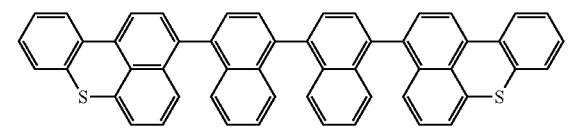
208

208
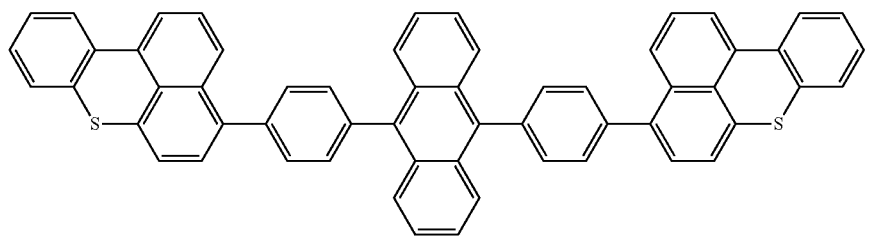
209
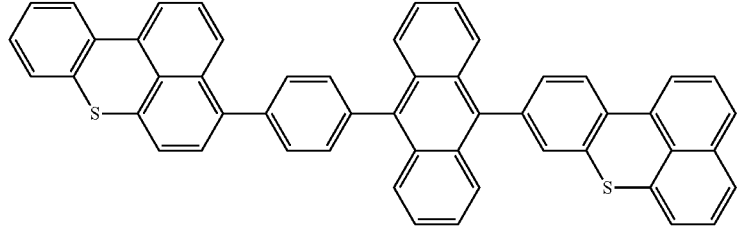
210
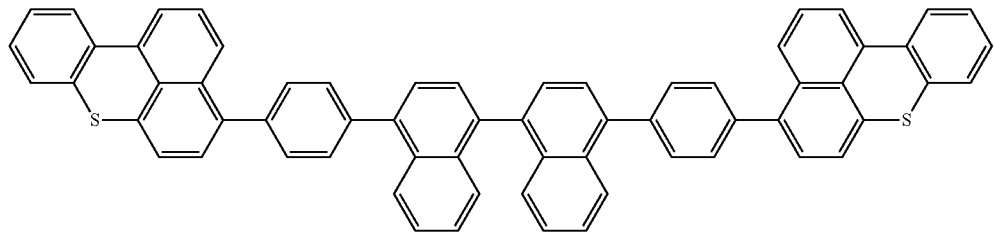
211
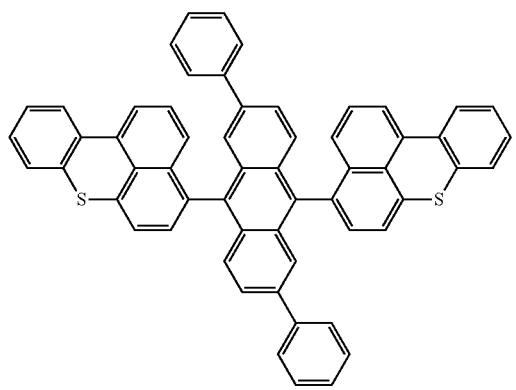
212
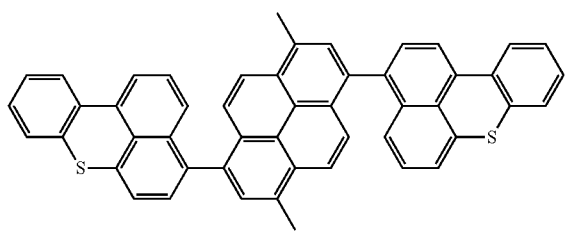
213
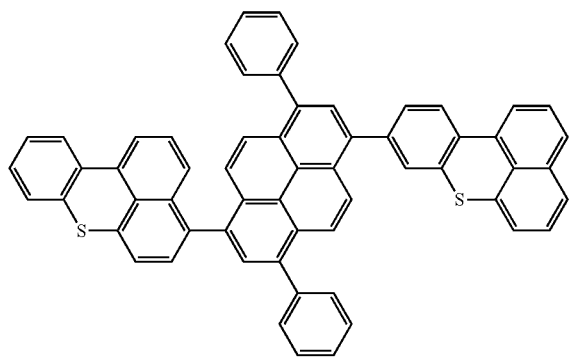
214
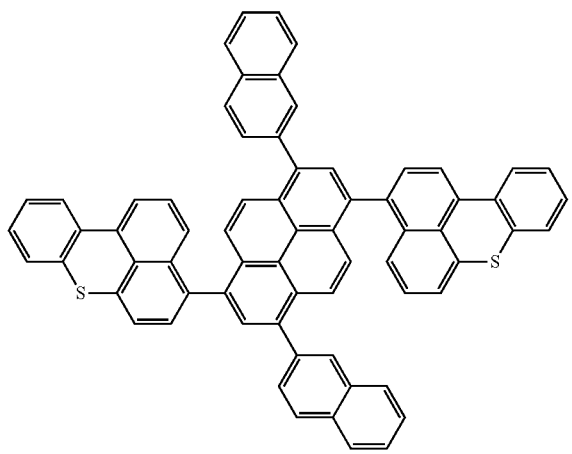

-continued

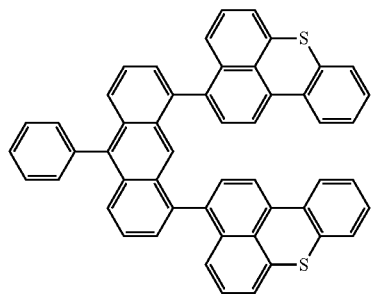
215

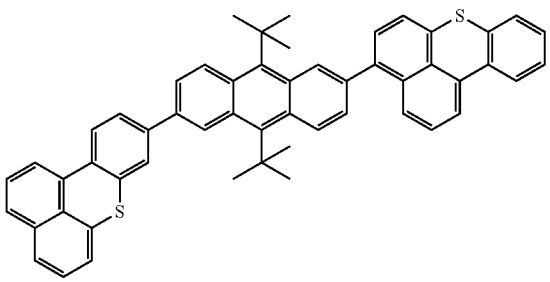
216

217

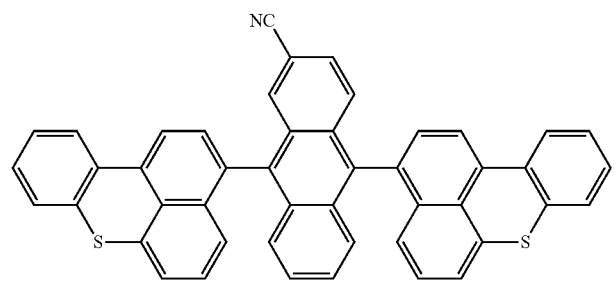

218

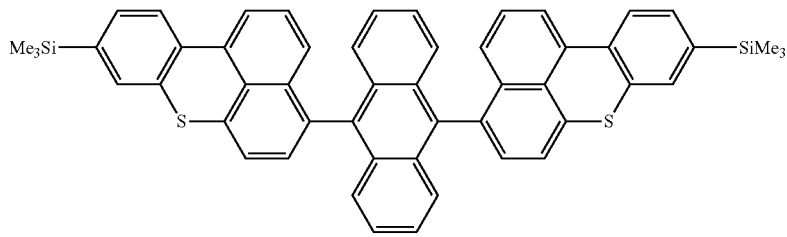

219

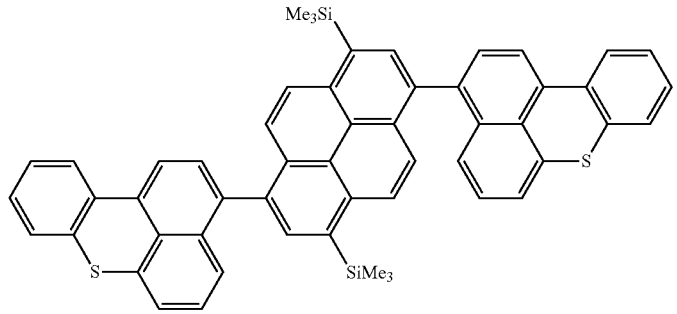

A saturated 6-membered ring in $Ar_1$ and $Ar_2$ in Formula 1 may include O or S, which are heteroatoms having an unshared electron pair. Accordingly, due to relatively low nucleophilic characteristics of the heteroatoms, an organic light-emitting device employing or including the condensed cyclic compound represented by Formula 1 may have high efficiency and long lifespan.

Accordingly, and organic light-emitting device including the compound represented by Formula 1 the may have a low driving voltage, high efficiency, high brightness, and long lifespan.

The condensed cyclic compound represented by Formula 1 may be synthesized by using a suitable organic synthetic method. A synthesis method of the condensed cyclic compound may be understood in view of the following embodiments.

The condensed cyclic compound of Formula 1 may be used or included between a pair of electrodes of an organic light-emitting device. For example, the condensed cyclic compound made be included in an emission layer. Accordingly, and organic light-emitting device according to an embodiment may include a first electrode; a second electrode facing the first electrode; and an organic layer between the first electrode and the second electrode and including an emission layer. The organic layer may include at least one of the condensed cyclic compounds described above.

The expression "(an organic layer) includes at least one condensed cyclic compounds" used herein may include a case in which "(an organic layer) includes one condensed cyclic compound of Formula 1 and a case in which two or more different condensed cyclic compounds of Formula 1.

For example, the organic layer may include, as the condensed cyclic compound, only Compound 1. In this regard, Compound 1 may exist in an emission layer of the organic light-emitting device. In another embodiment, the organic layer may include, as the condensed cyclic compound, Compound 1 and Compound 2. In this regard. Compound 1 and Compound 2 may exist in an identical layer (for example, Compound 1 and Compound 2 may all exist in an emission layer), or different layers (for example, Compound 1 may exist in a hole transport layer and Compound 2 may exist in an emission layer).

The organic layer may include, e.g., i) a hole transport region between the first electrode and the emission layer and includes at least one of a hole injection layer, a hole transport layer, a buffer layer, and an electron blocking layer, and ii) an electron transport region between the emission layer and the second electrode and includes at least one selected from a bole blocking layer, an electron transport layer, and an electron injection layer.

The emission layer may include the condensed cyclic compound represented by Formula 1. In an implementation, the condensed cyclic compound included in the emission layer may act as a host and the emission layer may further include a dopant. The dopant may be a dopant that is capable of emitting red light, green light, or blue light. The dopant may be a phosphorous dopant or a fluorescent dopant. According to an embodiment, the dopant may be a fluorescent dopant.

The term "organic layer" used herein refers to a single layer and/or a plurality of layers disposed between the first electrode and the second electrode of the organic light-emitting device. A material included in the "organic" layer is not limited to on organic material.

FIG. 1 illustrates a schematic view of an organic light-emitting device 10 according to an embodiment. The organic light-emitting device 10 may include a first electrode 110, an organic layer 150, and a second electrode 190.

Hereinafter, the structure of an organic light-emitting device according to an embodiment and a method of manufacturing an organic light-emitting device according to an embodiment will be described in connection with FIG. 1.

In FIG. 1, a substrate may be disposed under the first electrode 110 or above the second electrode 190. The substrate may be a glass substrate or transparent plastic substrate, each with excellent mechanical strength, thermal stability, transparency, surface smoothness, ease of handling, and water repellency.

The first electrode 110 may be formed by depositing or sputtering a material for forming the first electrode on the substrate. When the first electrode 110 is an anode, the material for the first electrode 110 may be selected from materials with a high work function to facilitate hole injection. The first electrode 110 may be a reflective electrode or a transmissive electrode. The material for the lust electrode 120 may be a transparent and highly conductive material, and examples of such a material may include indium tin oxide (ITO), indium zinc oxide (IZO), tin oxide ($SnO_2$), and zinc oxide (ZnO). When the first electrode 110 is a semi-transmissive electrode or a reflective electrode, as a material for forming the first electrode, at least one of magnesium (Mg), aluminum (Al), aluminum-lithium (Al—Li), calcium (Ca), magnesium-indium (Mg—In), magnesium-silver (Mg—Ag) may be used.

The first electrode 110 may have a single-layer structure, or a multi-layer structure including two or more layers. For example, the first electrode 110 may have a three-layered structure of ITO/Ag/ITO, but the structure of the first electrode 110 is not limited thereto.

An organic layer 150 may be disposed on the first electrode 110. The organic layer 150 may include an emission layer.

The organic layer 150 may further include a hole transport region between the first electrode and the emission layer, and/or an electron transport region between the emission layer and the second electrode.

The hole transport region may include at least one selected from a hole injection layer (HIL), a hole transport layer (HTL), a buffer layer, and an electron blocking layer (EBL), and the electron transport region may include at least one selected from a hole blocking layer (HBL), an electron transport layer (ETL), and an electron injection layer (EIL), but the hole transport region and the electron transport region are not limited thereto.

The hole transport region may have a single-layered structure formed of a single material, a single-layered structure formed of a plurality of different materials, or a multi-layered structure having a plurality of layers formed of a plurality of different materials.

For example, the hole transport region may have a single-layered structure formed of a plurality of different materials, or a structure of hole injection layer/hole transport layer, a structure of hole injection layer/hole transport layer/buffer layer, a structure of hole injection layer/buffer layer, a structure of hole transport layer/buffer layer, or a structure of hole injection layer/hole transport layer/electron blocking layer, wherein layers of each structure are sequentially stacked from the first electrode 110 in this stated order, but are not limited thereto.

When the hole transport region includes a hole injection layer, the hole injection layer may be formed on the first electrode 110 by using various methods, such as vacuum deposition, spin coating casting, a Langmuir-Blodgett (LB) method, ink-jet printing, laser-printing, or laser-induced thermal imaging.

When a hole injection layer is formed by vacuum deposition, for example, the vacuum deposition may be performed at a temperature of a deposition temperature of about 100 to about 500° C., at a vacuum degree of about $10^{-8}$ to about $10^{-3}$ torr, and at a deposition rate of about 0.01 to about 100 Å/sec in consideration of a compound for a hole injection layer to be deposited, and the structure of a hole injection layer to be formed.

When a hole injection layer is formed by spin coating, the spin coating may be performed at a coating rate of about 2000 rpm to about 5000 rpm, and at a temperature of about 80° C. to 200° C. in consideration of a compound for a hole injection layer to be deposited, and the structure of a hole injection layer to be formed.

When the hole transport region includes a hole transport layer, the hole transport layer may be formed on the first electrode 110 or the hole injection layer by using various methods, such as vacuum deposition, spin coating, casting, a LB method, ink-jet printing, laser-printing, or laser-induced thermal imaging. When the hole transport layer is formed by vacuum deposition or spin coating, deposition and coating conditions for the hole transport layer may be determined by referring to the deposition and coating conditions for the hole injection layer.

The hole transport region may include at least one selected from m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), (polyaniline)/poly(4-styrenesulfonate) (PANI/PSS), a compound represented by Formula 201 below, and a compound represented by Formula 202 below.

-continued
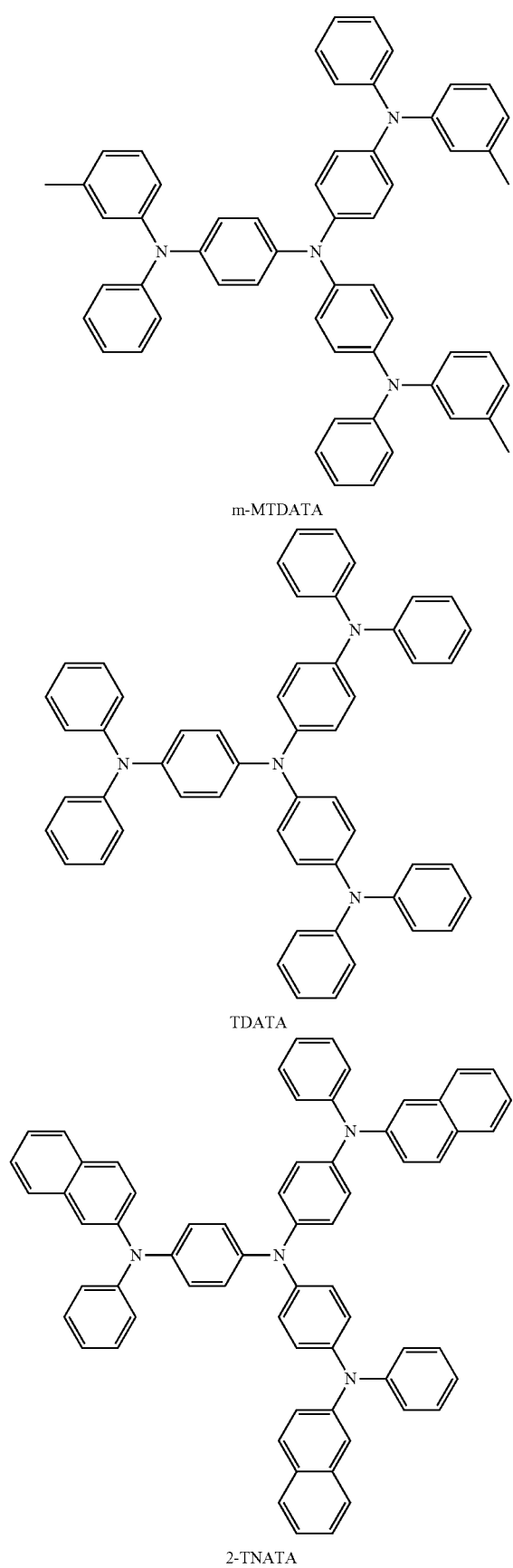
m-MTDATA
TDATA
2-TNATA
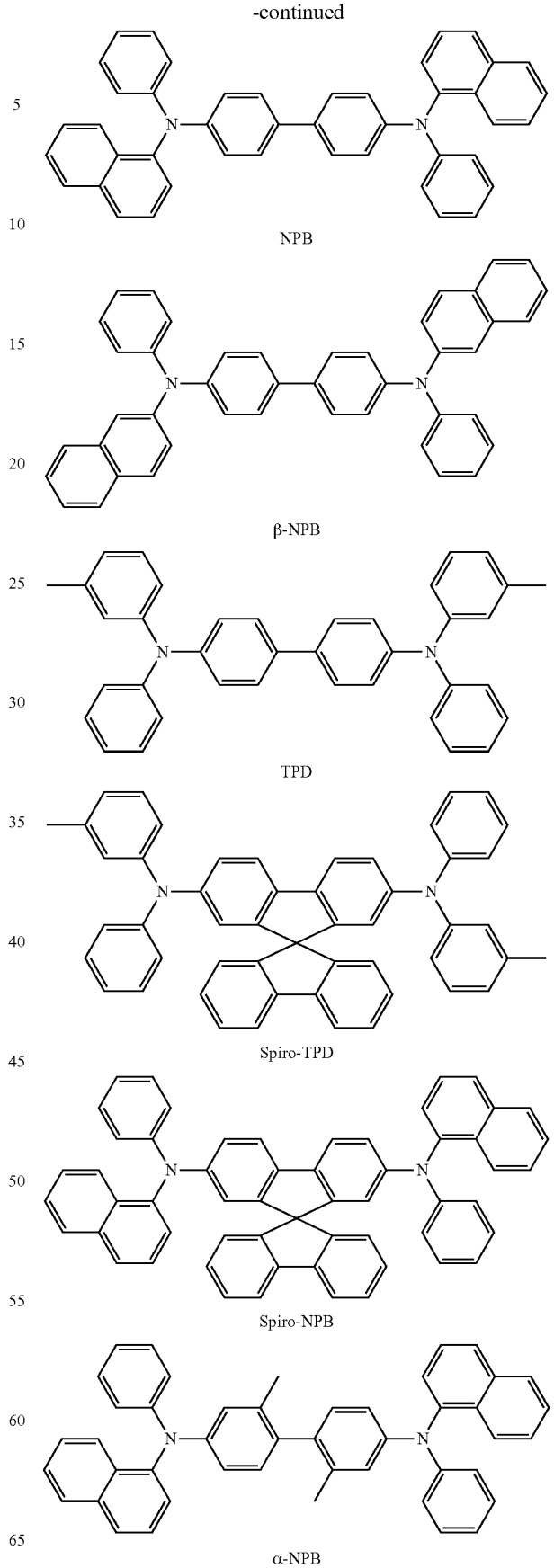
NPB
β-NPB
TPD
Spiro-TPD
Spiro-NPB
α-NPB

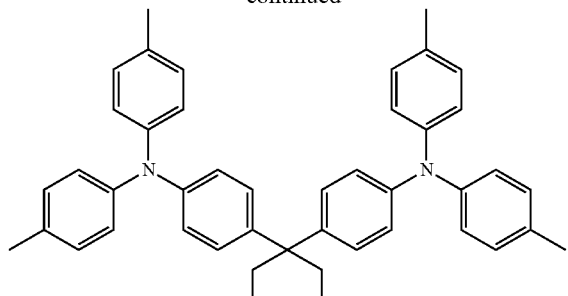

TAPC

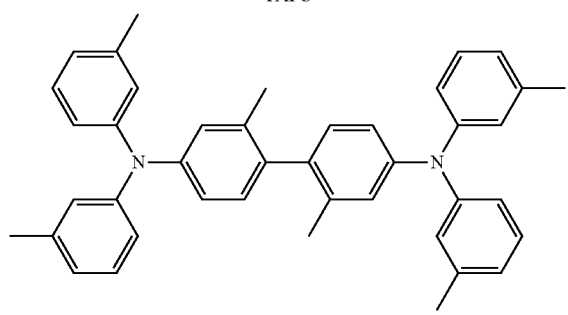

HMTPD

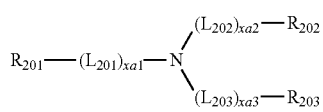

<Formula 201>

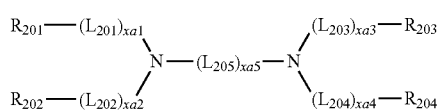

<Formula 202>

In Formulae 201 and 202, $L_{201}$ to $L_{205}$ may be understood by referring to the description provided herein in connection with $L_1$;

xa1 to xa4 may be each independently selected from 0, 1, 2, and 3;

xa5 may be selected from 1, 2, 3, 4, and 5; and $R_{201}$ to $R_{204}$ may be understood by referring to the description provided herein in connection with $R_{21}$.

In an implementation, in Formulae 201 and 202, $L_{201}$ to $L_{205}$ may be each independently selected from:

a phenylene group, a naphthylene group, a fluorenylene group, spiro-fluorenylene, fluorenylene group, a benzofluoene group, a dibenzofluoene group, a phenanthrenylene group, a anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene; and a phenylene group, a naphthylene group, a fluorenylene group, a spiro-fluorenylene group, a benzofluorenylene group, a dibenzofluorenylene group, a phenanthrenylene group, a anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, phenanthrenyl group, a anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may be each independently 0, 1, or 2;

xa5 may be 1, 2, or 3;

$R_{201}$ to $R_{204}$ are each independently selected from:

a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic add and a salt thereof, a phosphoric acid and a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but are not limited thereto.

The compound represented by Formula 201 may be represented by Formula 201A.

<Formula 201A>

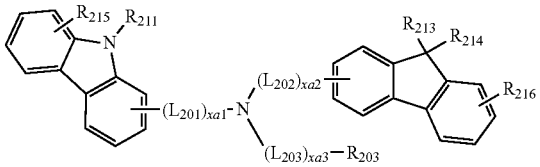

For example, the compound represented by Formula 201 may be represented by Formula 201A-1 below, but is not limited thereto:

<Formula 201A-1>

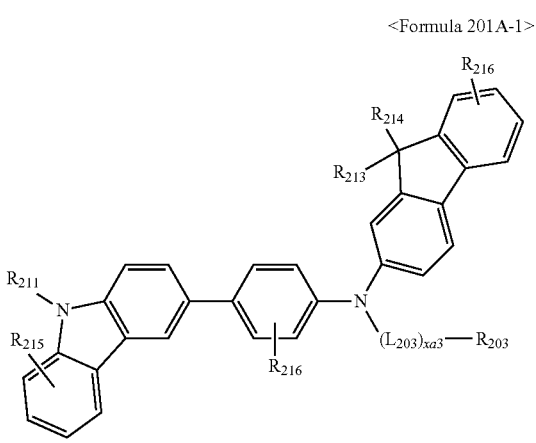

For example, the compound represented by Formula 202 may be represented by Formula 202A below, but is not limited thereto:

<Formula 202A>

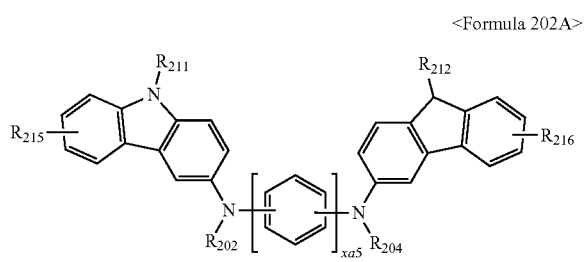

$L_{201}$ to $L_{203}$, xa1 to xa3, xa5, and $R_{202}$ to $R_{204}$ in Formulae 201A, 201A-1, and 202A are already described above, $R_{211}$ may be understood by referring to the description provided in connection with $R_{203}$, and $R_{213}$ to $R_{216}$ may be each independently selected from a hydrogen, a deuterium, —F, —Cl, —Br, —I, a hydroxyl group, cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl, a $C_2$-$C_{60}$ alkenyl, a $C_2$-$C_{60}$ alkynyl, a $C_1$-$C_{60}$ alkoxy, a $C_3$-$C_{10}$ cycloalkyl, a $C_3$-$C_{10}$ heterocycloalkyl, a $C_3$-$C_{10}$ cycloalkenyl, a $C_3$-$C_{10}$ heterocycloalkenyl, a $C_6$-$C_{60}$ aryl, a $C_6$-$C_{60}$ aryloxy, a $C_6$-$C_{60}$ arylthio, a $C_2$-$C_{60}$ heteroaryl, a monovalent non-aromatic condensed polycyclic group, and a monovalent non-aromatic condensed heteropolycyclic group.

For example, $L_{201}$ $L_{203}$ to in Formulae 201A, 201 A-1, and 202A may be each independently selected from:

a phenylene group, a naphthylene group, a fluorenylene group, a spiro-fluorenylene group, a benzofluorenylene group, a dibenzofluorenylene group, a phenanthrenylene group, a anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, to benzofluorenylene group, a dibenzofluorenylene group, a phenanthrenylene group, a anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 may be each independently 0 or 1;

$R_{203}$, $R_{211}$, and $R_{212}$ are each independently selected from:

a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic add and a salt thereof, a phosphoric acid and a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ are each independently selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic add and a salt thereof, a phosphoric acid and a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and $R_{215}$ and $R_{216}$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic add and a salt thereof, a phosphoric acid and a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xa5 may be 1 or 2.

$R_{213}$ and $R_{214}$ in Formulae 201A, and 201A-1 may bind to each other to form a saturated or unsaturated ring.

The compound represented by Formula 201, and the compound represented by Formula 202 may include compounds HT1 to HT20 illustrated below, but are not limited thereto.

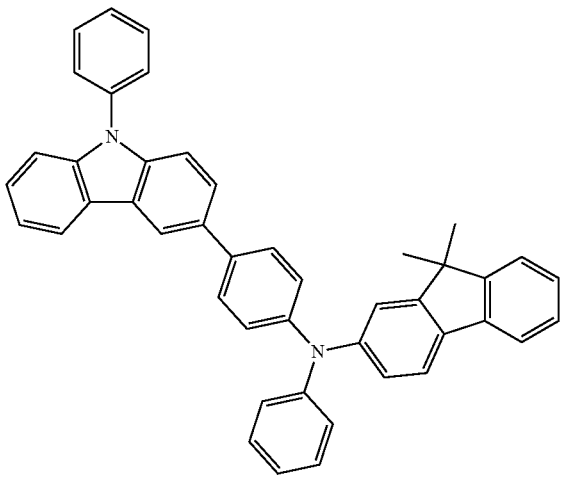

HT1

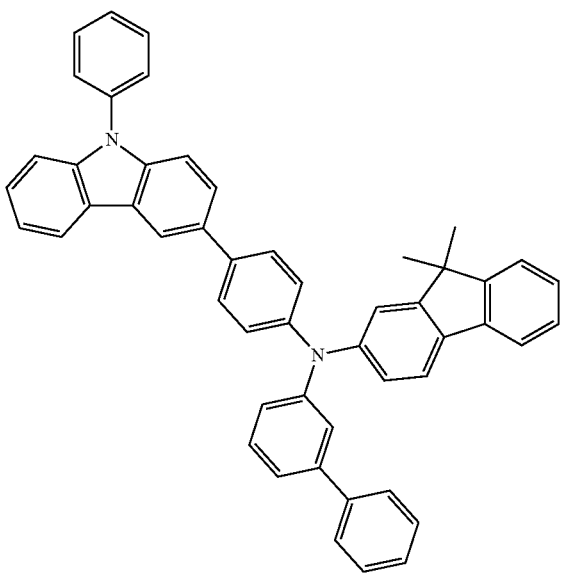

HT2

HT3
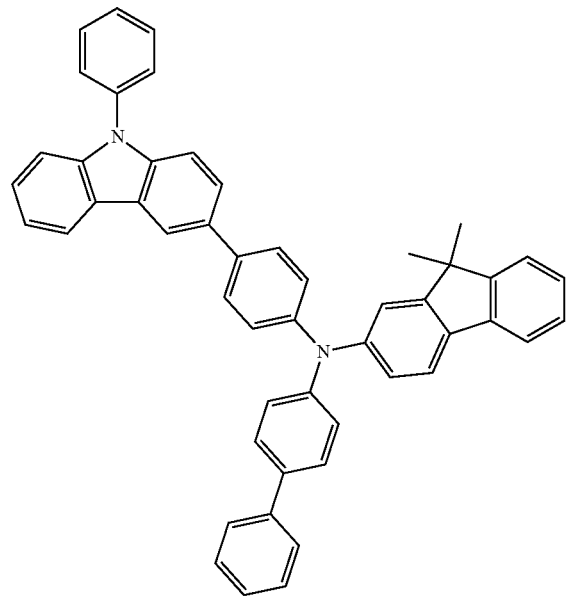
HT5
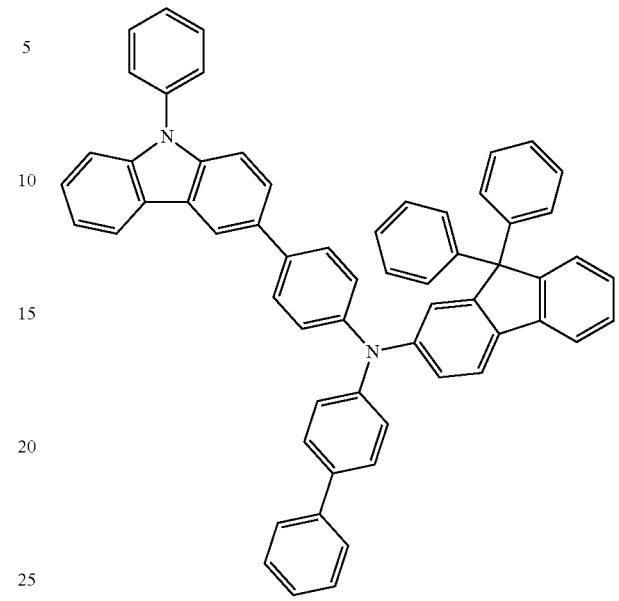
HT4
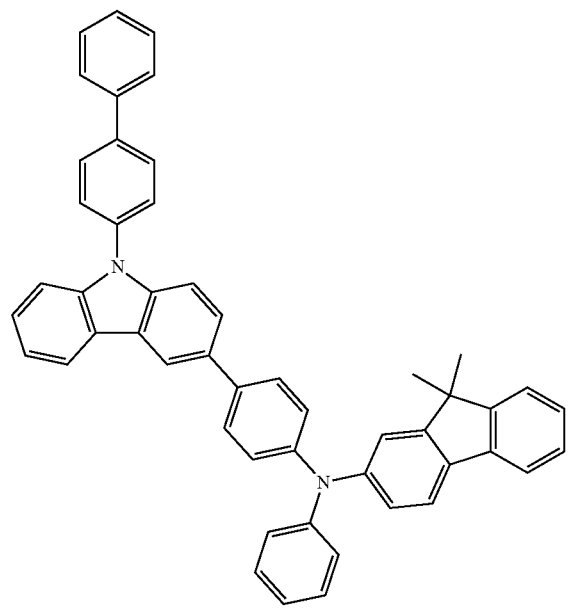
HT6
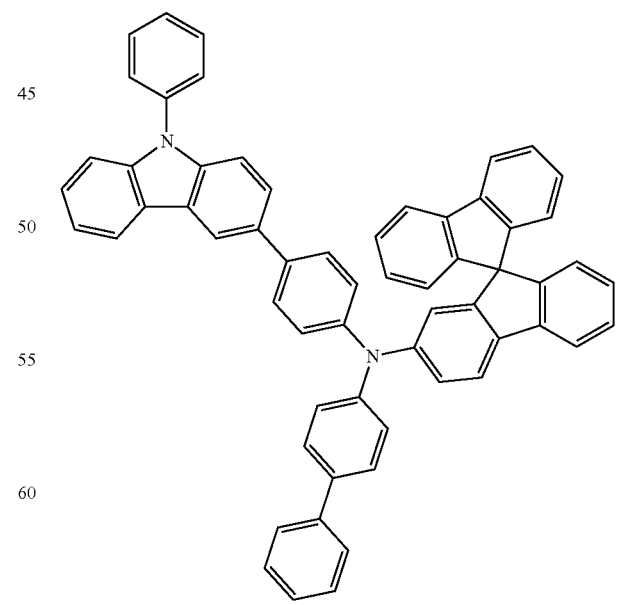

HT7
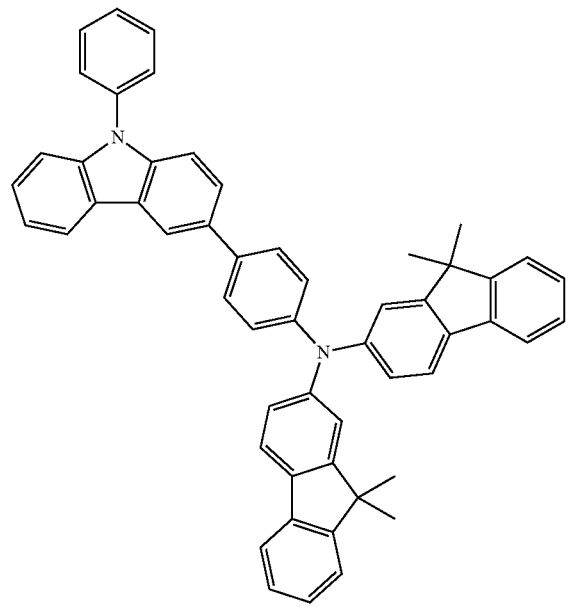
HT9
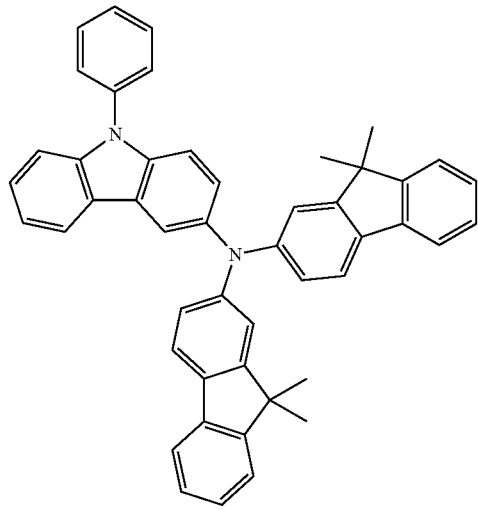
HT8
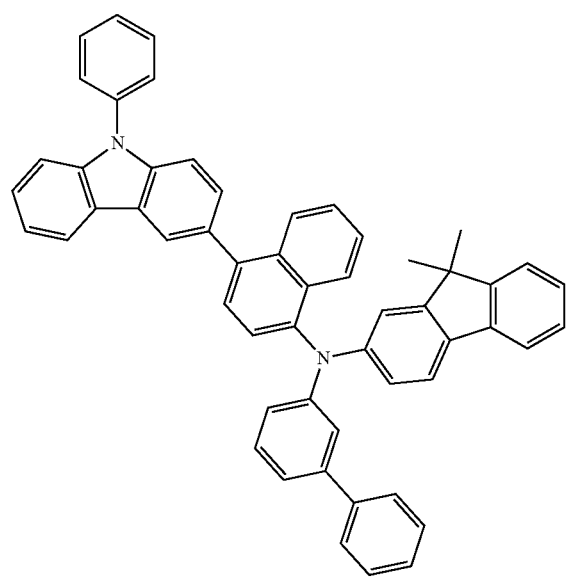
HT10
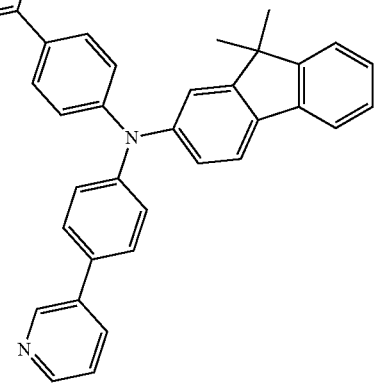

HT11
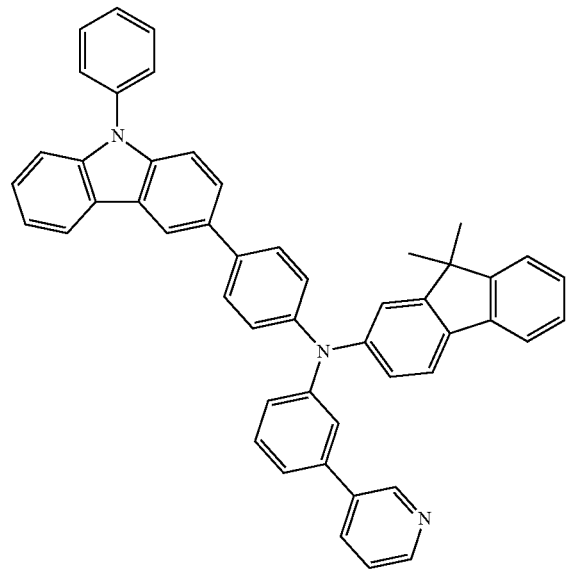
HT12
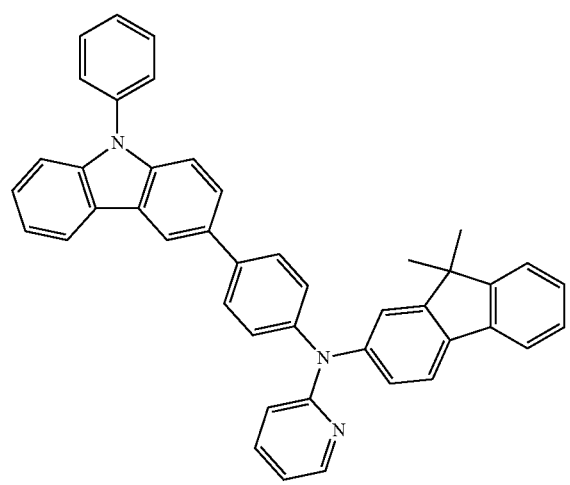
HT13
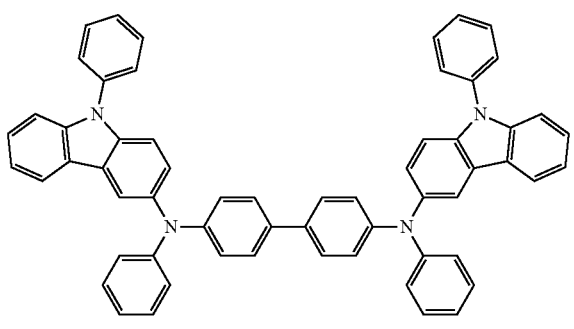
HT14
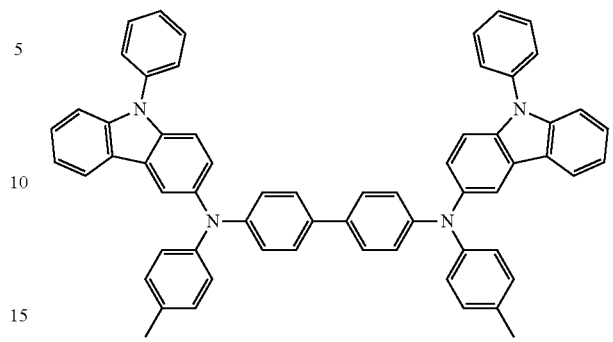
HT15
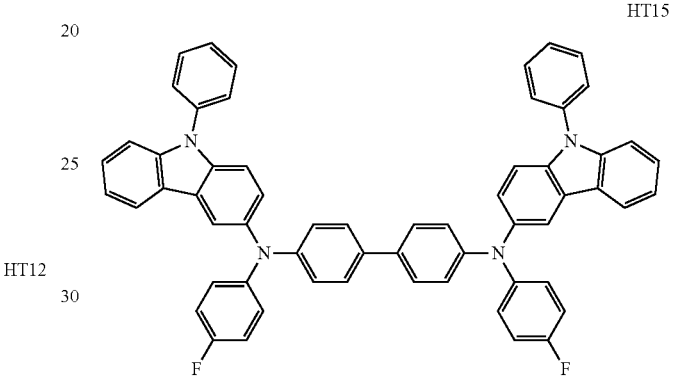
HT16
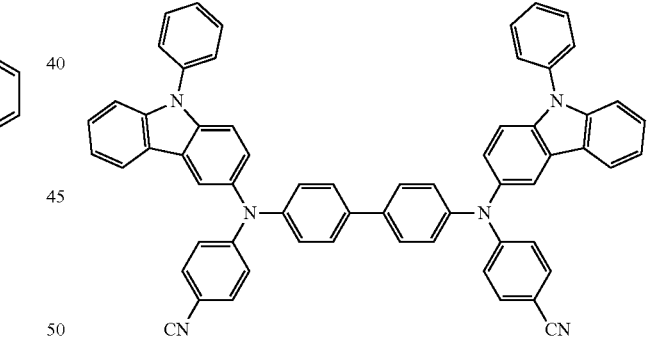
HT17
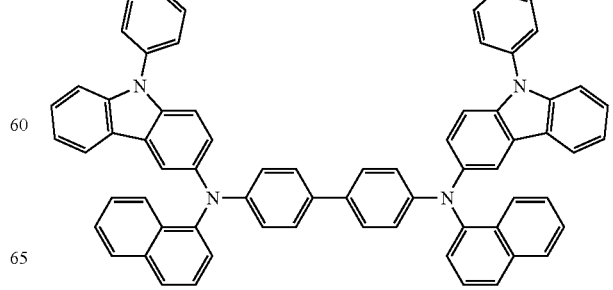

-continued

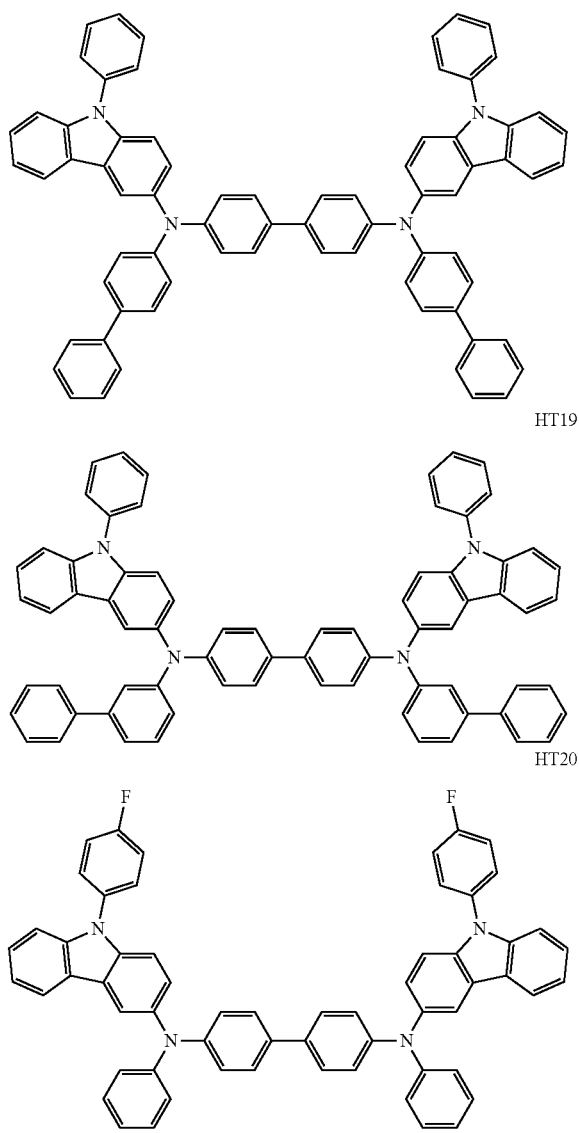

A thickness of the hole transport region may be about 100 Å to about 10,000 Å, e.g., about 100 Å to about 1000 Å. When the hole transport region includes both a hole injection layer and a hole transport layer, a thickness of the hole injection layer may be about 100 Å to about 10,000 Å, e.g., about 100 Å to about 1,000 Å, and a thickness of the hole transport layer may be about 50 Å to about 2,000 Å, e.g., about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogenously or non-homogenously dispersed in the hole transport region.

The charge-generation material may include, e.g., a p-dopant. The p-dopant may include one of a quinone derivative, a metal oxide, and a cyano group-containing compound, but is not limited thereto. For example, non-limiting examples of the p-dopant may include a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide, and Compound HT-D1 illustrated below, but are not limited thereto.

<Compound HT-D1>

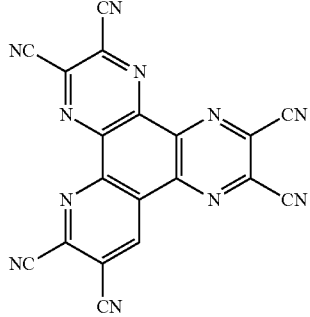

<F4-TCNQ>

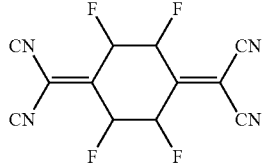

The hole transport region may further include, in addition to the hole injection layer and the hole transport layer, at least one of a buffer layer and an electron blocking layer. The buffer layer may help compensate for an optical resonance distance according to a wavelength of light emitted from the emission layer, light-emission efficiency of a formed organic light-emitting device may be improved. For use as a material included in the buffer layer, materials that are included in the hole transport region may be used. The electron blocking layer may help prevent injection of electrons from the electron transport region.

An emission layer may be formed on the first electrode 110 or the hole transport region by using various methods, such as vacuum deposition, spin coating, casting, a LB method, ink-jet printing, laser-printing, or laser-induced thermal imaging. When the emission layer is thrilled by vacuum deposition or spin coating, deposition and coaling conditions for the emission layer may be determined by referring to the deposition and coating conditions for the hole injection layer.

When the organic light-emitting device 10 is a full color organic light-emitting device, the emission layer may be patterned into a red emission layer, a green emission layer, and a blue emission layer, according to a sub pixel. In an implementation, the emission layer may have a stacked structure of a red emission layer, a green emission layer, and a blue emission layer, or may include a red-light emission material, a green-light emission material, and a blue-light emission material, which are mixed with each other in a single layer, to emit white light.

The emission layer may include a host and a dopant.

The host may include the condensed cyclic compound represented by Formula 1.

The host may further include, in addition to the condensed cyclic compound represented by Formula 1, at least one of TPBi, TBADN, ADN (also referred to as "DNA"), CBP, CDBP, and TCP.

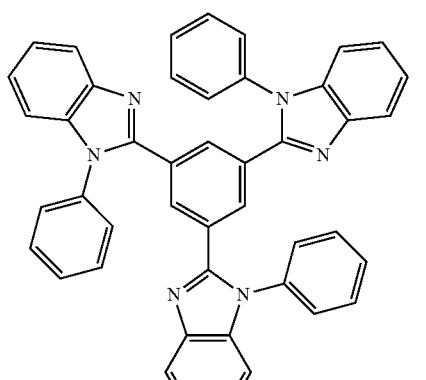

TPBi

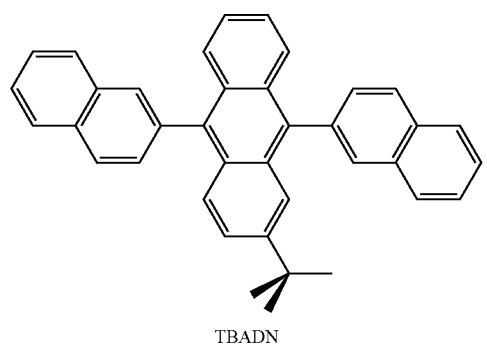

TBADN

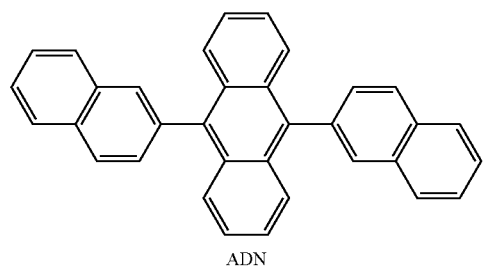

ADN

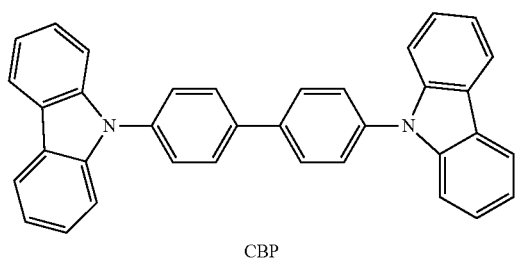

CBP

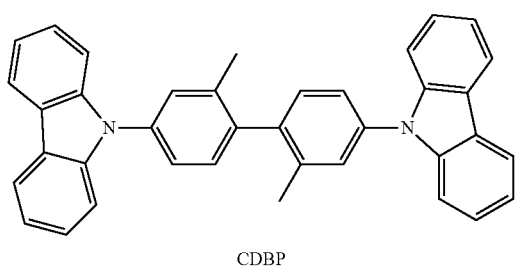

CDBP

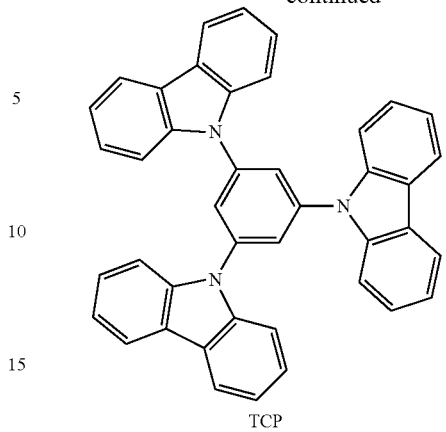

TCP

The dopant may be at least one selected from a fluorescent dopant and a phosphorescent dopant.

The phosphorescent dopant may include an organometallic complex represented by Formula 401 below.

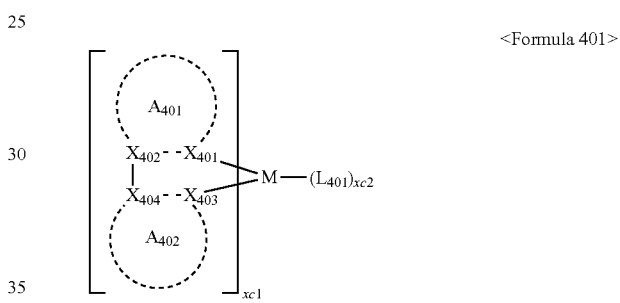

<Formula 401>

In Formula 401, M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may be each independently nitrogen or carbon.

$A_{401}$ and $A_{402}$ rings may be each independently selected from a substituted or unsubstituted benzene group, a substituted or unsubstituted naphthalene group, a substituted or unsubstituted fluorenene group, a substituted or unsubstituted spiro-fluorenene group, a substituted or unsubstituted indene group, a substituted or unsubstituted pyrrol group, a substituted or unsubstituted thiophene group, a substituted or unsubstituted furan group, a substituted or unsubstituted imidazole group, a substituted or unsubstituted pyrazole group, a substituted or unsubstituted thiazole group, a substituted or unsubstituted isothiazole group, a substituted or unsubstituted oxazole group, a substituted of unsubstituted isoxazole group, a substituted of unsubstituted pyridine group, a substituted or unsubstituted pyrazine group, a substituted or unsubstituted pyrimidine group, a substituted or unsubstituted pyridazine group, a substituted or unsubstituted quinoline group, a substituted or unsubstituted isoquinoline group, a substituted or unsubstituted benzoquinoline group, a substituted or unsubstituted quinoxaline group, a substituted or unsubstituted quinazoline group, a substituted or unsubstituted carbazol group, a substituted or unsubstituted benzoimidazole group, a substituted or unsubstituted benzofuran group, a substituted or unsubstituted benzothiophene group, a substituted or unsubstituted isobenzothiophene group, a substituted or unsubstituted benzooxazole group, a substituted or unsubstituted isobenzooxazole group, a substituted or unsubstituted triazole group, a substituted or unsubstituted oxadiazole group, a substituted or unsubstituted triazine group, a substituted or unsubstituted dibenzofuran group, and a substituted or unsubstituted dibenzothiophene group; and at least one substituent of the substituted benzene group, substituted naphthalene group, substituted fluorenene group, substituted spiro-fluorenene group, substituted indene group, substituted pyrrol group, substituted thiophene group, substituted furan group, substituted imidazole group, substituted pyrazole group, substituted thiazole group, substituted isothiazole group, substituted oxazole group, substituted isoxazole group, substituted pyridine group, substituted pyrazine group substituted pyrimidine group, substituted pyridazine group, substituted quinoline group, substituted isoquinoline group, substituted benzoqunioline group, substituted quinoxaline group, substituted quinazoline group, substituted carbazol group, substituted benzoimidazole group, substituted benzofuran group, substituted benzothiophene group, substituted isobenzothiophene group, substituted benzooxazole group, substituted isobenzooxazole group, substituted triazole group, substituted oxadiazole group, substituted triazine group, substituted dibenzofuran group, and substituted dibenzothiophene group may be selected from:

a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, —N($Q_{401}$)($Q_{402}$), —Si($Q_{403}$)($Q_{404}$)($Q_{405}$), and —B($Q_{406}$)($Q_{407}$);

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic hetero-condensed polycyclic group;

a $C_3$-$C_{10}$ cycloalkyl group, a $C_3$-$C_{10}$ heterocycloalkyl v, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic hetero-condensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a heteroaryl group, a monovalent non-aromatic condensed polycyclic group, a monovalent non-aromatic hetero-condensed polycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{423}$)($Q_{424}$)($Q_{425}$), and —B($Q_{426}$)($Q_{427}$); and $L_{401}$ may be an organic ligand;

xc1 is 1, 2, or 3; and xc2 is 0, 1, 2, or 3.

$L_{401}$ may be a monovalent, divalent, or trivalent organic ligand. For example, $L_{401}$ may be selected from a halogen ligand (for example, Cl or F), a diketone ligand (for example, acetylacetonate, 1,3-diphenyl-1,3-propandionate, 2,2,6,6-tetramethyl-3,5-heptandionate, or hexafluoroacetonate), a carboxylic acid ligand (for example, picolinate, dimethyl-3-pyrazolecarboxylate, or benzoate), a carbon monooxide ligand, an isonitrile ligand, a cyano ligand, and a phosphorous ligand (for example, phosphine, and phosphite), but is not limited thereto.

When $A_{401}$ in Formula 401 has two or more substituents, the substituents of $A_{401}$ may bind to each other to form a saturated or unsaturated ring.

When $A_{401}$ in Formula 402 has two or more substituents, the substituents of $A_{402}$ may bind to each other to form a saturated or unsaturated ring.

When xc1 in Formula 401 is two or more, a plurality of ligands

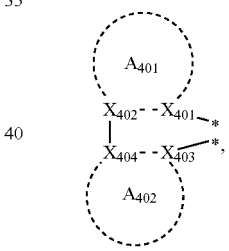

in Formula 401 may be identical or different. When xc1 in Formula 401 is two or more, $A_{401}$ and $A_{402}$ may be respectively directly connected to $A_{401}$ and $A_{402}$ of other neighboring ligands with or without a linker (for example, a $C_1$-$C_5$ alkylene, or —N(R')— (wherein R' may be a $C_1$-$C_{10}$ alkyl group or a $C_6$-$C_{20}$ aryl group) or —C(=O)—) therebetween.

The phosphorescent dopant may include at least one of Compounds PD1 to PD74 below, but is not limited thereto.

PD1

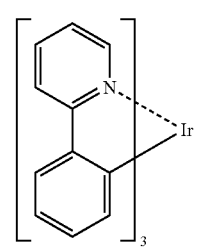

PD2 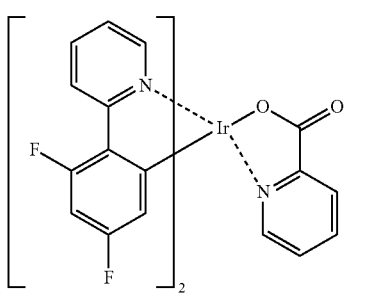
PD3 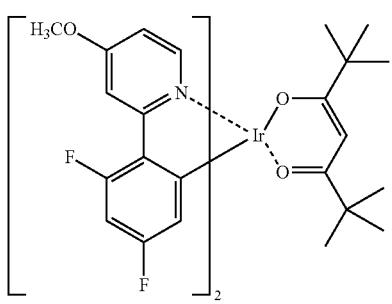
PD4 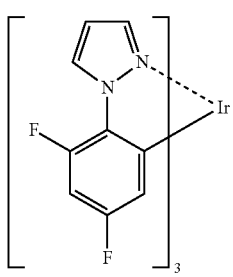
PD5 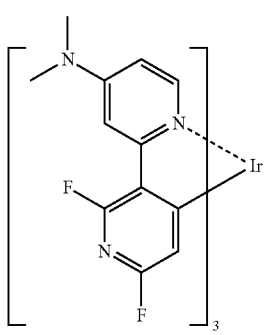
PD6 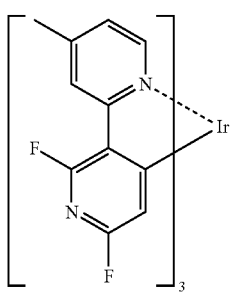
PD7 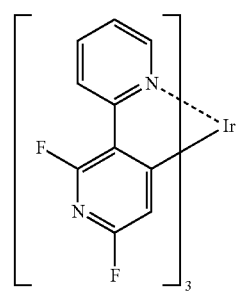
PD8 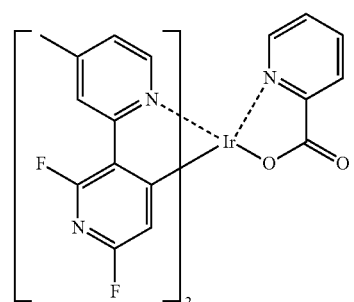
PD9 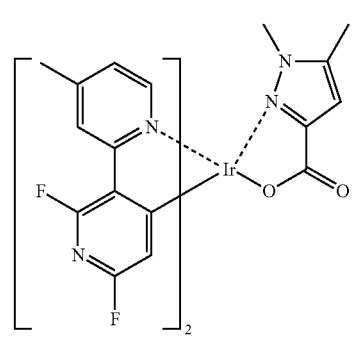
PD10 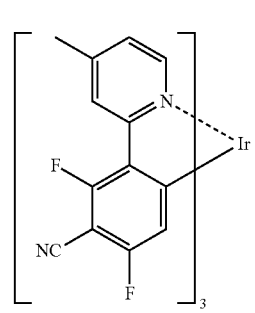
PD11 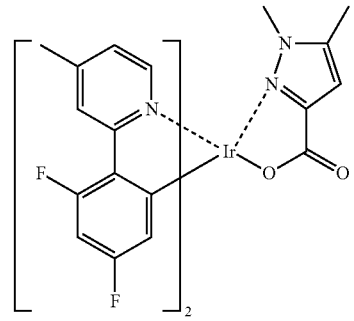

PD12 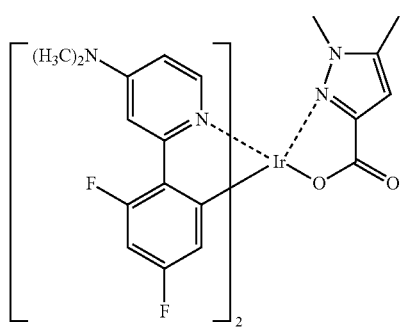
PD13 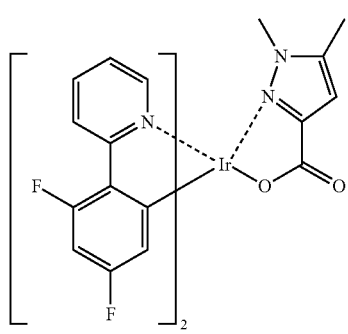
PD14 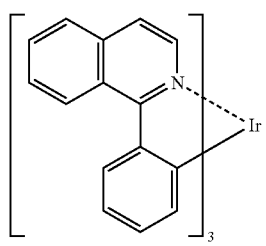
PD15 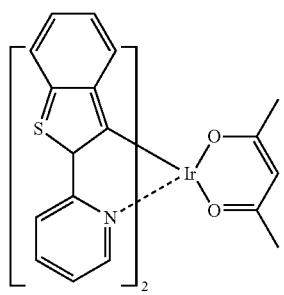
PD16 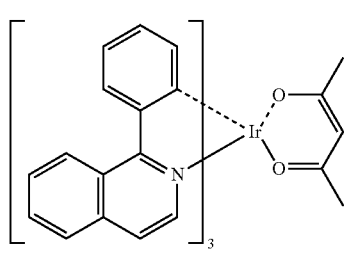
PD17 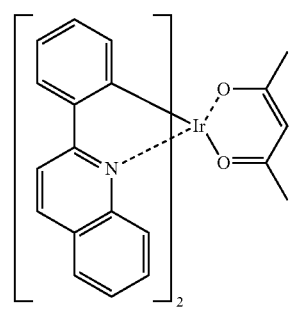
PD18 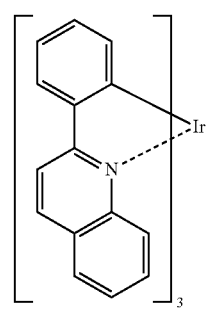
PD19 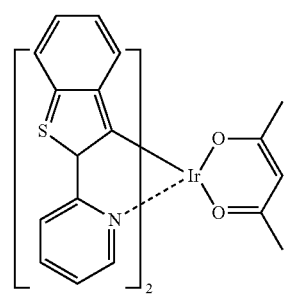
PD20 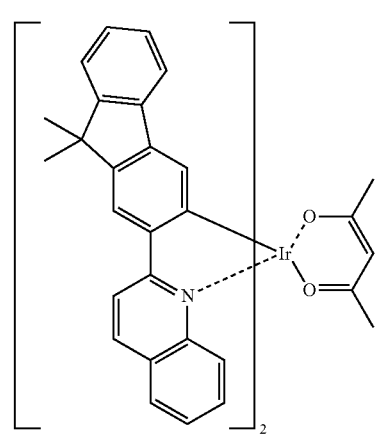

101
-continued
PD21
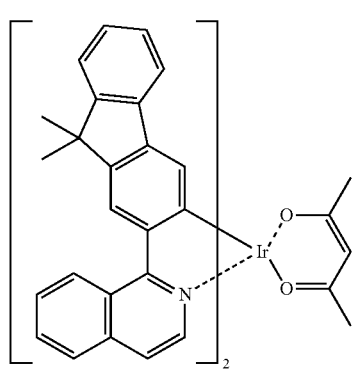
PD22
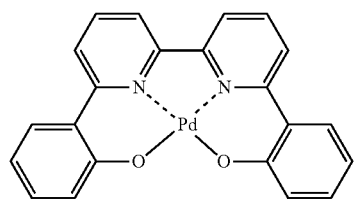
PD23
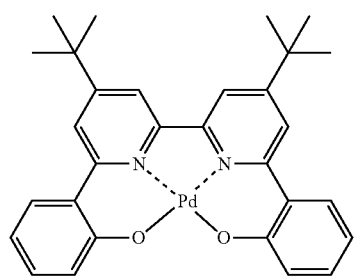
PD24
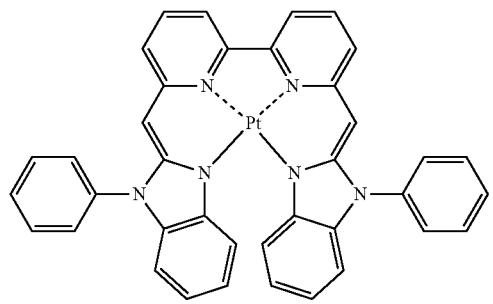
PD25
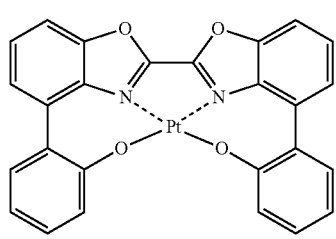
PD26
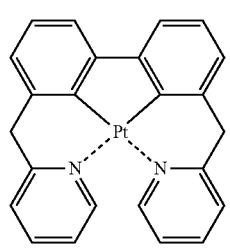
102
-continued
PD27
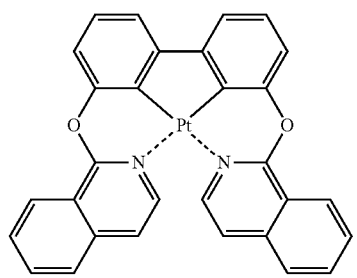
PD28
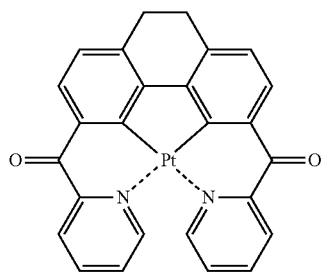
PD29
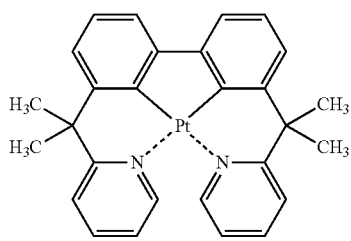
PD30
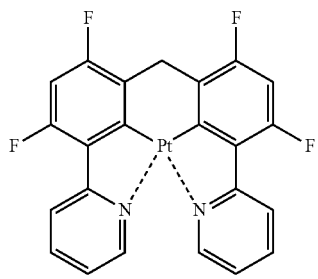
PD31
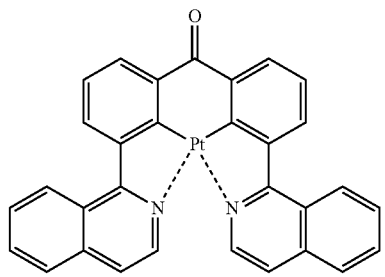
PD32
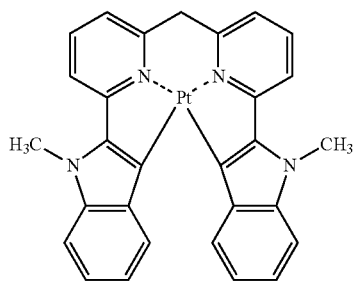

-continued
PD33 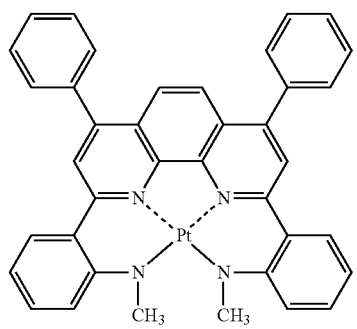
PD34 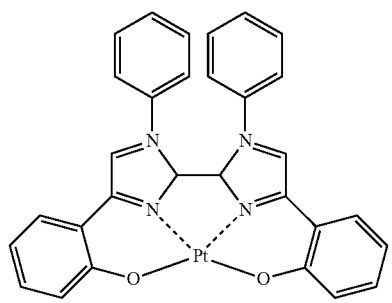
PD35 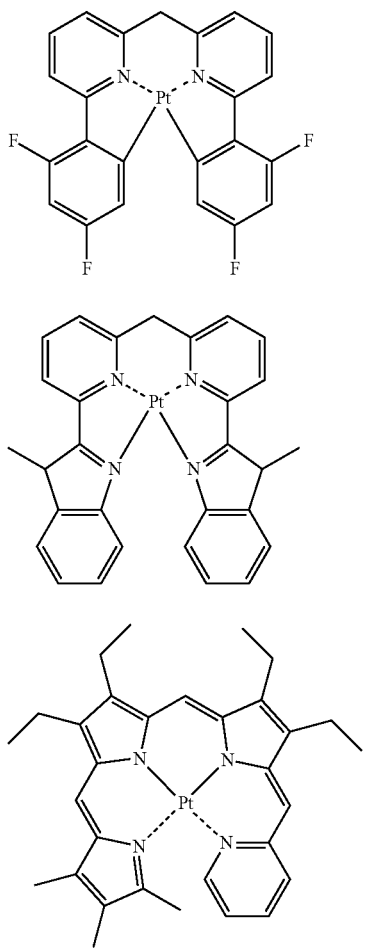
PD36 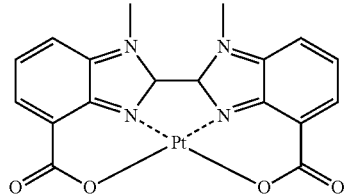
PD37 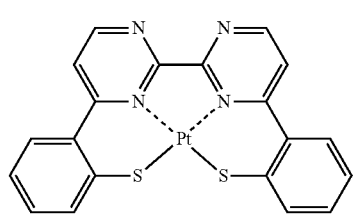
-continued
PD38 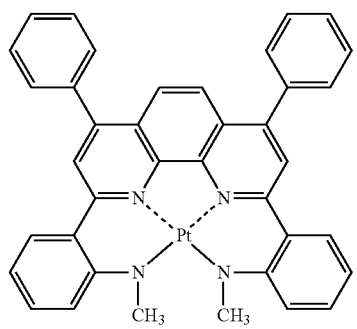
PD39 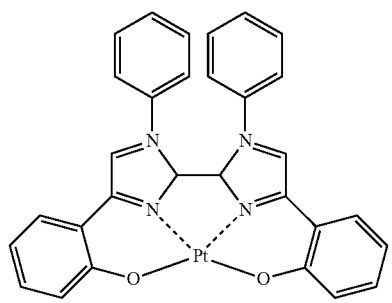
PD40 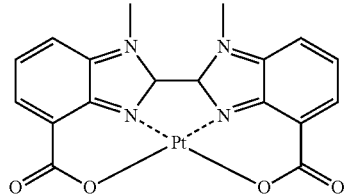
PD41 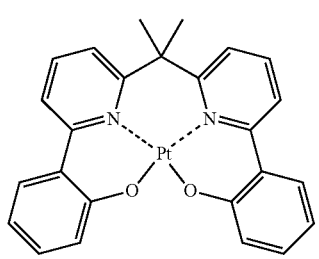
PD42 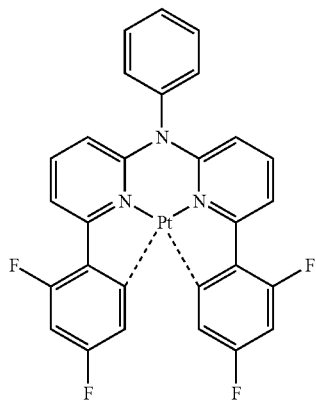

-continued
PD43
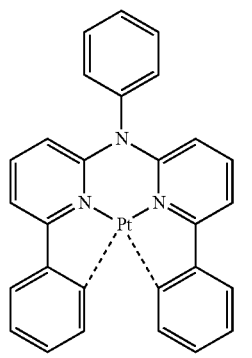
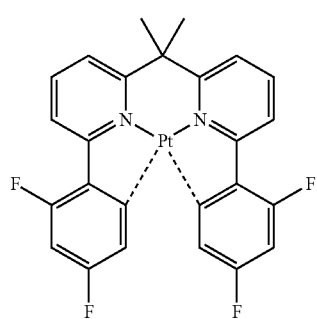
PD44
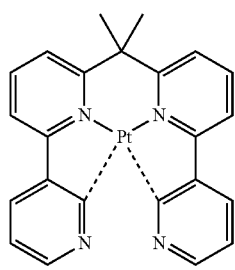
PD45
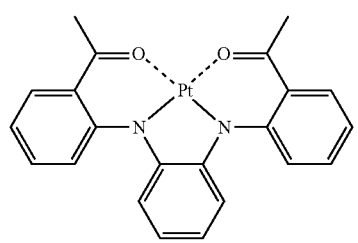
PD46
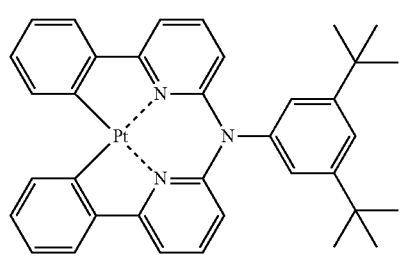
PD47
-continued
PD48
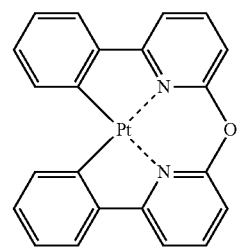
PD49
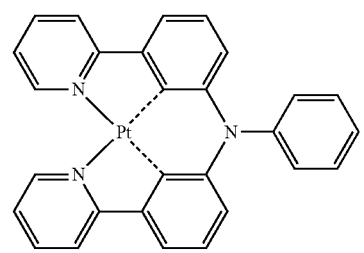
PD50
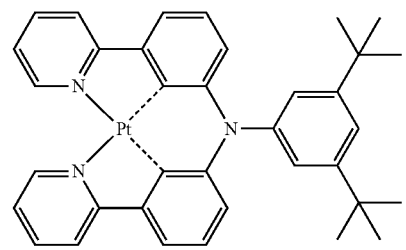
PD51
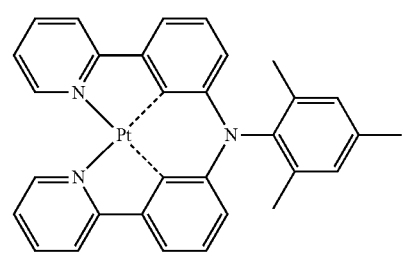
PD52
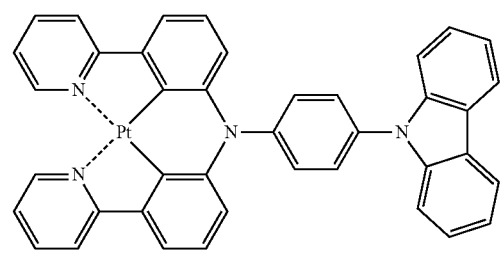
PD53
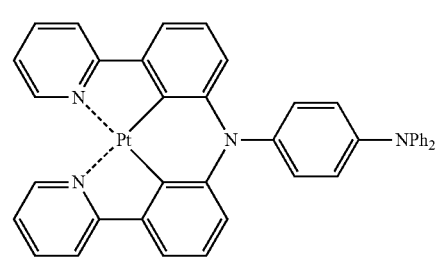

PD54 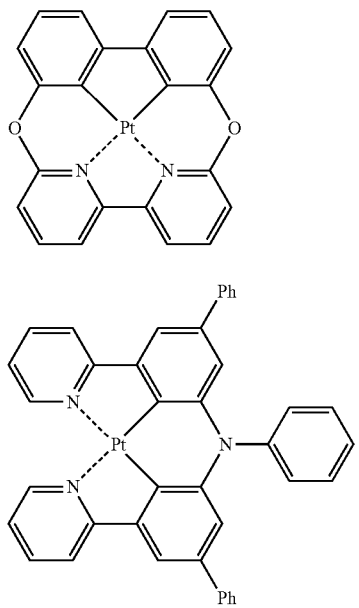
PD55 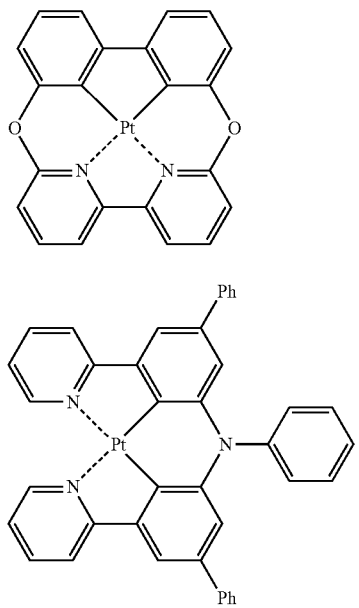
PD56 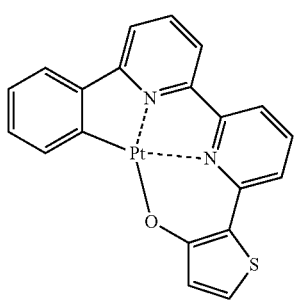
PD57 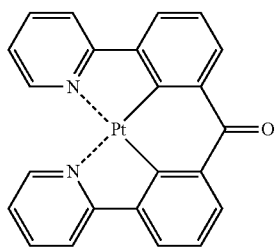
PD58 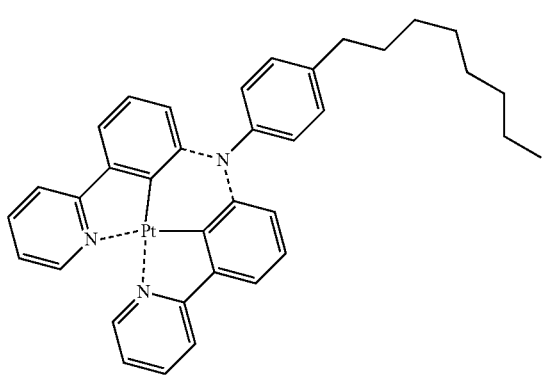
PD59 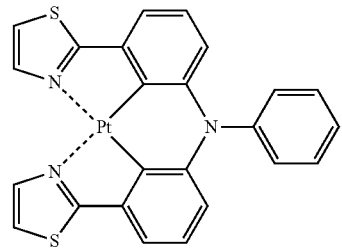
PD60 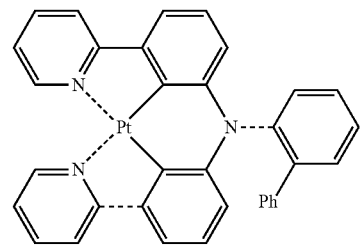
PD61 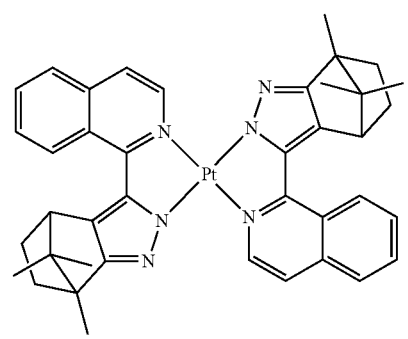
PD62 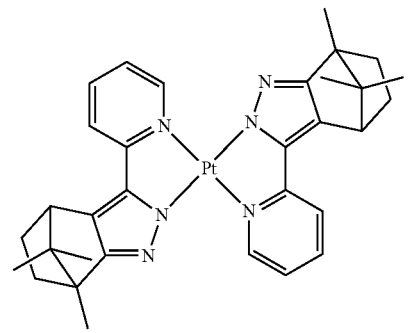
PD63 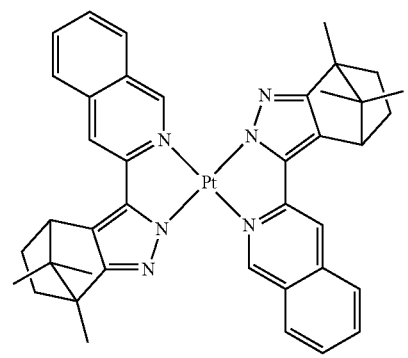

-continued
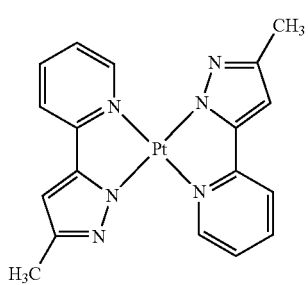
PD64
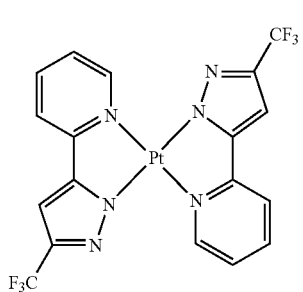
PD65
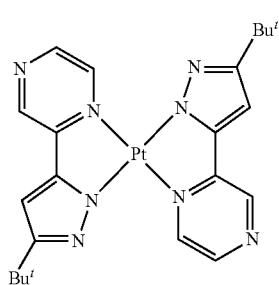
PD66
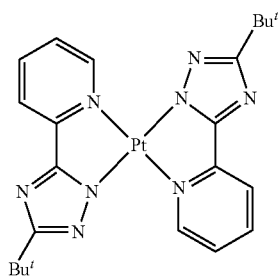
PD67
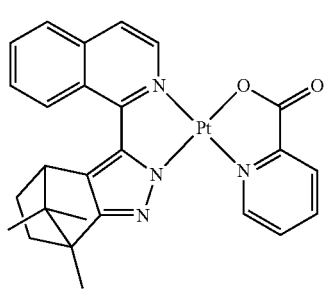
PD68
-continued
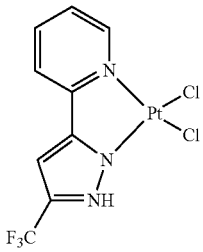
PD69
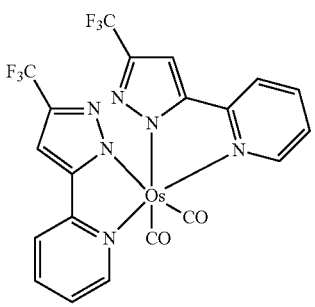
PD70
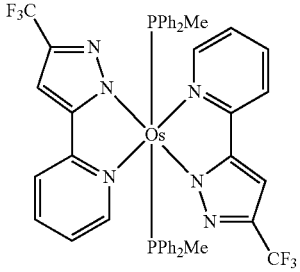
PD71
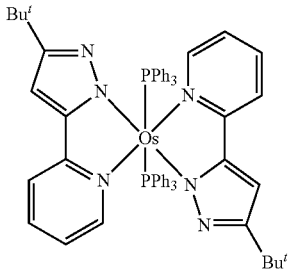
PD72
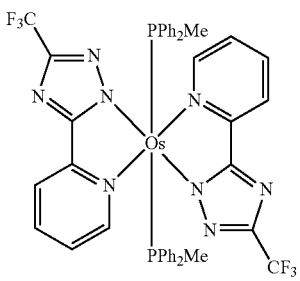
PD73

111
-continued
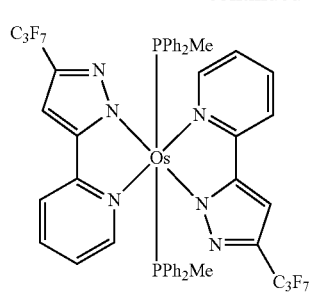
112
PD74
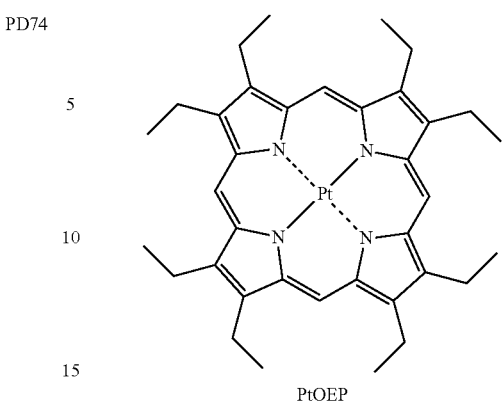
PtOEP
According to another embodiment, the phosphorescent dopant may include PtOEP:
The fluorescent dopant may include at least one selected from DPVBi, DPAVBi, TBPe, DCM, DCJTB, Coumarin 6, and C545T.
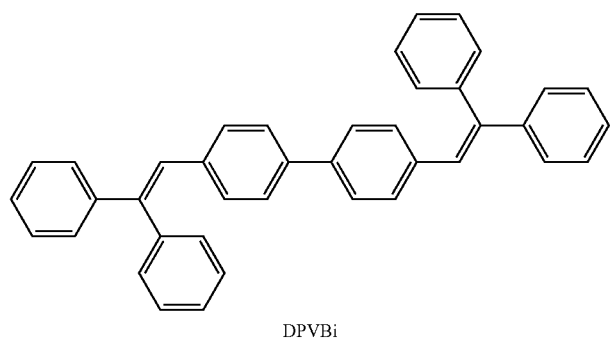
DPVBi
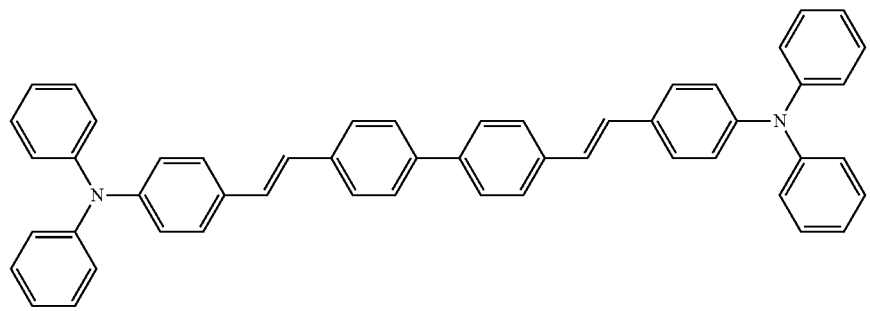
DPAVBi
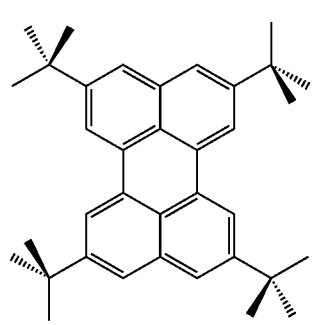
TBPe
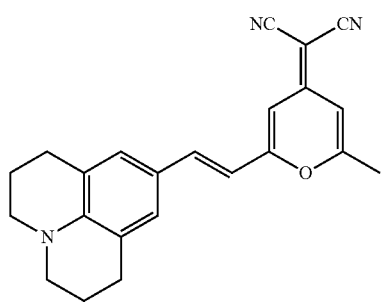
DCM
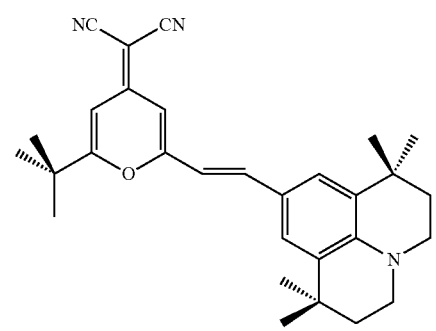
DCJTB

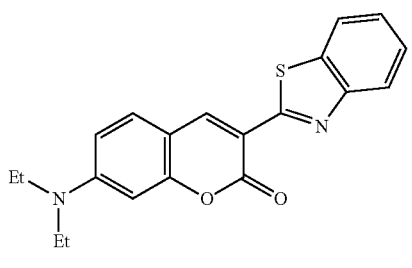
Coumarin 6

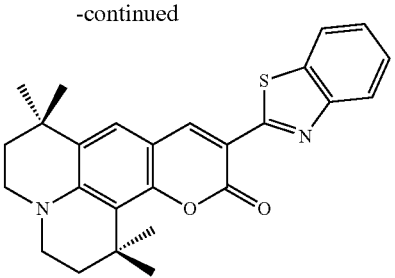
C545T

According to another embodiment, the fluorescent dopant may include a compound represented by Formula 501 below.

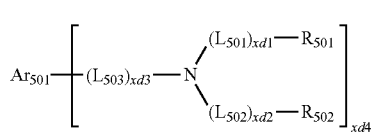
<Formula 501>

In Formula 501, $Ar_{501}$ may be selected from:

a naphthalene group, a heptalene group, a fluorenene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group;

a naphthalene group, a heptalene group, a fluorenene group, a spiro-fluorenene group, a benzofluorenene group, a dibenzofluorenene group, a phenalene group, a phenanthrene group, a anthracene group, a fluoranthene group, a triphenylene group, a pyrene group, a chrysene group, a naphthacene group, a picene group, a perylene group, a pentaphene group, and an indenoanthracene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) (wherein $Q_{301}$ to $Q_{303}$ are each independently selected from a hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group);

$L_{501}$ to $L_{503}$ may be understood by referring to the description provided herein in connection with $L_{201}$;

$R_{501}$ to $R_{502}$ may be each independently selected from:

a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic add and a salt thereof, a phosphoric acid and a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, a dibenzofuranyl group, and a dibenzothiophenyl group; and xd1 to xd3 may be each independently selected from 0, 1, 2, and 3; and xb4 may be selected from 1, 2, 3, and 4.

The fluorescent host may include at least one of Compounds FD1 to FD8.

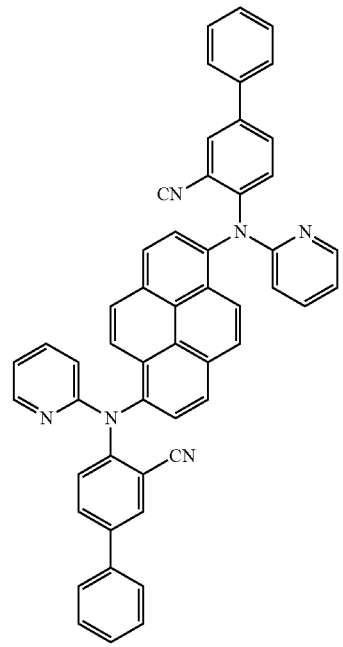
FD4

FD5

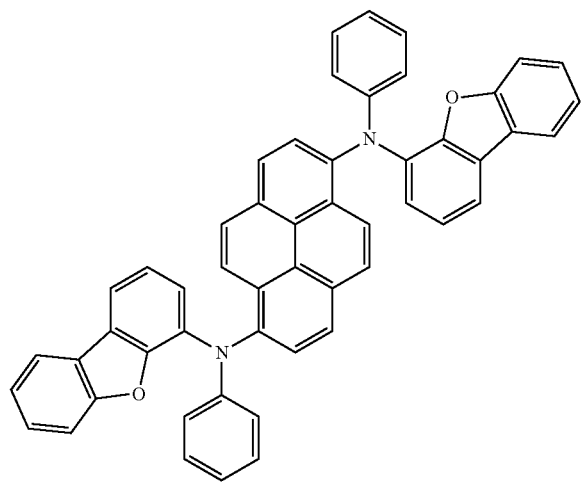

FD6

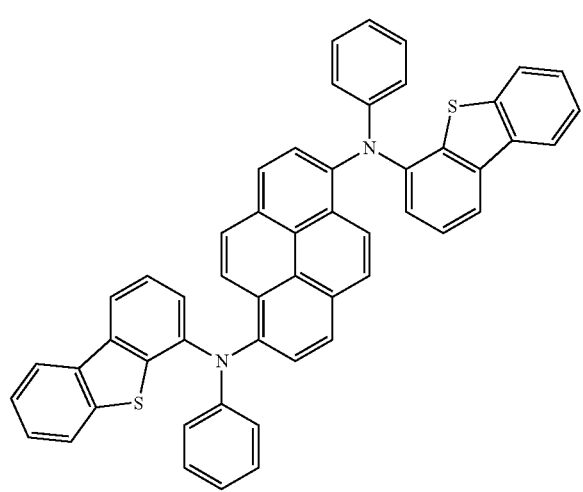

FD7

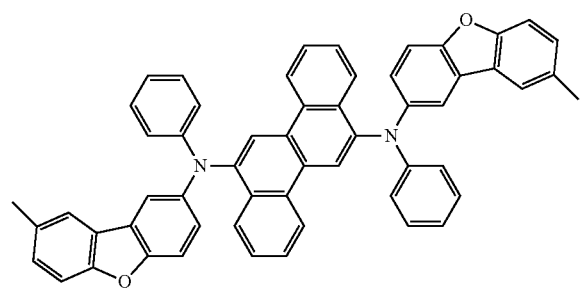

FD8

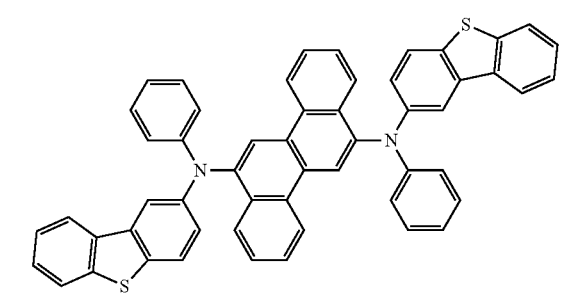

An amount of the dopant in the emission layer may be, e.g., about 0.01 to about 15 parts by weight, based on 100 parts by weight of the host, but is not limited thereto.

A thickness of the emission layer may be about 100 Å to about 1,000 Å, e.g., about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer (ETL), and an electron injection layer, but is not limited thereto.

For example, the electron transport region may have a structure of electron transport layers/electron injection layer or a structure of hole blocking layer/electron transport layer/electron injection layer, wherein layers of each structure are sequentially stacked from the emission layer in the stated order, but is not limited thereto.

According to an embodiment, the organic layer 150 of the organic light-emitting device may include an electron transport region between the emission layer and the second electrode 190, wherein the electron transport region may include the condensed cyclic compound represented by Formula 1.

The electron transport region may include a of blocking layer. The hole blocking layer may be formed when the emission layer includes a phosphorescent dopant, to help prevent diffusion of excitons or holes into an electron transport layer.

When the electron transport region includes a hole blocking layer, the hole blocking layer may be formed on the emission layer by using various methods, such as vacuum deposition spin coating casting is Langmuir-Blodgett (LB) method, ink-jet printing, laser-printing, or laser-induced thermal imaging. When the hole blocking layer is formed by vacuum deposition or spin coating, deposition and coating conditions for the hole blocking layer may be determined by referring to the deposition and coating conditions for the hole injection layer.

The hole blocking layer may include, e.g., at least one of BCP and Bphen, but is not limited thereto.

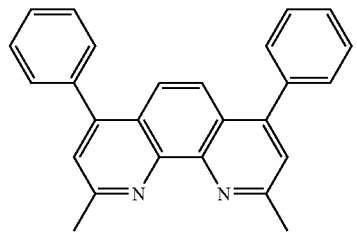

BCP

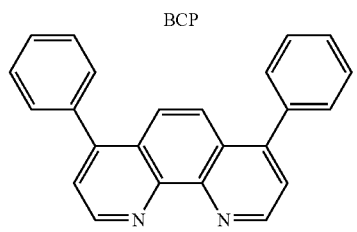

Bphen

A thickness of the hole blocking layer may be about 20 Å to about 1,000 Å, e.g., about 30 Å to about 300 Å. When the thickness of the hole blocking layer is within these ranges, the hole blocking layer may have excellent hole blocking characteristics without a substantial increase in driving voltage.

The electron transport region may include an electron transport layer. The electron transport layer may be formed on the emission layer or the hole blocking layer by using various methods, such as vacuum deposition, spin coating casting, a LB method, ink-jet printing, laser-printing, or laser-induced thermal imaging. When an electron transport layer is formed by vacuum deposition or spin coating, deposition and coating conditions for the electron transport layer may be determined by referring to the deposition and coating conditions for the hole injection layer.

The electron transport layer may further include, in addition to the condensed cyclic compound represented by Formula 1, at least one selected from BCP, Bphen, and Alq$_3$, Balq, TAZ, and NTAZ.

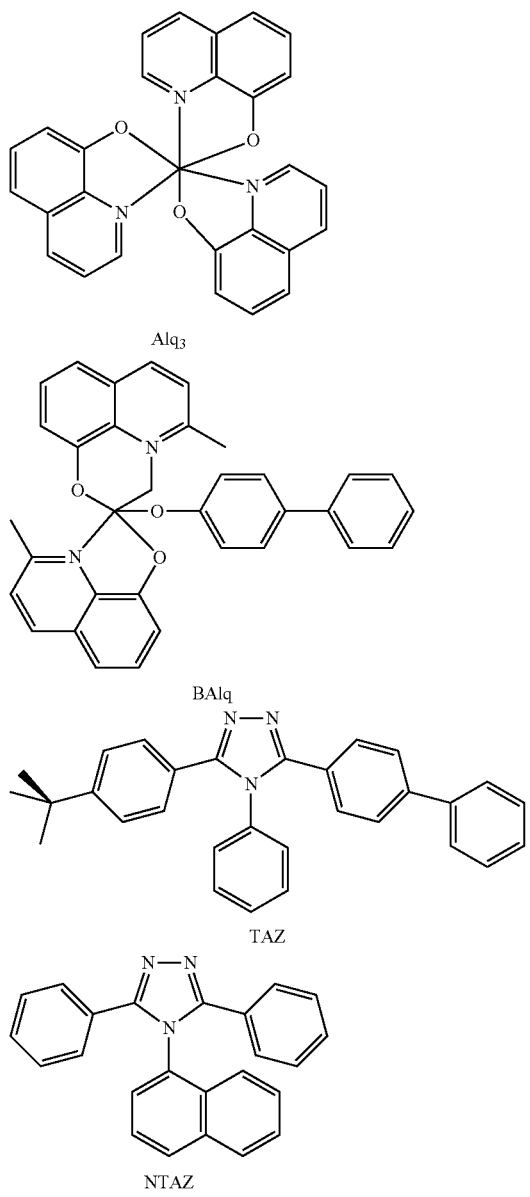

According to another embodiment, the electron transport layer may further include, the condensed cyclic compound represented by Formula 1, and at least one of compounds represented by Formula 601 below.

$$Ar_{601}\text{-}[(L_{601})_{xc1}\text{-}E_{601}]_{xc2} \qquad \text{<Formula 601>}$$

In Formula 601, $Ar_{601}$ may be selected from:

a naphthalene group, a heptalene group, a fluorenene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group;

a naphthalene group, a heptalene group, a fluorenene group, a spiro-fluorenene group, a benzofluorenene group, a dibenzofluorenene group, a phenalene group, a phenanthrene group, a anthracene group, a fluoranthene group, a triphenylene group, a pyrene group, a chrysene group, a naphthacene group, a picene group, a perylene group, a pentaphene group, and an indenoanthracene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) (wherein $Q_{301}$ to $Q_{303}$ are each independently selected from a hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group);

$L_{601}$ may be understood by referring to the description provided herein in connection with $L_{201}$;

$L_{601}$ may be selected from:

a pyrrolyl group, a thiophenyl group, a furanyl group, a imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, a indolyl group, a indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group; and a pyrrolyl group, a thiophenyl group, a furanyl group, a imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, a indolyl group, a indazolyl group, a purinyl group, a quinolinyl group, an isoquinolinyl group, a benzoquinolinyl group, a phthalazinyl group, a naphthyridinyl group, a quinoxalinyl group, a quinzolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a pentalenyl group, an indeyl group, a naphthyl group, an azulenyl group, a heptalenyl group, a indacenyl group, an acenaphthyl group, a fluorenyl group, a spiro-fluorenyl group, a benzofluorenyl group, a dibenzofluorenyl group, a phenalenyl group, a phenanthrenyl group, a anthracenyl group, a fluoranthenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl, group, a ovalenyl group, a pyrrolyl group, a thiophenyl group, a furanyl group, a imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, a indolyl group, a indazolyl group, a purinyl group, a quinolinyl group, an isoquinolinyl group, a benzoquinolinyl group, a phthalazinyl group, a naphthyridinyl group, a quinoxalinyl group, a quinzolinyl group, a cinnolinyl group, a carbazolyl group, a phenanthridinyl group, a acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group; and xe1 may be selected from 0, 1, 2, and 3 and
xe2 may be selected from 1, 2, 3, and 4.

According to another embodiment, the electron transport layer may further include, the condensed cyclic compound represented by Formula 1, and at least one of compounds represented by Formula 602 below.

<Formula 602>

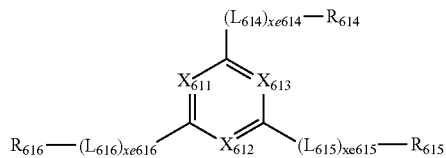

In Formula 602, $X_{611}$ is N or C-$(L_{611})_{xe611}$-$R_{611}$, $X_{612}$ is N or C-$(L_{612})_{xe612}$-$R_{612}$, $X_{613}$ is N or C-$(L_{613})_{xe613}$-$R_{613}$ and, at least one of $X_{611}$ to $X_{613}$ is N;

$L_{611}$ to $L_{616}$ may be understood by referring to the description provided herein in connection with $L_{201}$;

$R_{611}$ and $R_{616}$ may be each independently selected from:

a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic add and a salt thereof, a phosphoric acid and a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xe611 to xe616 may be each independently selected from 0, 1, 2, and 3.

The compound represented by Formula 601 and the compound represented by Formula 602 may include at least one of Compounds ET1 to ET15 illustrated below.

ET1

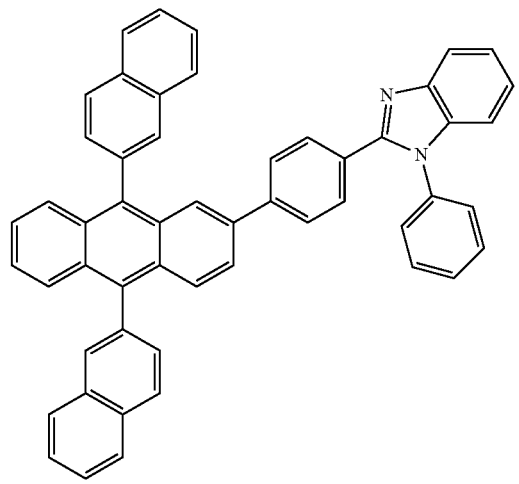

121
-continued
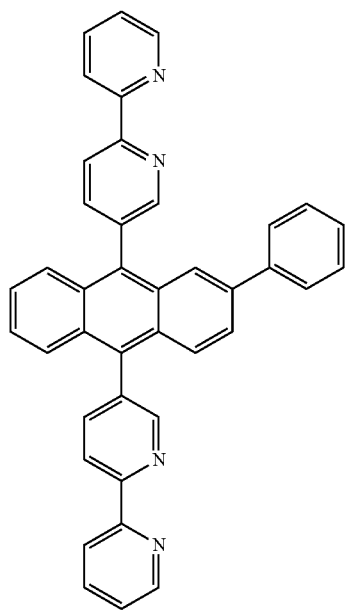
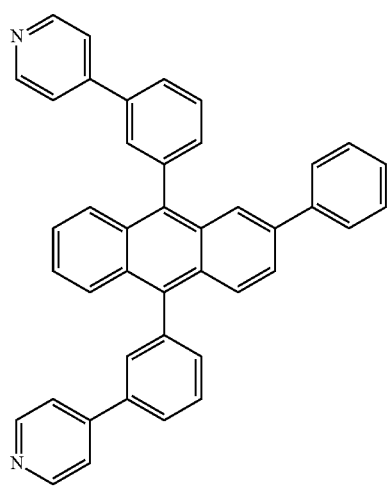
ET3
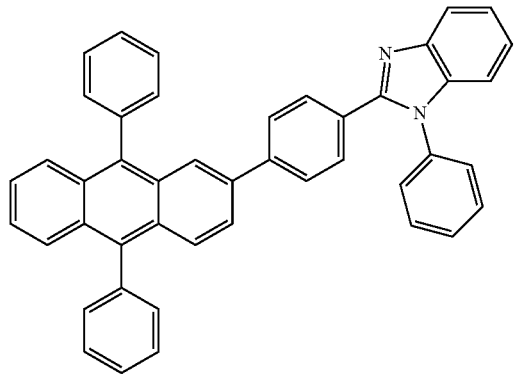
ET4
122
-continued
ET2
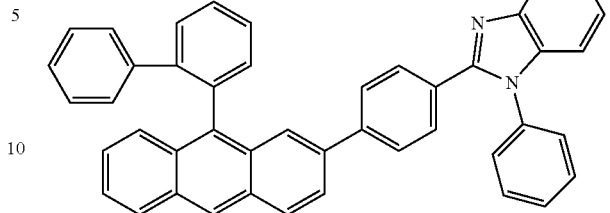
ET5
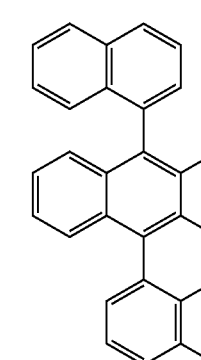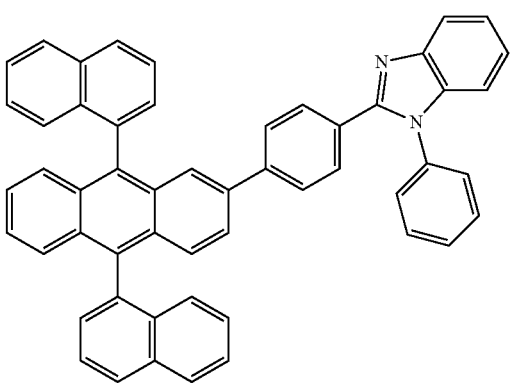
ET6
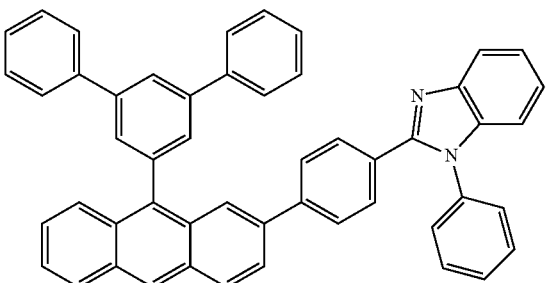
ET7
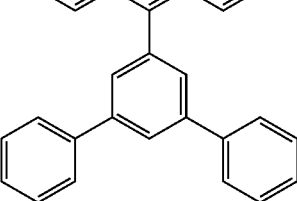

ET8
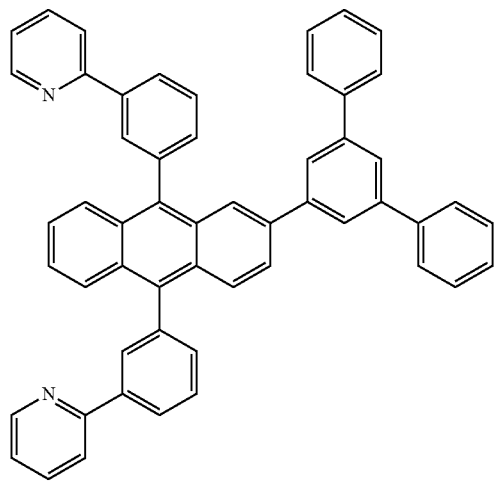
ET9
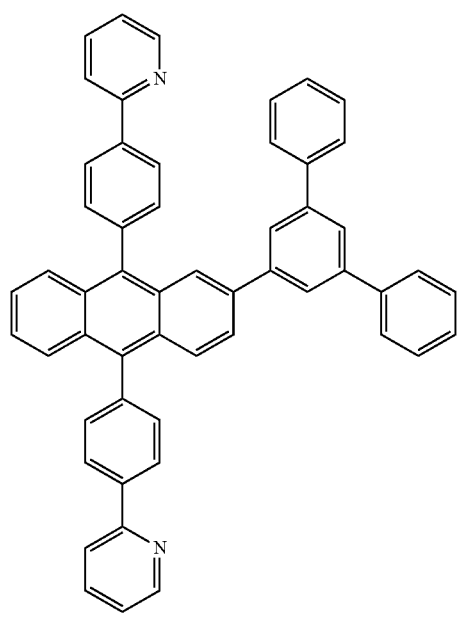
ET10
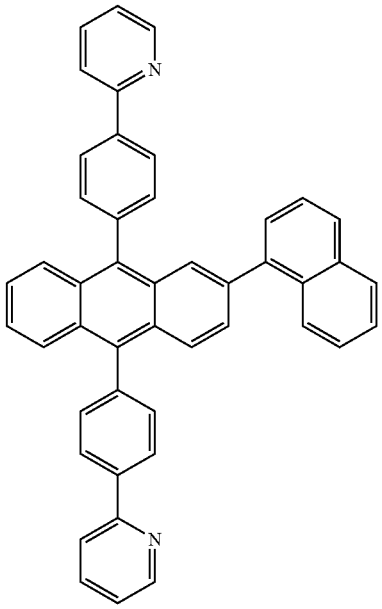
ET11
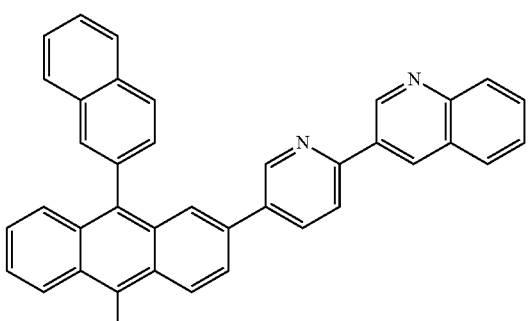
ET12
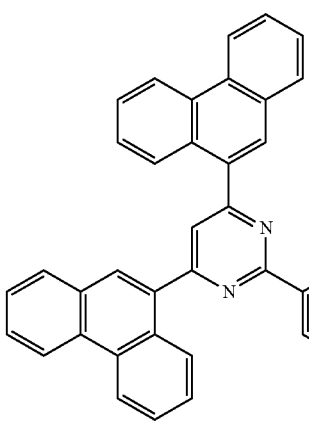

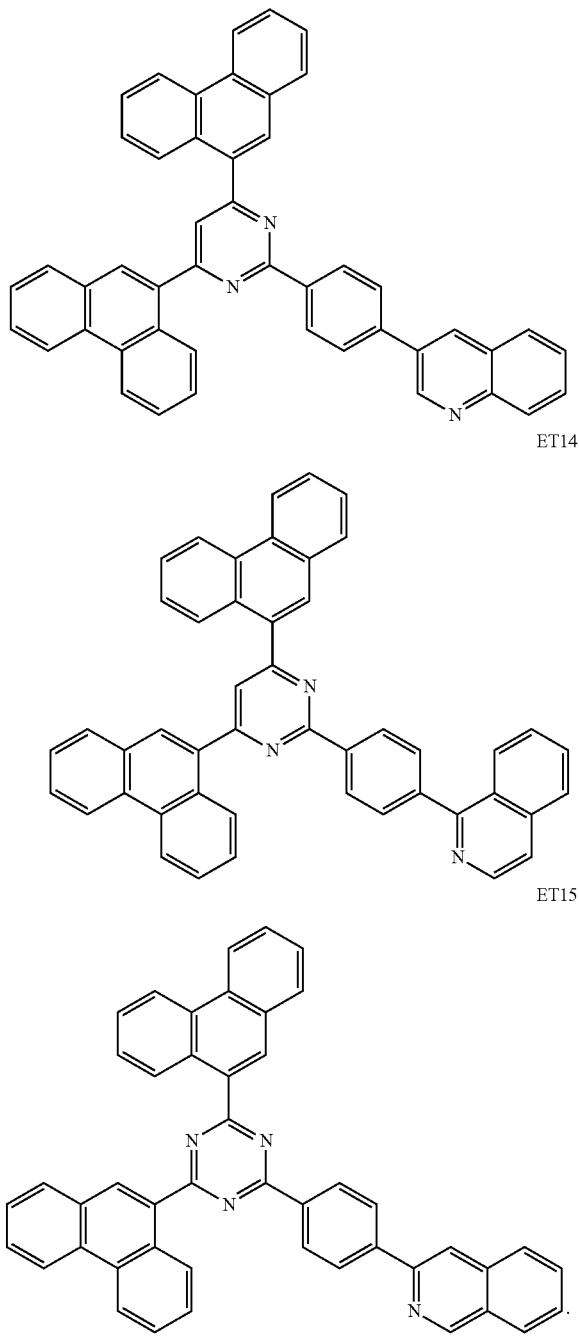

A thickness of the electron transport layer may be about 100 Å to about 1,000 Å, e.g., about 150 Å to about 500 Å. When the thickness of the electron transport layer is within the range described above, the electron transport layer may have satisfactory electron transportation characteristics without a substantial increase in driving voltage.

In an implementation, the electron transport layer may further include, in addition to the materials described above, a metal-containing material.

The metal-containing material may include a Li complex. The Li complex may include, for example, Compound ET-D1 (lithium quinolate, LiQ) or ET-D2.

The electron transport region may include an electron injection layer that allows electrons to be easily provided from the second electrode 190.

The electron injection layer may be formed on the electron transport layer by using various methods, such as vacuum deposition, spin coating casting, a LB method, ink-jet printing, laser-printing, or laser-induced thermal imaging. When an electron injection layer is formed by vacuum deposition or spin coating, deposition and coating conditions for the electron injection layer may be determined by referring to the deposition and coating conditions for the hole injection layer.

The electron injection layer may include at least one selected from, LiF, NaCl, CsF, $Li_2O$, BaO, and LiQ.

A thickness of the electron injection layer may be about 1 Å to about 100 Å, e.g., about 3 Å to about 90 Å. When the thickness of the electron injection layer is within the range described above, the electron injection layer may have satisfactory electron transportation characteristics without a substantial increase in driving voltage.

The second electrode 190 may be disposed on the organic layer 150 having such a structure. The second electrode 190 may be a cathode which is an electron injection electrode, and in this regard, a material for the second electrode 190 may include metal, an alloy, an electrically conductive compound, and a mixture thereof, which have a relatively low work function. Detailed examples of the second electrode 190 may include lithium (Li), magnesium (Mg), aluminum (Al), aluminum-lithium (Al—Li), calcium (Ca), magnesium-indium (Mg—In), or magnesium-silver (Mg—Ag). According to another embodiment, the material for forming the second electrode 190 may include ITO or IZO. The second electrode 190 may be a reflective electrode, a semi-transmissive electrode, or a transmissive electrode.

Hereinbefore, the organic light-emitting device has been described with reference to FIG. 1, but is not limited thereto.

A $C_1$-$C_{60}$ alkyl group used herein refers to a linear or branched aliphatic hydrocarbon monovalent group having 1 to 60 carbon atoms, and detailed examples thereof are a methyl group, a ethyl group, a propyl group, an isobutyl group, a sec-butyl group, a ter-butyl group, a pentyl group, an iso-amyl group, and a hexyl group. A $C_1$-$C_{60}$ alkylene group used herein refers to a divalent group having the same structure as the $C_1$-$C_{60}$ alkyl group.

A $C_1$-$C_{60}$ alkoxy group used herein refers to a monovalent group represented by —$OA_{101}$ (wherein $A_{101}$ is the $C_1$-$C_{60}$ alkyl), and detailed examples thereof are a methoxy group, an ethoxy group, and an isopropyloxy group.

A $C_2$-$C_{60}$ alkenyl group used herein refers to a hydrocarbon group formed by substituting at least one carbon double bond in the middle or terminal of the $C_2$-$C_{60}$ alkyl group, and detailed examples thereof are an ethenyl group, a prophenyl group, and a butenyl group. A $C_2$-$C_{60}$ alkenylene group used herein refers to a divalent group having the same structure as the $C_2$-$C_{60}$ alkenyl group.

A $C_2$-$C_{60}$ alkynyl group used herein refers to a hydrocarbon group formed by substituting at least one carbon trip bond in the middle or terminal of the $C_2$-$C_{60}$ alkyl group, and detailed examples thereof are an ethynyl group, and a propynyl group. A $C_2$-$C_{60}$ alkynylene group used herein refers to a divalent group having the same structure as the $C_2$-$C_{60}$ alkynyl group.

A $C_3$-$C_{10}$ cycloalkyl group used herein refers to a monovalent hydrocarbon monocyclic group having 3 to 10 carbon atoms, and detailed examples thereof are a cyclopropyl group, a cyclobutyl group, a cyclopentyl group, a cyclohexyl group, and a cycloheptyl group. A $C_3$-$C_{10}$ cycloalkylene group used herein refers to a divalent group having the same structure as the $C_3$-$C_{10}$ cycloalkyl group.

A $C_3$-$C_{10}$ heterocycloalkyl group used herein refers to a monovalent monocyclic group having at least one hetero atom selected from N, O, P, and S as a ring-forming atom and 3 to 10 carbon atoms, and detailed examples thereof are a tetrahydrofuranyl group, and a tetrahydrothiophenyl group. A $C_3$-$C_{10}$ heterocycloalkylene group used herein refers to a divalent group having the same structure as the $C_3$-$C_{10}$ heterocycloalkyl group.

A $C_3$-$C_{10}$ cycloalkenyl group used herein refers to a monovalent monocyclic group that has 3 to 10 carbon atoms and at least one double bond in the ring thereof and does not have aromacity, and detailed examples thereof are a cyclopentenyl group, a cyclohexenyl group, and a cycloheptenyl group. A $C_3$-$C_{10}$ cycloalkenylene group used herein refers to a divalent group having the same structure as the $C_3$-$C_{10}$ cycloalkenyl group.

A $C_3$-$C_{10}$ heterocycloalkenyl group used herein refers to a monovalent monocyclic group that has at least one hetero atom selected from N, O, P, and S as a ring-forming atom, 3 to 10 carbon atoms, and at least one double bond in its ring. Detailed examples of the $C_3$-$C_{10}$ heterocycloalkenyl group are a 2,3-hydrofuranyl group and a 2,3-hydrothiophenyl group. A $C_3$-$C_{10}$ heterocycloalkenylene group used herein refers to a divalent group having the same structure as the $C_3$-$C_{10}$ heterocycloalkenyl group.

A $C_6$-$C_{60}$ aryl group used herein refers to a monovalent group having carbocyclic aromatic system having 6 to 60 carbon atoms, and a $C_6$-$C_{60}$ arylene group used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_2$-$C_{60}$ heteroaryl group used herein refers to a monavalent group having a carboncyclic aromatic system that has at least one hetero atom selected from N, O, P, and S as a ring-forming atom, and 2 to 60 carbon atoms. A $C_2$-$C_{60}$ heteroarylene group used herein refers to a divalent group having a carbocyclic aromatic stytem that has at least one hetero atom selected from N, O, P, and S as a ring-forming atom, and 2 to 60 carbon atoms. Detailed examples of the $C_2$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl and the $C_2$-$C_{60}$ heteroarylene each include two or more rings, the rings may be fused to each other.

A $C_6$-$C_{60}$ aryloxy group used herein indicates —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl), A monovalent non-aromatic condensed polycyclic group used herein refers to a monovalent group that has two or more rings condensed to each other, only carbon atoms as a ring forming atom, and non-aromacity in the entire molecular structure. Detailed examples of the monovalent non-aromatic condensed polycyclic group are a fluorenyl group. A divalent non-aromatic condensed polycyclic group used herein refers to a divalent group having the same structure as the monovalent non-aromatic condensed polycyclic group.

A monovalent non-aromatic condensed heteropolycyclic group used herein refers to a monovalent group that has two or more rings condensed to each other, has a hetero atom selected from N, O P, and S, other than carbon atoms, as a ring forming atom, and has non-aromacity in the entire molecular structure. Detailed examples of the monovalent non-aromatic condensed heteropolycyclic group are a carbazolyl group. A divalent non-aromatic condensed heteropolycyclic group used herein refers to a divalent group having the same structure as the monovalent non-aromatic condensed heteropolycyclic group.

The term "Ph" used herein refers to phenyl, the term "Me" used herein refers to methyl, the "Et" used herein refers to ethyl and the term "ter-Bu" or "But" used herein refers to tert-butyl.

Hereinafter, an organic light-emitting device according to an embodiment will be described in detail with reference to Synthesis Examples and Examples. The wording "B was used instead of A" used in describing Synthesis Examples means that a molar equivalent of A was identical to a molar equivalent of B.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLE

Synthesis Example 1: Synthesis of Compound 1

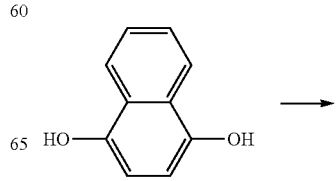

129
-continued

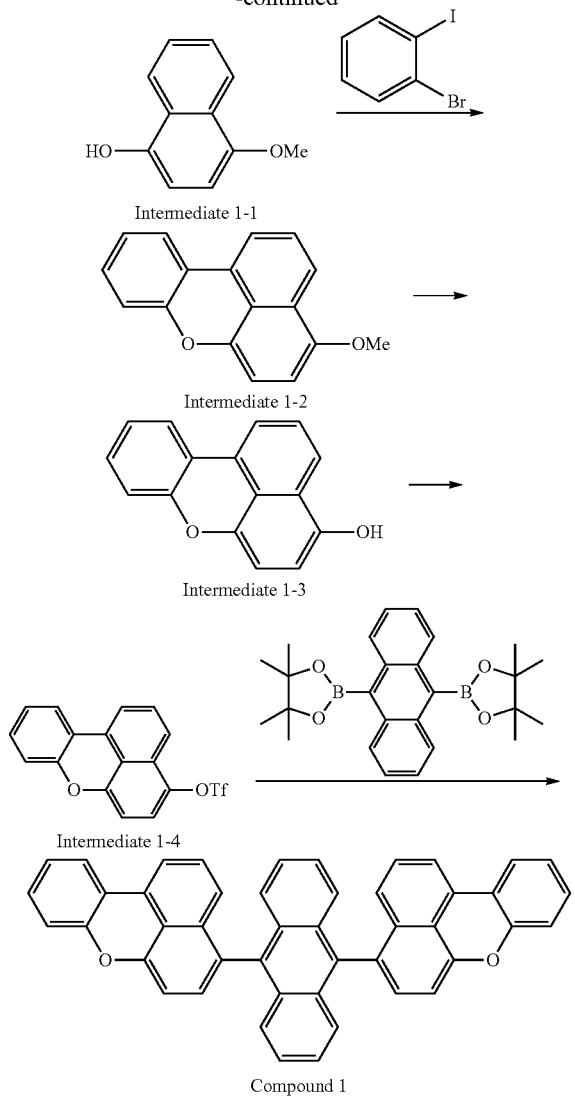

Intermediate 1-1

Intermediate 1-2

Intermediate 1-3

Intermediate 1-4

Compound 1

Synthesis of Intermediate 1-1

18 g of 1,4-dihydroxynaphthalene was dissolved in 1 L of acetone, and then, 31 g of potassium carbonate and 11 g of methyl iodide were added thereto and then the mixture was stirred at room (e.g., ambient) temperature for 24 hours. The reaction solution was filtered, and the obtained filtrate was concentrated and the result was separation-purified by silica gel column chromatography to obtain Intermediate 1-1 (6.1 g, 45%), Synthesis of Intermediate 1-2

6.1 g of Intermediate 1-1 was dissolved in 230 mL of DMF, and then, 252 mg of Pd(OAc)$_2$, 320 mg of PPh$_3$, 23 g of CsCO$_3$, and 1-bromo-2-iodobenzene were added thereto, and the mixture was refluxed at a temperature of 140° C. while stirring. After 15 hours, the temperature was lowered to at room temperature and 70 mL of water was added thereto to stop the reaction. Ethyl acetate was used to perform an extrcation process thereon three times, and then, an organic solution was dried and concentrated by using anhydrous magnesium sulfate, and the result was separation-purified by using silica gel column chromatography to obtain Intermediate 1-2 (4.48 g, 67%).

130

Synthesis of Intermediate 1-3

4.5 g of Intermediate 1-2 was diluted in 100 mL of dichloromethane, and then, 2.5 ml of tribromoborone was slowly dropped thereto. After 3 hours, a saturated sodium bicarbonate solvent was used to stop the reaction and the reaction solution was divided into layers. An organic layer was dried using anhydrous magnesium sulfate and concentrated under reduced pressure, and the result was purified by silica gel column chromatography to obtain Intermediate 1-3 (3.48 g, 87%).

Synthesis of Intermediate 1-4

2.8 g of Intermediate 1-3 was diluted with 60 ml of dichloromethane, and then, 3.32 ml of triethylamine was dropped thereto. Then, 1.76 ml of anhydrous trifluoroacetic acid was slowly dropped thereto. After 3 hours, water was used to stop the reaction, and an organic layer was isolated and dried using anhydrous magnesium sulfate and concentrated under reduced pressure, and the result was purified by silica gel column chromatography to obtain Intermediate 1-4 (3.43 g, 63%)

Synthesis of Compound 1

3.43 g of Intermediate 1-4 and 3.18 g of 9,10-bis(4,4,5,5-tetramethyl-1,3,2-dioxaborolan-2-yl)anthracene were diluted with 100 ml of THF and 50 mP of water. 860 mg of Pd(PPh$_3$)$_4$ and 6.2 g of potassium carbonate were added thereto, and then, at a temperature of 65° C., the mixture was refluxed for 17 hours. The result was extracted three times by using ethyl acetate, and an organic layer was dried by using anhydrous magnesium sulfate, and concentrated under reduced pressure and the residual was purified by silica gel column chromatography to obtain Compound 1 (5 g, 92%).

Synthesis Example 2: Synthesis of Compound 5

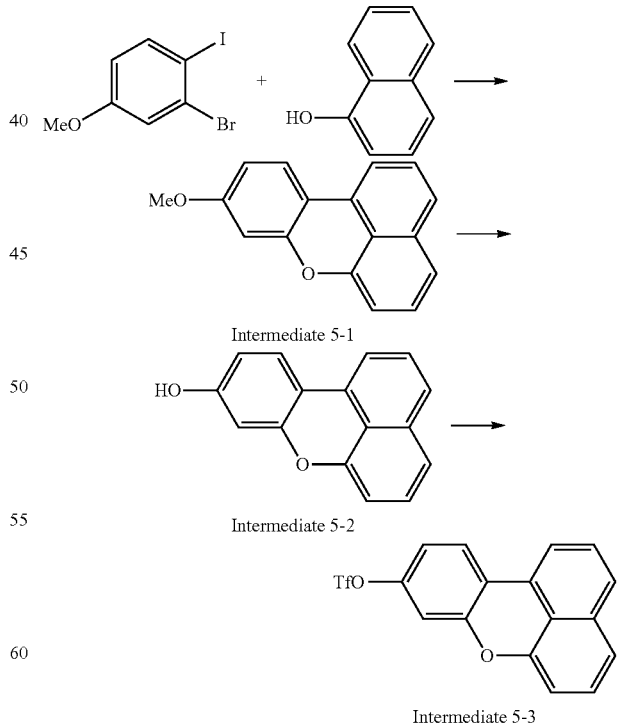

Intermediate 5-1

Intermediate 5-2

Intermediate 5-3

Synthesis of Intermediate 5-1

Intermediate 5-1 (3.6 g, 76%) was synthesized in the same manner as in synthesizing Intermediate 1-2 of Synthesis Example 1, except that 6 g of 1-hydroxynaphthalene and 2.7 g of 1-bromo-4-iodo-anisole were used instead of intermediate 1-1 and 1-bromo-2-iodobenzene.

Synthesis of Intermediate 5-2

Intermediate 5-2 (2.8 g, 81%) was synthesized in the same manner as in synthesizing Intermediate 1-3 of Synthesis Example 1, except that 3.6 g of Intermediate 5-1 was used instead of Intermediate 1-2.

Synthesis of Intermediate 5-3

Intermediate 5-3 (4 g, 92%) was synthesized in the same manner as in synthesizing Intermediate 1-4 of Synthesis Example 1, except that Intermediate 5-2 was used instead of Intermediate 1-3.

nesium sulfate and then, concentrated under reduced pressure, and the result was purified by silica gel column chromatography to obtain Intermediate 5-4 (5.1 g, 67%).

Synthesis of Intermediate 5-5

5.1 g of Intermediate 5-4 was diluted in 130 ml of tetrahydrofuran, and then, at a temperature of −78° C., n-BuLi (2.4M, 4.93 ml) was slowly dropped thereto. After stirring for one hour while the temperature was maintained, 3 ml of 2-isopropoxy-4,4,5,5-tertamethyl-1,3,2-dioxaborane was dropped thereto. The temperature was slowly raised to at room temperature. After 15 hours, water was used to stop the reaction, and then, an organic layer was isolated by using ethylacetate. The obtained organic layer was dried by using

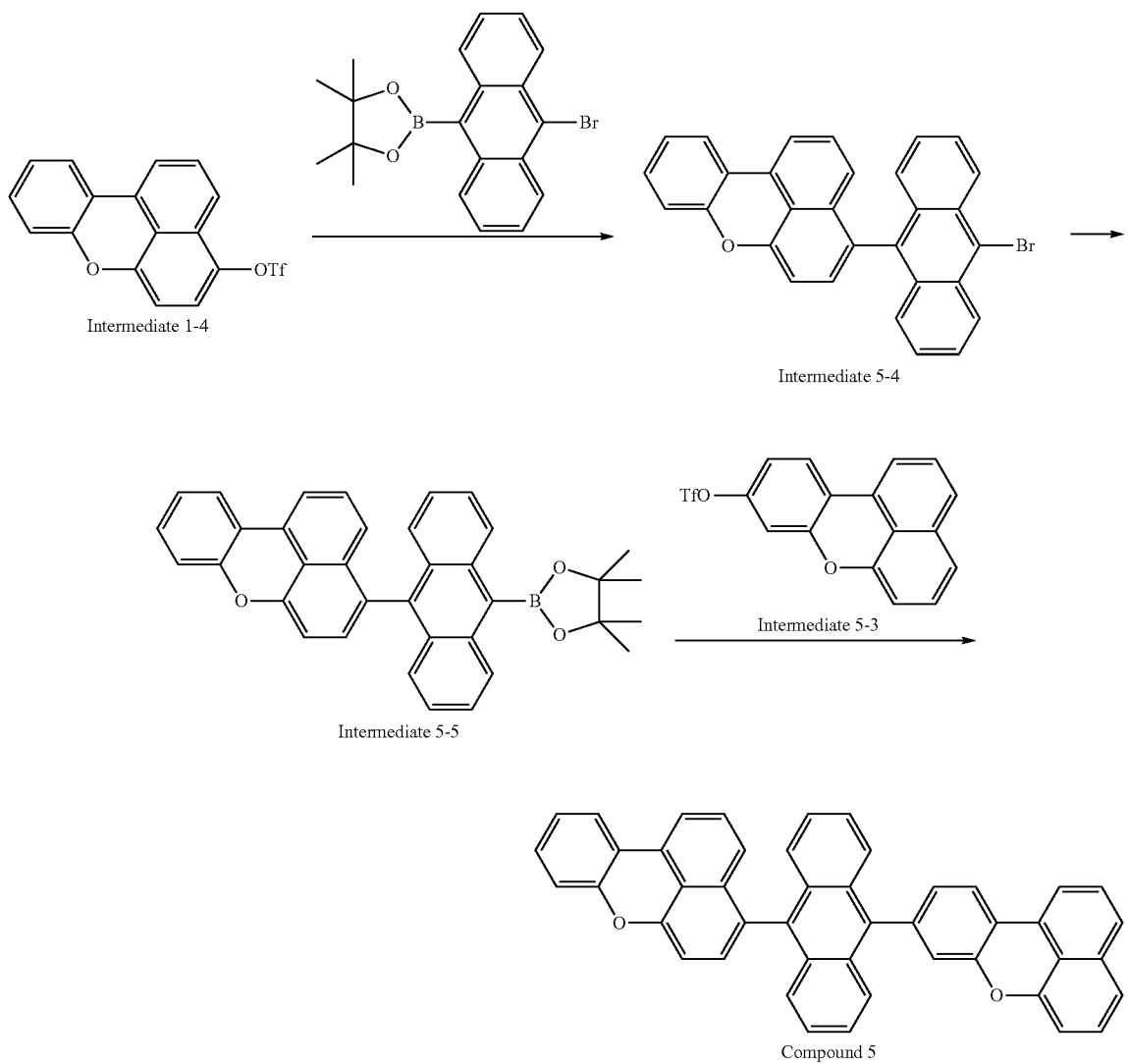

Synthesis of Intermediate 5-4

6 g of Intermediate 1-4 and 3 g of 2-(10-bromoanthracene-9-yl)-4,4,5,5-tetramethyl-1,3,2-dioxabororene were diluted with 100 ml of tetrahydrofuran and 50 ml of water, and then, 947 mg of Pd(PPh$_3$)$_4$ and 6.8 g of potassium carbonate were added thereto, and then, at a temperature of 70° C., the mixture was refluxed while stirring. After 15 hours, the temperature was lowered to room temperature, and ethyl acetate was used to isolate on organic layer. The obtained organic layer was dried by using anhydrous maganhydrous magnesium sulfate and then, concentrated under reduced pressure, and the result was purified by silica gel column chromatography to obtain Intermediate 5-5 (4.1 g, 73%).

Synthesis of Compound 5

Compound 5 (2.8 g, 59%) was obtained in the same manner as used to synthesize Intermediate 5-4, except that Intermediate 5-3 and Intermediate 5-5 were respectively used instead of Intermediate 1-4 and 2-(10-bromoanthracene-9-yl)-4,4,5,5-tetramethyl-1,3,2-dioxabororene.

Synthesis Example 3: Synthesis of Compound 9

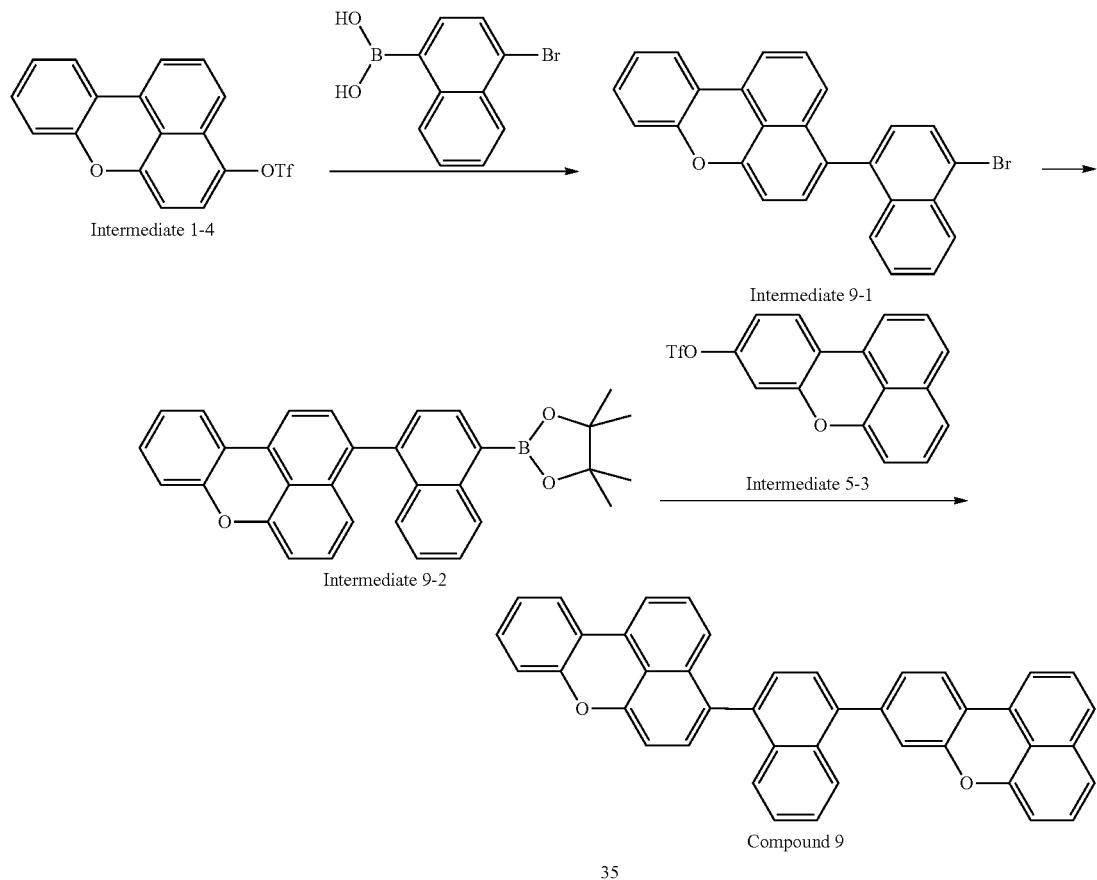

Synthesis of Intermediate 9-1

Intermediate 9-1 (12 g, 67%) was obtained in the same manner as used to synthesize Intermediate 5-4 of Synthesis Example 2, except that 2.1 g of (4-bromonaphthalene-1-yl) boronic acid was used instead of 3 g of 2-(10-bromoanthracene-9-yl)-4,4,5,5-tetramethyl-1,3,2-dioxabororene and the amount of Intermediate 1-4 was 4.7 g.

Synthesis of Intermediate 9-2

Intermediate 9-2 (2.2 g, 90%) was synthesized in the same manner as in synthesizing Intermediate 5-5 of Synthesis Example 2, except that 2.2 g of Intermediate 9-1 was used instead of Intermediate 5-4.

Synthesis of Compound 9

Intermediate 9 (1.9 g, 82%) was synthesized in the same manner as in synthesizing Compound 5 of Synthesis Example 2, except that Intermediate 9-2 was used instead of Intermediate 5-5.

Synthesis Example 4: Synthesis of Compound 10

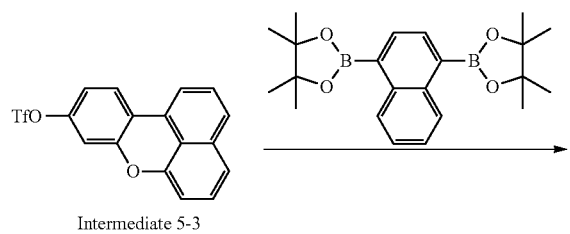

-continued

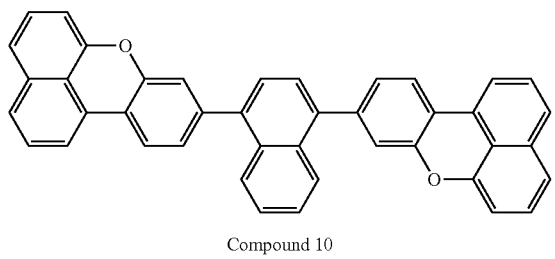

Compound 10

Compound 10 (1.7 g, 58%) was obtained in the same manner as used to synthesize Intermediate 5-4 of Synthesis Example 2, except that 4 g of Intermediate 5-3 and 2 g of 1,4-bis(4,4,5,5-tetramethyl-1,3,2-dioxaborene-2-yl)naphthalene were respectively used instead of Intermediate 1-4 and 2(10-bromoanthracene-9-yl)-4,4,5,5-tetramethyl-1,3,2-dioxabororene.

Synthesis Example 5: Synthesis of Compound 15
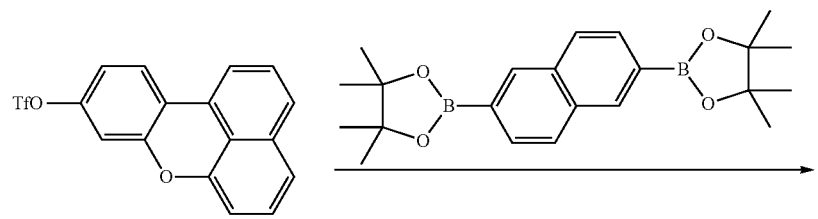
Intermediate 5-3
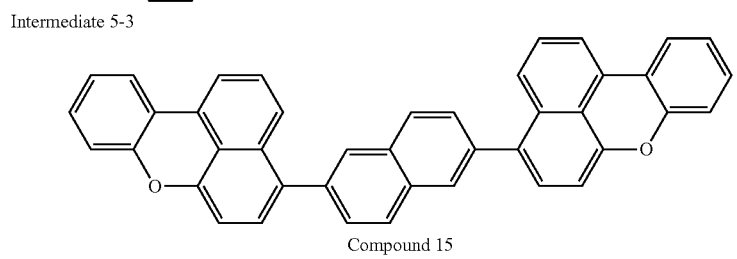
Compound 15
Compound 15 (2.1 g, 72%) was obtained in the same manner as in Synthesis Example 4, except that 2,6-bis(4,4,5,5-tetramethyl-1,3,2-dioxaborene-2-yl)naphthalene was used instead of 1,4-bis(4,4,5,5-tetramethyl-1,3,2-dioxaborene-2-yl)naphthalene.
Synthesis Example 6: Synthesis of Compound 23
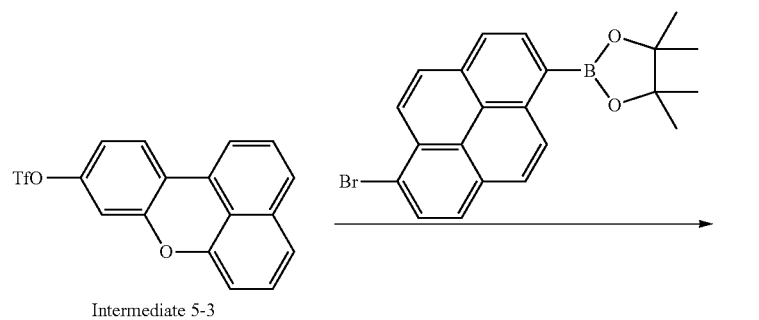
Intermediate 5-3
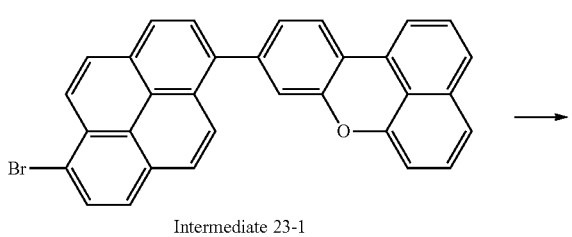
Intermediate 23-1
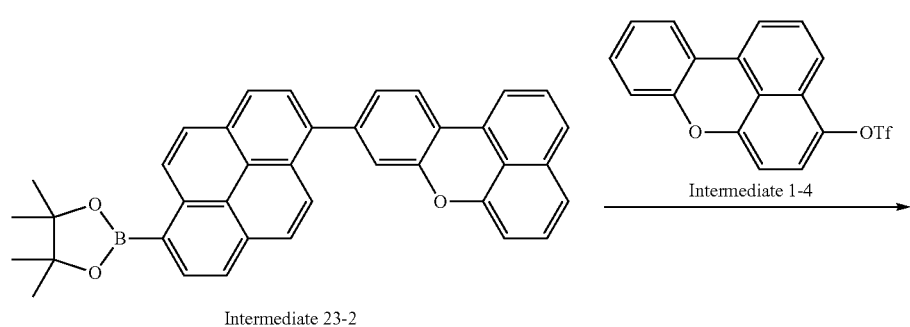
Intermediate 23-2

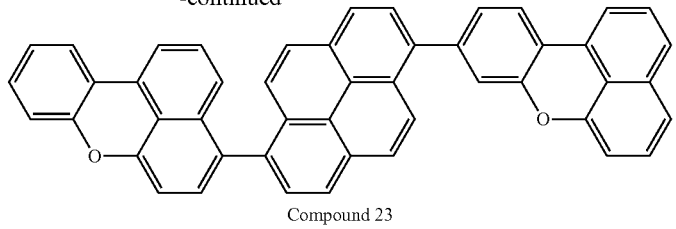
Compound 23

Synthesis of Intermediate 23-1

Intermediate 23-1 (2 g, 68%) was obtained in the same manner as used to synthesize Intermediate 5-4 of Synthesis Example 2, except that 3 g of Intermediate 5-3 and 2.4 g of 2-(6-bromopyrene-1-yl)-4,4,5,5-tetramethyl-1,3,2-dioxaborene were respectively used instead of Intermediate 1-4 and 2-(10-bromoanthracene-9-yl)-4,4,5,5-tetramethyl-1,3,2-dioxabororene.

Synthesis of Intermediate 23-2

Intermediate 23-2 (1.76 g, 81%) was synthesized in the same manner as in synthesizing Intermediate 5-5 of Synthesis Example 2, except that 2 g of Intermediate 23-1 was used instead of Intermediate 5-4.

Synthesis of Compound 23

Compound 23 (1.4 g, 69%) was obtained in the same manner as used to synthesize Compound 5 in Synthesis Example 2, except that 1.76 g of Intermediate 23-2 and 1.2 g of Intermediate 1-4 were respectively used instead of Intermediate 5-5 and Intermediate 5-3.

Synthesis Example 7: Synthesis of Compound 21

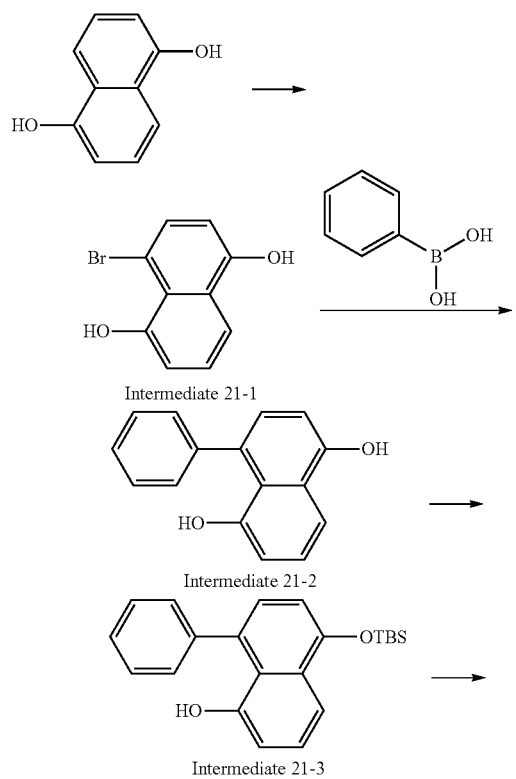

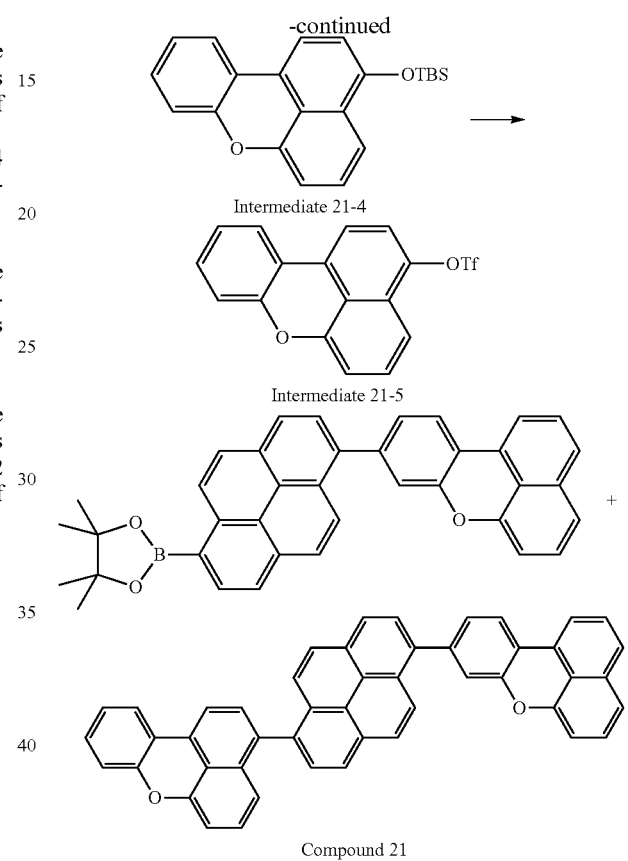
Compound 21

Synthesis of Intermediate 21-1

5 g of 1-5-dihydroxynaphthalene was dissolved in 100 ml of acetonitrile, and then, 5.5 g of N-bromosuccimide diluted in 100 ml of acetonitrile was slowly dropped thereon at a temperature of 0° C. After 3 hours of stirring while the temperature was maintained, water was used to stop the reaction, and an organic solvent was removed therefrom by distillation under reduced pressure. The obtained result was extracted by using ethyl acetate, and then, dried using anhydrous magnesium sulfate and concentrated under reduced pressure, and the obtained result was purified by silica gel column chromatography to obtain Intermediate 21-1 (5.8 g, 78%).

Synthesis of Intermediate 21-2

Intermediate 21-2 (5.1 g, 89%) was obtained in the same manner as used to synthesize Intermediate 5-4 of Synthesis Example 2, except that 5.8 g of Intermediate 21-1 and 3.5 g of phenylboronic acid were respectively used instead of Intermediate 1-4 and 2-(10-bromoanthracene-9-yl)-4,4,5,5-tetramethyl-1,3,2-dioxabororene.

Synthesis of Intermediate 21-3

5.1 g of Intermediate 21-2 was diluted in dichloromethane, and then, 5.1 ml of triethylamine and 3.2 g of tert-butyldimethylchlorosilane were slowly dropped thereto. After 3 hours, water was used to stop the reaction, and an organic layer was isolated therefrom. The obtained organic layer was dried by using anhydrous magnesium sulfate and then, concentrated under reduced pressure, and the result was purified by silica gel column chromatography to obtain Intermediate 21-3 (7 g, 91%).

Synthesis of Intermediate 21-4

7 g of Intermediate 21-3 was diluted in 100 ml of nitrobenzene, and then, 4.7 g of Cu(I)O was dropped thereto, and the result was relaxed at a temperature of 180° C. while stirring. After 48 hours, the reaction temperature was slowly lowered to room temperature, and then, nitrobenzene was removed therefrom by distillation under reduced pressure, and the obtained result was purified by silica gel column chromatography to obtain Intermediate 21-4 (4 g, 57%)

Synthesis of Intermediate 21-5

4 g of Intermediate 21-4 was diluted in 80 ml of dichloromethane, and then 10 ml of TFA was dropped thereto. After 8 hours, triethylamine was used to stop the reaction, and an organic solution was removed by distillation under reduced pressure, and the residual was separation-purified by silica gel column chromatography. The obtained compound was diluted in 100 ml of dichloromethane, and then, (4.7 ml) of triethylamine and (4.7 g) of anhydrous trifluoroacethyl acid were added thereto, and the mixture was stirred at a temperature of 0° C. After 1 hour, water was used to stop the reaction, and an organic layer was isolated therefrom by using dichloromethane. The isolated organic layer was dried using anhydrous magnesium sulfate, and then, distilled under reduced pressure, and the obtained result was purified by silica gel column chromatogaphy to obtain Intermediate 21-5 (2.7 g, 64%).

Synthesis of Compound 21

Compound 21 (3.6 g, 78%) was synthesized in the same manner as in synthesizing Compound 23 of Synthesis Example 6, except that 2.7 g of Intermediate 21-5 was used instead of Intermediate 1-4.

Synthesis Example 8: Synthesis of Compound 38

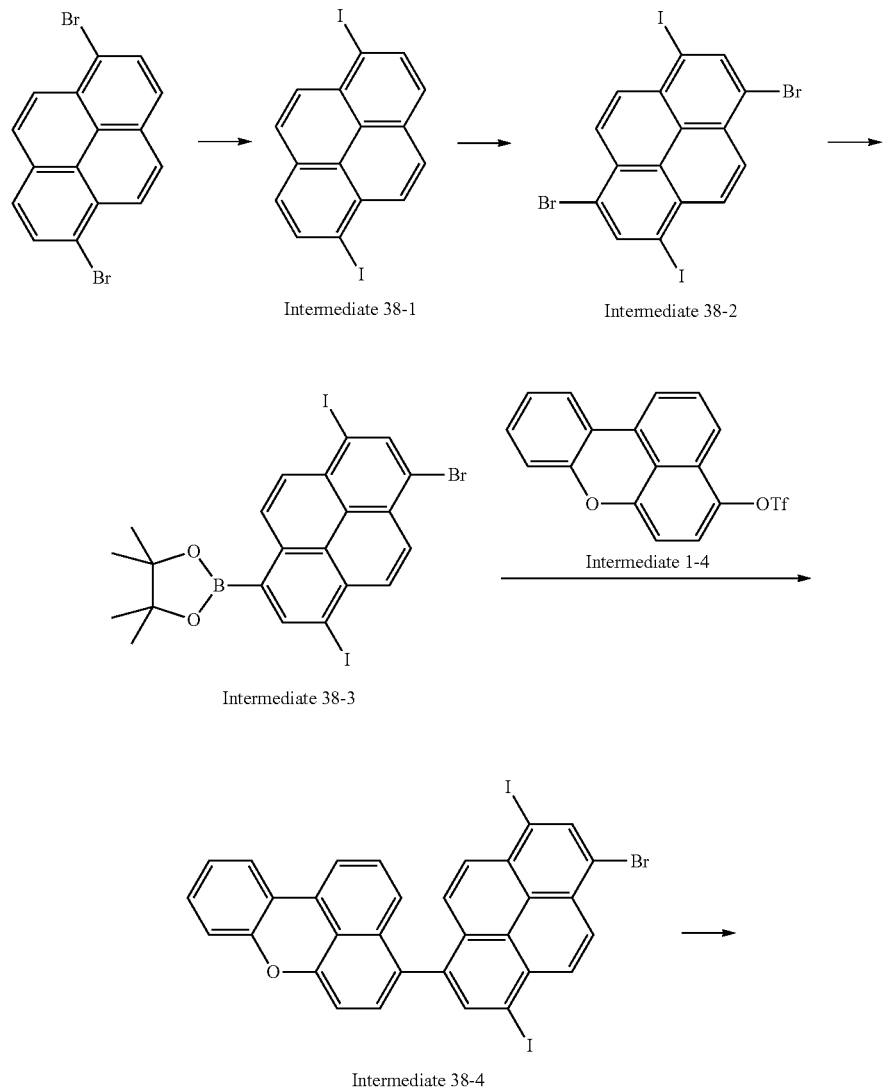

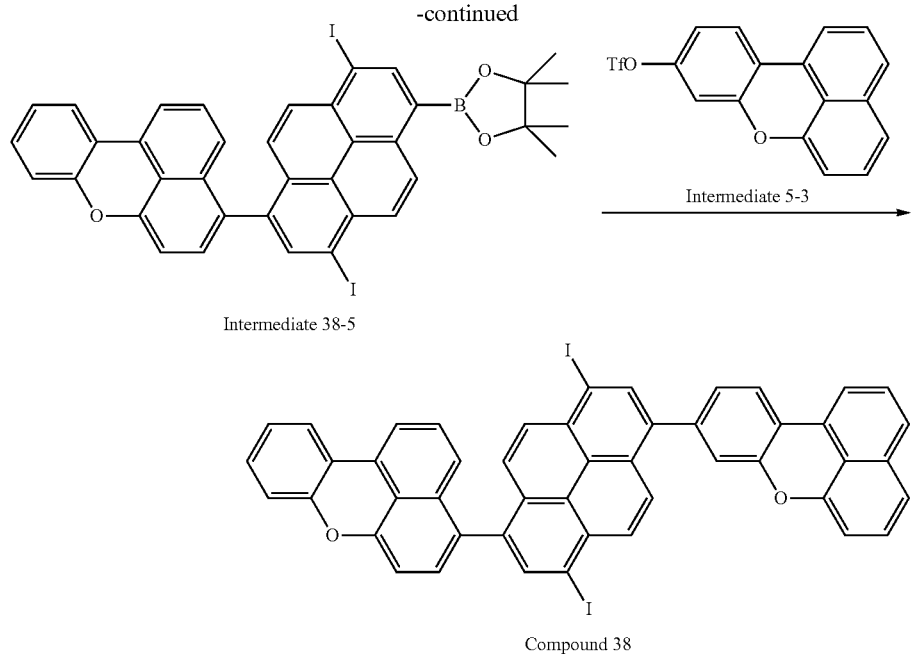

Intermediate 38-5

Compound 38

Synthesis of Intermediate 38-1

10 g of 1,6-dibromopyrene was completely dissolved in 1,000 ml of tetrahydrofuran, and then, at a temperature of −78° C., n-BuLi (2.4M, 46 ml) was slowly dropped thereto, and the mixture was stirred one hour while the temperature was maintained. At the same temperature, 19.6 g of iodomethane was dropped thereto, and then, the temperature was slowly raised to room temperature, and then, after mixing for 15 hours, a saturated ammonium chloride aqueous solution was used to stop the reaction. An organic layer collected by performing an extraction process three times by using ethyl acetate was dried by using anhydrous magnesium sulfate, and distilled under reduced pressure, and the result was purified by silica gel column chromatography to obtain Intermediate 38-1 (3 g, 48%).

Synthesis of Intermediate 38-2

3 g of Intermediate 38-1 was diluted in 300 ml of dichloromethane, and then, 4.85 g of N-bromosuccinimide was added thereto, and the mixture was stirred for 15 hours. The reaction solution was filtered under reduced pressure and the obtained result was washed with dichloromethane to obtain Intermediate 38-2 (4.8 g, 94%).

Synthesis of Intermediate 38-3

Intermediate 38-3 (4.2 g, 78%) was synthesized in the same manner as in synthesizing Intermediate 5-5 of Synthesis Example 2, except that 4.8 g of Intermediate 38-2 was used instead of Intermediate 5-4.

Synthesis et Intermediate 38-4

Intermediate 38-4 (3.9 g, 76%) was obtained in the same manner as used to synthesize Intermediate 5-4 of Synthesis Example 2, except that 4.2 g of Intermediate 38-3 was used instead of 2-(10-bromoanthracene-9-yl)-4,4,5,5-tetramethyl-1,3,2-dioxabororene and the amount of Intermediate 1-4 was 4.5 g.

Synthesis of Intermediate 38-5

Intermediate 38-2 (3.6 g, 86%) was synthesized in the same manner as in synthesizing Intermediate 38-3, except that 3.9 g of Intermediate 38-4 was used instead of Intermediate 38-2.

Synthesis of Compound 38

Compound 38 (3.2 g, 72%) was synthesized in the same manner as in synthesizing Compound 5 of Synthesis Example 2, except that 3.9 g of Intermediate 38-5 was used instead of Intermediate 5-5.

Synthesis Example 9: Synthesis of Compound 44

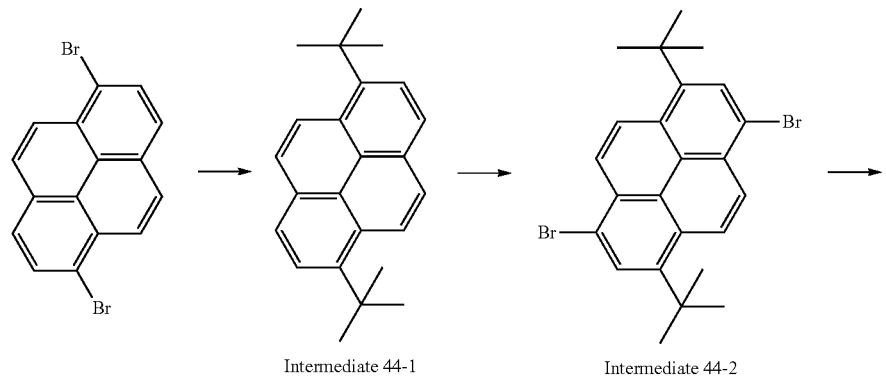

Intermediate 44-1

Intermediate 44-2

-continued
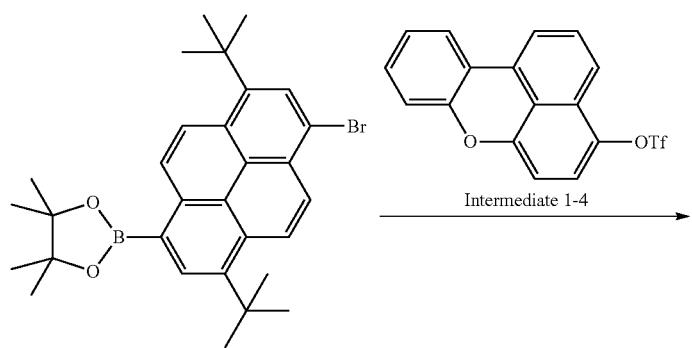
Intermediate 44-3 Intermediate 1-4
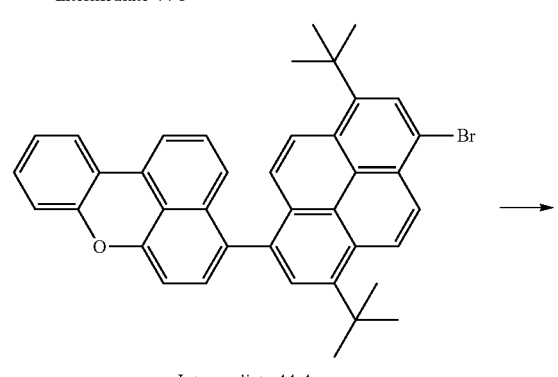
Intermediate 44-4
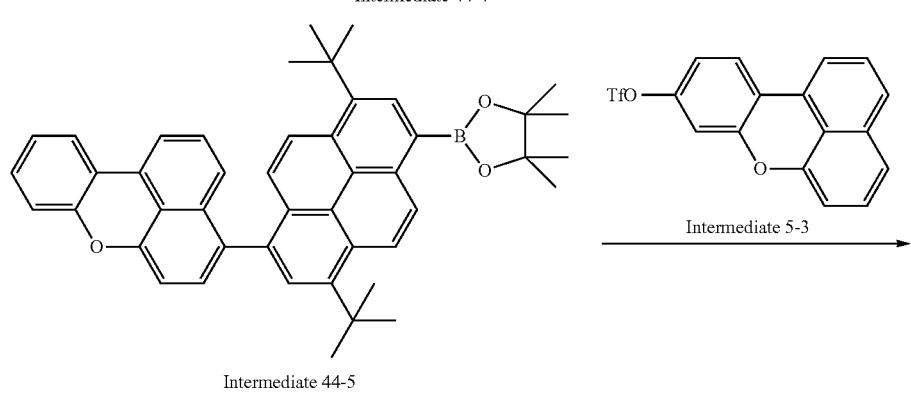
Intermediate 44-5 Intermediate 5-3
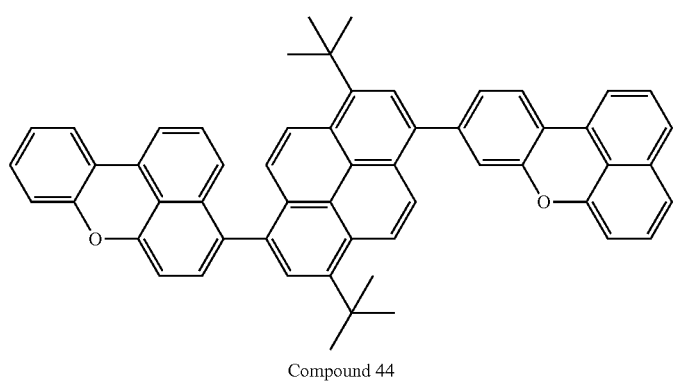
Compound 44

Synthesis of Intermediate 44-1

Intermediate 44-1 (3.5 g, 81%) was obtained in the same manner as used to synthesize Intermediate 38-1 in Synthesis Example 8, except that 5 g of 1,6-dibromopyrene and 3.1 g of t-butylboronic acid were used instead of 10 g of 1,6-dibromopyrene and iodomethane.

Synthesis of Intermediate 44-2

Intermediate 44-2 (5 g, 96%) was synthesized in the same manner as in synthesizing Intermediate 38-1 of Synthesis Example 8, except that 3.5 g of Intermediate 44-1 was used instead of intermediate 38-1.

Synthesis of Intermediate 44-3

Intermediate 44-3 (4.1 g, 76%) was synthesized in the same manner as in synthesizing Intermediate 38-3 of Synthesis Example 8, except that 5 g of Intermediate 44-2 was used instead of Intermediate 38-2.

Synthesis of Intermediate 44-4

Intermediate 44-4 (4.1 g, 85%) was obtained in the same manner as used to synthesize Intermediate 5-4 of Synthesis Example 2, except that 4.1 g of Intermediate 44-3 was used instead of 2-(10-bromoanthracene-9-yl)-4,4,5,5-tetramethyl-1,3,2-dioxabororene and the amount of Intermediate 1-4 was 3.1 g.

Synthesis of Intermediate 44-5

Intermediate 44-5 (3.4 g, 77%) was synthesized in the same manner as in synthesizing Intermediate 5-5 of Synthesis Example 2, except that 4.1 g of Intermediate 44-4 was used instead of Intermediate 5-4.

Synthesis of Compound 44

Compound 44 (2.6 g, 66%) was obtained in the same manner as used to synthesize Intermediate 5-4 of Synthesis Example 2, except that 2.1 g of Intermediate 5-3 and 3.4 g of Intermediate 44-5 were respectively used instead of Intermediate 1-4 and 2-(10-bromoanthracene-9-yl)-4,4,5,5-tetramethyl-1,3,2-dioxabororene.

Synthesis Example 10: Synthesis of Compound 51

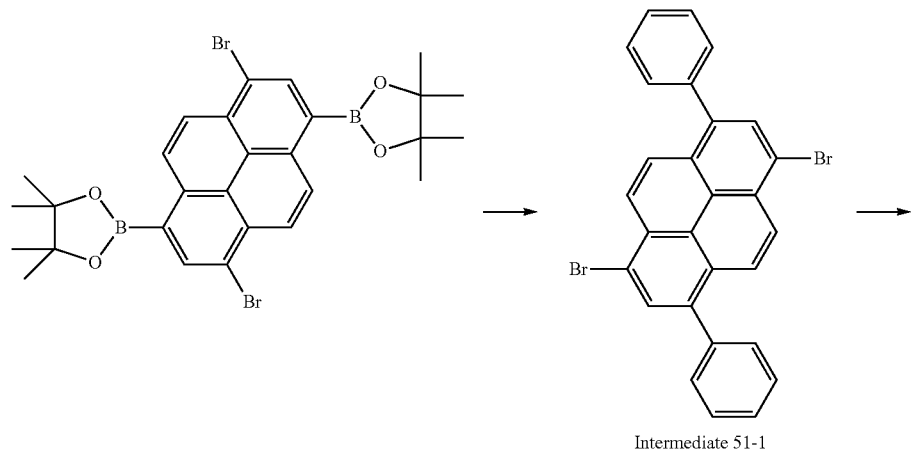

Intermediate 51-1

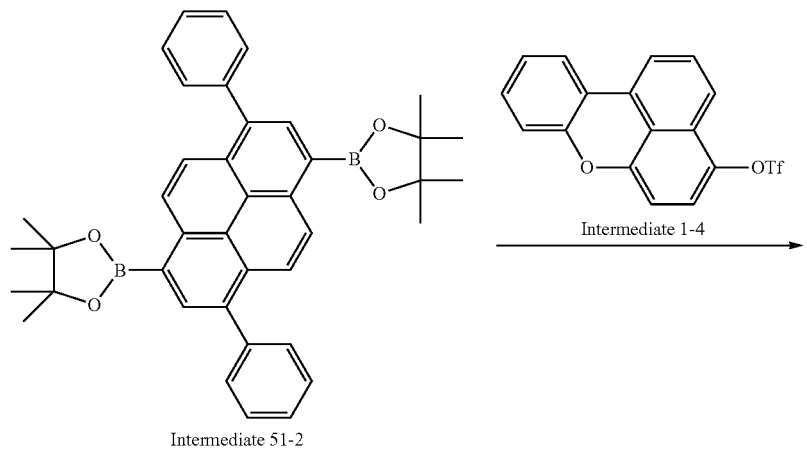

Intermediate 51-2

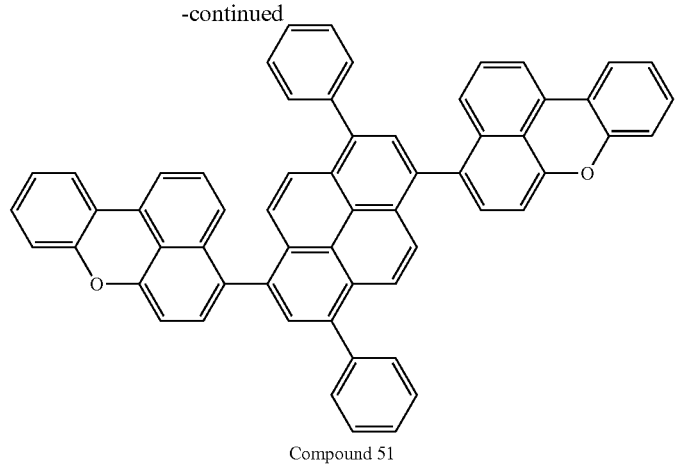

Compound 51

Synthesis of Intermediate 51-1

Intermediate 51-1 (2.1 g, 43%) was obtained in the same manner as used to synthesize Intermediate 44-1 of Synthesis Example 9, except that 5.7 g of 2,2'-(3,8-dibromompyrene-1,6-diyl)bis(4,4,5,5-tetramethyl-1,3,2-dioxaborolane) and 7.6 g of iodobenzene were respectively used instead of 1,6-dibromopyrene and t-butylburonic acid.

Synthesis of Intermediate 51-2

Intermediate 51-2 (3.3 g, 76%) was synthesized in the same manner as in synthesizing intermediate 5-5 of Synthesis Example 2, except that 2.1 of Intermediate 51-1 was used instead of Intermediate 5-4.

Synthesis of Compound 51

Compound 51 (3.2 g, 73%) was obtained in the same manner as used to synthesize Intermediate 5-4 of Synthesis Example 2, except that 3.3 g of Intermediate 51-2 was used instead of 2-(10-bromoanthracene-9-yl)-4,4,5,5-tetramethyl-1,3,2-dioxabororene and the amount of Intermediate 1-4 was 4.5 g.

Synthesis Example 11: Synthesis of Compound 57

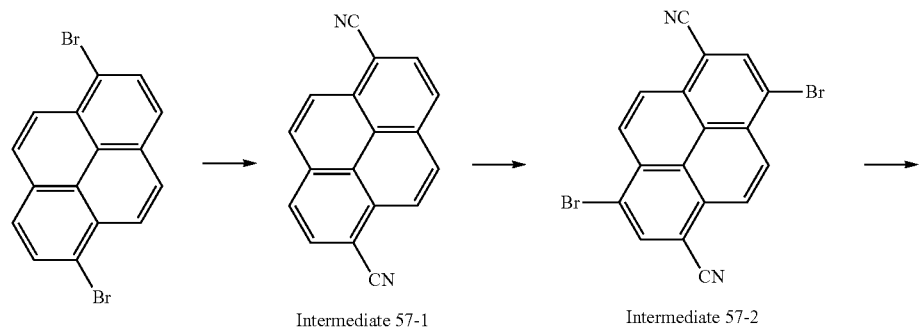

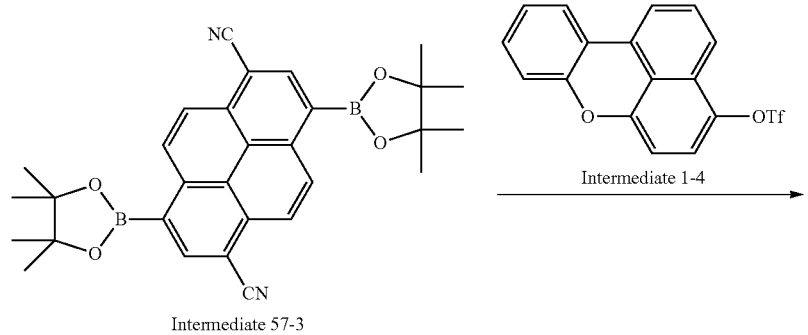

-continued

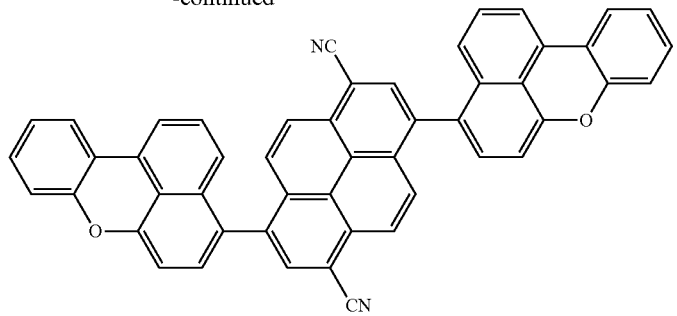

Compound 57

Synthesis of Intermediate 57-1

3 g of 1,6-dibromopyrene was diluted in 60 ml of dimethylformamide, and then 2 g of CuCN was dropped thereto, and the mixture was refluxed at a temperature of 150° C. while stirring. After 24 hours, the temperature was decreased to room temperature and then, water was used to stop the reaction, and then the reaction product was extracted by using ethyl acetate. The extracted organic layer was dried by using anhydrous magnesium sulfate, and then, distilled under reduced pressure, and the result was separation-purified by silica gel column chromatography to obtain Intermediate 57-1 (2.1 g, 99%).

Synthesis of Intermediate 57-2

Intermediate 57-2 (3 g, 89%) was synthesized in the same manner as in synthesizing Intermediate 44-2 of Synthesis Example 9, except that 2.1 g of Intermediate 57-1 was used instead of Intermediate 44-1.

Synthesis of Intermediate 57-3

Intermediate 57-3 (2.6 g, 70%) was synthesized in the same manner as in synthesizing Intermediate 44-3 of Synthesis Example 9, except that 3 g of Intermediate 57-2 was used instead of Intermediate 44-2.

Synthesis of Compound 57

Compound 57 (2.6 g, 74%) was obtained in the same manner as used to synthesize Intermediate 5-4 of Synthesis Example 2, except that 2.6 g of Intermediate 57-3 was used instead of 2-(10-bromoanthracene-9-yl)-4,4,5,5-tetramethyl-1,3,2-dioxabororene and the amount of Intermediate 1-4 was 4.2 g.

Synthesis Example 12: Synthesiss of Compound 62

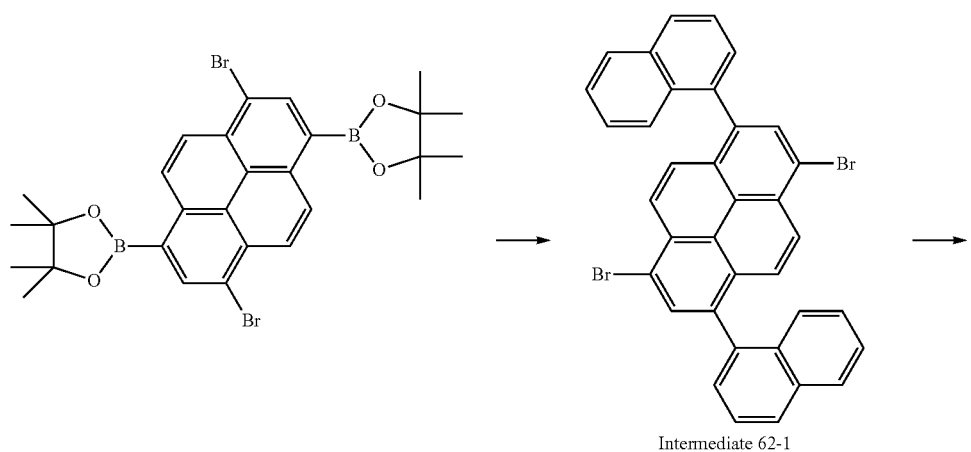

Intermediate 62-1

-continued
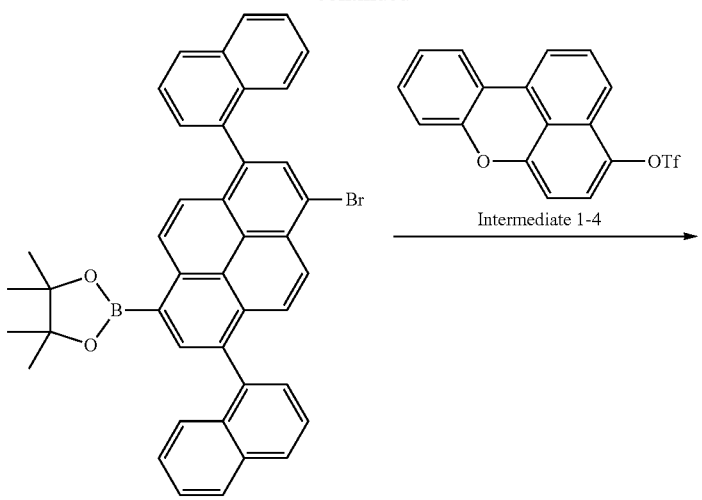
Intermediate 62-2
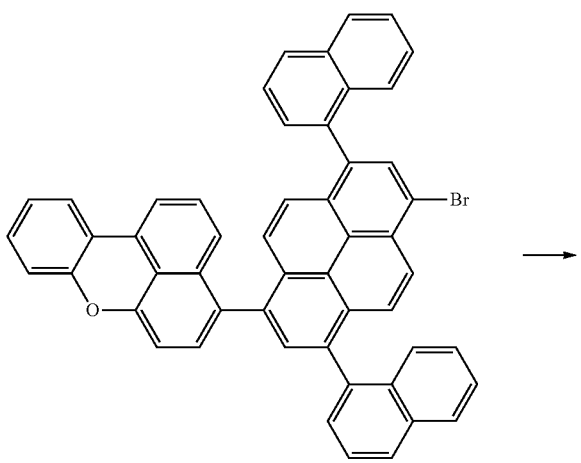
Intermediate 62-3
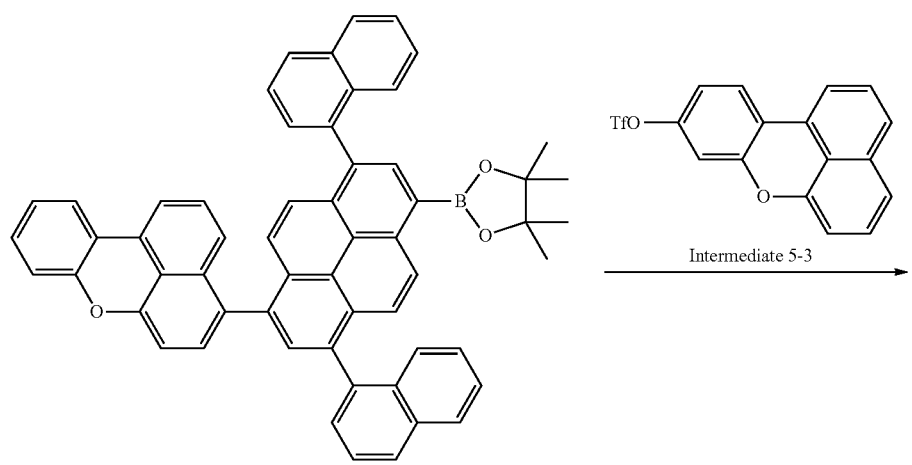
Intermediate 62-4

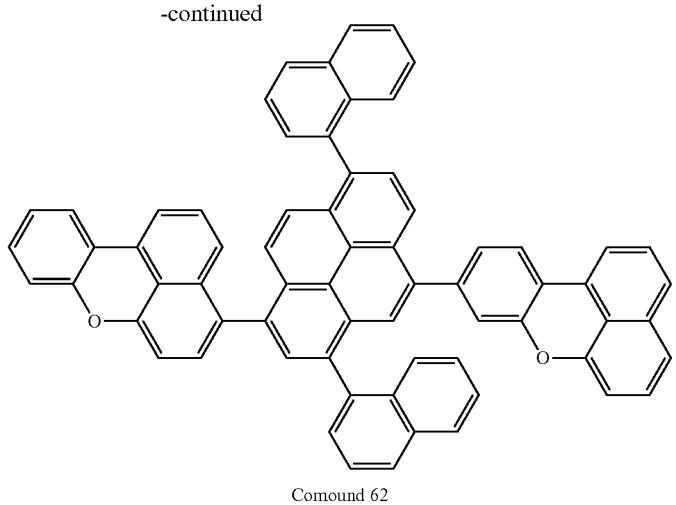

Comound 62

Synthesis of Intermediate 62-1

Intermediate 62-1 (3.3 g, 37%) was synthesized in the same manner as in synthesizing Intermediate 51-1 of Synthesis Example 10, except that 12 g of 1-bromonaphthalene was used instead of iodobenzene.

Synthesis of Intermediate 62-2

Intermediate 62-2 (2.7 g, 77%) was synthesized in the same manner as in synthesizing Intermediate 5-5 of Synthesis Example 2, except that 3.3 g of Intermediate 62-1 was used instead of Intermediate 5-4.

Synthesis of Intermediate 62-3

Intermediate 62-3 (2.5 g, 81%) was obtained in the same manner as used to synthesize Intermediate 5-4 of Synthesis Example 2, except that 2.7 g of Intermediate 62-2 was used instead of 2-(10-bromoanthracene-9-yl)-4,4,5,5-tetramethyl-1,3,2-dioxabororene and the amount of Intermediate 1-4 was 3 g.

Synthesis of Intermediate 62-4

Intermediate 62-4 (1.9 g, 71%) was synthesized in the same manner as in synthesizing Intermediate 5-5 of Synthesis Example 2, except that 2.5 g of Intermediate 62-3 was used instead of Intermediate 5-4.

Synthesiss of Compound 62

Compound 62 (1.7 g, 81%) was obtained in the same manner as used to synthesize Intermediate 5-4 of Synthesis Example 2, except that 1.9 g of Intermediate 62-3 and 1.2 g of Intermediate 5-3 were respectively used instead of 2-(10-bromoanthracene-9-yl)-4,4,5,5-tetramethyl-1,3,2-dioxabororene and Intermediate 1-4.

Synthesis Example 13: Synthesis of Compound 75

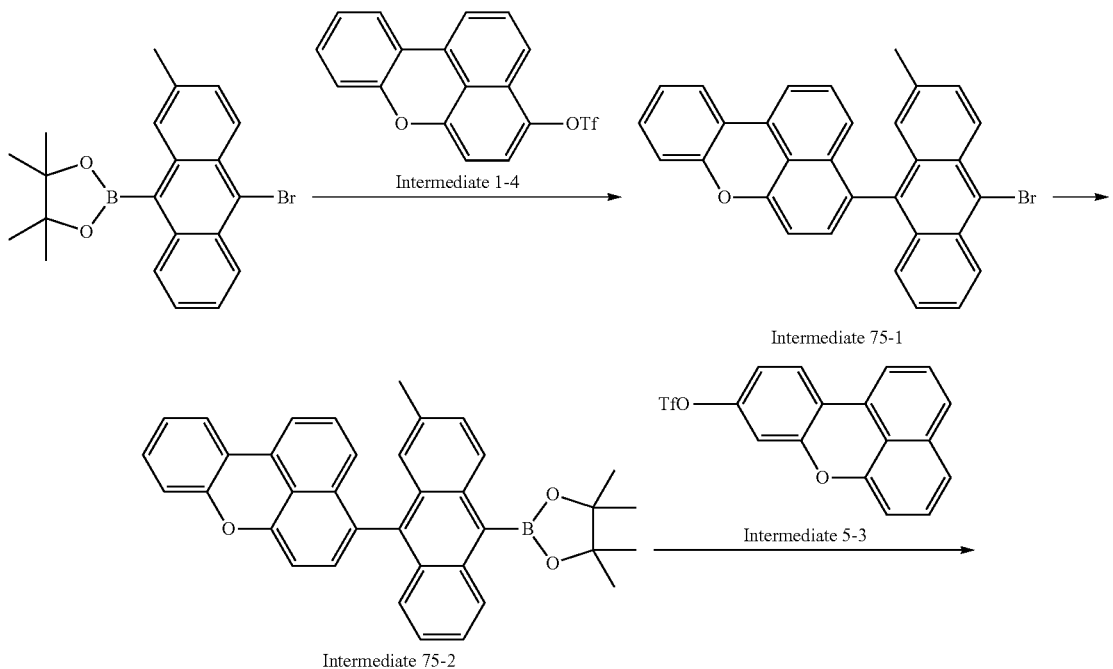

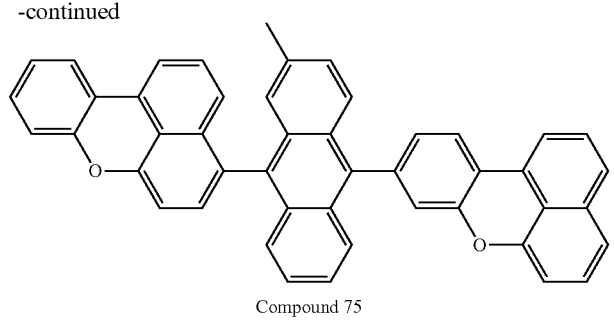

Compound 75

Synthesis of Intermediate 75-1

Intermediate 75-1 (2.3 g, 61%) was obtained in the same manner as used to synthesize Intermediate 5-4 of Synthesis Example 2, except that 2-(10-bromo-2-methylanthracen-9-yl)-4,4,5,5-tetramethyl-1,3,2-dioxaborolane was used instead of 2-(10-bromoanthracene-9-yl)-4,4,5,5-tetramethyl-1,3,2-dioxabororene.

Synthesis of Intermediate 75-2

Intermediate 75-2 (2.1 g, 83%) was synthesized in the same manner as in synthesizing Intermediate 5-5 of Synthesis Example 2, except that 2.3 g of Intermediate 75-1 was used instead of Intermediate 5-4.

Synthesis of Compound 75

Compound 75 (2.1 g, 85%) was obtained in the same manner as used to synthesize Intermediate 5-4 of Synthesis Example 2, except that 2.1 g of Intermediate 75-2 and 1.6 g of Intermediate 5-3 were respectively used instead of 2-(10-bromoanthracene-9-yl)-4,4,5,5-tetramethyl-1,3,2-dioxabororene and Intermediate 1-4.

Synthesis Example 14: Synthesis of Compound 116

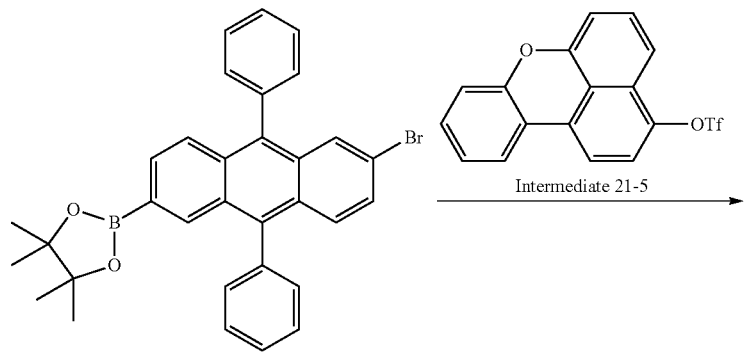

Intermediate 21-5

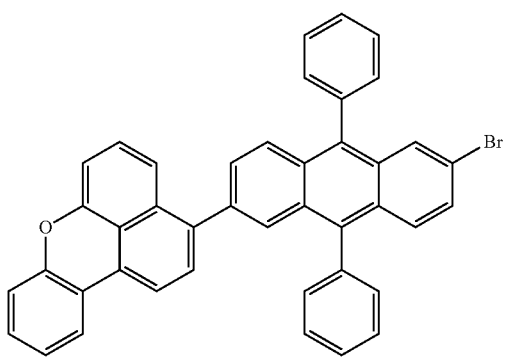

Intermediate 116-1

-continued

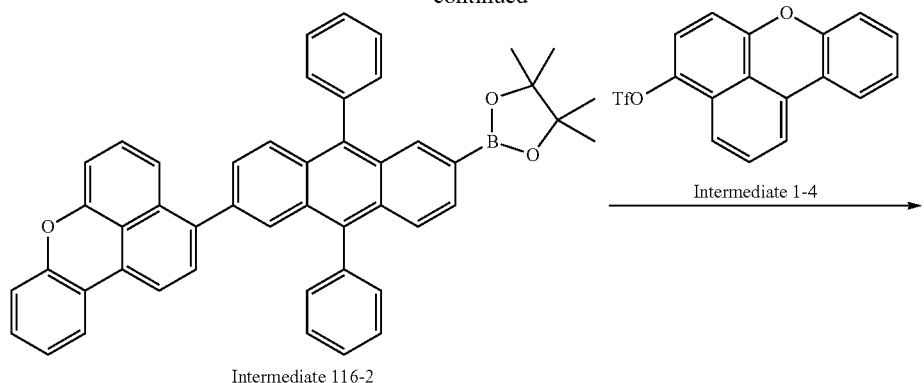

Intermediate 116-2

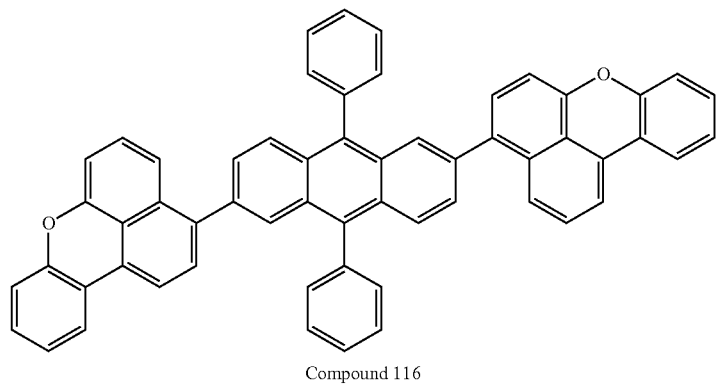

Compound 116

Synthesis of Intermediate 116-1

Intermediate 116-1 (3.5 g, 78%) was obtained in the same manner as used to synthesize Intermediate 5-4 of Synthesis Example 2, except that 4 g of 2-(6-bromo-9,10-diphenylanthracen-2-yl)-4,4,5,5-tetramethyl-1,3,2-dioxaborolane and 5.4 g of Intermediate 21-5 were respectively used instead of 2-(10-bromoanthracene-9-yl) -4,4,5,5-tetramethyl-1,3,2-dioxabororene and Intermediate 1-4.

Synthesis of Intermediate 116-2

Intermediate 116-2 (3.1 g, 81%) was synthesized in the same manner as in synthesizing Intermediate 5-5 of Synthesis Example 2, except that 3.5 g of Intermediate 116-1 was used instead of Intermediate 5-4.

Synthesis of Compound 116

Compound 116 (2.7 g, 76%) was obtained in the same manner as used to synthesize Intermediate 5-4 of Synthesis Example 2, except that 3.1 g of Intermediate 116-2 was used instead of 2-(10-bromoanthracene-9-yl)-4,4,5,5-tetramethyl-1,3,2-dioxabororene and the amount of Intermediate 1-4 was 1.9 g.

Synthesis Example 15: Synthesis of Compound 123

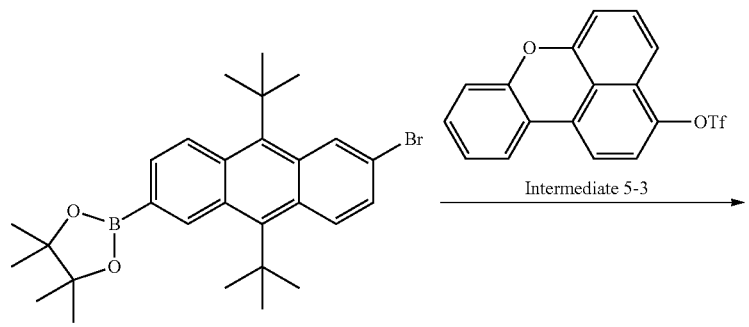

-continued

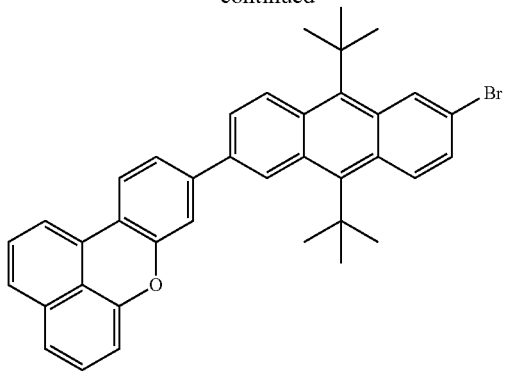

Intermediate 123-1

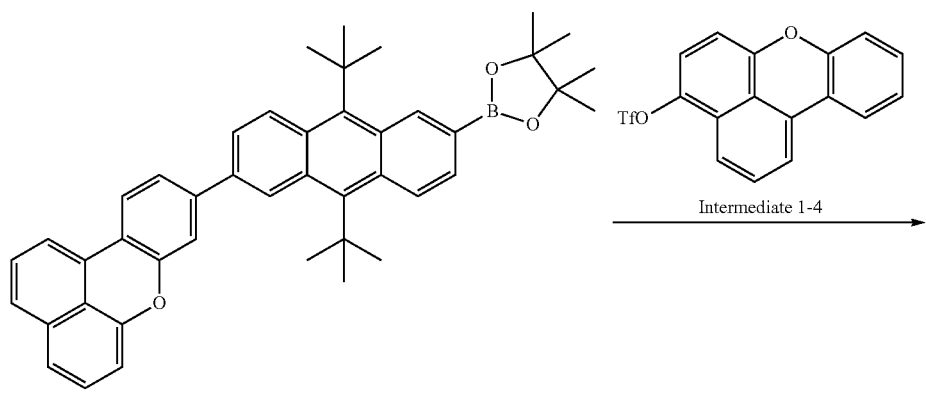

Intermediate 123-2

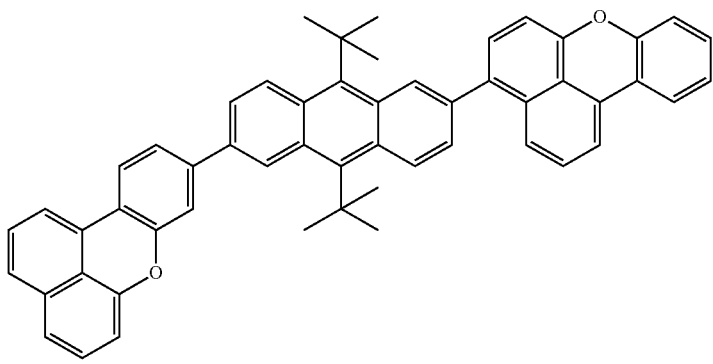

Compound 123

Synthesis of Intermediate 123-1

Intermediate 123-1 (3 g, 64%) was obtained in the same manner as used to synthesize Intermediate 5-4 of Synthesis Example 2, except that 4 g of 2-(6-bromo-9,10-diphenylanthracen-2-yl)-4,4,5,5-tetramethyl-1,3,2-dioxaborolane and 6 g of Intermediate 5-3 were respectively used instead of 2-(10-bromoanthracene-9-yl)-4,4,5,5-tetramethyl-1,3,2-dioxabororene and Intermediate 1-4.

Synthesis of Intermediate 123-2

Intermediate 123-2 (2.5 g, 77%) was synthesized in the same manner as in synthesizing Intermediate 5-5 of Synthesis Example 2, except that 3 g of Intermediate 123-1 was used instead of Intermediate 5-4.

Synthesiss of Compound 123

Compound 123 (2.4 g, 84%) was obtained in the same manner as used to synthesize Intermediate 5-4 of Synthesis Example 2, except that 2.5 g of Intermediate 123-2 was used instead of 2-(10-bromoanthracene-9-yl)-4,4,5,5-tetramethyl-1,3,2-dioxabororene and the amount of Intermediate 1-4 was 2 g.

Synthesis Example 16: Synthesis of Compound 155

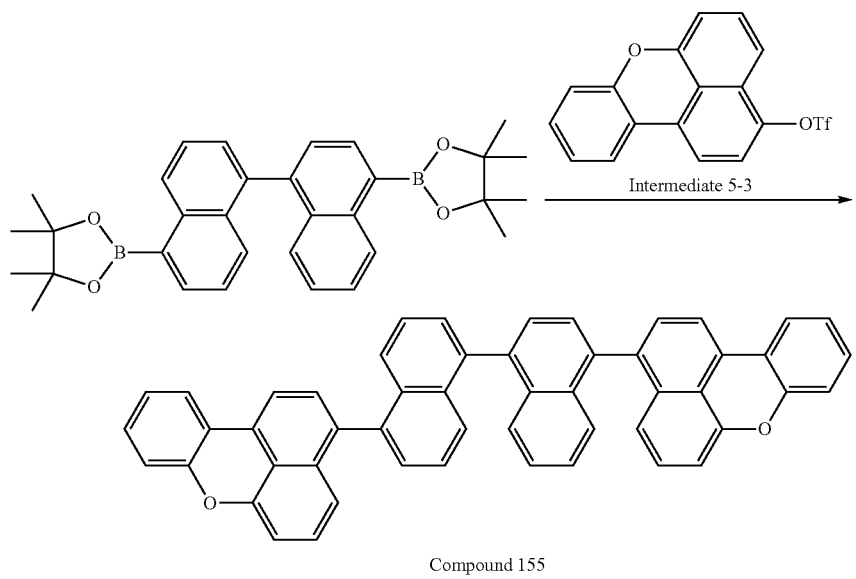

Intermediate 155 (2.4 g, 78%) was obtained in the same manner as used to synthesize Intermediate 5-4 of Synthesis Example 2, except that 2.3 g of 2,2'-([1,1'-binaphthalene]-4,5'-diyl)bis(4,4,5,5-tetramethyl-1,3,2-dioxaborolane and 3.4 g of Intermediate 5-3 were respectively used instead of 2-(10-bromoanthracene-9-yl)4,4,5,5-tetramethyl-1,3,2-dioxabororene and Intermediate 1-4.

Synthesis Example 17: Compound 159

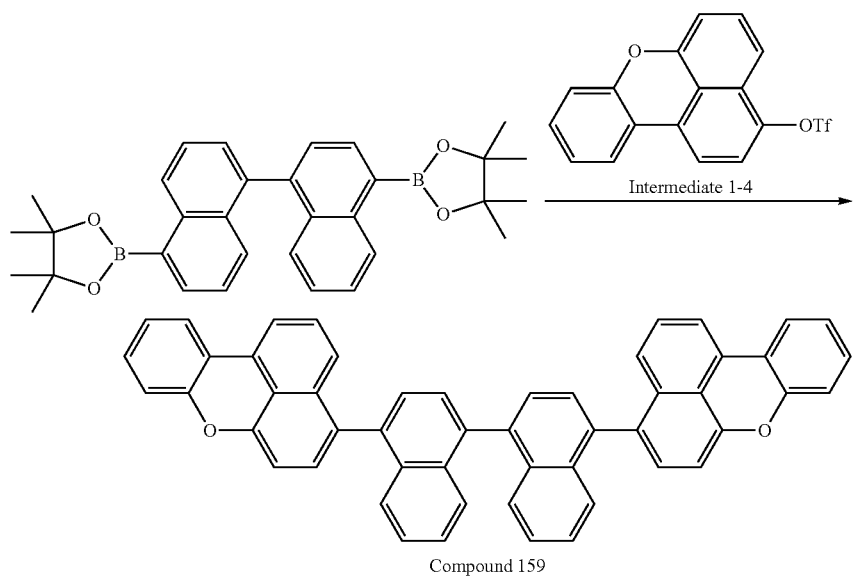

Compound 159 (2.8 g, 86%) was obtained in the same manner as used to synthesize Intermediate 5-4 of Synthesis Example 2, except that 2.3 g of 4,4'-bis(4,4,5,5-tetramethyl-1,3,2-dioxaborolan-2-yl)-1,1'-binaphthalene was used instead of 2-(10-bromoanthracene-9-yl)-4,4,5,5-tetramethyl-1,3,2-dioxabororene and the amount of Intermediate 1-4 was 3.4 g.

Synthesis Example 18: Synthesis of Compound 161
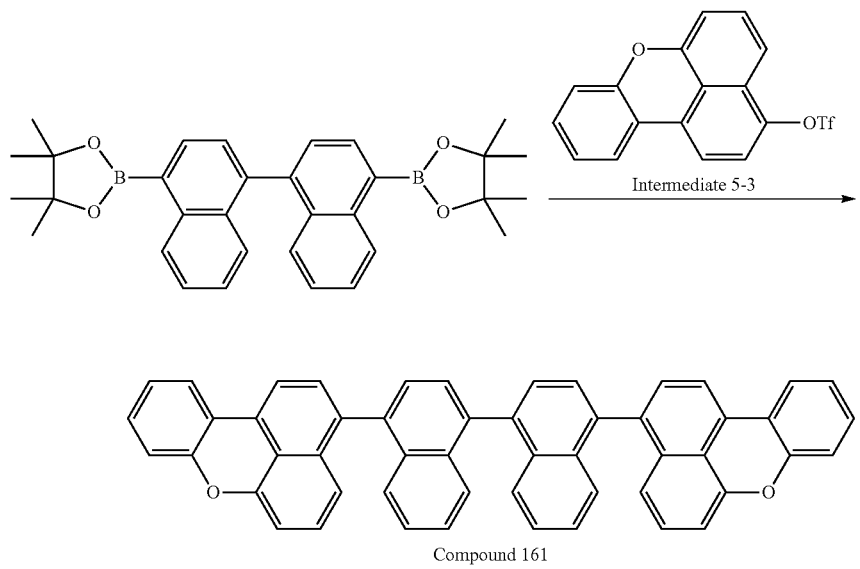
Compound 161 (2.2 g, 70%) was obtained in the same manner as in synthesizing Compound 17, except that 3.4 g of Intermediate 5-3 was used instead of Intermediate 1-4.
Synthesis Example 19: Synthesis of Compound 178
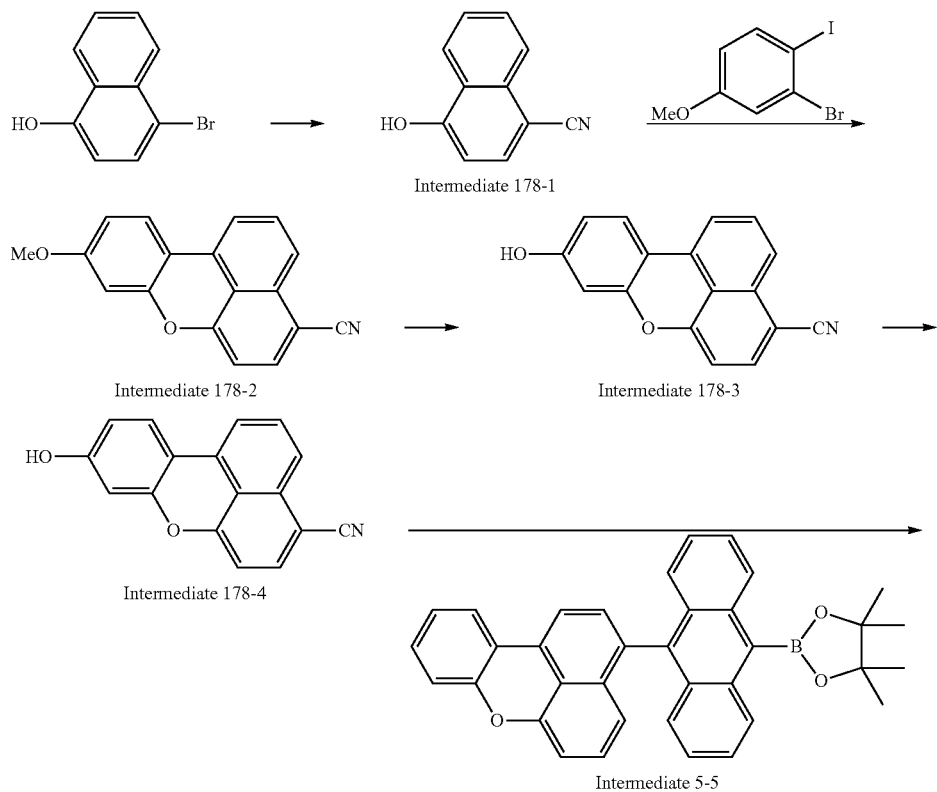

-continued

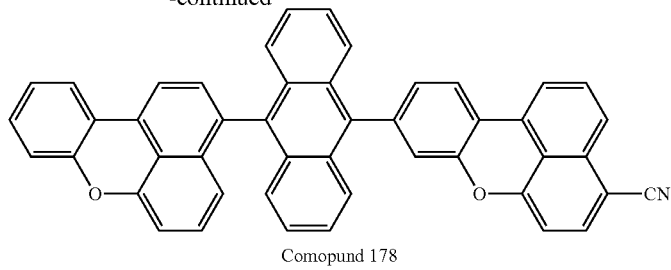

Comopund 178

Synthesis of Intermediate 178-1

Intermediate 178-1 (2 g, 88%) was synthesized in the same manner as in synthesizing Intermediate 57-1 of Synthesis Example 11, except that 3 g of 4-bromonaphthalene-1-ol was used instead of 1,6-dibromopyrene.

Synthesis of Intermediate 178-2

Intermediate 178-2 (2.5 g, 76%) was synthesized in the same manner as in synthesizing Intermediate 1-2 of Synthesis Example 1, except that 2 g of Intermediate 178-1 was used instead of Intermediate 1-1.

Synthesis of Intermediate 178-3

Intermediate 178-3 (2.1 g, 91%) was synthesized in the same manner as in synthesizing Intermediate 1-3 of Synthesis Example 1, except that 2.5 g of Intermediate 178-2 was used instead of Intermediate 1-2.

Synthesis of Intermediate 178-4

Intermediate 178-4 (2.9 g, 92%) was synthesized in the same manner as in synthesizing Intermediate 5-3 of Synthesis Example 2, except that 2.1 g of Intermediate 178-3 was used instead of Intermediate 5-2.

Synthesis of Compound 178

Compound 178 (3.3 g, 71%) was obtained in the same manner as used to synthesize Intermediate 5-4 of Synthesis Example 2, except that 2.9 g of Intermediate 178-4 and 3.8 g of Intermediate 5-5 were respectively used instead of Intermediate 1-4 and 2-(10-bromoanthracene-9-yl)-4,4,5,5-tetramethyl-1,3,2-dioxabororene.

Synthesis Example 20: Synthesis of Compound 182

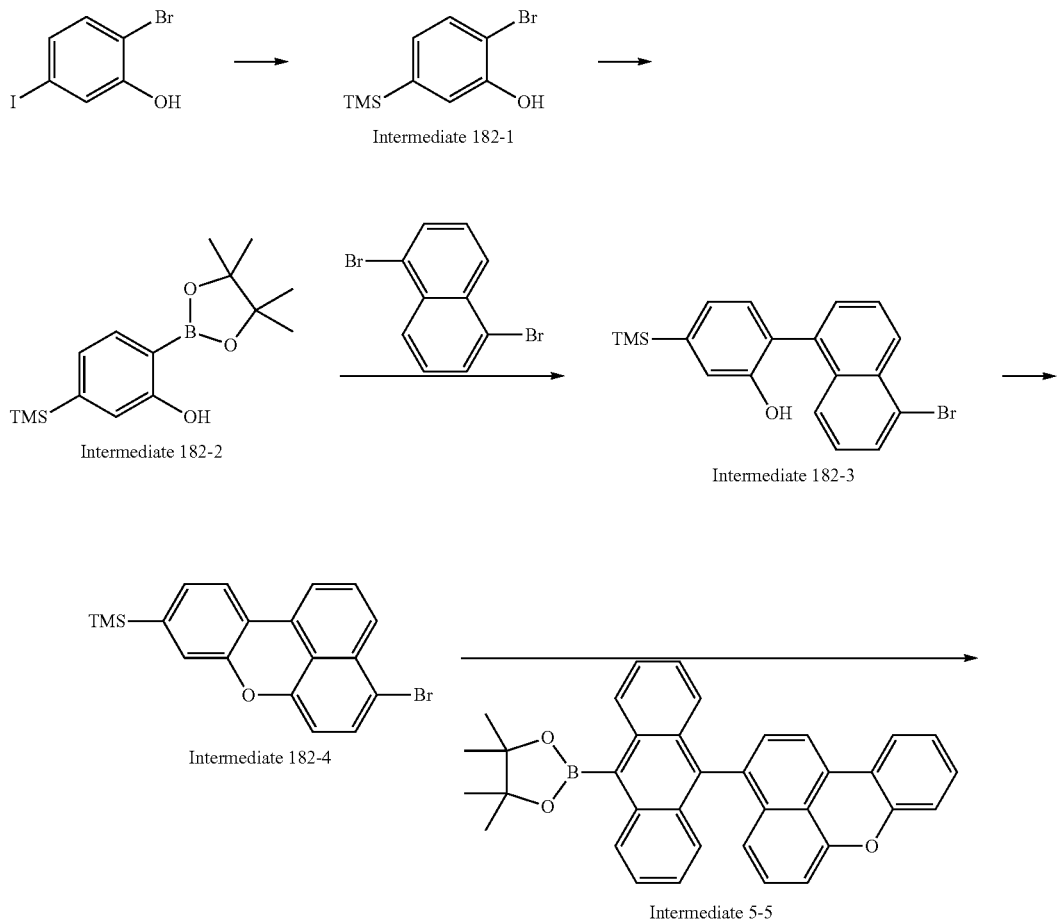

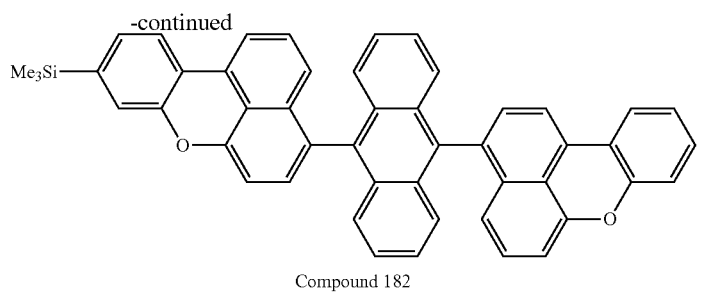

Compound 182

Synthesis Intermediate 182-1

7 g of 2-bromo-5-iodophenol was dissolved in 100 ml of tetrahydrofuran, and then, at a temperature of −78° C., n-BuLi (2.4M, 18.7 ml) was slowly dropped thereto. While the temperature was maintained, the mixture was stirred for 30 minutes and then, 5.1 g of chloro trimethylsilane was slowly dropped thereto, and then, at room temperature, the mixture was stirred for 1 hour. The reaction was stopped by adding saturated ammonium chloride aqueous solution thereto, and then, the reaction product was extracted three times by using ethyl acetate. An organic layer obtained therefrom was dried by using anhydrous magnesium sulfide, and then, distilled under reduced pressure, and then, the result was separated and purified by silica gel chromatography to obtain Intermediate 182-1 (2.1 g, 37%).

Synthesis of Intermediate 182-2

2.1 g of Intermediate 182-1 was dissolved in 4 ml dimethylformamid, and then, 0.350 g of 1,1'-bis(diphenylphosphino)ferrocene]dichloropalladium(II), 2.2 g of bis(pinacolato)diboron, and 2.5 g of potassium acetate were added thereto, and the mixture was refluxed at a temperature of 80° C. for 2 hours while stirring. The reaction product was slowly cooled at room temperature, and then, water was added thereto to stop the reaction, and then the result was extracted three times by using ethyl acetate. An organic layer obtained therefrom was dried by using anhydrous magnesium sulfide, and then, distilled under reduced pressure, and then, the result was separated and purified by silica gel chromatography to obtain Intermediate 182-2 (2.1 g, 84%).

Synthesis of Intermediate 182-3

Compound 182-3 (2.1 g, 77%) was obtained in the same manner as used to synthesize Intermediate 5-4 of Synthesis Example 2, except that 2.1 g of Intermediate 182-2 and 1.8 g of 1,5-dibromonaphthalene were respectively used instead of 2-(10-bromoanthracene-9-yl)-4,4,5,5-tetramethyl-1,3,2-dioxabororene and Intermediate 1-4.

Synthesis of Intermediate 182-4

Intermediate 182-4 (1.4 g, 67%) was synthesized in the same manner as in synthesizing Intermediate 21-4 of Synthesis Example 7, except that 2.1 g of Intermediate 182-3 was used instead of Intermediate 21-3.

Synthesis of Compound 182

Compound 182 (1.7 g, 69%) was synthesized in the same manner as in synthesizing Compound 178 of Synthesis Example 20, except that 1.4 g of Intermediate 182-4 was used instead of Intermediate 178-4.

Synthesis Example 21: Synthesiss of Compound 194

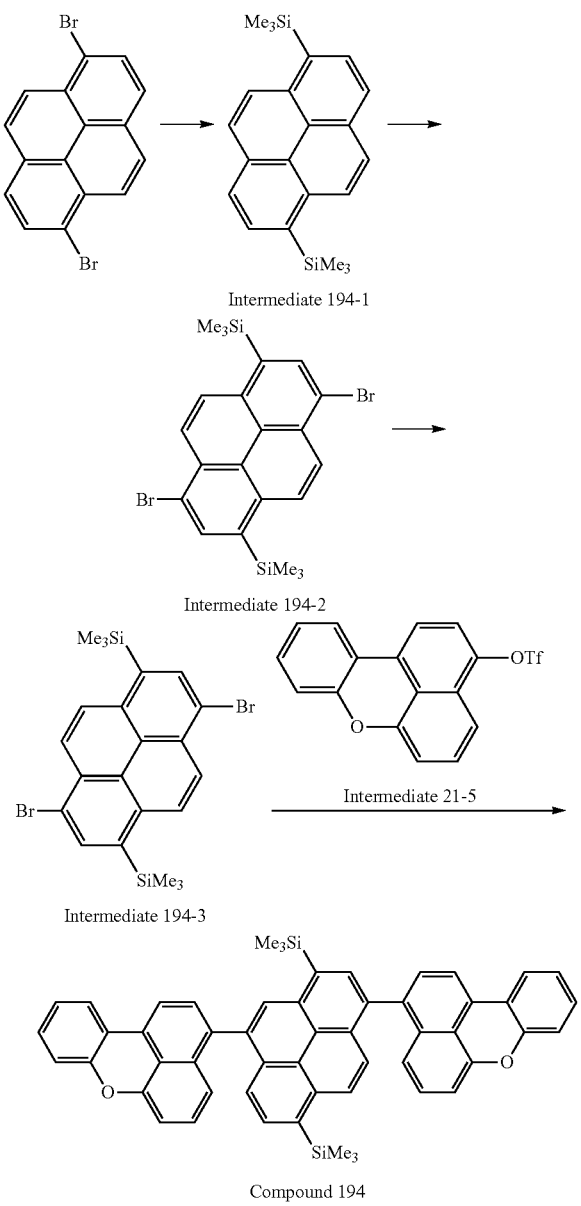

Compound 194

Synthesis of Intermediate 194-1

7 g of 1,6-dibromopyrene was completely dissolved in 1000 ml of tetrahydrofuran, and then, at a temperature of −78° C., n-BuLi (2.4M, 32 ml) was slowly dropped thereto, and the mixture was stirred one hour while the temperature was maintained. At the same temperature, 8.5 g of trimethylchlorosilane was dropped thereto, and then, the temperature was slowly raised to room temperature, and then, after mixing for 15 hours, a saturated ammonium chloride aqueous solution was used to stop the reaction. An organic layer collected by performing an extraction process three times by using ethyl acetate was dried by using anhydrous magnesium sulfate, and distilled under reduced pressure, and the result was purified by silica gel column chromotography to obtain Intermediate 194-1 (4.3 g, 64%).

Synthesis of Intermediate 194-2

Intermediate 194-2 (5.7 g, 91%) was synthesized in the same manner as in synthesizing Intermediate 38-2 of Synthesis Example 8, except that 4.3 g of Intermediate 194-1 was used instead of Intermediate 38-1.

Synthesis of Intermediate 194-3

Intermediate 194-3 (4.6 g, 68%) was synthesized in the same manner as in synthesizing Intermediate 5-5 of Synthesis Example 2, except that 5.7 g of Intermediate 194-2 was used instead of Intermediate 5-4.

Synthesiss of Compound 194

Compound 194 (4.4 g, 73%) was obtained in the same manner as used to synthesize Intermediate 5-4 of Synthesis Example 2, except that 4.6 g of Intermediate 194-3 and 6 g of Intermediate 21-5 were respectively used instead of 2-(10-bromoanthracene-9-yl)-4,4,5,5-tetramethyl-1,3,2-dioxabororene and Intermediate 1-4.

Synthesis Example 22: Compound 196

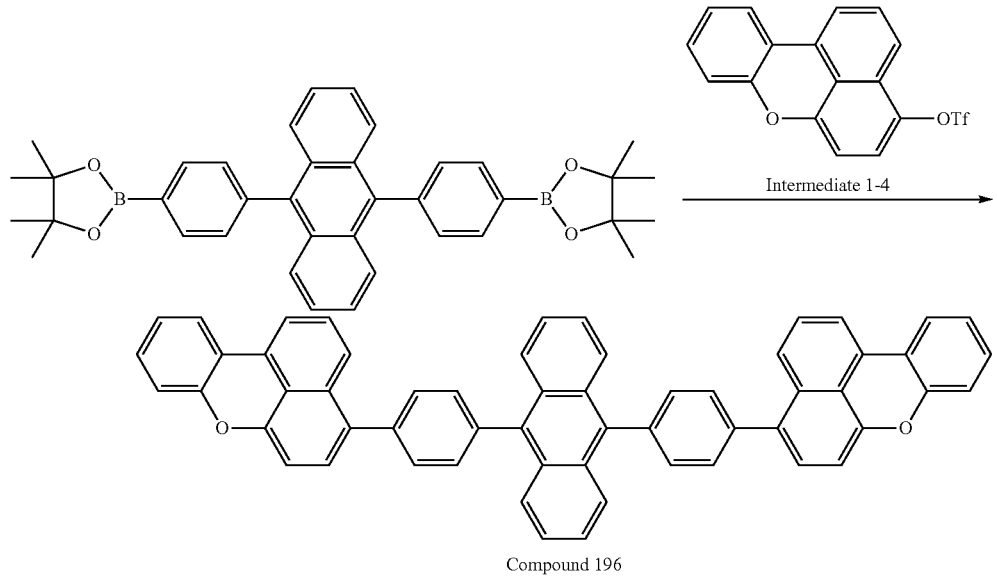

Compound 196

Compound 196 (2.8 g, 73%) was obtained in the same manner as used to synthesize Intermediate 5-4 of Synthesis Example 2, except that 3 g of 9,10-bis(4-(4,4,5,5-tetramethyl-1,3,2-dioxaborolan-2-yl)phenyl)anthracene was used instead of 2-(10-bromoanthracene-9-yl)-4,4,5,5-tetramethyl-1,3,2-dioxabororene and the amount of Intermediate 1-4 was 3.8 g.

Synthesis Example 23: Synthesis of Compound 202

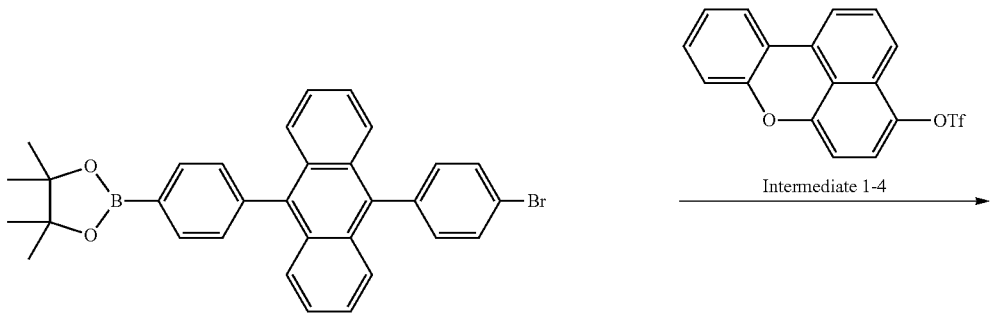

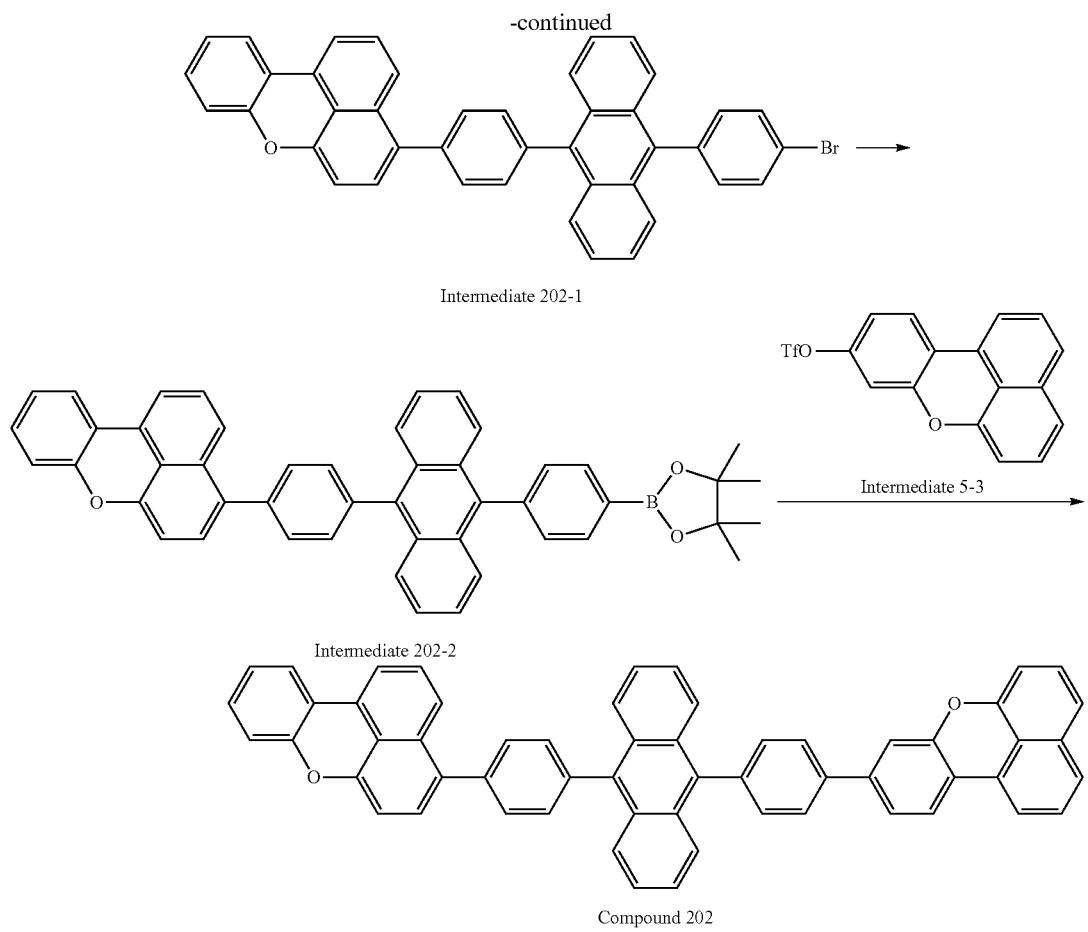

Intermediate 202-1

Intermediate 202-2

Compound 202

Synthesis of Intermediate 202-1

Intermediate 202-1 (2.3 g, 67%) was obtained in the same manner as used to synthesize Intermediate 5-4 of Synthesis Example 2, except that 3 g of 2-(4-(10-(4-bromophenyl)anthracen-9-yl)phenyl)-4,4,5,5-tetramethyl-1,3,2-dioxaborolane was used instead of 2-(10-bromoanthracene-9-yl)-4,4,4-tetramethyl-1,3,2-dioxabororene and the amount of Intermediate 1-4 was 3 g.

Synthesis of Intermediate 202-2

Intermediate 202-2 (1.8 g, 71%) was synthesized in the same manner as in synthesizing Intermediate 5-5 of Synthesis Example 2, except that 2.3 g of Intermediate 202-1 was used instead of Intermediate 5-4.

Synthesis of Intermediate 202

Compound 202 (1.8 g, 90%) was obtained in the same manner as used to synthesize Intermediate 5-4 of Synthesis Example 2, except that 1.8 g of Intermediate 202-2 and 1.1 g of Intermediate 5-3 were respectively used instead of 2-(10-bromoanthracene-9-yl)-4,4,5,5-tetramethyl-1,3,2-dioxabororene and Intermediate 1-4.

Synthesis Example 24: Compound 209

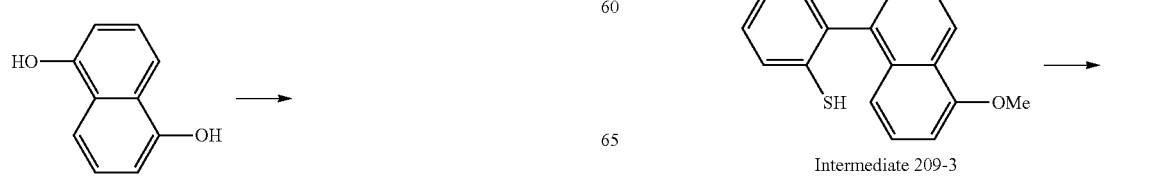

Intermediate 209-1

Intermediate 209-2

Intermediate 209-3

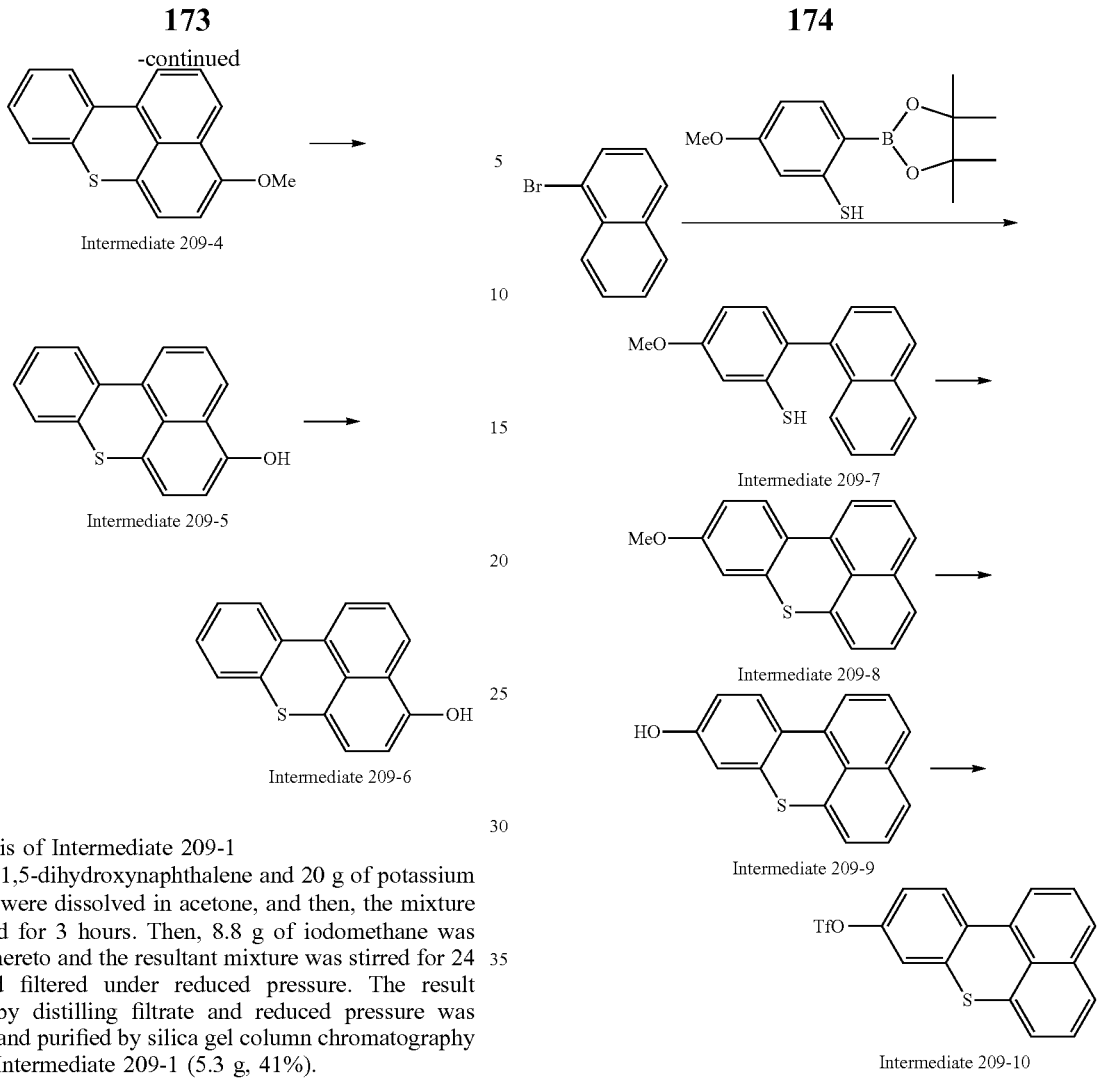

Synthesis of Intermediate 209-1

10 g of 1,5-dihydroxynaphthalene and 20 g of potassium carbonate were dissolved in acetone, and then, the mixture was stirred for 3 hours. Then, 8.8 g of iodomethane was dropped thereto and the resultant mixture was stirred for 24 hours and filtered under reduced pressure. The result obtained by distilling filtrate and reduced pressure was separated and purified by silica gel column chromatography to obtain Intermediate 209-1 (5.3 g, 41%).

Synthesis of Intermediate 209-2

Intermediate 209-2 (8.2 g, 88%) was synthesized in the same manner as in synthesizing Intermediate 5-3 of Synthesis Example 2, except that 5.3 g of Intermediate 209-1 was used instead of Intermediate 5-2.

Synthesis of Intermediate 209-3

Compound 209 (5.6 g, 78%) was obtained in the same manner as used to synthesize Intermediate 5-4 of Synthesis Example 2, except that 8.2 g of Intermediate 209-2 and 6.3 g of 2-(4,4,5,5-tetramethyl-1,3,2-dioxaborolan-2-yl)benzenethiol were respectively used instead of Intermediate 1-4 and 2-(10-bromoanthracene-9-yl)-4,4,5,5-tetramethyl-1,3,2-dioxabororene.

Synthesis of Intermediate 209-4

Intermediate 209-4 (3.5 g, 63%) was synthesized in the same manner as in synthesizing Intermediate 21-4 of Synthesis Example 7, except that 5.6 g of Intermediate 209-3 was used instead of Intermediate 21-3.

Synthesis of Intermediate 209-5

Intermediate 209-2 (3 g, 93%) was synthesized in the same manner as in synthesizing Intermediate 1-3 of Synthesis Example 1, except that 3.5 g of Intermediate 209-4 was used instead of Intermediate 1-2.

Synthesis of Intermediate 209-6

Intermediate 209-6 (3.7 g, 81%) was synthesized in the same manner as in synthesizing Intermediate 5-3 of Synthesis Example 2, except that 3 g of Intermediate 209-5 was used instead of Intermediate 5-2.

Synthesis of Intermediate 209-7

Intermediate 209-7 (6.5 g, 72%) was obtained in the same manner as used to synthesize Intermediate 4,4-4 of Synthesis Example 2, except that 7 g of 1-bromonaphthalene and 9 g of 5-methoxy-2-(4,4,5,5-tetramethyl-1,3,2-dioxaborolan-2-yl)benzenethiol were respectively used instead of 2-(10-bromoanthracene-9-yl)-4,4,5,5-tetramethyl-1,3,2-dioxabororene and Intermediate 1-4.

Synthesis of Intermediate 209-8

Intermediate 209-8 (4.5 g, 70%) was synthesized in the same manner as in synthesizing Intermediate 21-4 of Synthesis Example 7, except that 6.5 g of Intermediate 209-7 was used instead of Intermediate 21-3.

Synthesis of Intermediate 209-9

Intermediate 209-9 (3.7 g, 88%) was synthesized in the same manner as in synthesizing Intermediate 1-3 of Synthesis Example 1, except that 4.5 g of Intermediate 209-8 was used instead of Intermediate 1-2.

Synthesis of Intermediate 209-10

Intermediate 209-10 (4.9 g, 86%) was synthesized in the same manner as in synthesizing Intermediate 5-3 of Synthesis Example 2, except that 3.7 g of Intermediate 209-9 was used instead of Intermediate 5-2.

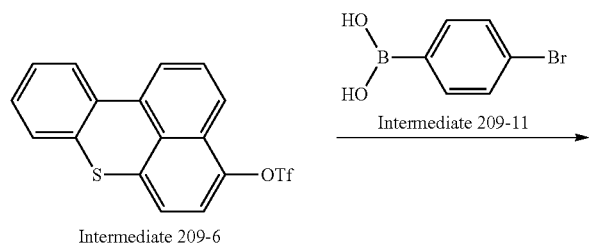

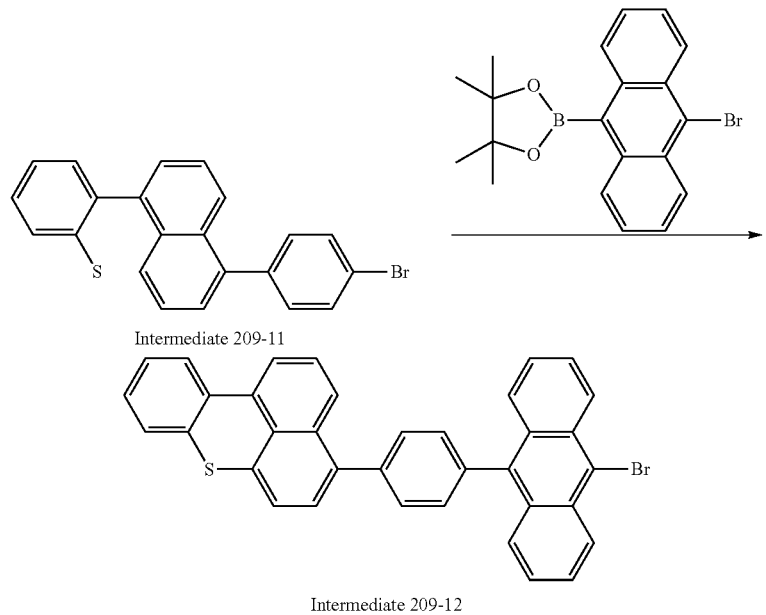

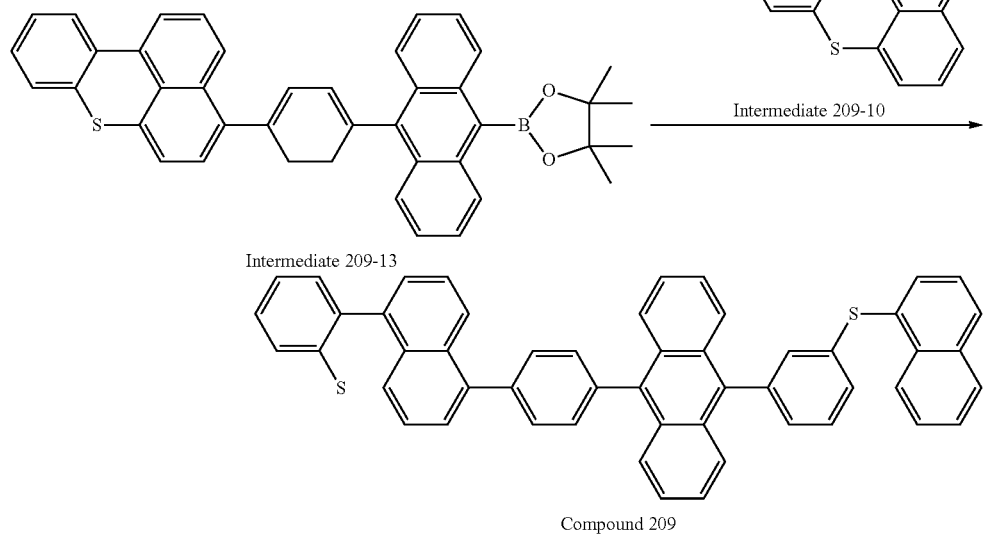

Synthesis of Intermediate 209-11

Compound 209 (2.8 g, 75%) was obtained in the same manner as used to synthesize Intermediate 5-4 of Synthesis Example 2, except that 3.7 g of Intermediate 209-6 and 1.9 g of (4-bromophenyl)boronic acid were respectively used instead of Intermediate 1-4 and 2-(10-bromoanthracene-9-yl)-4,4,5,5-tetramethyl-1,3,2-dioxabororene.

Synthesis of Intermediate 209-12

Intermediate 209-12 (3.1 g, 76%) was obtained in the same manner as used to synthesize Intermediate 5-4 of Synthesis Example 2, except that 2.8 g of Intermediate 209-11 was used instead of Intermediate 1-4 and the amount of 2-(10-bromoanthracen-9-yl)-4,4,5,5-tetramethyl-1,3,2-dioxaborolane was 2.7 g.

Synthesis of Intermediate 209-13

Intermediate 209-13 (2.7 g, 81%) was synthesized in the same manner as in synthesizing Intermediate 5-5 of Synthesis Example 2, except that 3.1 g of Intermediate 209-12 was used instead of Intermediate 5-4.

Synthesiss of Compound 209

Compound 209 (2.5 g, 77%) was obtained in the same manner as used to synthesize Intermediate 5-4 of Synthesis Example 2, except that 2.7 g of Intermediate 209-13 and 1.7 g of Intermediate 209-10 were respectively used instead of 2-(10-bromoanthracene-9-yl)-4,4,5,5-tetramethyl-1,3,2-dioxabororene and Intermediate 1-4.

Synthesis Example 25: Synthesis of Compound 210

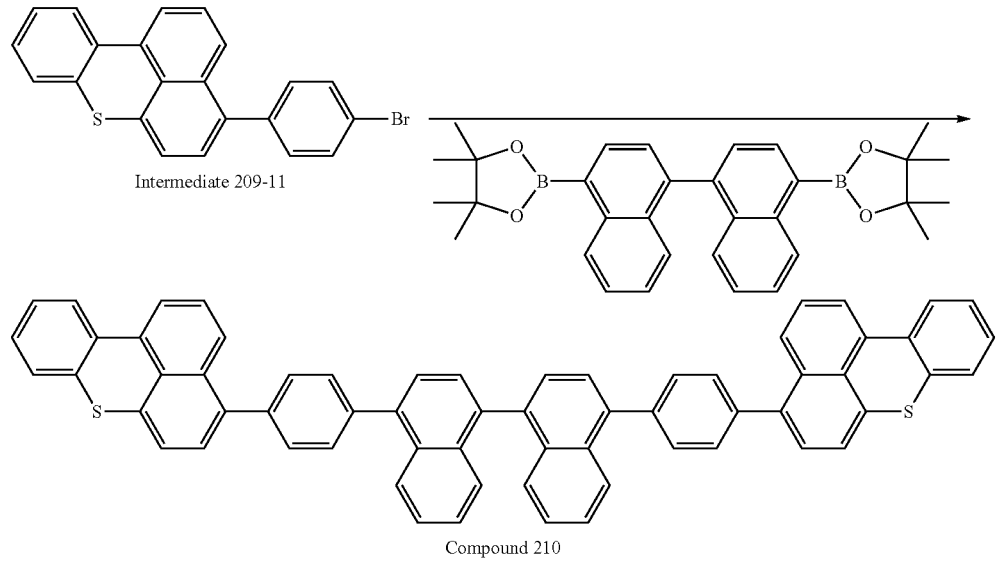

Compound 210 (4.5 g, 67%) was obtained in the same manner as used to synthesize Intermediate 5-4 of Synthesis Example 2, except that 3 g of Intermediate 209-11 and 1.9 g of 4,4'-bis(4,4,5,5-tetramethyl-1,3,2-dioxaborolan-2-yl)-1,1'-binaphthalene were respectively used instead of Intermediate 1-4 and 2-(10-bromoanthracene-9-yl)-4,4,5,5-tetramethyl-1,3,2-dioxabororene.

$^1$H NMR and MS/FAB results of the synthesized compounds are shown in Table 1 below.

Synthesis methods for other compounds than the compounds shown in Table 1 may be considered by referring to synthetic paths and source materials of Synthesis Examples 1 to 25.

| Compound | 1H NMR (CDCl3, 400 MHz) | LC/MS found | LC/MS calc. |
|---|---|---|---|
| 1 | 8.26 (dd, 2H), 8.12 (dd, 2H), 7.84-7.79 (m, 6H), 7.64 (t, 2H), 7.40 (dd, 1H), 7.35-7.29 (m, 6H), 7.25-7.21 (m, 3H), 7.09 (dd, 2H), 7.06-7.04 (m, 2H) | 610.30 | 610.19 |
| 5 | 8.58 (d, 2H), 8.12 (dd, 2H), 8.03 (dd, 2H), 7.94 (d, 2H), 7.83 (dd, 2H), 7.78 (d, 2H), 7.70 (d, 1H), 7.61-7.49 (m, 3H), 7.40-7.23 (m, 6H), 7.09 (td, 2H), 6.98 (d, 2H), 6.91 (dd, 2H) | 610.28 | 610.19 |
| 9 | 8.18 (dd, 2H), 8.12 (d, 2H), 8.03-8.01 (m, 2H), 7.97 (d, 2H), 7.94-7.69 (m, 1H), 7.69-7.45 (m, 4H), 7.39 (t, 2H), 7.35 (dd, 2H), 7.16 (d, 2H), 7.09 (td, 2H), 7.02-6.89 (m, 3H) | 560.60 | 560.18 |
| 10 | 8.02-8.01 (m, 4H), 7.97 (m, 4H), 7.90-7.88 (m, 2H), 7.68 (s, 2H), 7.61-7.49 (m, 6H), 7.39 (t, 2H), 7.02-6.96 (m, 2H), 6.91 (dd, 2H) | 560.49 | 560.18 |
| 15 | 8.19 (dd, 2H), 8.13 (m, 2H), 8.12 (dd, 2H), 8.03 (m, 1H), 8.01 (m, 1H), 7.83-7.82 (dd, 2H), 7.65 (t, 2H), 7.55 (dd, 2H), 7.53 (dd, 2H), 7.38-7.31 (m, 2H), 7.25 (m, 2H), 7.16 (d, 2H), 7.09 (td, 2H) | 560.41 | 560.18 |
| 21 | 8.45 (d, 2H), 8.12 (dd, 2H), 8.07-8.88 (m, 6H), 7.76 (d, 1H), 7.61-7.49 (m, 4H), 7.41 (m, 2H), 7.35-7.32 (m, 2H), 7.26 (dd, 1H), 7.09 (td, 2H), 6.95 (dd, 1H), 6.91 (dd, 1H) | 634.28 | 634.19 |
| 23 | 8.16 (dd, 2H), 8.12 (dd, 2H), 8.07-7.89 (m, 6H), 7.76 (d, 2H), 7.65-7.49 (m, 4H), 7.45 (t, 1H), 7.41 (d, 1H), 7.35td (1H), 7.32 (dd, 2H), 7.19 (d, 2H), 7.09 (td, 2H), 6.91 (dd, 1H) | 634.31 | 634.19 |

-continued

| Compound | 1H NMR (CDCl3, 400 MHz) | LC/MS found | LC/MS calc. |
|---|---|---|---|
| 38 | 8.16 (dd, 2H), 8.12 (dd, 2H), 8.07-7.89 (m, 2H), 7.95 (d, 2H), 7.76 (d, 1H), 7.65-7.49 (m, 4H), 7.45-7.41 (m, 2H), 7.35-7.30 (m, 2H), 7.25 (d, 1H), 7.13 (d, 2H), 7.09 (td, 2H), 6.91 (dd, 2H), 2.74 (s, 3H), 2.69 (s, 3H) | 662.39 | 662.22 |
| 44 | 8.16 (dd, 2H), 8.12-8.10 (m, 2H), 8.03 (d, 2H), 7.90-7.88 (m, 2H), 7.79-7.68 (m, 3H), 7.65-7.49 (m, 4H), 7.49 (dd, 1H), 7.35-7.32 (m, 2H), 7.25-7.23 (m, 2H), 7.14-7.05 (2H), 6.91 (dd, 2H), 1.51 (s, 18H) | 746.93 | 746.95 |
| 51 | 8.16 (dd, 2H), 8.14-8.07 (m, 8H), 7.65 (t, 2H), 7.53-7.48 (m, 10H), 7.45-7.40 (m, 3H), 7.35-7.31 (m, 2H), 7.25-7.19 (m, 4H), 7.12-7.04 (m, 3H) | 788.97 | 788.95 |
| 57 | 8.64 (s, 2H), 8.24-8.02 (m, 8H), 7.63-7.54 (m, 4H), 7.35 (m, 8H), 7.09-7.05 (m, 2H) | 684.26 | 684.18 |
| 62 | 8.30 (d, 2H), 8.26 (s, 2H), 8.16-8.10 (m, 6H), 8.05-7.93 (m, 6H), 7.66-7.75 (m, 5H), 7.69-7.49 (m, 11H), 7.35-7.18 (m, 12H), 7.09-7.01 (m, 3H), 6.91 (d, 2H) | 887.21 | 887.05 |
| 75 | 8.26 (d, 2H), 8.12 (d, 2H), 8.03 (d, 2H), 7.96-7.89 (m, 2H), 7.83 (d, 2H), 7.76 (m, 2H), 7.65-7.49 (m, 2H), 7.43-7.30 (m, 5H), 7.26-7.21 (m, 2H), 7.10 (m, 2H), 6.91 (d, 2H), 2.49 (s, 3H) | 624.49 | 624.21 |
| 116 | 8.38 (d, 2H), 8.19-8.11 (m, 4H), 8.00 (d, 2H), 7.90-7.69 (m, 4H), 7.82 (m, 4H), 7.65 (m, 1H), 7.55-7.46 (m, 6H), 7.41-7.32 (m, 4H), 7.25-7.16 (m, 3H), 7.09 (td, 2H), 6.92 (d, 2H) | 726.91 | 726.26 |
| 123 | 8.48 (d, 2H), 8.21 (d, 2H), 8.19 (dd, 1H), 8.03 (d, 2H), 7.98 (d, 1H), 7.61 (d, 2H), 7.68 (d, 2H), 7.59-7.43 (m, 4H), 7.41 (d, 2H), 7.36-7.18 (m, 2H), 7.02 (t, 2H), 6.91 (d, 2H), 1.49 (s, 18H) | 722.98 | 722.32 |
| 155 | 8.45 (d, 2H), 8.32 (d, 1H), 8.12 (dd, 2H), 7.88 (d, 1H), 7.69-8.49 (m, 12H), 7.32 (m, 2H), 7.35-7.32 (m, 2H), 7.25 (m, 2H), 7.09 (td, 2H), 7.01 (m, 2H), 6.93 (d, 2H) | 686.87 | 686.22 |
| 159 | 8.18 (dd, 2H), 8.12 (dd, 2H), 7.69-7.61 (m, 6H), 7.56 (m, 2H), 7.51-7.48 (m, 2H), 7.45-7.39 (m, 4H), 7.35-7.31 (m, 2H), 7.25-7.21 (m, 2H), 7.16-7.14 (m, 2H), 7.09 (td, 2H), 7.00-6.93 (m, 4H) | 686.79 | 686.22 |
| 161 | 8.45 (d, 2H), 8.12 (dd, 2H), 7.88 (d, 1H), 7.69-7.49 (m, 12H), 7.42 (m, 2H), 7.35-7.31 (m, 2H), 7.25 (m, 2H), 7.09 (td, 2H), 7.01 (m, 2H), 6.93 (d, 2H) | 686.98 | 686.22 |
| 182 | 8.56 (d, 2H), 8.41 (d, 2H), 8.12 (d, 2H), 7.68 (d, 2H), 7.83 (m, 4H), 7.70-7.53 (m, 3H), 7.42-7.23)(m, 6H), 7.09 (td, 2H), 6.99 (m, 2H), 0.21 (s, 9H) | 683.10 | 682.89 |
| 194 | 8.80 (d, 2H), 8.50 (d, 4H), 8.42 (s, 2H), 8.12 (dd, 2H), 7.66-7.55 (m, 4H), 7.35-7.23 (m, 6H), 7.09 (td, 2H), 6.95 (dd, 2H), 0.28 (s, 18H) | 779.10 | 778.27 |
| 196 | 8.19 (d, 2H), 8.12 (d, 2H), 7.72-7.65 (m, 8H), 7.65-m7.51 (m, 8H), 7.35-7.23 (m, 10H), 7.15 (d, 2H), 7.09 (td, 2H) | 762.81 | 762.26 |
| 197 | 8.19 (d, 2H), 8.12 (d, 2H), 8.03 (m, 2H), 7.91-7.84 (m, 6H), 7.72-7.49 (m, 9H), 7.45 (m, 1H), 7.35-7.23 (m, 6H)7.15 (m, 2H), 7.09 (td, 2H), 6.91 (dd, 2H) | 763.01 | 762.26 |
| 202 | 8.19 (d, 2H), 8.12 (d, 2H), 7.76-7.53 (m, 12H), 7.50 (m, 2H), 7.45 (m, 2H), 7.39-7.31 (m, 6H), 7.25 (m, 2H), 7.15 (m, 2H), 7.09 (t, 2H), 7.01-6.94 (m, 4H) | 838.87 | 838.29 |
| 209 | 8.27 (d, 2H), 8.17 (m, 2H), 8.13 (m, 2H), 7.90-7.61 (m, 6H), 7.72-7.69 (m, 8H), 7.67-7.43 (m, 6H), 7.38-7.29 (m, 4H) | 718.82 | 718.18 |
| 210 | 8.29 (d, 2H), 7.90 (m, 4H), 7.76-7.61 (m, 18H), 7.56 (d, 1H), 7.55 (d, 1H), 7.41-7.32 (m, 8H), 7.02-6.95 (m, 4H) | 871.10 | 870.24 |

Example 1

An anode was prepared by cutting a glass substrate with a Corning 15 Ωcm² (1,200 Å) ITO layer formed thereon to a size of 50 mm×50 mm×0.7 mm, ultrasonically cleaning the glass substrate by using isopropyl alcohol and pure water for 5 minutes each, and then irradiating UV light for 30 minutes thereto and exposing to ozone to clean. Then, the anode was loaded into a vacuum deposition apparatus.

2-TNATA was deposited on the ITO layer acting as an anode to form a hole injection layer having a thickness of 600 Å, and then, NPB was deposited on the hole injection layer to form a hole transport layer having is thickness of 300 Å, and then, Compound 1 (host) and C545T (dopant) were co-deposited at a weight ratio of 98:2 on the hole transport layer to form an emission layer having a thickness of 300 Å.

Thereafter, Alq₃ was deposited on the emission layer to form an electron transport layer having a thickness of 300 Å, and LiF was deposited on the electron transport layer to form an electron injection layer having a thickness of 10 Å, and Al was deposited on the electron injection layer to form a cathode having a thickness of 3000 Å, thereby completing the manufacture of an organic light-emitting device.

Example 2

An organic light-emitting device was manufactured in the same manner as in Example 1, except that in forming an emission layer, as a host, Compound 21 was used instead of Compound 1.

Example 3

An organic light-emitting device was manufactured in the same manner as in Example 1, except that in forming an emission layer, as a host, Compound 44 was used instead of Compound 1.

Example 4

An organic light-emitting device was manufactured in the same manner as in Example 1, except that in forming an emission layer, as a host, Compound 159 was used instead of Compound 1.

Example 5

An organic light-emitting device was manufactured in the same manner as in Example 1, except that in forming an emission layer, as a host, Compound 161 was used instead of Compound 1.

Example 6

An organic light-emitting device was manufactured in the same manner as in Example 1, except that in forming an emission layer, as a host, Compound 203 was used instead of Compound 1.

Example 7

An organic light-emitting device was manufactured in the same manner as in Example 1, except that in forming an emission layer, as a host, Compound 9 was used instead of Compound 1, and as a dopant, DPAVBi was used instead of C545T.

Example 8

An organic light-emitting device was manufactured in the same manner as in Example 7, except that in forming an emission layer, as a host, Compound 196 was used instead of Compound 1.

Example 9

An organic light-emitting device was manufactured in the same manner as in Example 7, except that in forming an emission layer, as a host, Compound 197 was used instead of Compound 9.

Example 10

An organic light-emitting device was manufactured in the same manner as in Example 7, except that in forming an emission layer, as a host, Compound 202 was used instead of Compound 9.

Example 11

An organic light-emitting device was manufactured in the same manner as in Example 7, except that in forming an emission layer, as a host, Compound 209 was used instead of Compound 9.

Example 12

An organic light-emitting device was manufactured in the same manner as in Example 7, except that in forming am emission layer, as a host, Compound 210 was used instead of Compound 9.

Comparative Example 1

An organic light-emitting device was manufactured in the same manner as in Example 1, except that in forming an emission layer, as a host, $Alq_3$ was used instead of Compound 1.

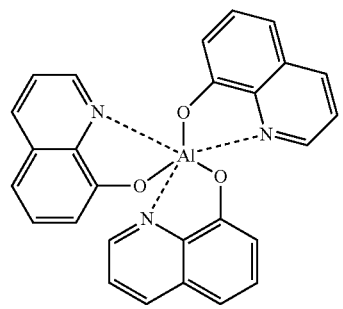

$Alq_3$

Comparative Example 2

An organic light-emitting device was manufactured in the same manner as in Example 7, except that in forming an emission layer, as a host, ADN was used instead of Compound 9.

Comparative Example 3

An organic light-emitting device was manufactured in the same manner as in Example 1, except that in forming an emission layer, as a host, Compound A was used instead of Compound 1.

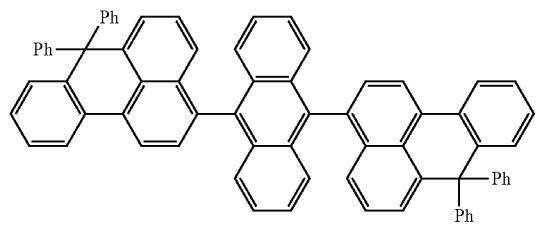

<Compound A (Ph indicates a phenyl group)>

Comparative Example 4

An organic light-emitting device was manufactured in the same manner as in Example 7, except that in forming an emission layer, as a host, Compound B was used instead of Compound 9.

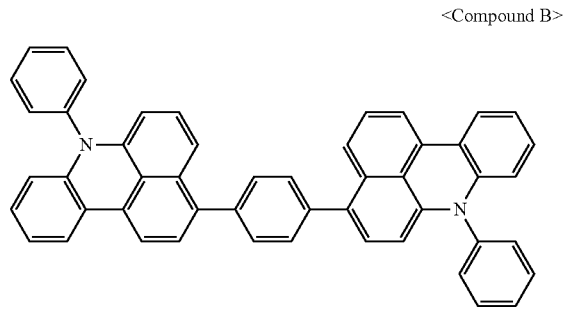 [SMILES: c1ccc(N2c3ccccc3-c3ccc(-c4ccc(-c5ccc6c7c(cccc57)-c5ccccc5N6c5ccccc5)cc4)c4cccc2c34)cc1]

<Compound B>

Evaluation Example 1

The driving voltage, current density, brightness, efficiency, and half-lifespan of the organic light-emitting devices manufactured according to Examples 1 to 12, and Comparative Examples 1 to 4 were measured by using Kethley SMU 236 and a brightness photometer PR650, and results thereof are shown in Table 2. The half-lifespan is a period of time that is taken until the brightness of the organic light-emitting device 50% of initial brightness.

TABLE 2

| | Host | Dopant | Driving voltage (V) | Current Density (mA/cm$^2$) | Brightness (cd/m$^2$) | Efficiency (cd/A) | Emission color | Half lifespan (hr @ 100 mA/cm$^2$) |
|---|---|---|---|---|---|---|---|---|
| Example 1 | Compound 1 | C545T | 6.48 | 50 | 7835 | 15.67 | Green | 451 |
| Example 2 | Compound 21 | C545T | 6.27 | 50 | 7795 | 15.59 | Green | 437 |
| Example 3 | Compound 44 | C545T | 6.76 | 50 | 7655 | 15.31 | Green | 419 |
| Example 4 | Compound 159 | C545T | 6.99 | 50 | 7485 | 14.97 | Green | 390 |
| Example 5 | Compound 161 | C545T | 6.83 | 50 | 7395 | 14.79 | Green | 420 |
| Example 6 | Compound 203 | C545T | 6.23 | 50 | 7248 | 14.50 | Green | 410 |
| Example 7 | Compound 9 | DPAVBi | 6.17 | 50 | 3105 | 6.21 | Blue | 287 |
| Example 8 | Compound 196 | DPAVBi | 6.11 | 50 | 3215 | 6.43 | Blue | 298 |
| Example 9 | Compound 197 | DPAVBi | 5.98 | 50 | 3400 | 6.80 | Blue | 276 |
| Example 10 | Compound 202 | DPAVBi | 6.03 | 50 | 3455 | 6.91 | Blue | 287 |
| Example 11 | Compound 209 | DPAVBi | 6.34 | 50 | 3321 | 6.64 | Blue | 276 |
| Example 12 | Compound 210 | DPAVBi | 6.58 | 50 | 3343 | 6.69 | Blue | 265 |
| Comparative Example 1 | Alq3 | C545T | 7.85 | 50 | 5641 | 13.12 | Green | 351 |
| Comparative Example 2 | ADN | DPAVBi | 7.35 | 50 | 2065 | 4.13 | Blue | 145 |
| Comparative Example 3 | Compound A | C545T | 8.23 | 50 | 4090 | 8.18 | Green | 210 |
| Comparative Example 4 | Compound B | DPAVBi | 3.45 | 50 | 1335 | 2.67 | Blue | 114 |

In Table 2, it may be seen that the driving voltage, current density, brightness, efficiency, and half lifespan of the organic light-emitting devices of Examples 1 to 6 were higher than the driving voltage, current density, brightness, efficiency, and half lifespan of the organic light-emitting devices of Comparative Examples 1 and 3. The driving voltage, current density, brightness, efficiency, and half lifespan of the organic light-emitting devices of Examples 7 to 12 were higher than the driving voltage, current density, brightness, efficiency, and half lifespan of the organic light-emitting devices of Comparative Examples 2 and 4.

An organic light-emitting device including the condensed cyclic compound according an embodiment may have a low driving voltage, high efficiency, high color purity, and long lifespan.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicted. Accordingly, it will be understood by those of skill in the art that various changes in form and details may be made without departing from the spirit and scope of the present invention as set forth in the following claims.

What is claimed is:

1. A condensed cyclic compound represented by Formula 1 below:

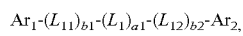  <Formula 1> wherein, in Formula 1, L$_1$, L$_{11}$, and L$_{12}$ are each independently selected from a substituted or unsubstituted C$_3$-C$_{10}$ cycloalkylene group, a substituted or unsubstituted C$_3$-C$_{10}$ heterocycloalkylene group, a substituted or unsubstituted C$_3$-C$_{10}$ cycloalkenylene group, a substituted or unsubstituted C$_3$-C$_{10}$ heterocycloalkenylene group, a substituted or unsubstituted C$_6$-C$_{60}$ arylene group, a substituted or unsubstituted C$_2$-C$_{60}$ heteroarylene group, a substituted or unsubstituted divalent non-aromatic condensed polycyclic group, and a substituted or unsubstituted divalent non-aromatic hetero-condensed polycyclic group;

a1 is an integer selected from 1 to 5;

b1 and b2 are each independently an integer selected from 0 to 5;

Ar$_1$ is represented by one of Formula 2A or Formula 2B, below; and

Ar$_2$ is represented by one of Formula 2C or Formula 2D, below;

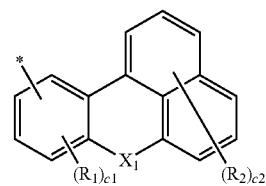  <Formula 2A>

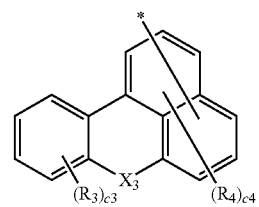  <Formula 2B>

<Formula 2C>

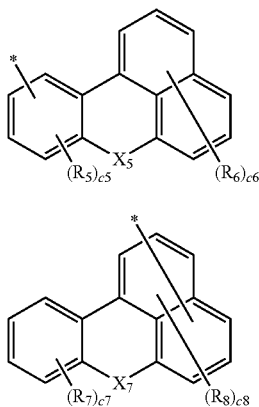

<Formula 2D> wherein, in Formula 1 and Formulae 2A to 2D, $X_1$, $X_3$, $X_5$, and $X_7$ are each independently O or S;

$R_1$ to $R_8$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic hetero-condensed polycyclic group, —N($Q_1$)($Q_2$), —Si($Q_3$)($Q_4$)($Q_5$), and —B($Q_6$)($Q_7$);

c1 and c5 are each independently an integer selected from 0 to 3;

c2 and c6 are each independently an integer selected from 0 to 6;

c3 and c7 are each independently an integer selected from 0 to 4;

c4 and c8 are each independently an integer selected from 0 to 5;

in Formulae 2A and 2B, * indicates a binding site to $L_1$ in Formula 1 or a binding site to $L_{11}$ in Formula 1;

in Formulae 2C and 2D, * indicates a binding site to $L_1$ in Formula 1 or a binding site to $L_{12}$ in Formula 1;

at least one substituent of the substituted $C_3$-$C_{10}$ cycloalkylene group, the substituted $C_3$-$C_{10}$ heterocycloalkylene group, the substituted $C_3$-$C_{10}$ cycloalkenylene group, the substituted $C_3$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic hetero-condensed polycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy, the substituted $C_3$-$C_{10}$ cycloalkyl group, the substituted $C_3$-$C_{10}$ heterocycloalkyl group, the substituted $C_3$-$C_{10}$ cycloalkenyl group, the substituted $C_3$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic hetero-condensed polycyclic group is selected from:

a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic hetero-condensed polycyclic group;

a $C_3$-$C_{10}$ cycloalkyl group, a $C_3$-$C_{10}$ heterocycloalkyl v, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic hetero-condensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$); and $Q_1$ to $Q_7$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic hetero-condensed polycyclic group.

2. The condensed cyclic compound as claimed in claim 1, wherein $L_1$, $L_{11}$, and $L_{12}$ are independently selected from a substituted or unsubstituted $C_6$-$C_{20}$ arylene group.

3. The condensed cyclic compound as claimed in claim 1, wherein $L_1$, $L_{11}$, and $L_{12}$ are each independently selected from:

a phenylene group, a pentalenylene group, an indeylene group, a naphthylene group, an azulenylene group, a heptalenylene group, a indacenylene group, an acenaphthylene group, a fluorenylene group, a spiro-fluorenylene group, a benzofluorenylene group, a dibenzofluorenylene group, a phenalenylene group, a phenanthrenylene group, a anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, a ovalenylene group, a pyrrolylene group, a thiophenylene group, a furanylene group, a imidazolylene group, a pyrazolylene group, a thiazolylene group, an isothiazolylene group, a oxazolylene group, an isooxazolylene group, a pyridinylene group, a pyrazinylene group, a pyrimidinylene group, a pyridazinylene group, an isoindolylene group, a indolylene group, a indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzaimidazolylene group, a benzofuranylene group, a benzothiophenylene group, an isobenzothiazolylene group, a benzooxalylene group, an isobenzooxazolylene group, a triazolylene group, a tetrazolylene group, a oxadiazolylene group, a triazinylene group, a dibenzofuranylene group, a dibenzothiophenylene group, a benzooarbazolylene group, a dibenzocarbazolylene group, a thiadiazolylene group, and an imidazopyridinylene group; and a phenylene group, a pentalenylene group, an indacenylene group, a naphthylene group, an azulenylene group, a heptalenylene group, a indacenylene group, an acenaphthylene group, a fluorenylene group, a spiro-fluoronylene group, a benzofluorenylene group, a dibenzofluorenylene group, a phenalenylene group, a phenanthrenylene group, a anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, a ovalenylene group, a pyrrolylene group, a thiophenylene group, a furanylene group, a imidazolylene group, a pyrazolylene group, a thiazolylene group, an isothiazolylene group, a oxazolylene group, an isooxazolylene group, a pyridinylene group, a pyrazinylene group, a pyrimdinylene group, a pyridazinylene group, an isoindolylene group, a indolylene group, a indazolylene group, purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, as phenanthridinylene group, a acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, a oxadiazolylene group, a triazinylene group, a dibenzofuranylene group, a dibenzothiophenylene group, a benzocarbazolylene group, a dibenzocarbazolylene and imidapyridinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof; a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indeyl group, a naphthyl group, an azulenyl group, a heptalenyl group, a indacenyl group, an acenaphthyl group, a fluorenyl group, a spiro-fluorenyl group, a benzofluorenyl group, a dibenzylfluorenyl group, a phenalenyl group, a phenanthrenyl group, a anthracenyl group, a fluorantenyl group, a triphenylenyl group, a pyrenyl group, a chrysenyl group, a naphthacenyl, group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, a imidazolyl group, a pyrazolyl group, a thiazolyl group, an isothiazolyl group, a oxazolyl group, an isooxazolyl group, a pyridinyl group, a pyrazinyl group, as pydinyl group, a pyridazinyl group, an isoindolyl group, a indolyl group, a indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, a acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl, group, a tetrazolyl group, a oxadiazolyl group, to triazinyl group, is dibenzofuranyl group, a dibenzothiophenyl group, a benzocarbazolyl group, a dibenzocarbazolyl group, a thiadiazolyl group, an imidazopyridinyl group, and —Si($Q_{33}$)($Q_{34}$)($Q_{35}$), in which $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a pyridinyl group, a pyrimidinyl group, and a triazinyl group.

4. The condensed cyclic compound as claimed in claim 1, wherein $L_1$, $L_{11}$, and $L_{12}$ are each independently a group represented by one of Formulae 3-1 to 3-24 below:
Formula 3-1
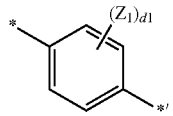
Formula 3-2
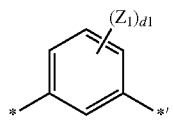
Formula 3-3
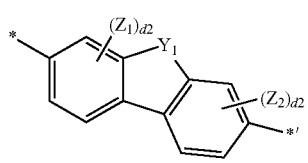
Formula 3-4
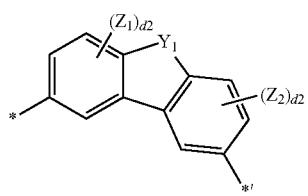
Formula 3-5
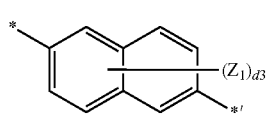
Formula 3-6
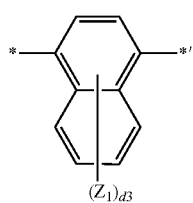
Formula 3-7
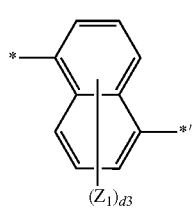
Formula 3-8
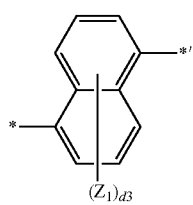
Formula 3-9
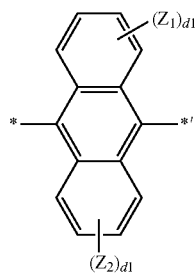
Formula 3-10
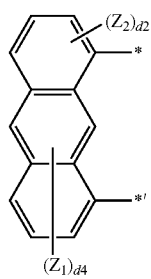
Formula 3-11
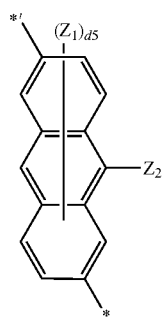
Formula 3-12
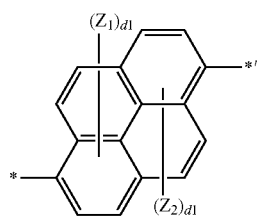
Formula 3-13
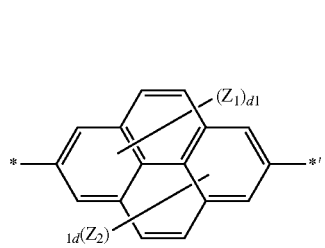
Formula 3-14
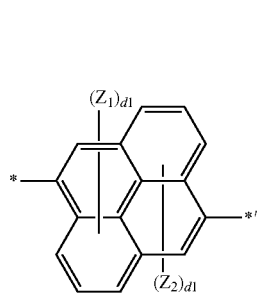

-continued

Formula 3-15
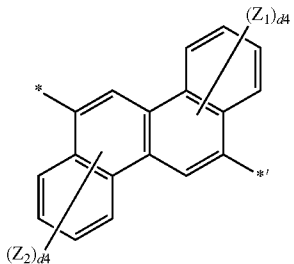

Formula 3-16
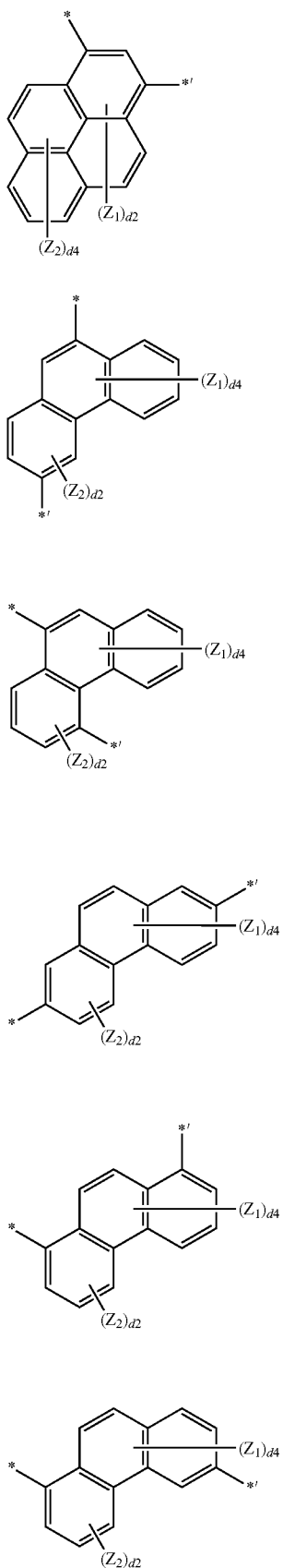

Formula 3-17

Formula 3-18

Formula 3-19

Formula 3-20

Formula 3-21
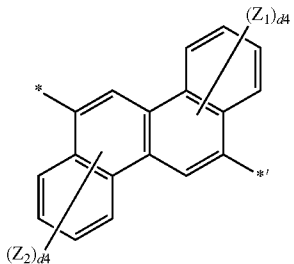

Formula 3-22
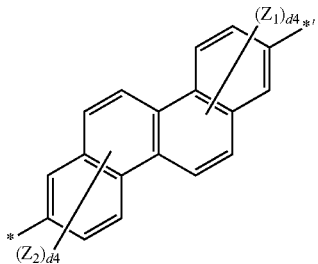

Formula 3-23
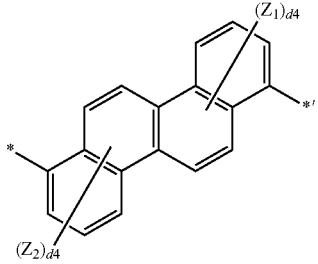

Formula 3-24
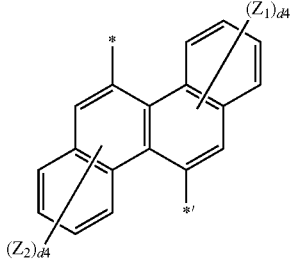

wherein, in Formulae 3-1 to 3-24,
Y$_1$ is O, S, C(Z$_3$)(Z$_4$), N(Z$_5$), or Si(Z$_6$)(Z$_7$);
Z$_1$ to Z$_7$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a C$_1$-C$_{20}$ alkyl group, a C$_1$-C$_{20}$ alkoxy group, a phenyl group, a pentalenyl group, an indeyl group, a naphthyl group, an azulenyl group, a heptalenyl group, a indacenyl group, an acenaphthyl group, a fluorenyl group, a spiro-fluorenyl group a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, a imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, a indolyl group, a indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, a acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and —Si($Q_{33}$)($Q_{34}$)($Q_{35}$);

$Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a pyridinyl group, a pyrimidinyl group, and a triazinyl group;

d1 is an integer selected from 1 to 4;

d2 is an integer selected from 1 to 3;

d3 is an integer selected from 1 to 6;

d4 is an integer selected from 1 to 5;

d5 is an integer selected from 1 to 7; and

\* and \*' represent binding sites.

5. The condensed cyclic compound as claimed in claim 4, wherein $Z_1$ to $Z_7$ are each independently selected from a hydrogen, a deuterium, —F, —Cl, —Br, —I, a hydroxyl group, a cyano group, a nitro group, an amino group, an amidino group, a hydrazine group, a hydrozone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a trizinyl group, a quinolinyl group, an isoquinolinyl group, a quinoxalinyl group, a quinazolinyl group, a cinnolinyl group, a quinazolinyl group, and —Si($Q_{33}$)($Q_{34}$)($Q_{35}$), in which $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a pyridinyl group, a pyrimidinyl group, and a triazinyl group.

6. The condensed cyclic compound as claimed in claim 1, wherein:

a1 is 1 or 2; and b1 and b2 are each independently 0, 1, or 2.

7. The condensed cyclic compound as claimed in claim 1, wherein a moiety represented by -($L_1$)$_{a1}$- in Formula 1 is represented by any one of Formulae 4-1 to 4-17:

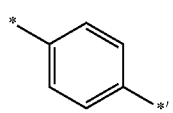

Formula 4-1

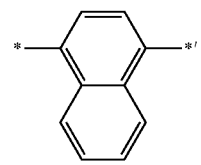

Formula 4-2

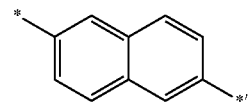

Formula 4-3

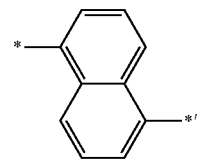

Formula 4-4

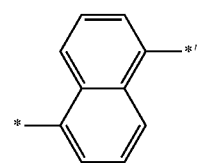

Formula 4-5

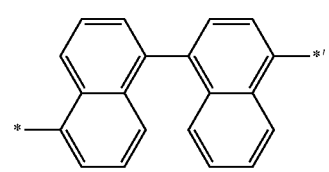

Formula 4-6

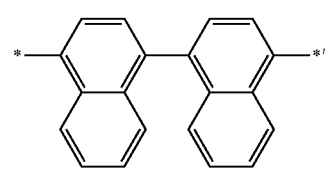

Formula 4-7

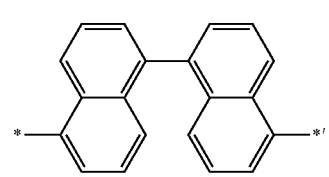

Formula 4-8

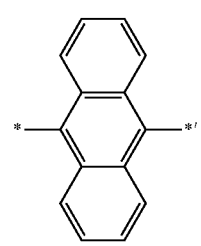

Formula 4-9

-continued

Formula 4-10
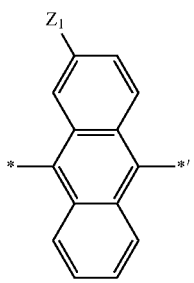

Formula 4-11
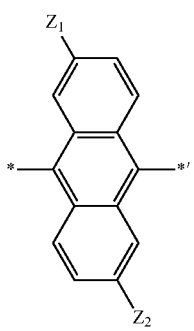

Formula 4-12
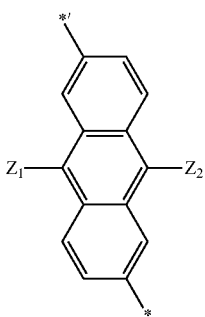

Formula 4-13
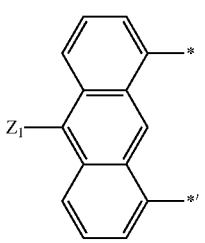

Formula 4-14
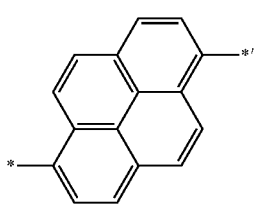

-continued

Formula 4-15
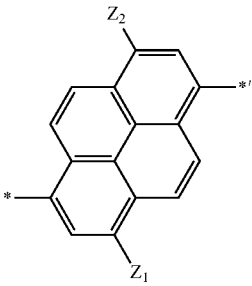

Formula 4-16
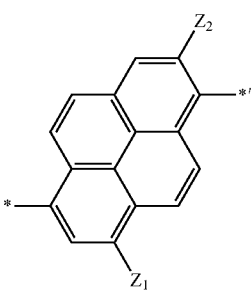

Formula 4-17
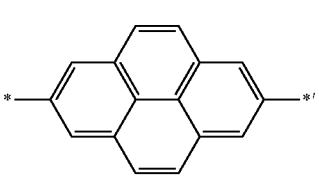

wherein in Formulae 4-1 to 4-17, $Z_1$ and $Z_2$ are each independently selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a quinoxalinyl group, a quinazolinyl group, a cinnolinyl group, a quinazolinyl group, and —Si($Q_{33}$)($Q_{34}$)($Q_{35}$), in which $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a pyridinyl group, a pyrimidinyl group, and a triazinyl group; and

* and *' represent binding sites.

8. The condensed cyclic compound as claimed in claim 1, wherein:
b1=0 and b2=0;
b1=0 and b2=1;
b1=1 and b2=0, or
b1=1 and b2=1.

9. The condensed cyclic compound as claimed in claim 4, wherein:
at least one of b1 or b2 is an integer of 1 or greater, and $L_{11}$ and $L_{12}$ are each independently represented by one of Formulae 3-1, 3-2, and 3-5 to 3-8.

10. The condensed cyclic compound as claimed in claim 1, wherein:
Ar₁ is represented by one of Formula 2A-1, Formula 2B-1, Formula 2B-2, or Formula 2B-3 below; and
Ar₂ is represented by one of Formula 2C-1, Formula 2D-1, Formula 2D-2, or Formula 2D-3 below;

<Formula 2A-1>
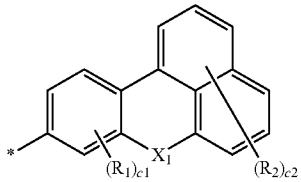

<Formula 2B-1>
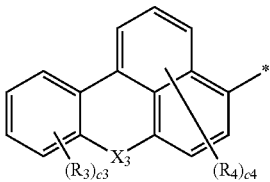

<Formula 2B-2>
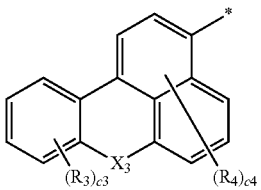

<Formula 2B-3>
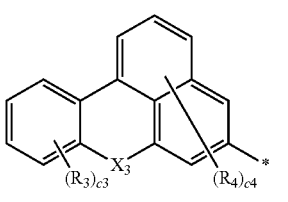

<Formula 2C-1>
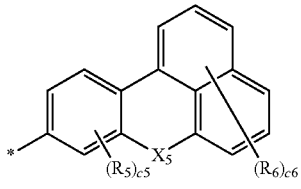

<Formula 2D-1>
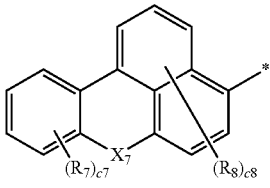

<Formula 2D-2>
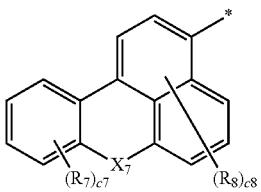

<Formula 2D-3>
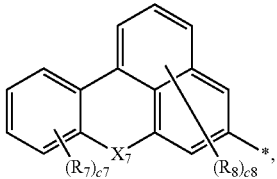

wherein $X_1$, $X_3$, $X_5$, $X_7$, $R_1$ to $R_8$, and c1 to c8 are the same as those defined with respect to Formulae 2A to 2D.

11. The condensed cyclic compound as claimed in claim 1, wherein $R_1$ to $R_8$ are each independently selected from:
a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, and a $C_1$-$C_{20}$ alkoxy group;
a phenyl group, a pentalenyl group, an indeyl group, a naphthyl group, an azulenyl group, a heptalenyl group, a indacenyl group, an acenaphthyl group, as fluorenyl group, a spiro-fluorenyl group, a benzofluorenyl group, a dibenzofluorenyl group, a phenalenyl group, a phenanthrenyl group, a anthracenyl group, a fluoranthenyl group, a triphenylenyl group, a pyrenyl group, a chrysenyl group, a naphthacenyl group, a picenyl group, a perylenyl group, is pentaphenyl group, a hexacenyl group, a pentacenyl group, a rubicenyl group, a coronenyl group, a ovalenyl group, a pyrrolyl group, a thiophenyl group, a furanyl group, a imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, a indolyl group, a indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, a acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, a thiadiazolyl group, and an imidazopyridinyl group; and
a phenyl group, a pentalenyl group, an indeyl group, a naphthyl group, an azulenyl group, a heptalenyl group, a indacenyl group, an acenaphthyl group, a fluorenyl group, a spiro-fluorenyl group, a benzofluorenyl group, a dibenzofluorenyl group, a phenalenyl group, a phenanthrenyl group, a anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, a imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, a indolyl group, a indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, a acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group a triazolyl group, a tetrazolyl group, a oxadiazolyl group, a triazinyl group, a dibenzofuranyl group, a dibenzothiophenyl group, a benzocarbazolyl group, a dibenzocarbazolyl grow, and an imidazopyridinyl group, each substituted with at least one selected from a deuterium, —F, —C —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, —Si($Q_{33}$)($Q_{34}$)($Q_{35}$), a phenyl group, a pentalenyl group, an indeyl group, a naphthyl group, an azulenyl group, a heptalenyl group, a indacenyl group, an acenaphthyl group, a fluorenyl group, a spiro-fluorenyl group, a benzofluorenyl group, a dibenzofluorenyl group, a phenalenyl group, a phenanthrenyl group, a anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, a imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, a indolyl group, a indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, a acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, a thiadiazolyl group, and an imidazopyridinyl group; and —Si($Q_3$)($Q_4$)($Q_5$); and wherein $Q_3$ to $Q_5$ and $Q_{33}$ to $Q_{35}$ each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a pyridinyl group, a pyrimidinyl group, and a triazinyl group.

12. The condensed cyclic compound as claimed in claim 1, wherein the condensed cyclic compound represented by Formula 1 is represented by one of Formulae 1A to 1G:

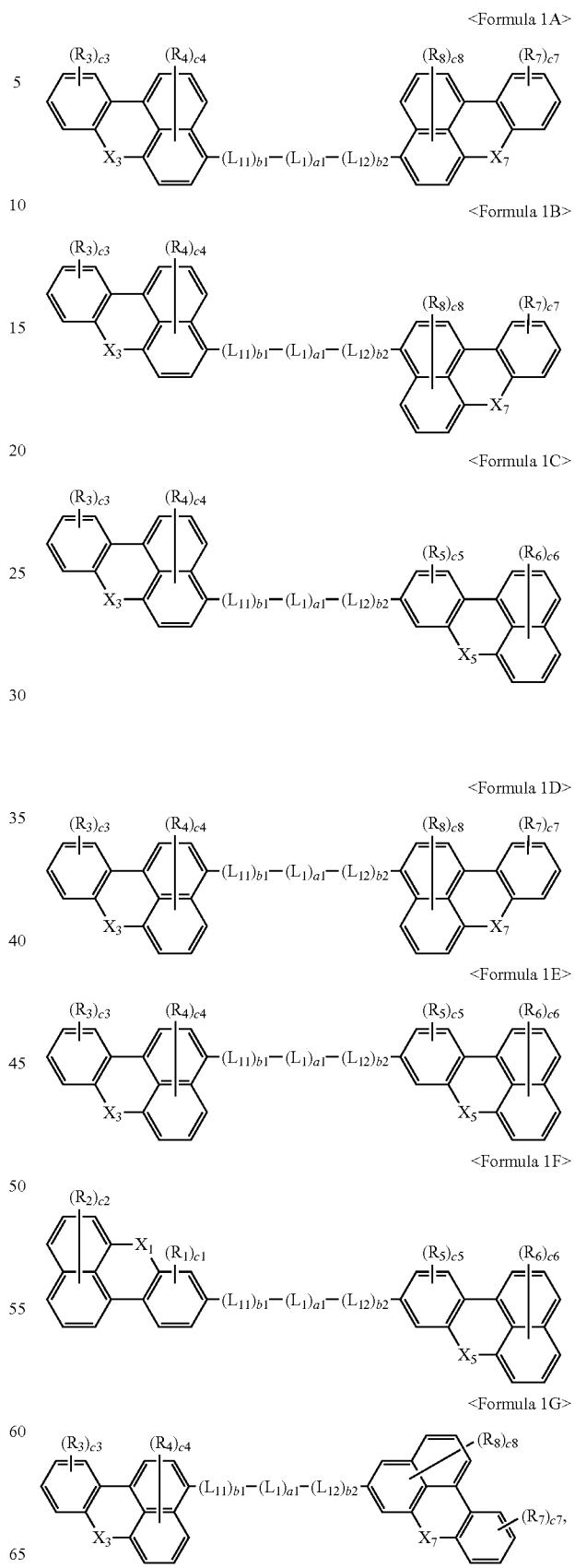

wherein, $L_1$, $L_{11}$, $L_{12}$, $X_1$, $X_3$, $X_5$, $X_7$, $R_1$ to $R_8$, a1, b1, b2, and c1 to c8 are the same as those defined with respect to Formulae 1 and 2A to 2D.

13. The condensed cyclic compound as claimed in claim 12, wherein:

$R_1$ to $R_8$ are each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, and a $C_1$-$C_{20}$ alkoxy group;

a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a quinoxalinyl group, a quinazolinyl group, a cinnolinyl group, and a quinazolinyl group;

a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a quinoxalinyl group, a quinazolinyl group, a cinnolinyl group, and a quinazolinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, —Si($Q_{33}$)($Q_{34}$)($Q_{35}$), a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a quinoxalinyl group, a quinazolinyl group, a cinnolinyl group, and a quinazolinyl group; and —Si($Q_3$)($Q_4$)($Q_5$);

wherein $Q_3$ to $Q_5$ and $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a pyridinyl group, a pyrimidinyl group, and a triazinyl group; and wherein c1 to c8 are each independently 0, 1, or 2.

14. The condensed cyclic compound as claimed in claim 1, wherein the compound represented by Formula 1 is one of Compounds 1 to 219 below:

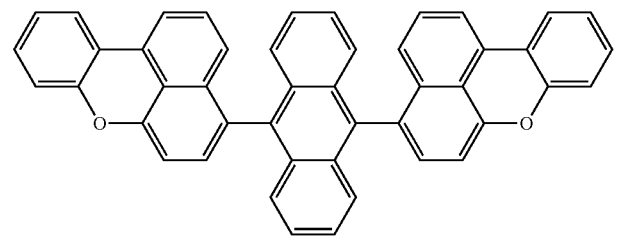

1

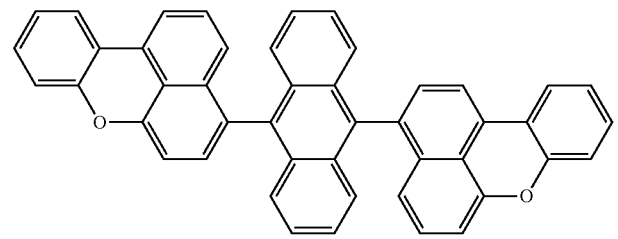

2

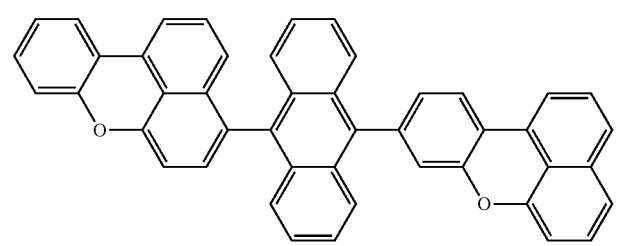

3

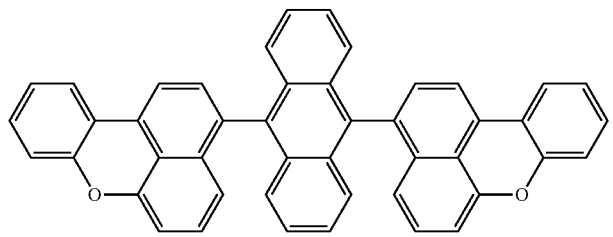

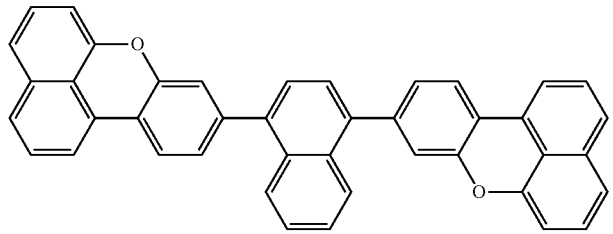
10
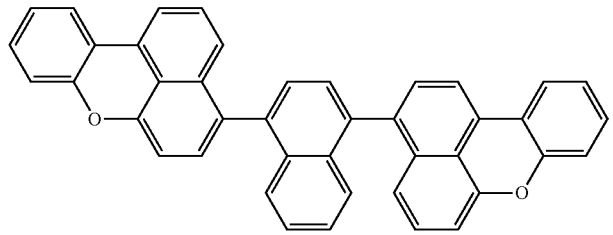
11
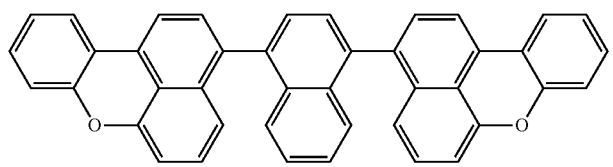
12
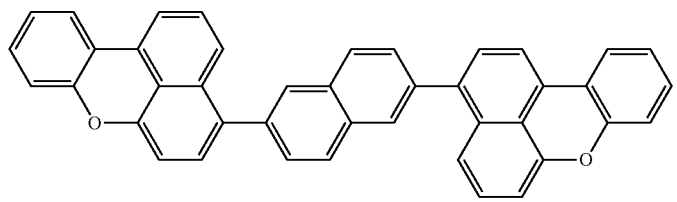
13
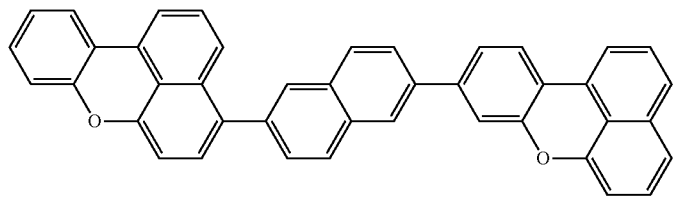
14
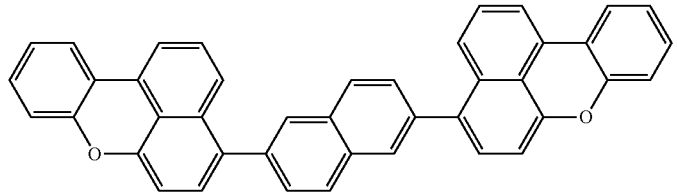
15
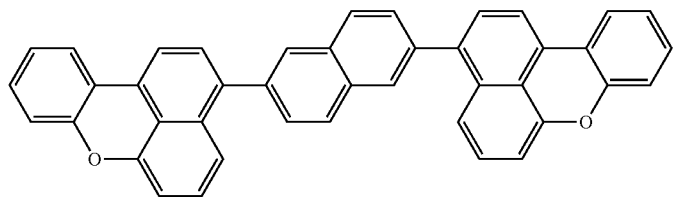
16

-continued
17
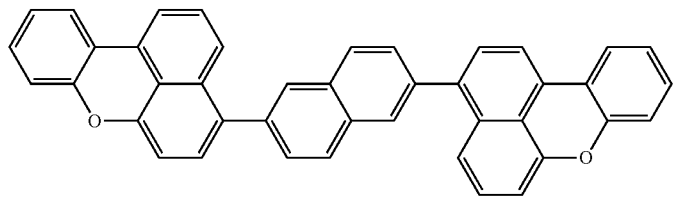
18
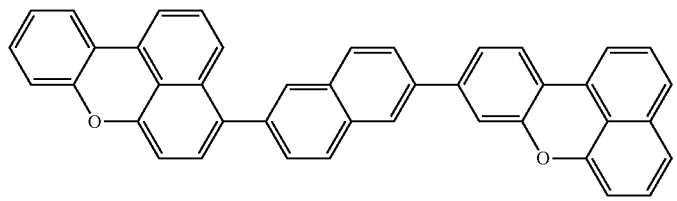
19
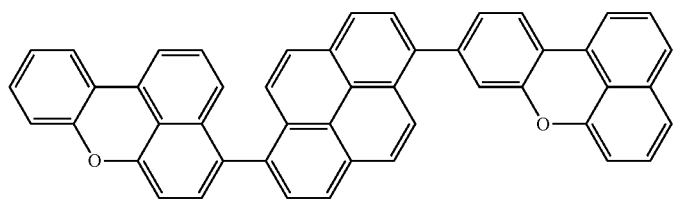
20
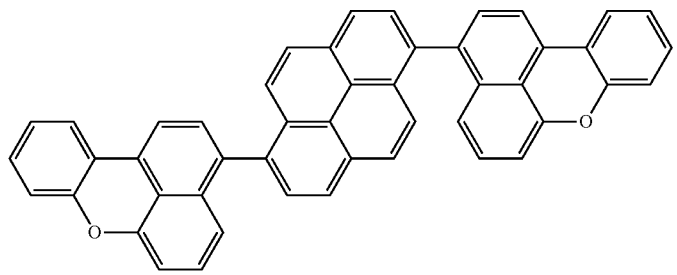
21
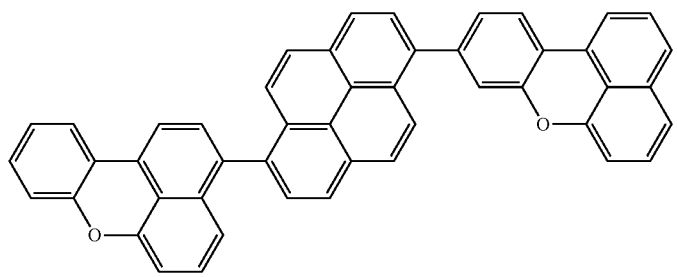
22
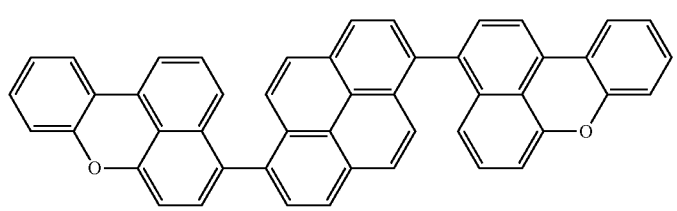
23
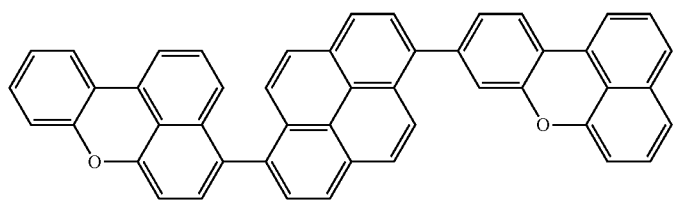

24
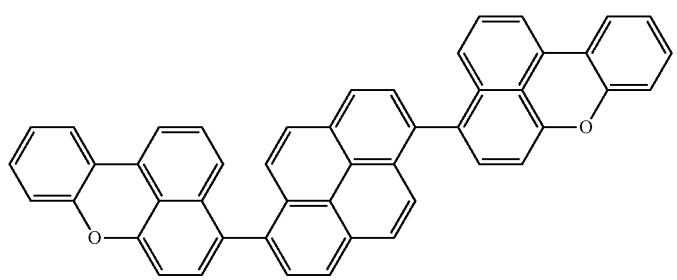
25
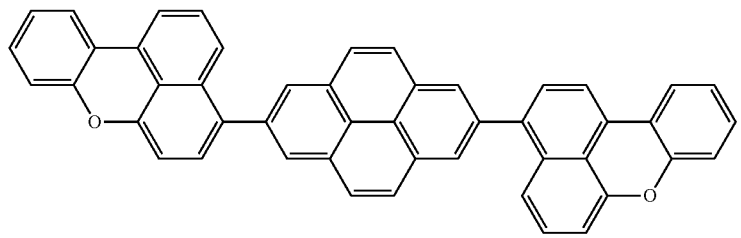
26
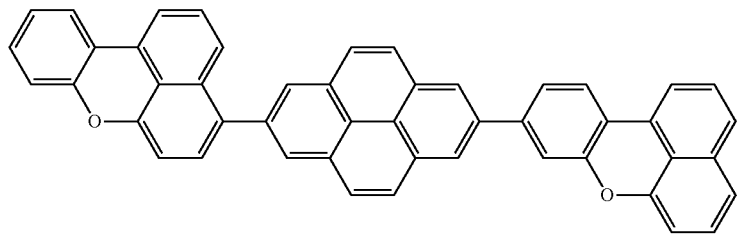
27
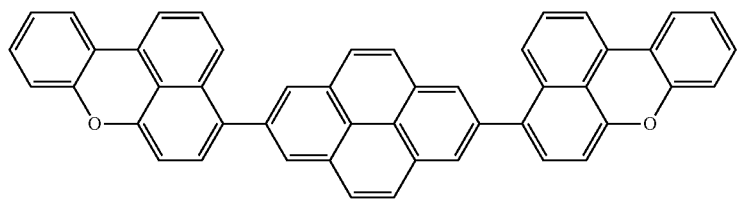
28
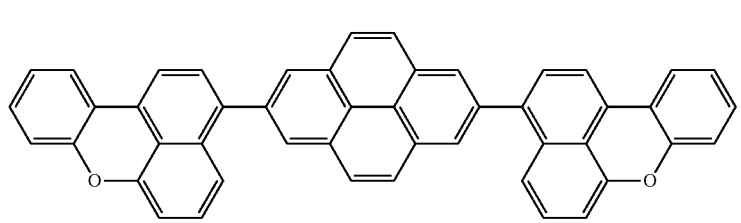
29
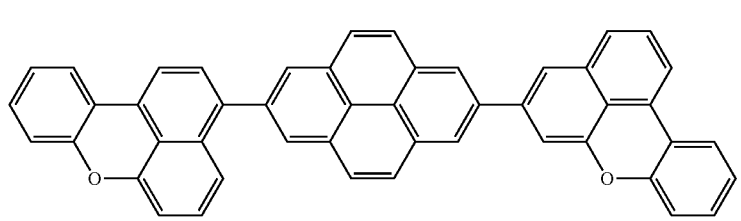
30
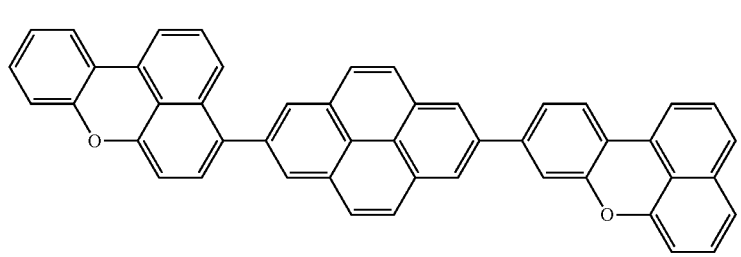

31
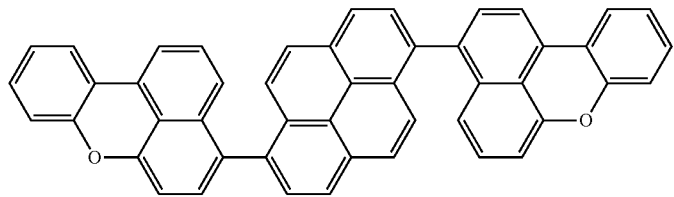
32
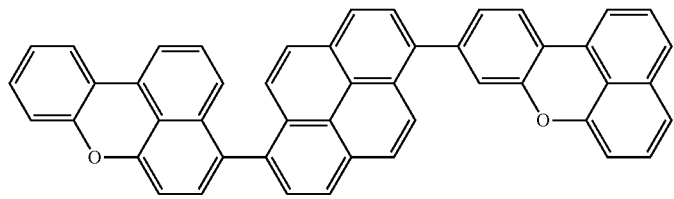
33
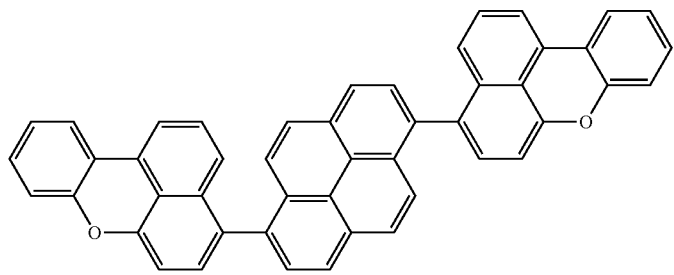
34
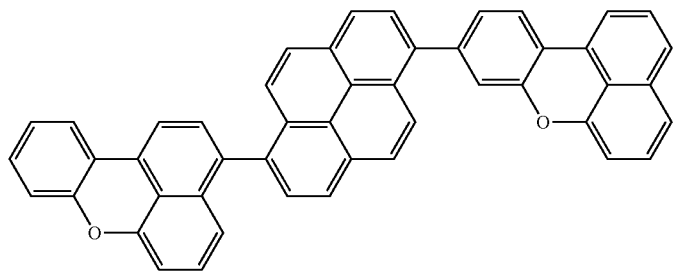
35
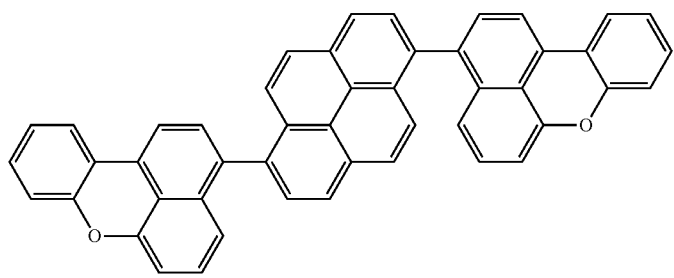
36
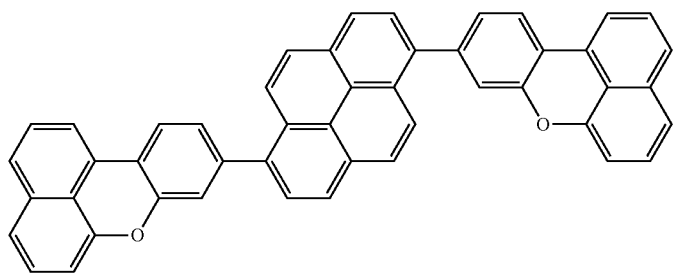

37
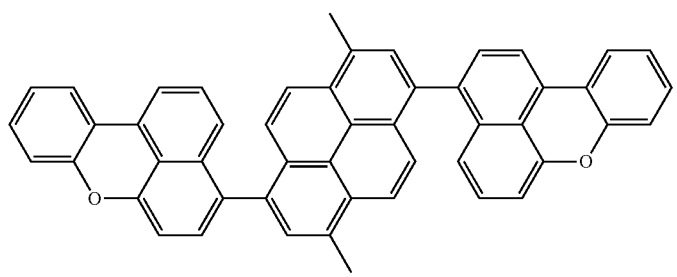
38
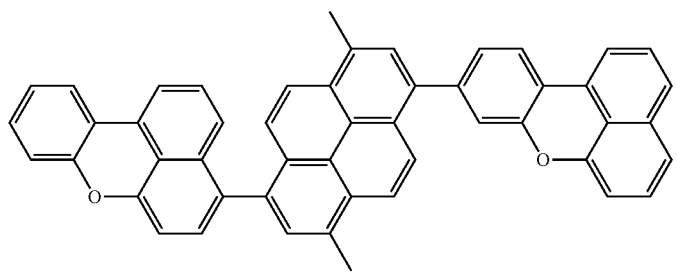
39
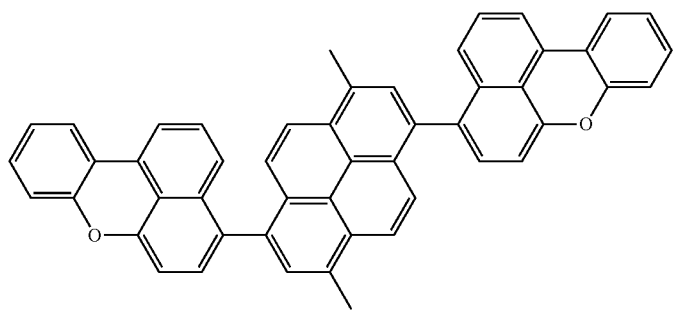
40
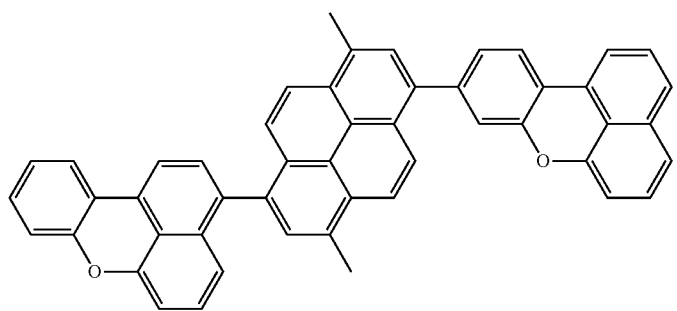
41
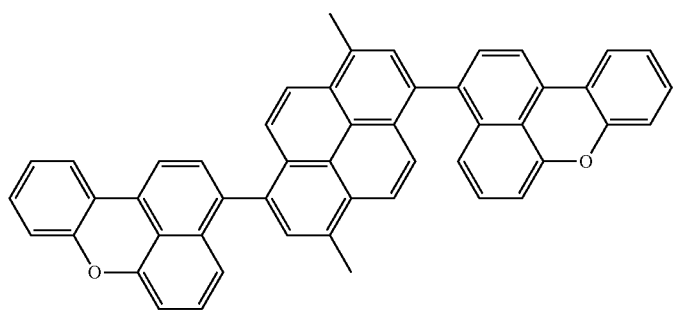

-continued
42
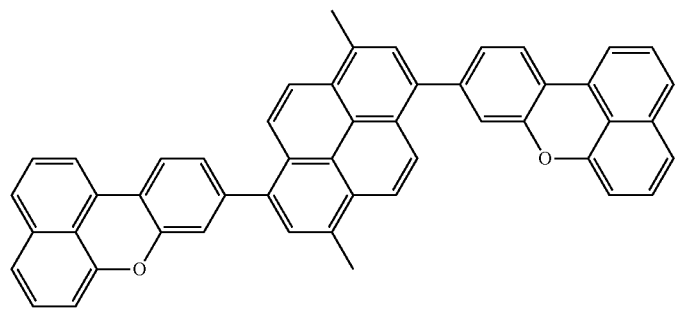
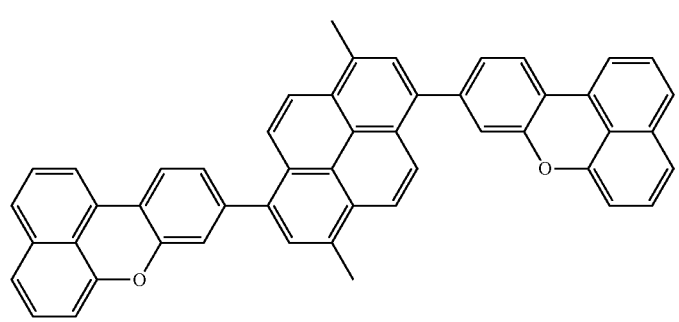
43
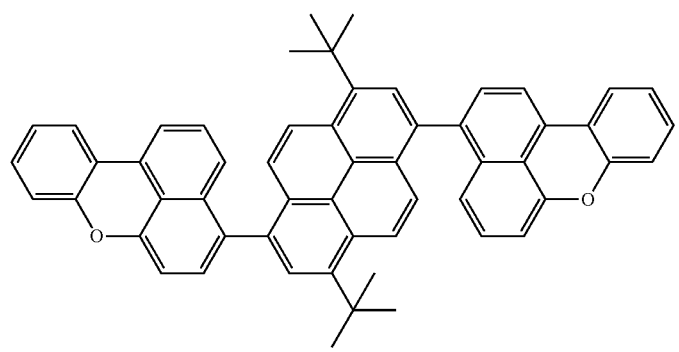
44
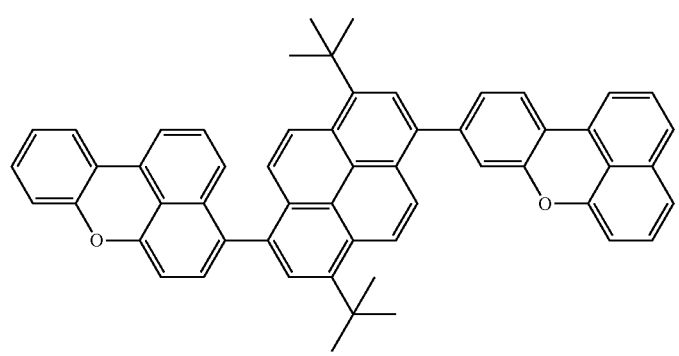

-continued
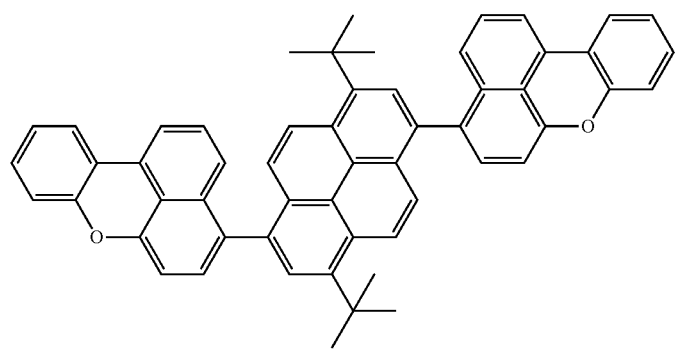
45
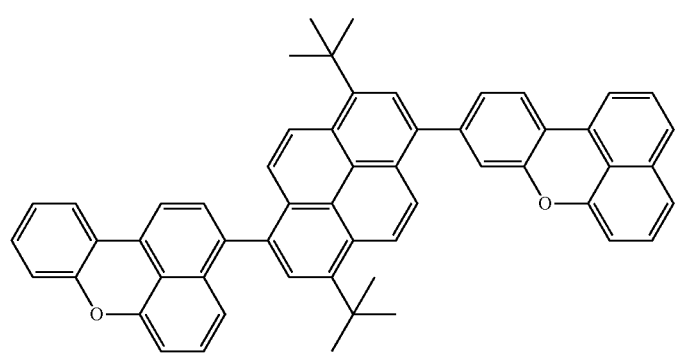
46
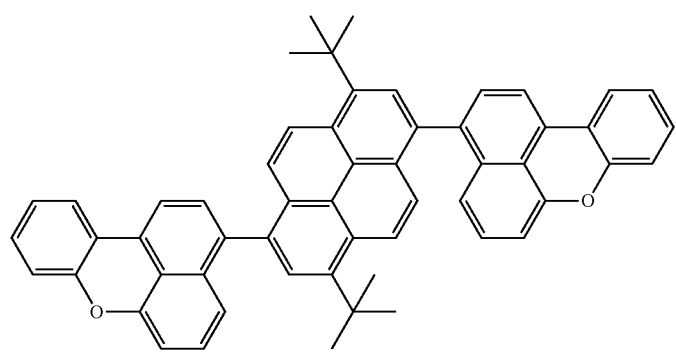
47
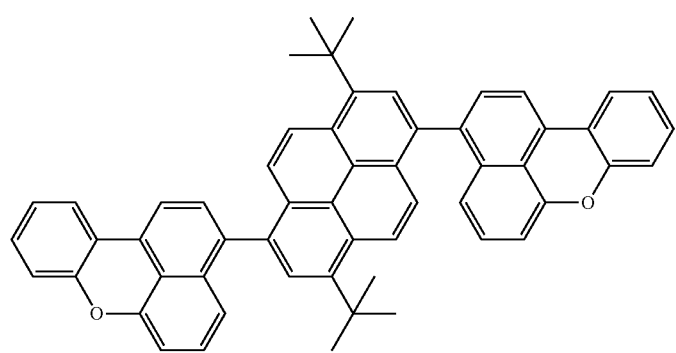
47

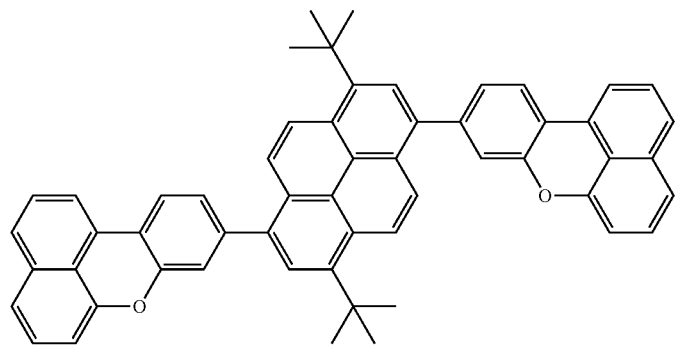
48
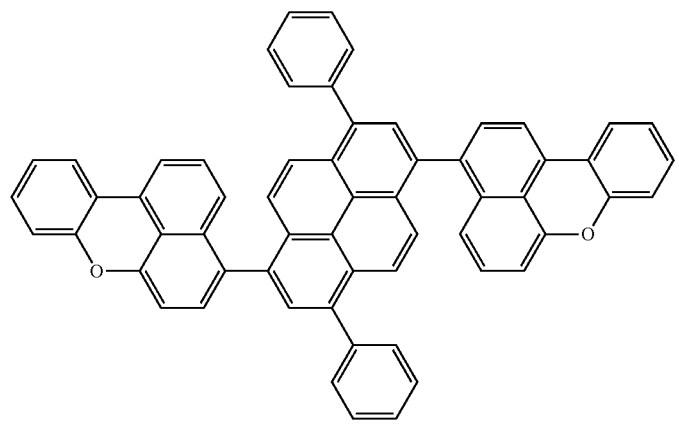
49
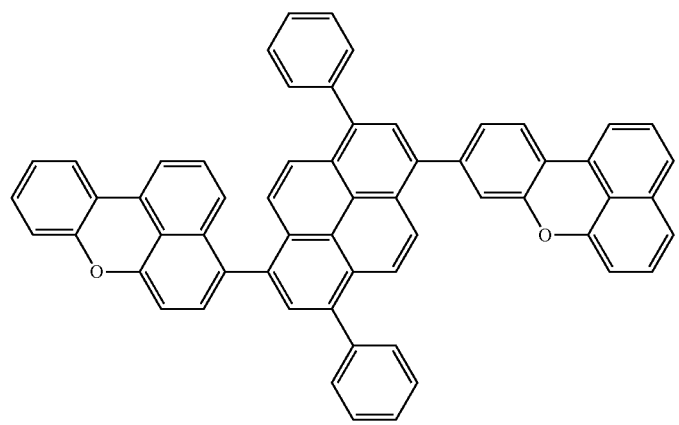
50
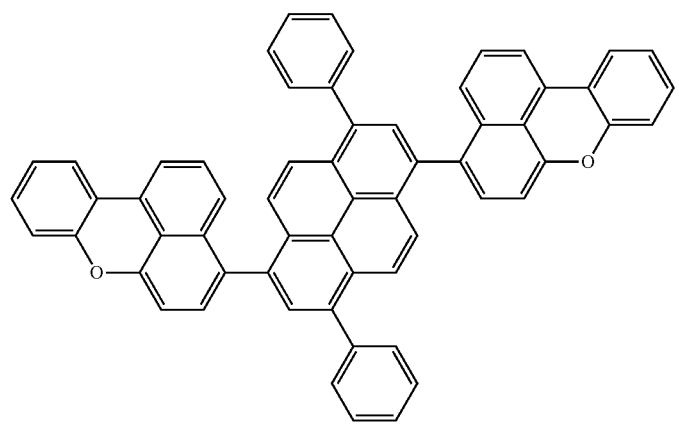
51

-continued
52
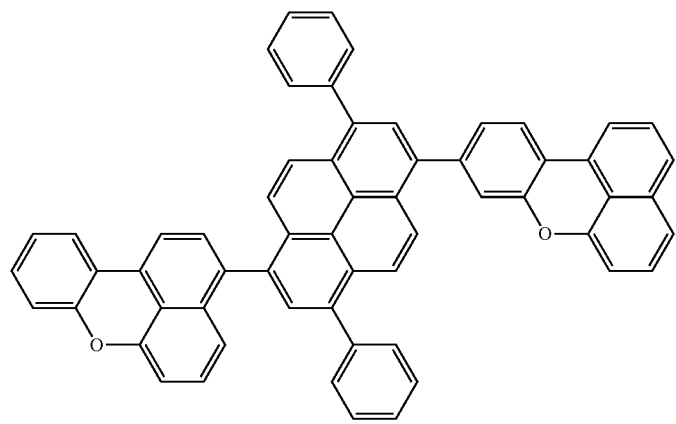
53
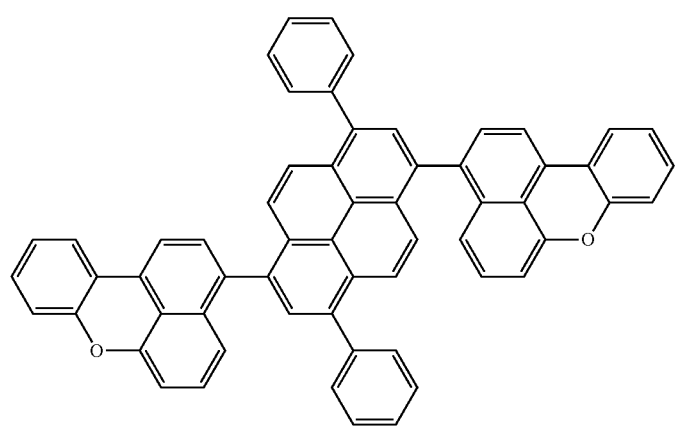
54
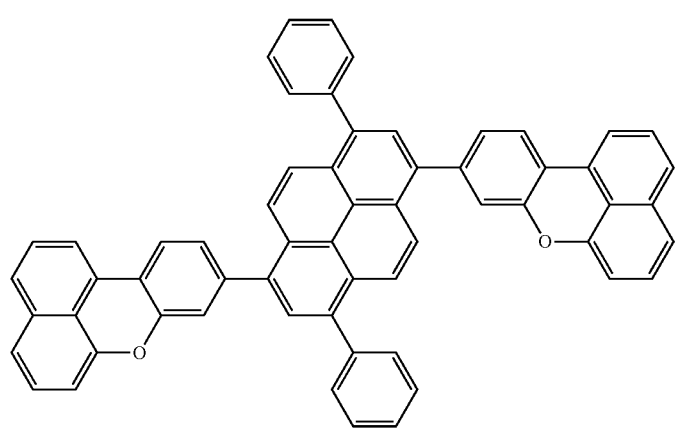
55
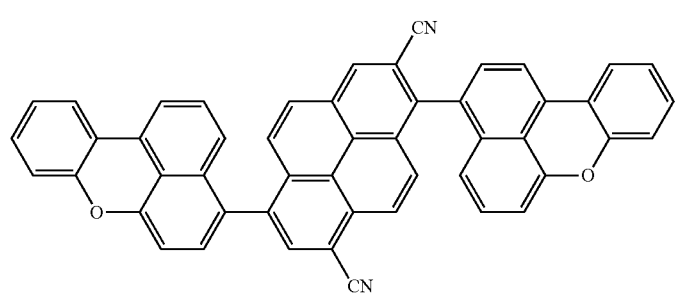

-continued
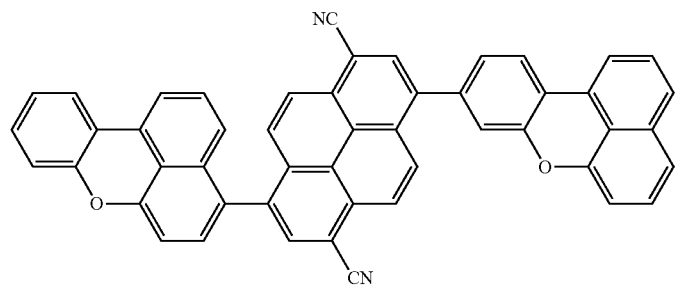
56
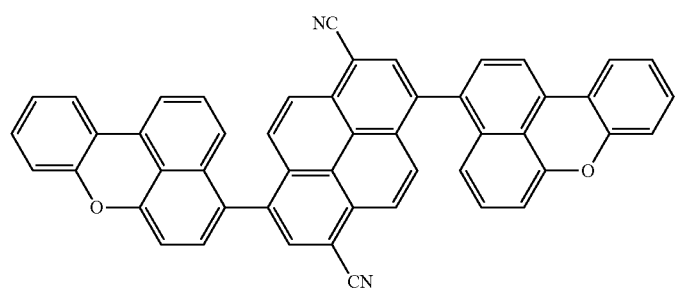
57
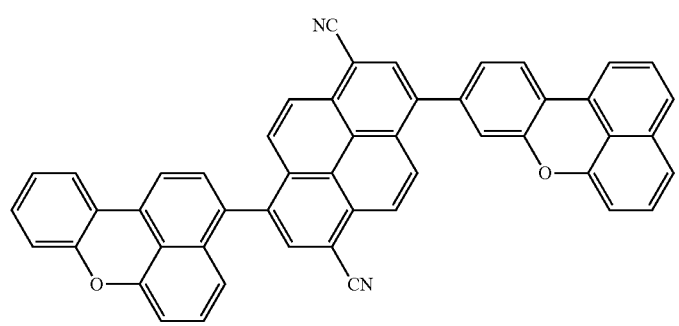
58
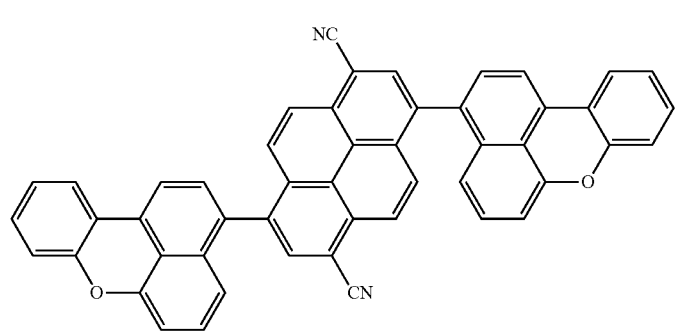
59
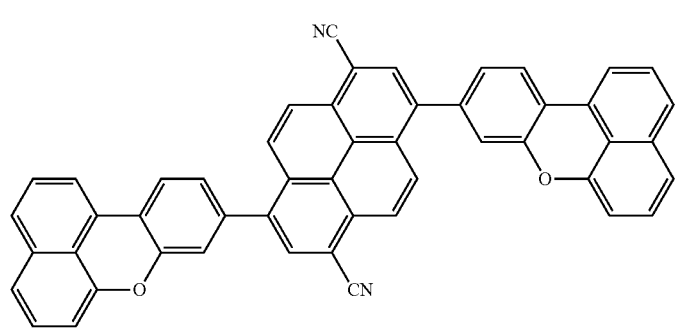
60

61
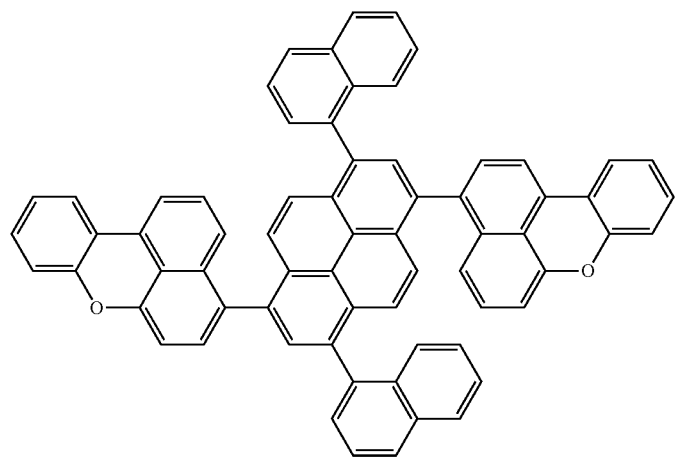
62
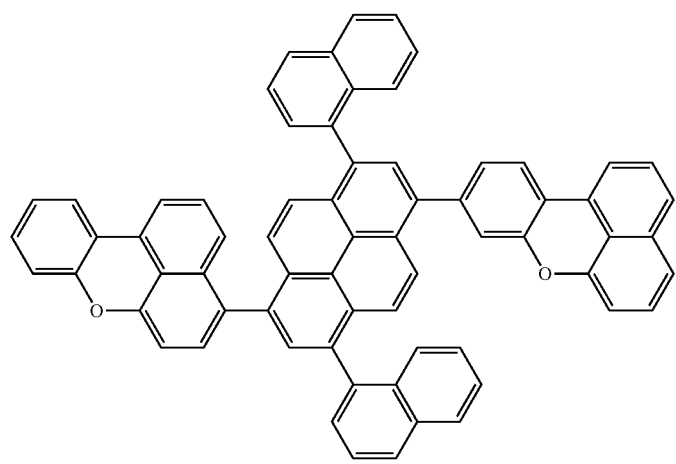
63
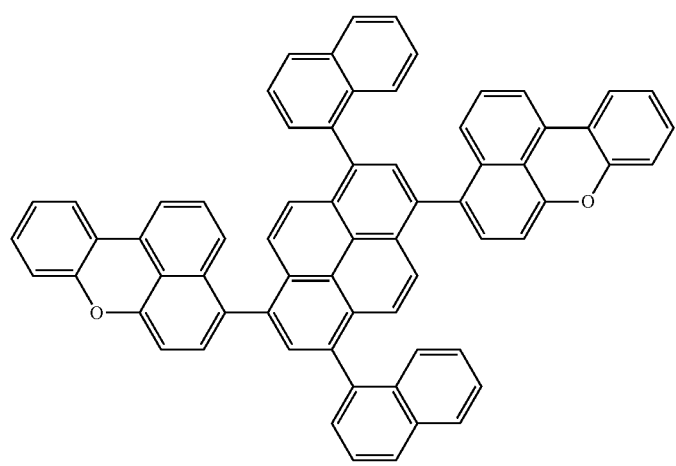

64
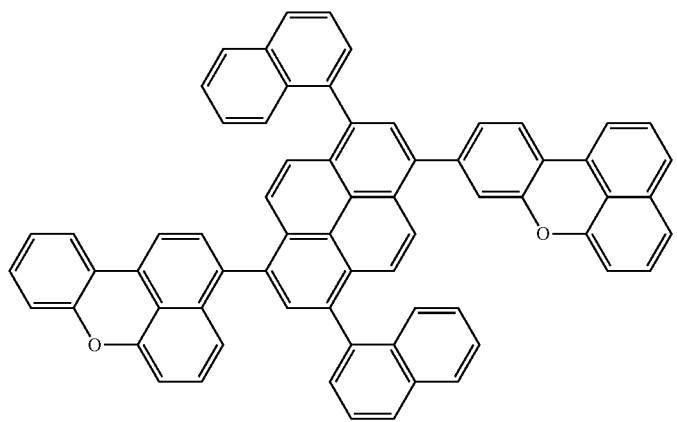
65
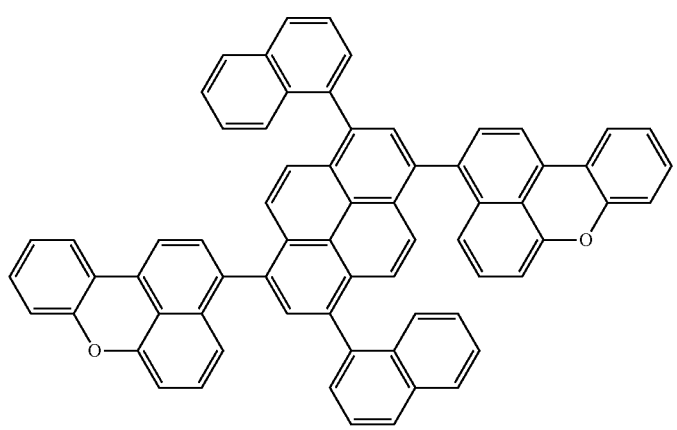
66
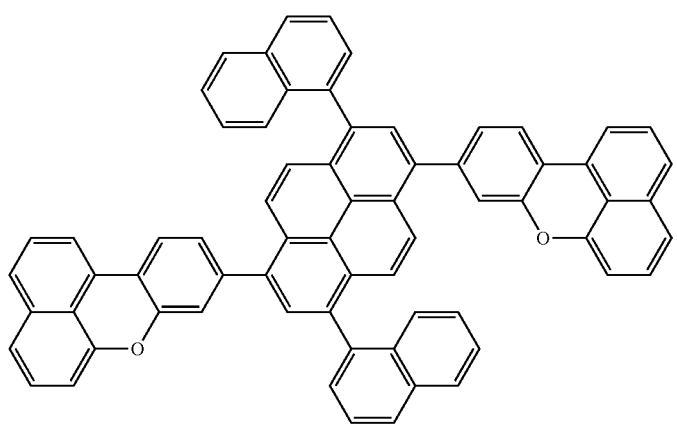

67
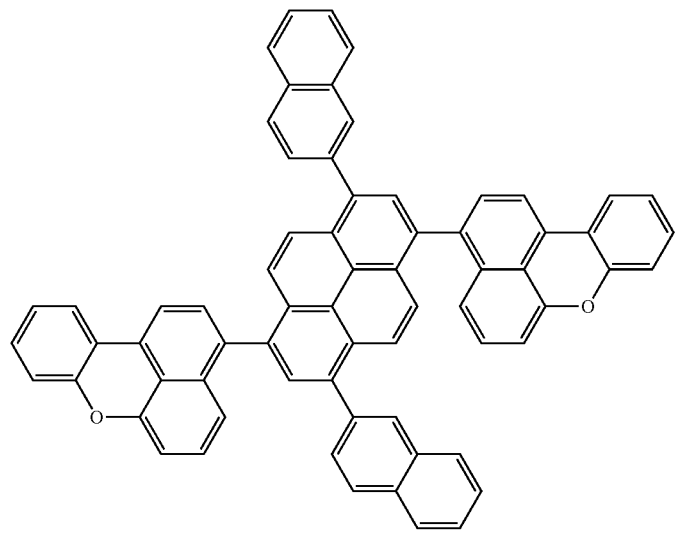
68
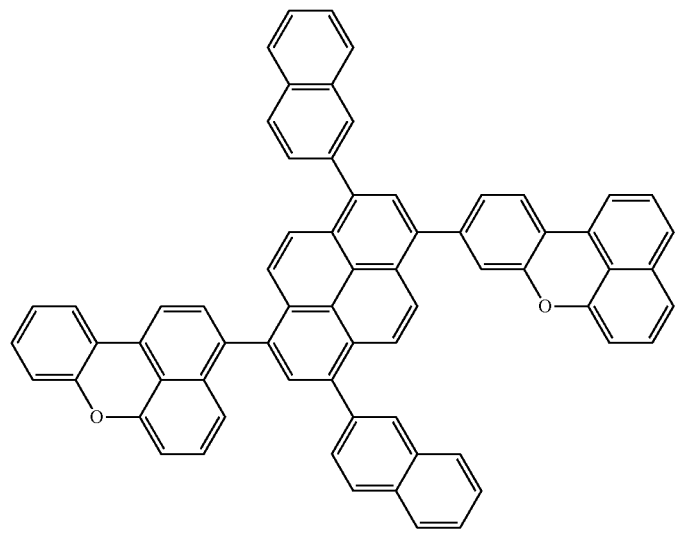
69
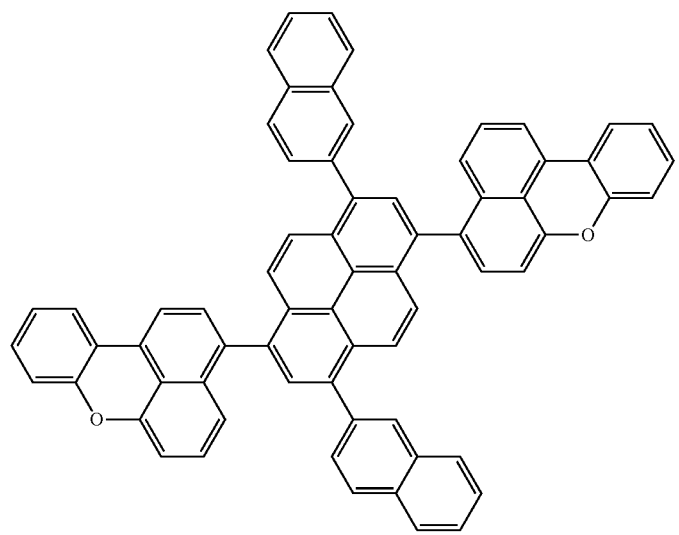

70
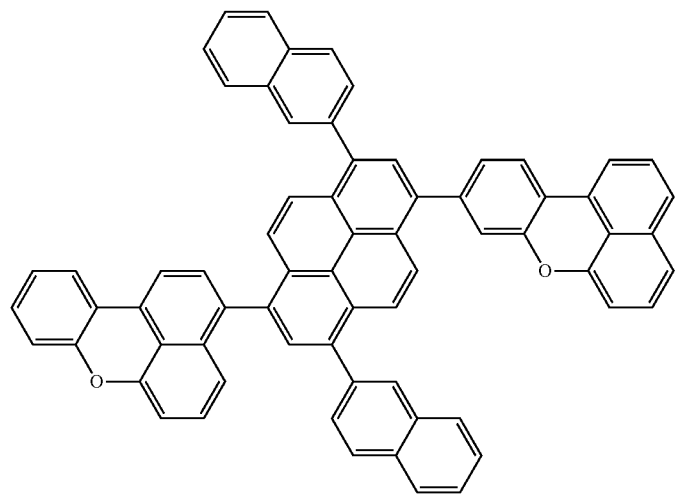
71
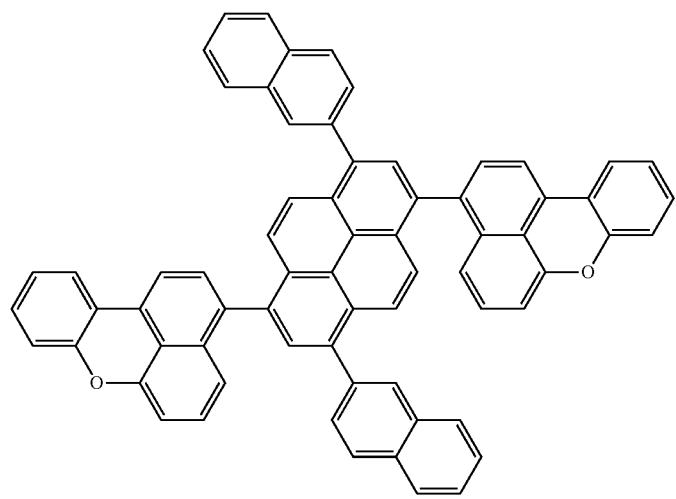
72
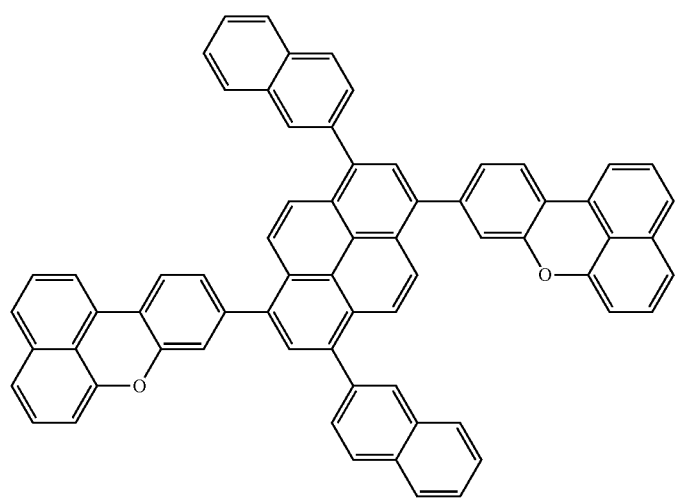

73
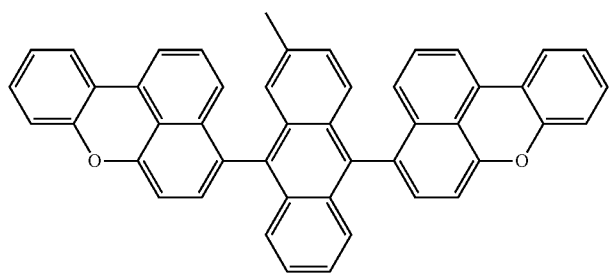
74
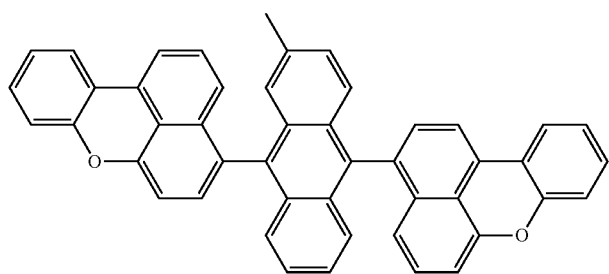
75
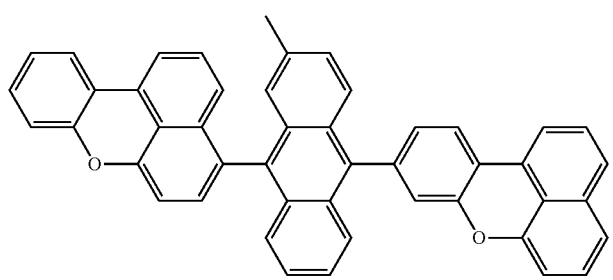
76
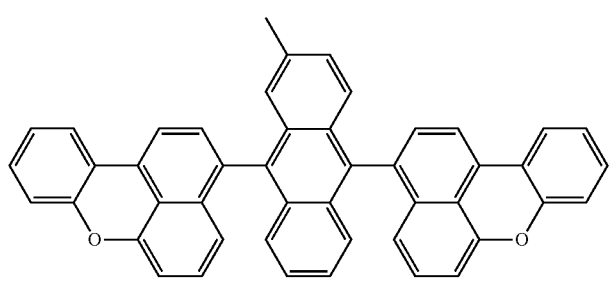
77
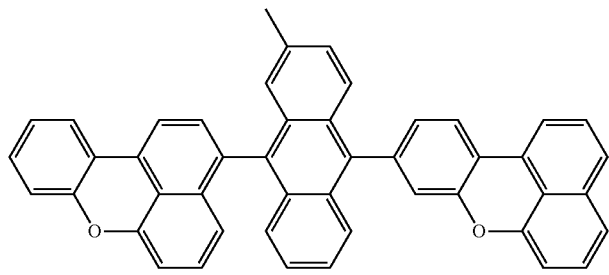

-continued
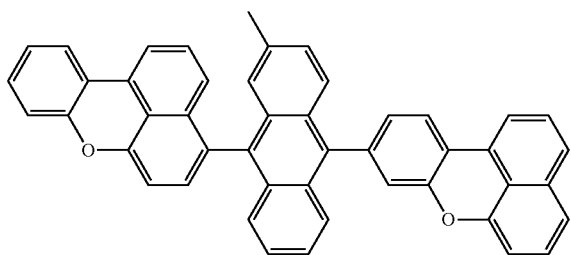
78
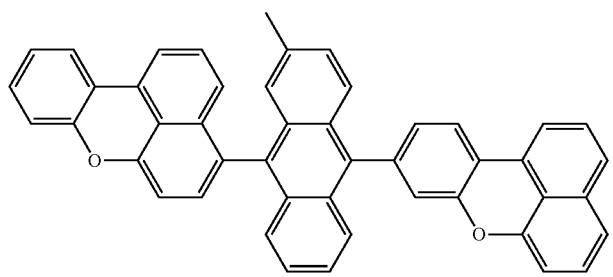
79
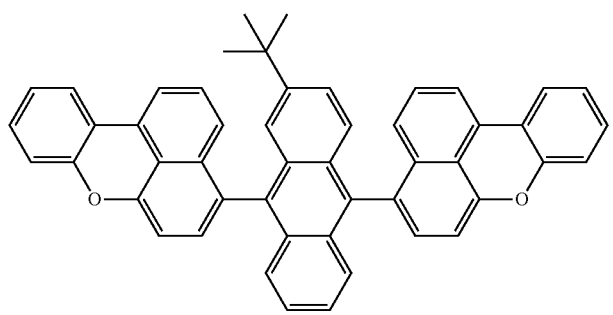
80
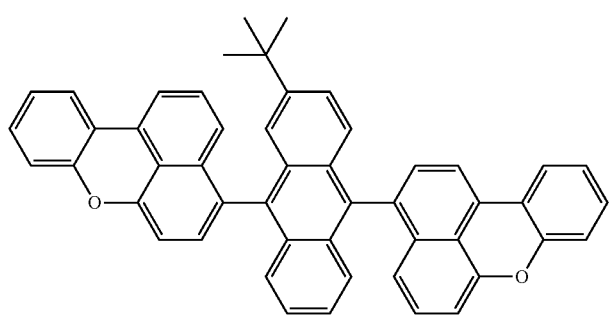
81
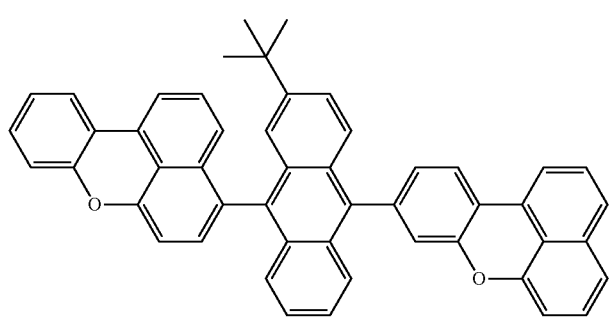

82
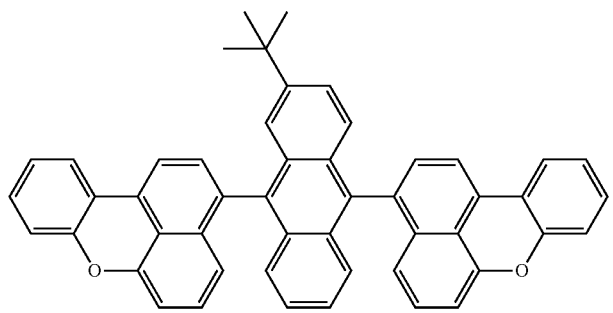
83
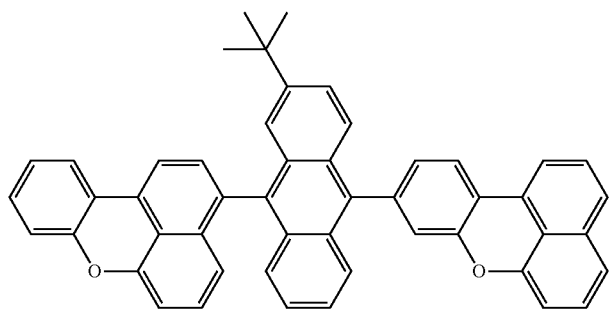
84
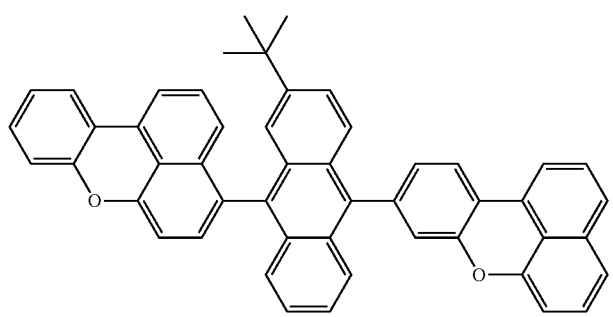
85
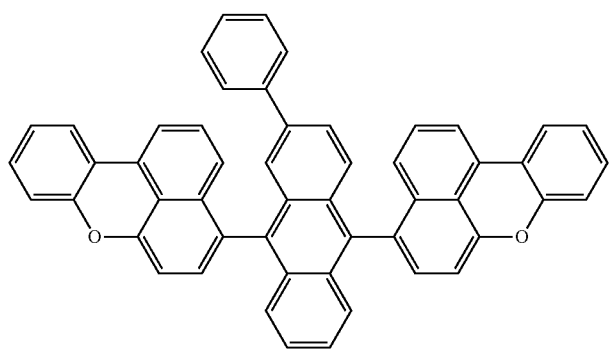
86
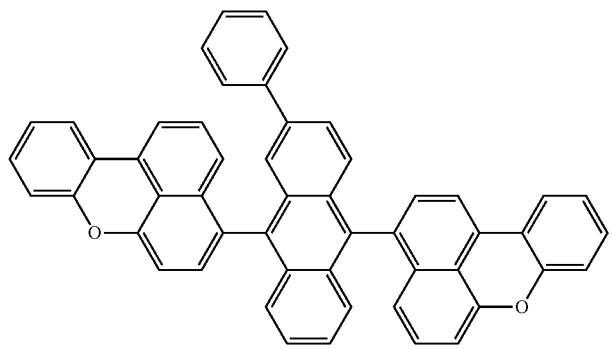

87
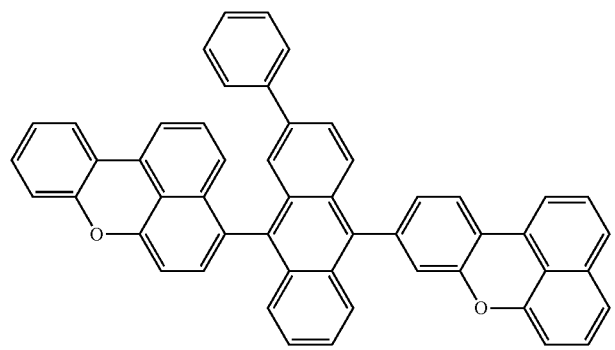
88
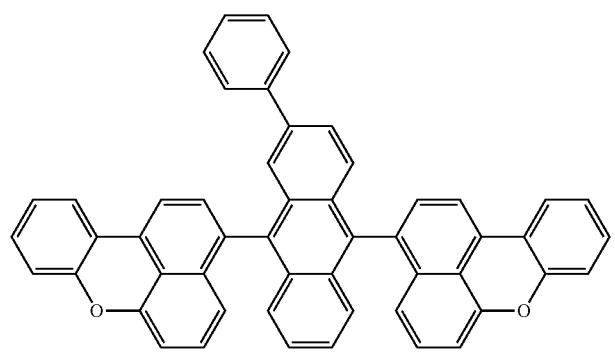
89
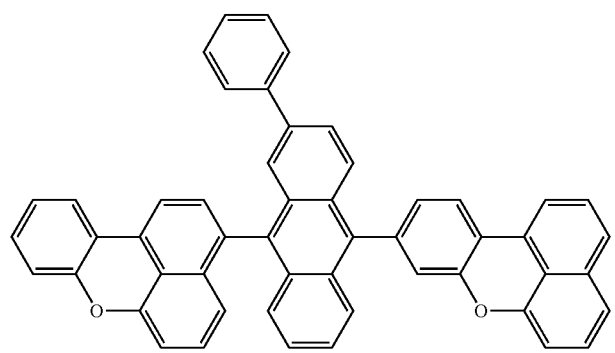
90
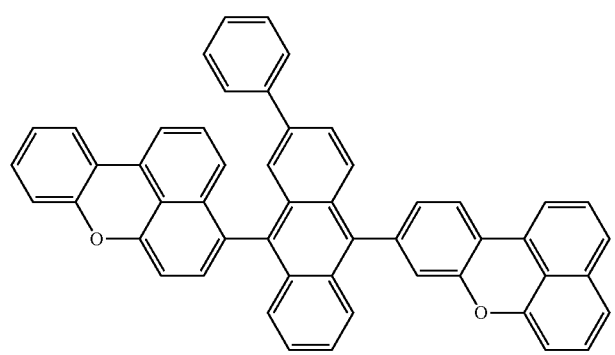

91
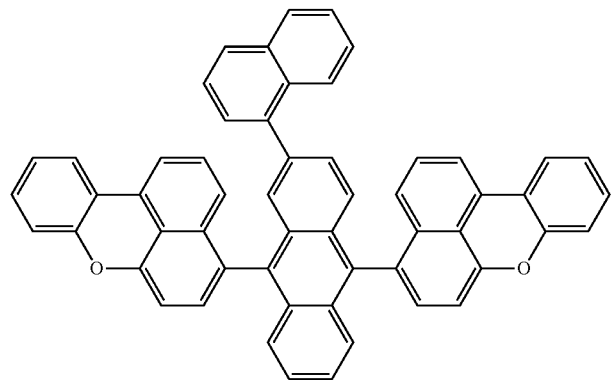
92
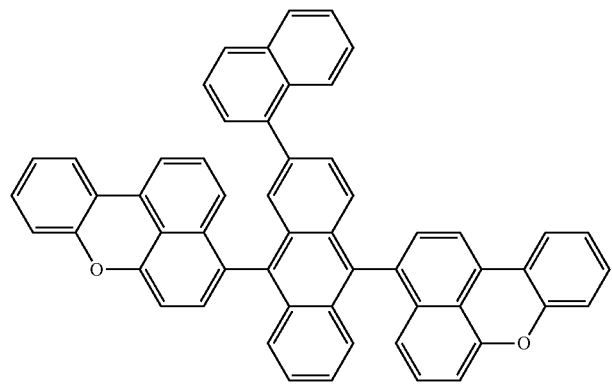
93
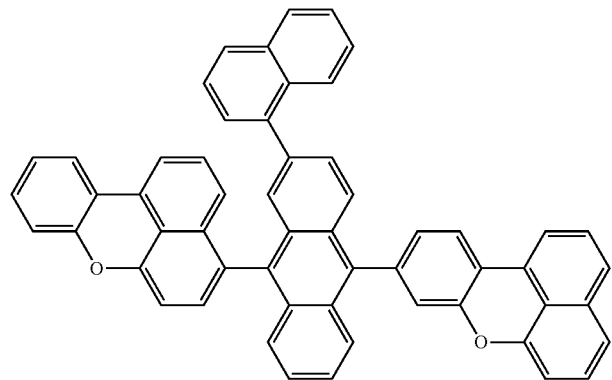
94
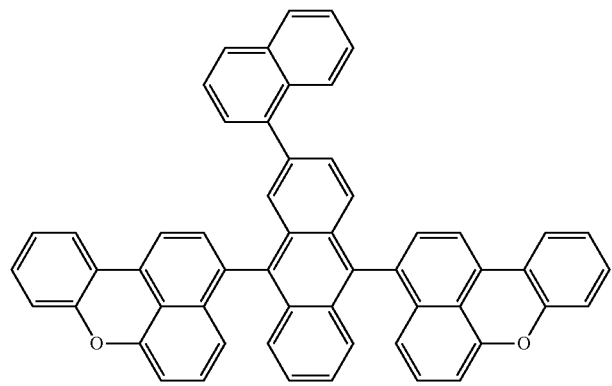

95
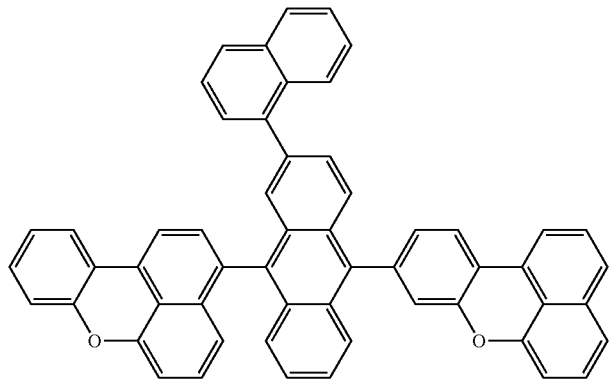
96
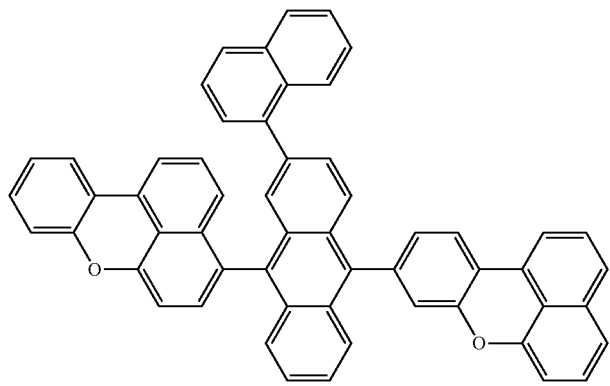
97
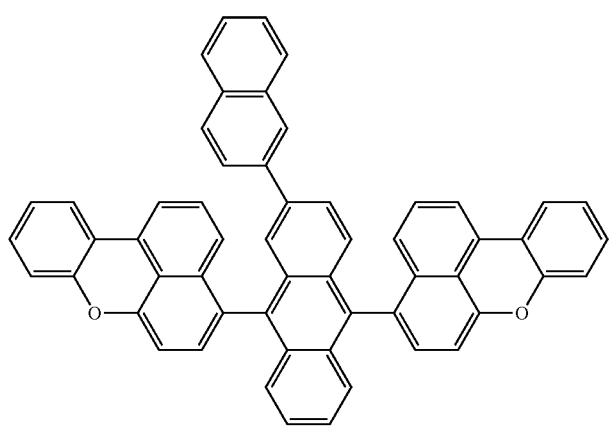
98
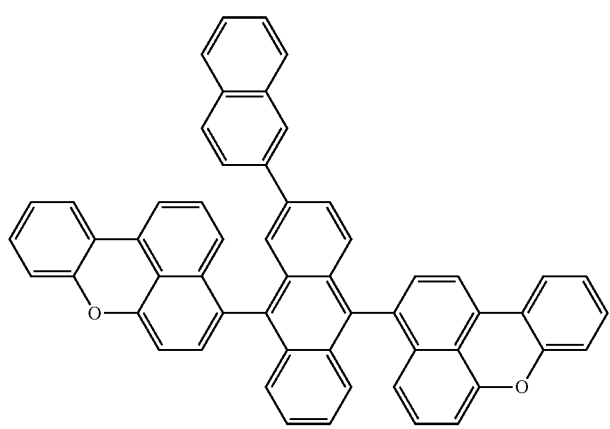

-continued
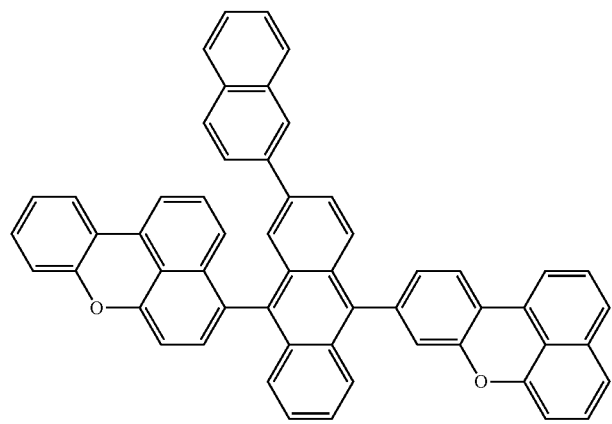
99
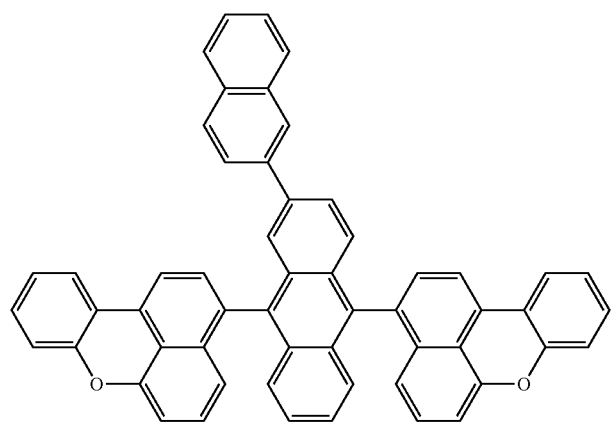
100
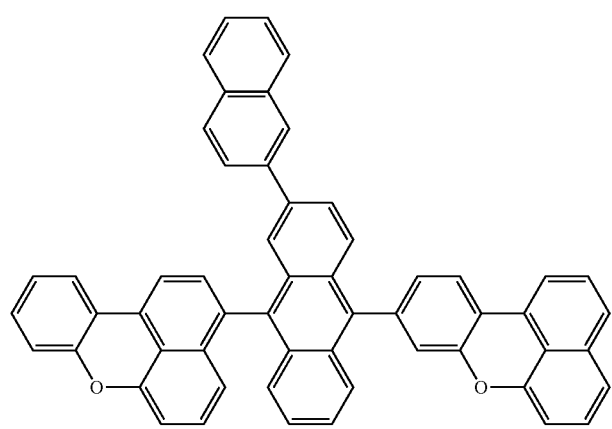
101

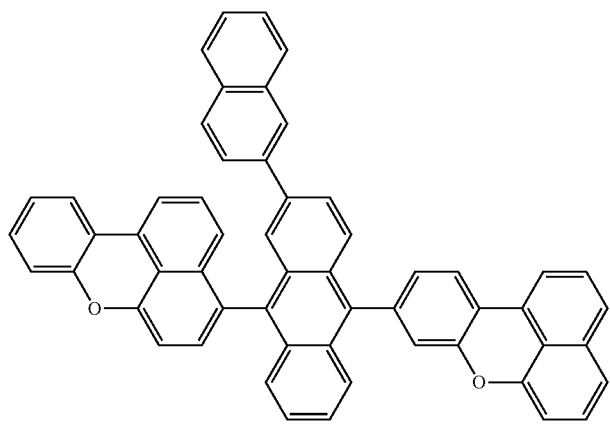
102
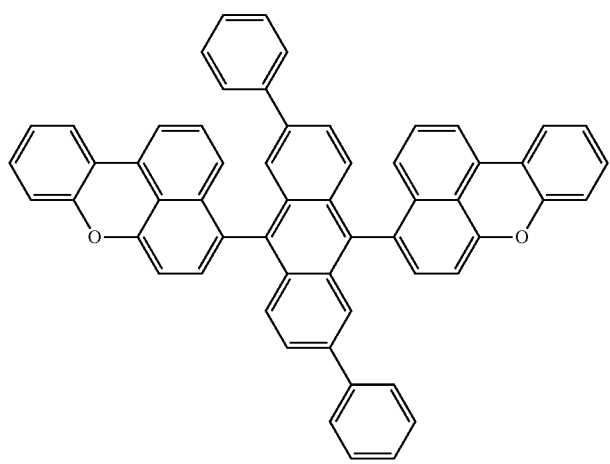
103
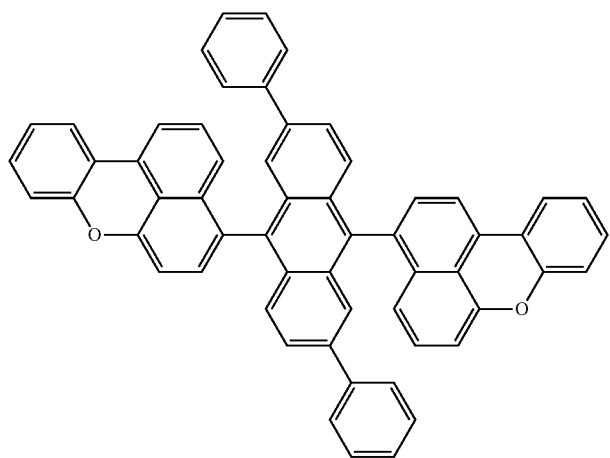
104

105
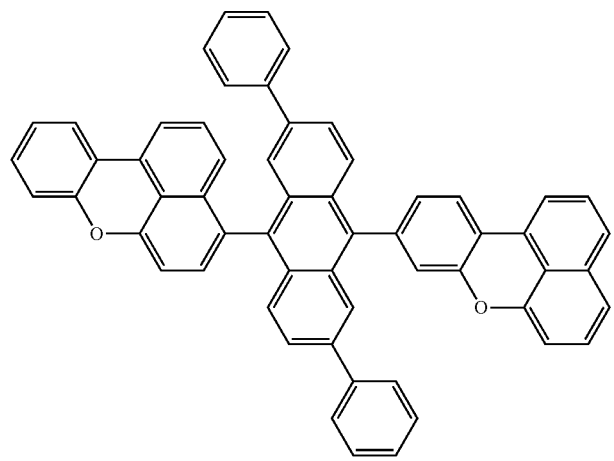
106
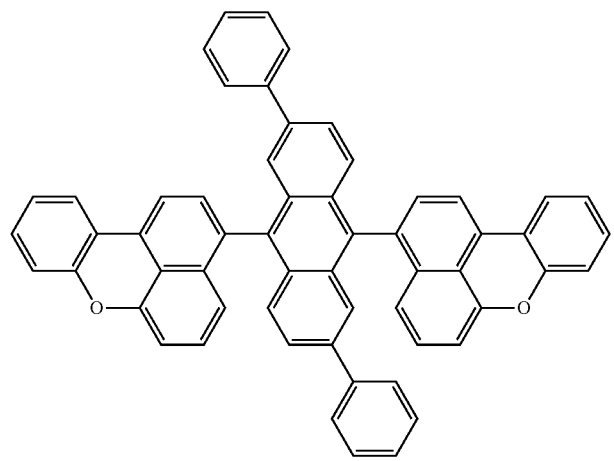
107
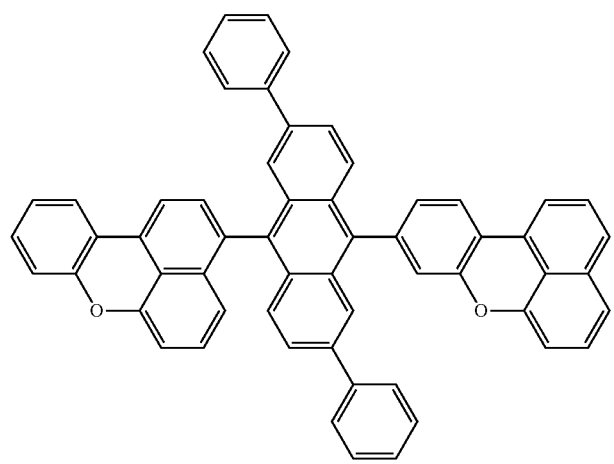

108
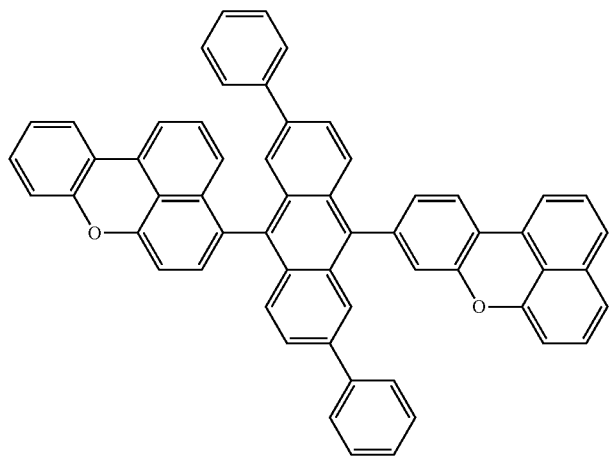
109
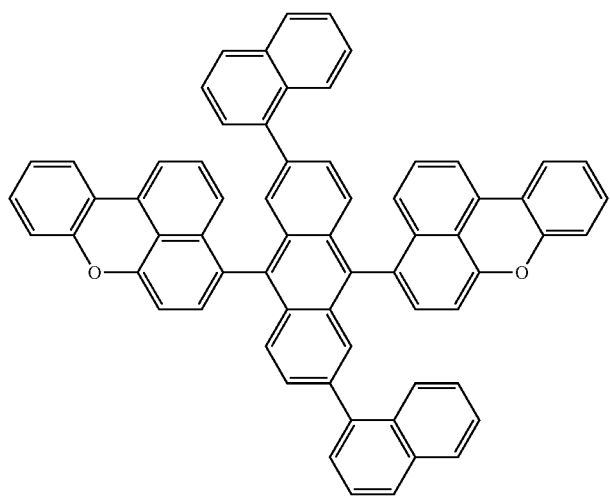
110
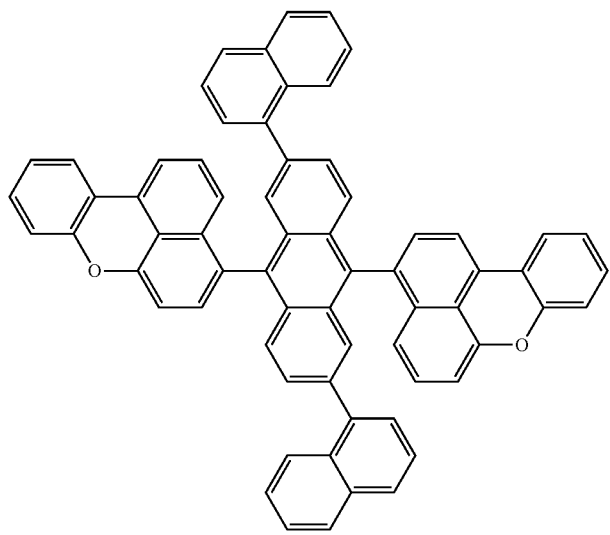

-continued
111
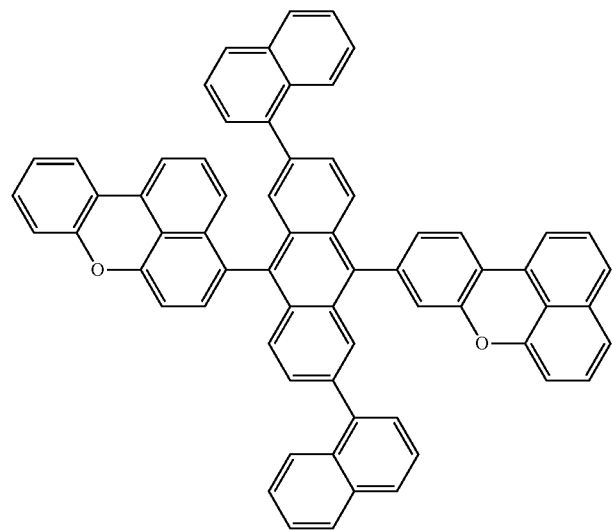
112
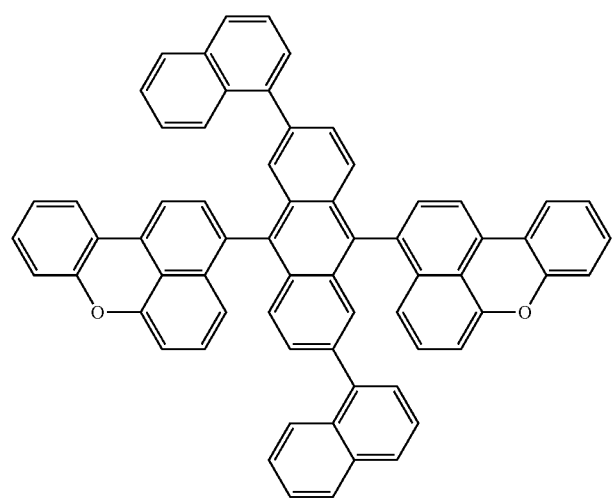
113
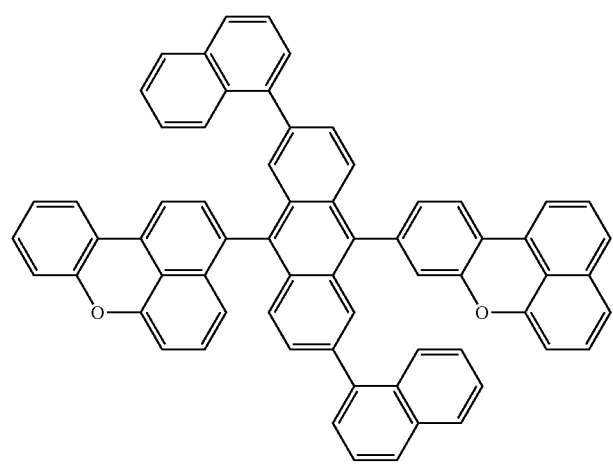

-continued
114
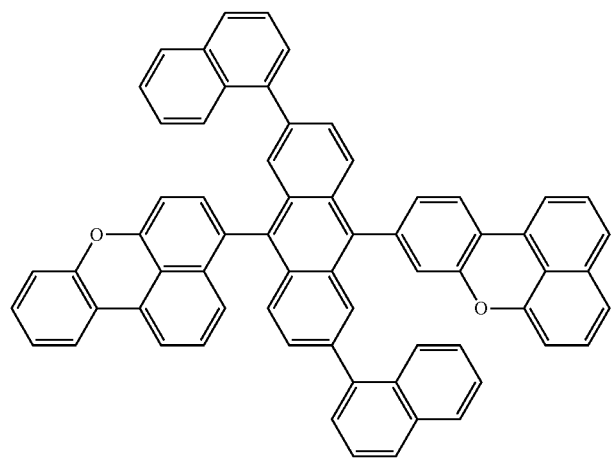
115
116
117

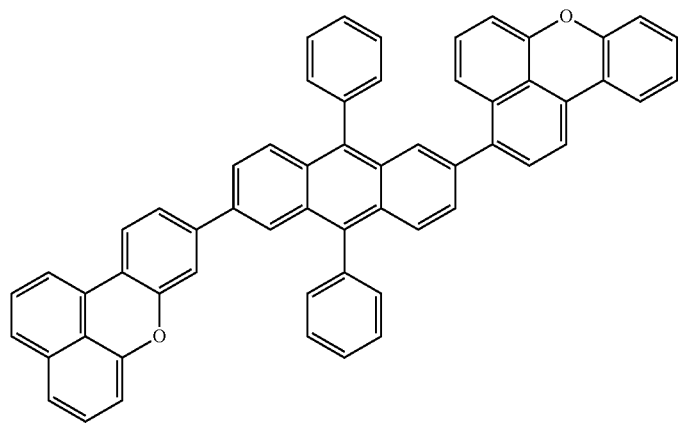
118
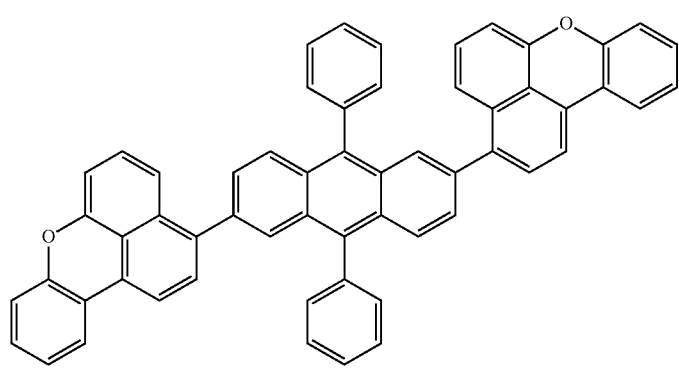
119
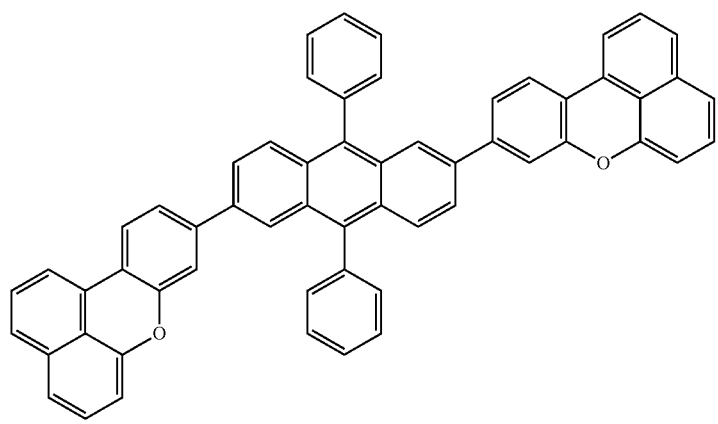
120
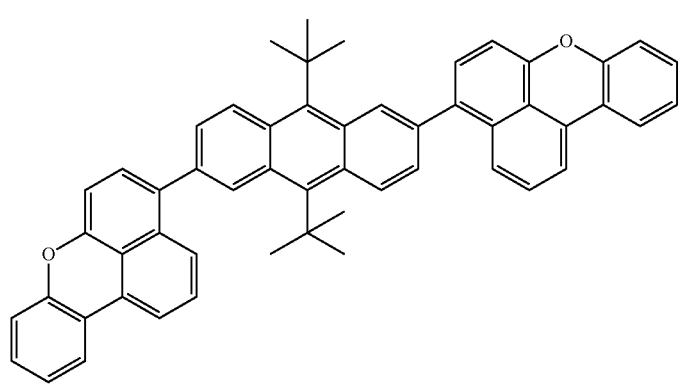
121

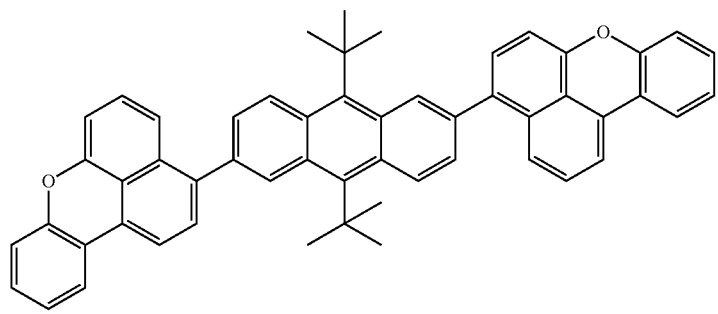
122
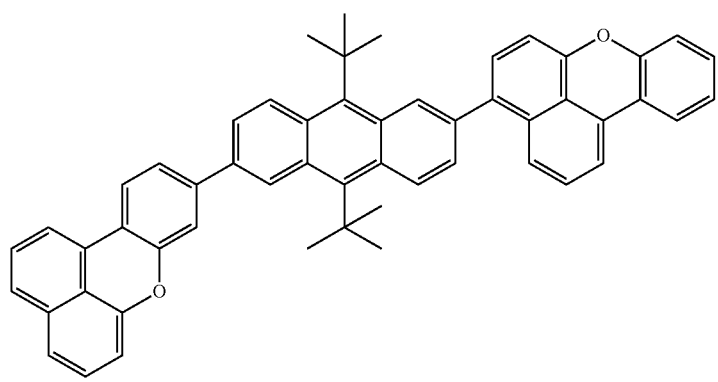
123
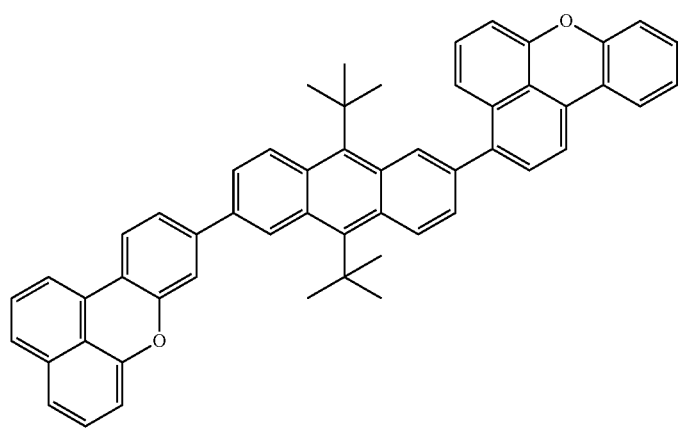
124
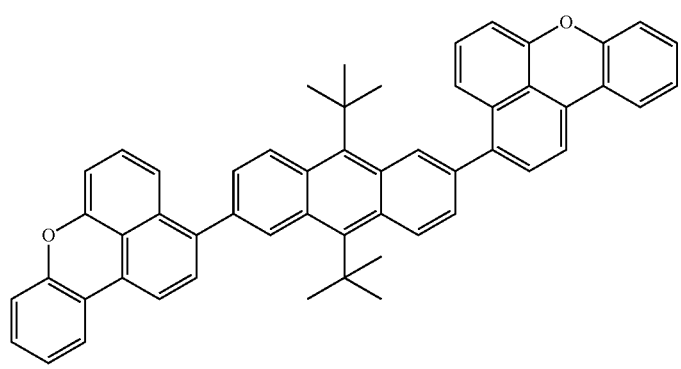
125

-continued
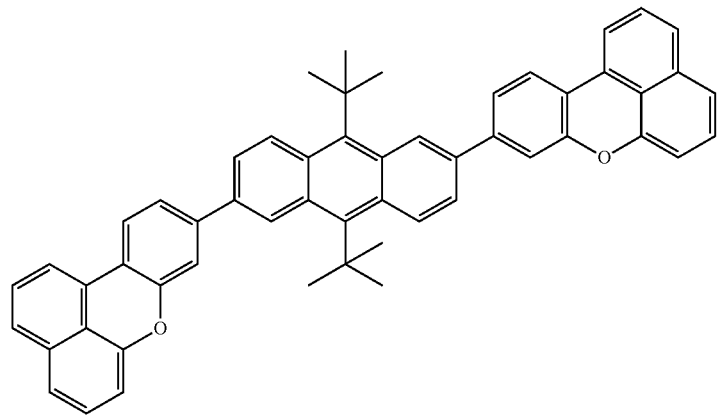
126
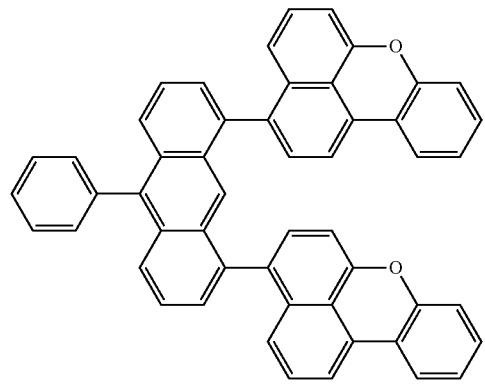
127
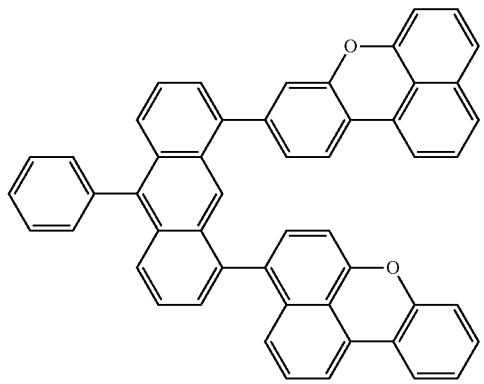
128
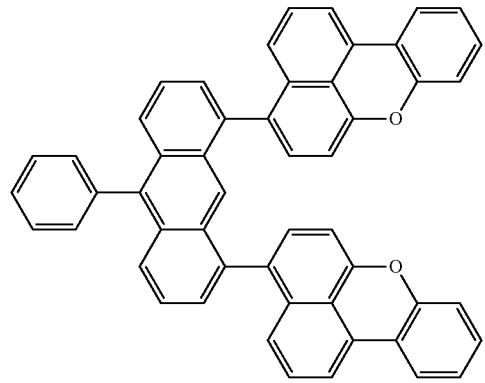
129
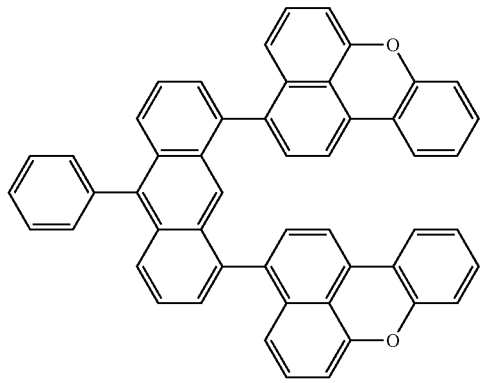
130
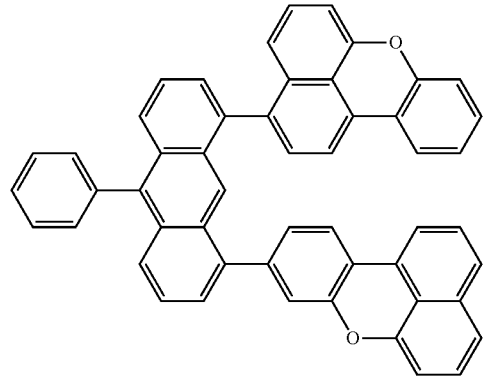
131
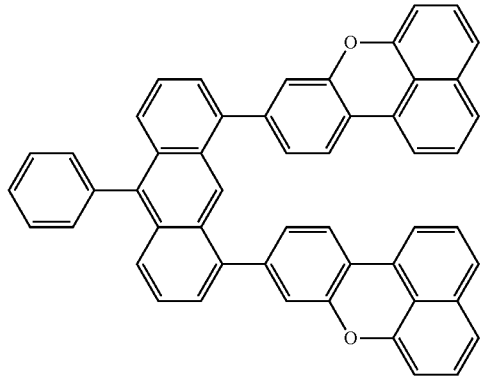
132

-continued
133
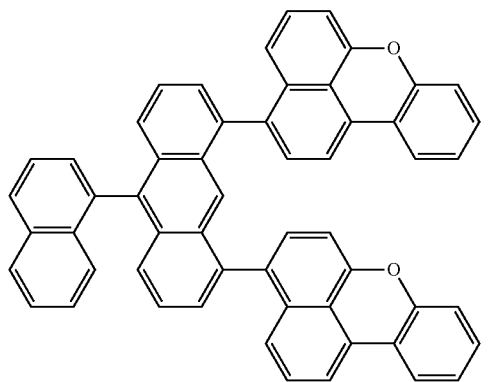
134
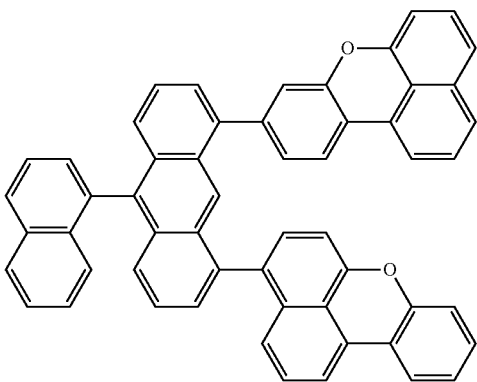
135
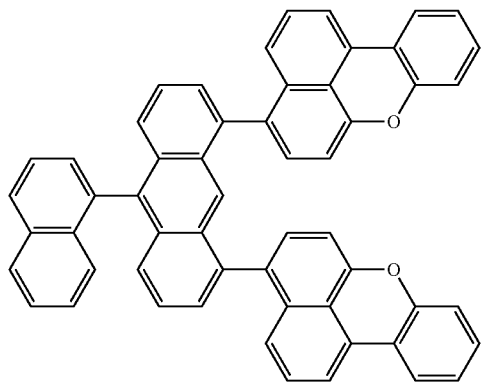
136
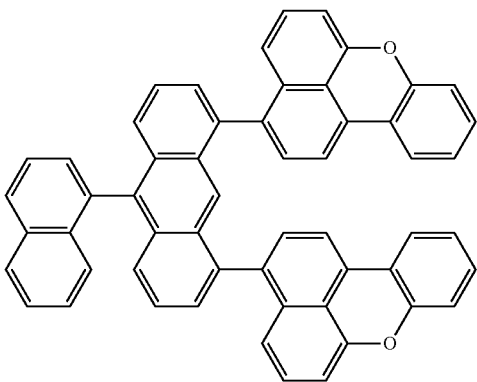
137
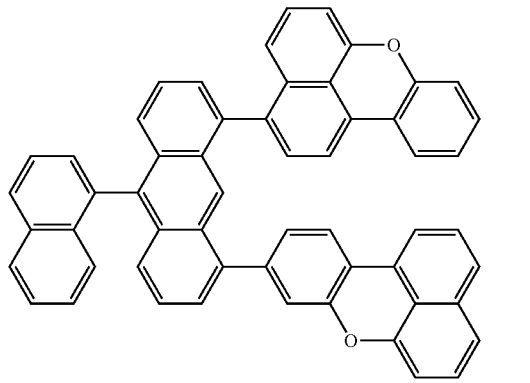
138
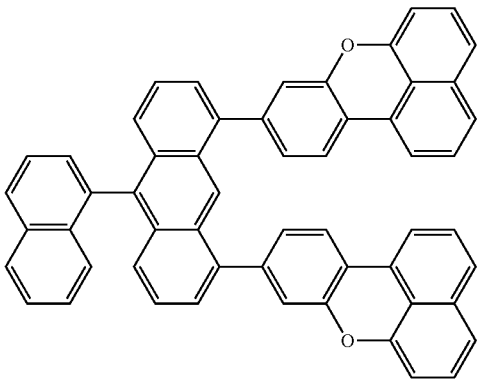
139
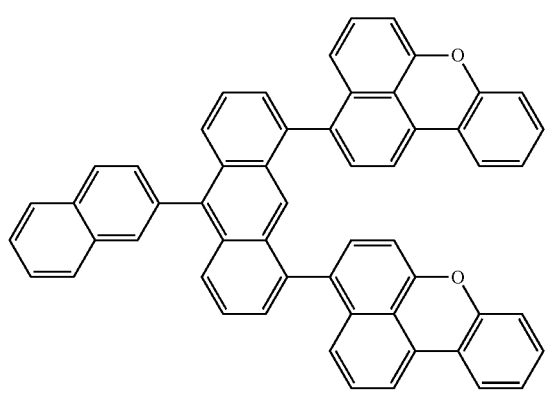
140
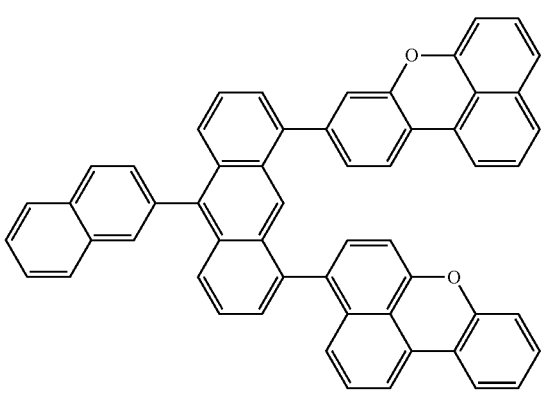

141
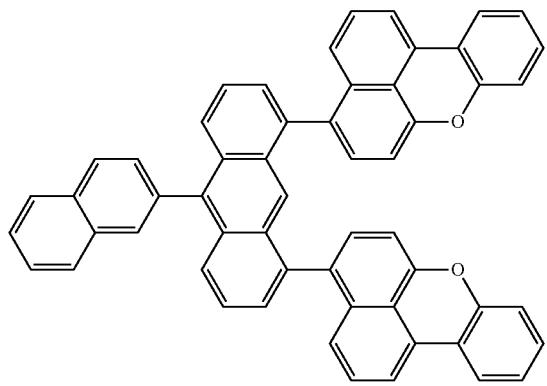
142
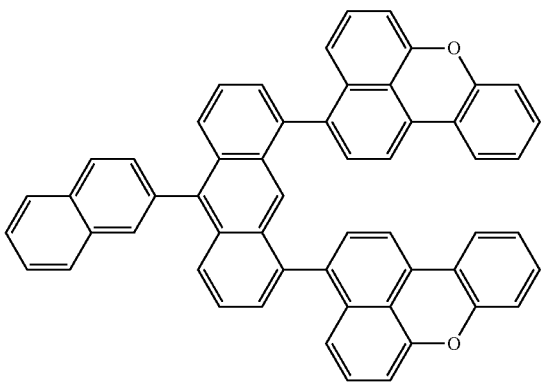
143
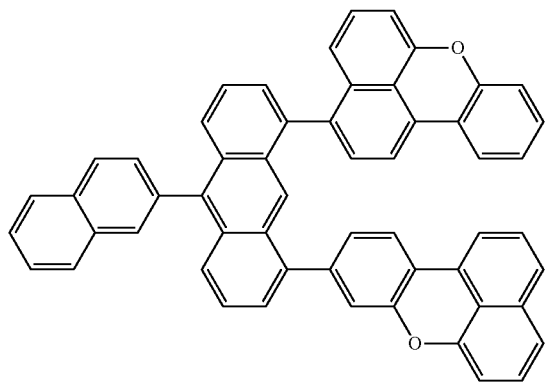
144
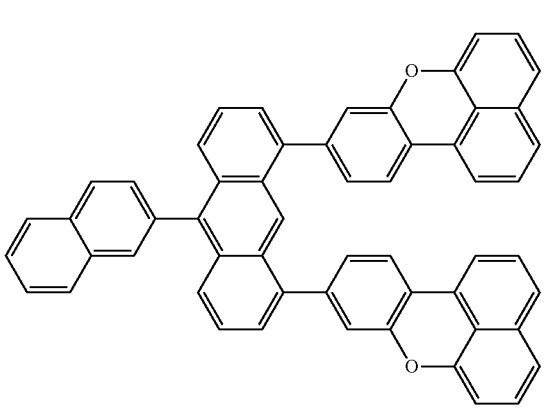
145
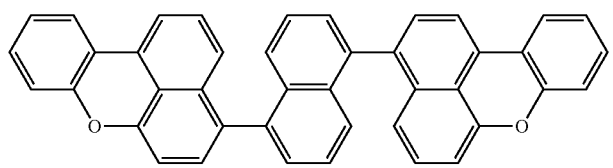
146
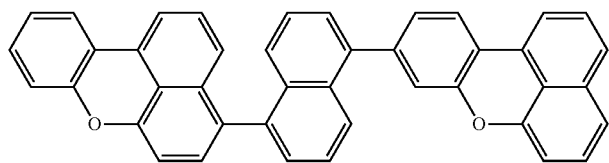
147
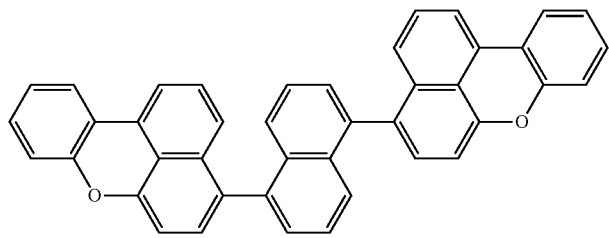
148
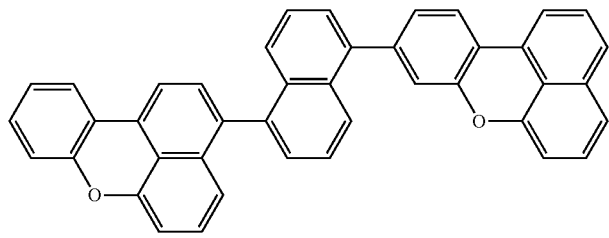

149
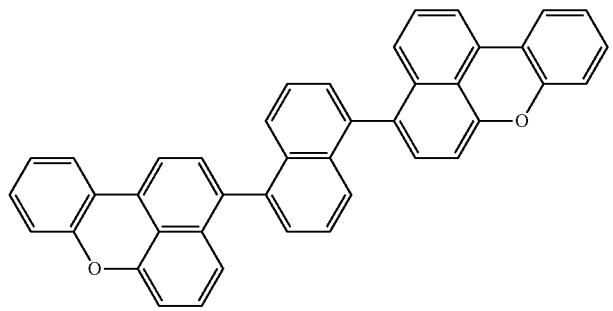
150
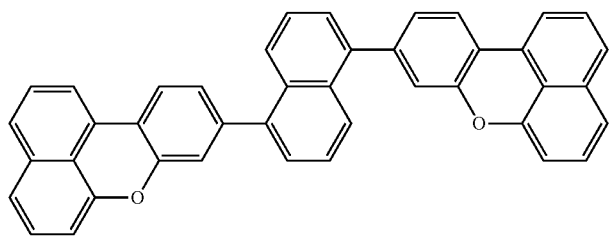
151
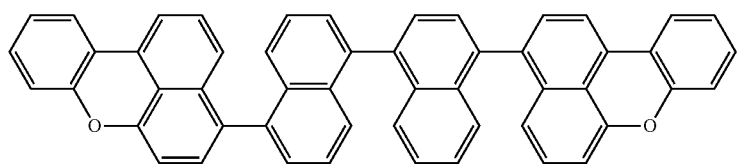
152
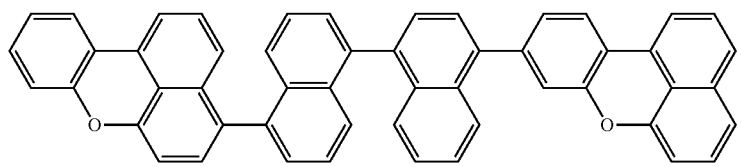
153
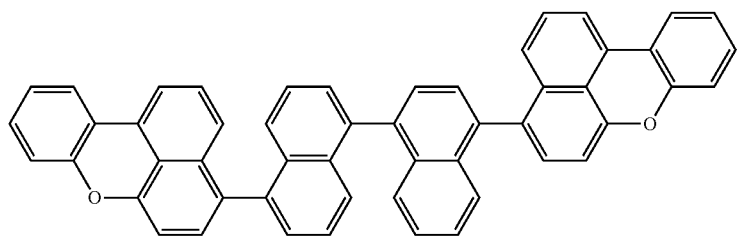
154
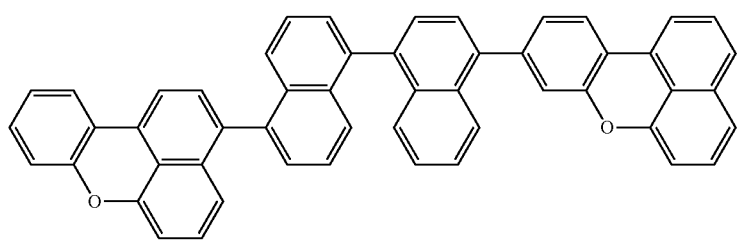
155
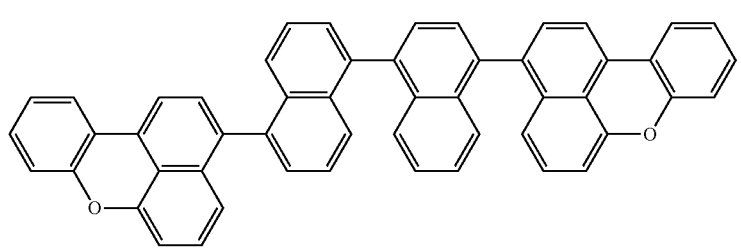

-continued
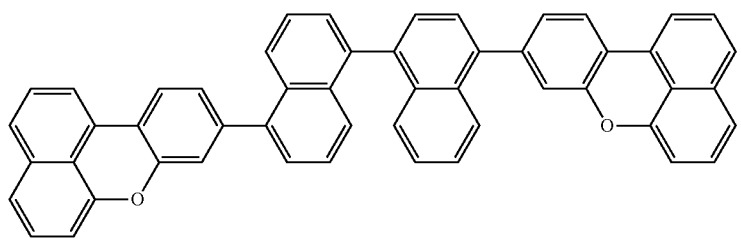
156
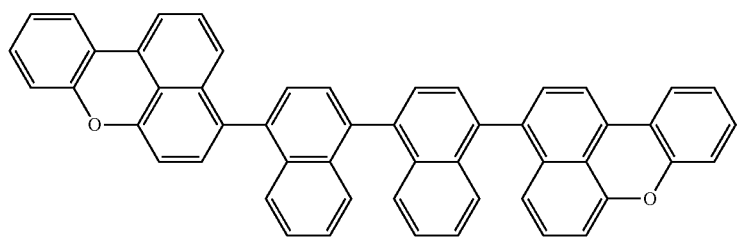
157
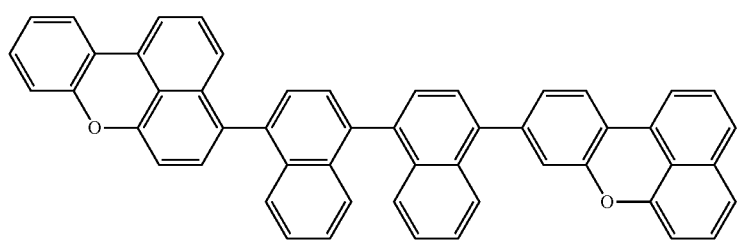
158
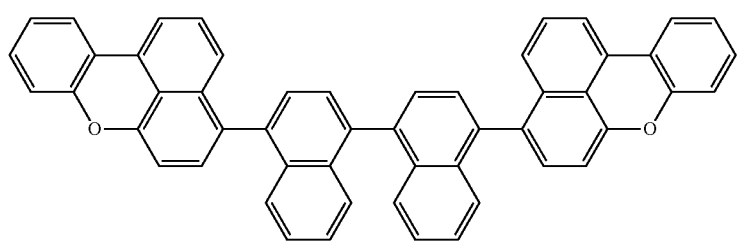
159
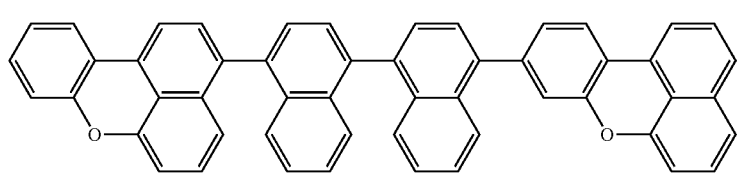
160
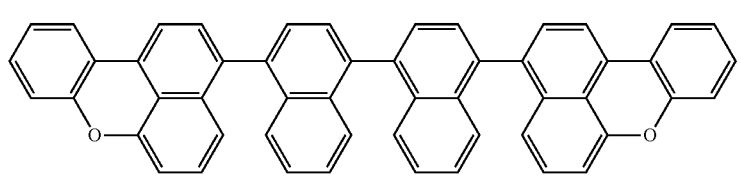
161
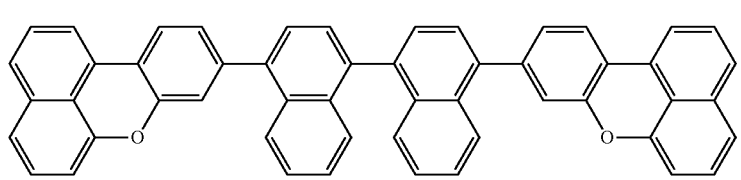
162

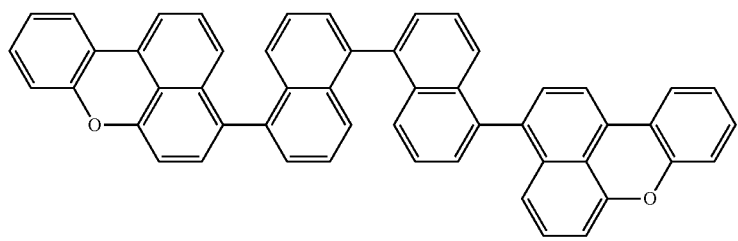
163
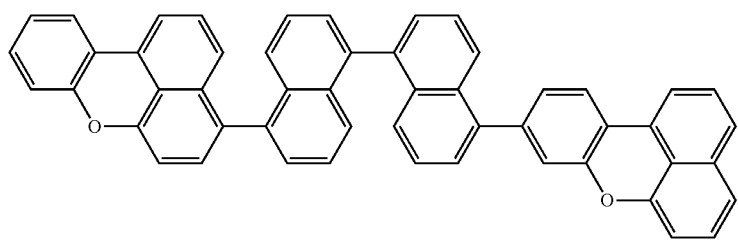
164
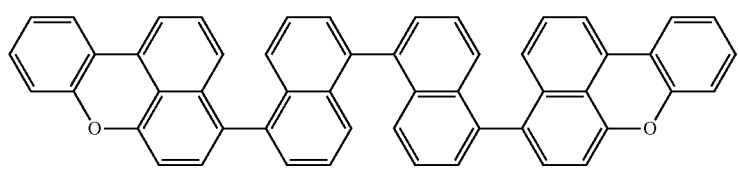
165
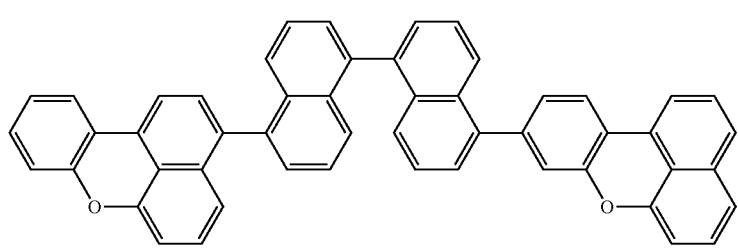
166
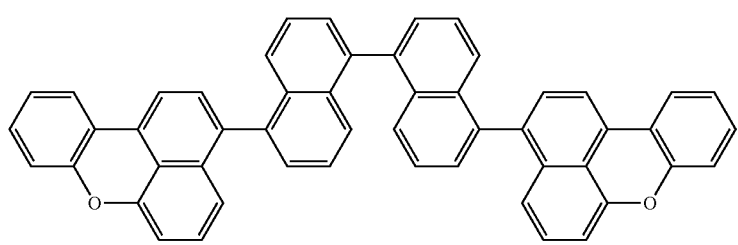
167
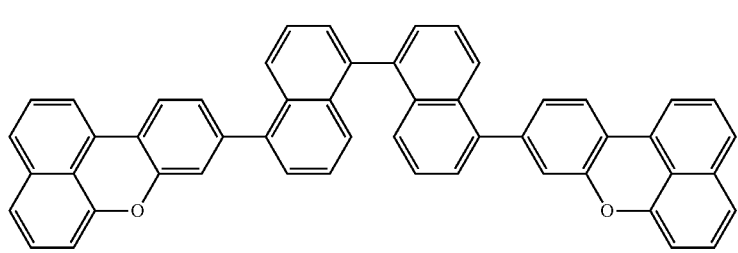
168

169
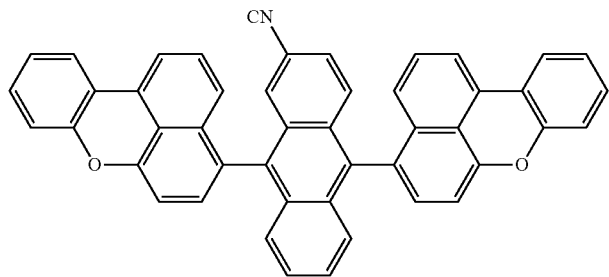
170
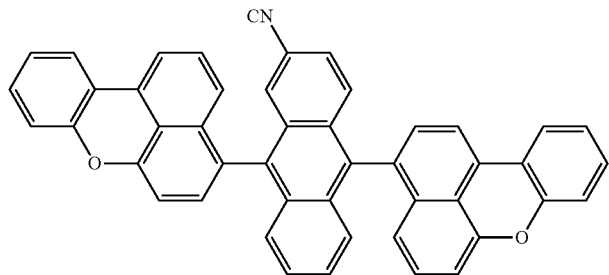
171
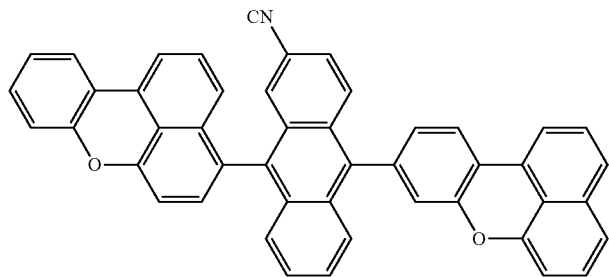
172
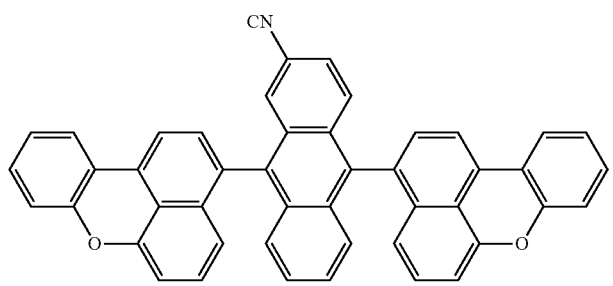
173
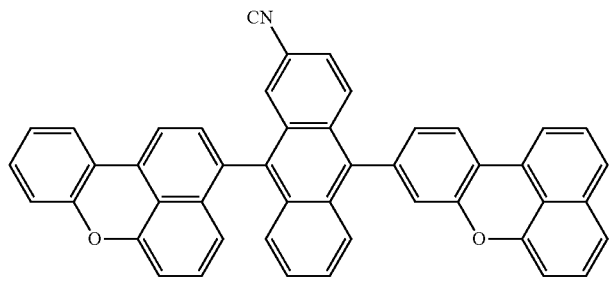

-continued
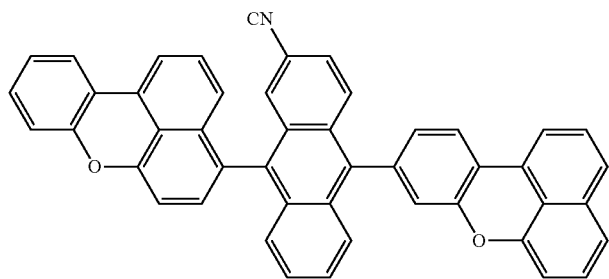
174
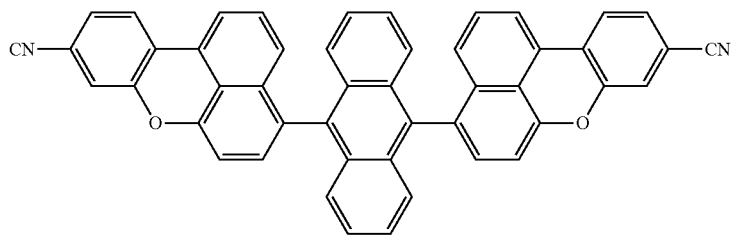
175
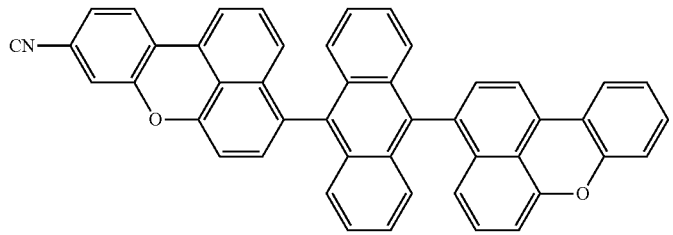
176
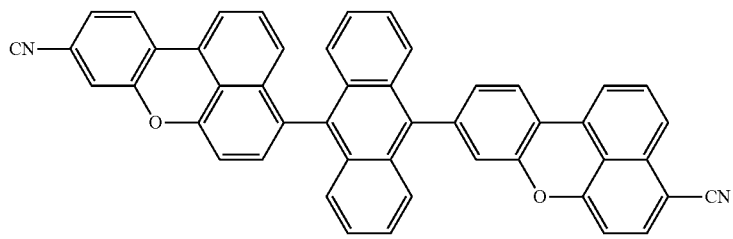
177
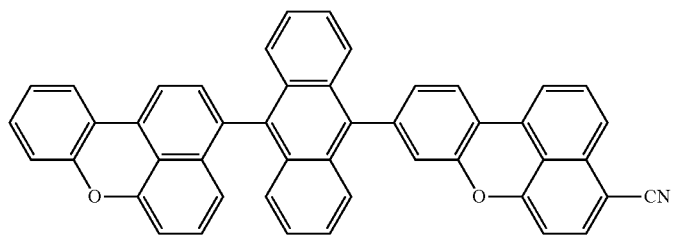
178
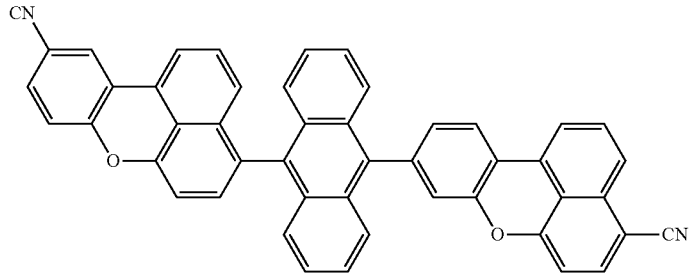
179

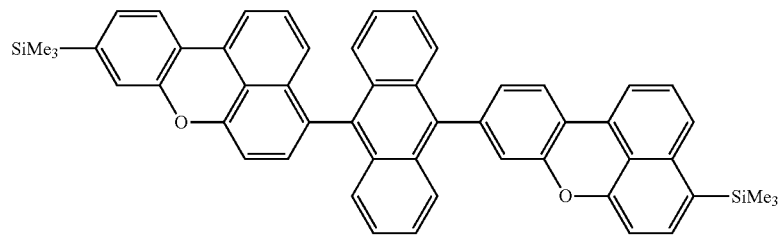
180
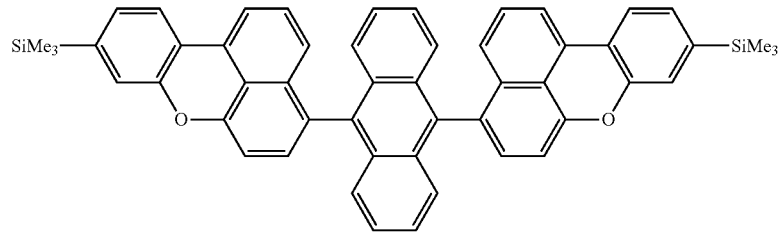
181
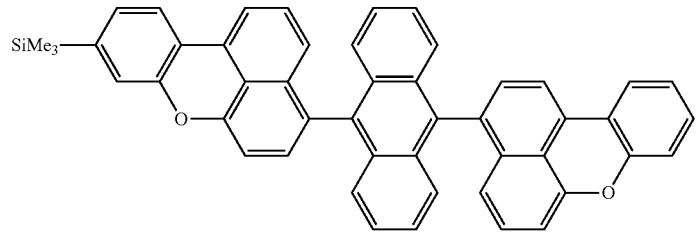
182
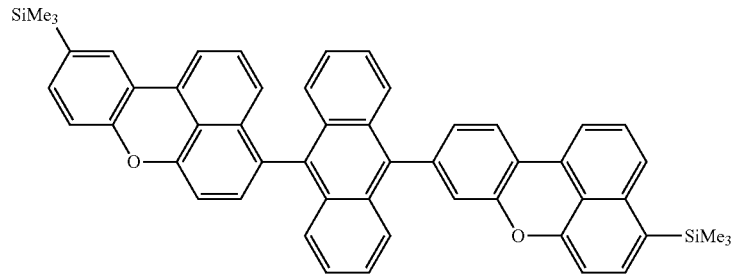
183
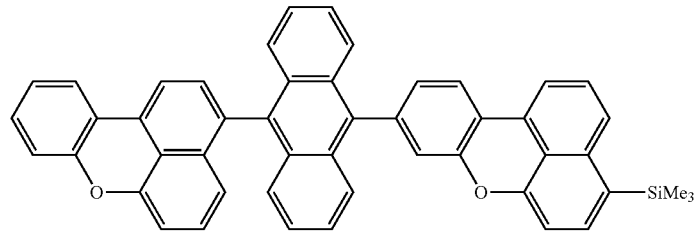
184
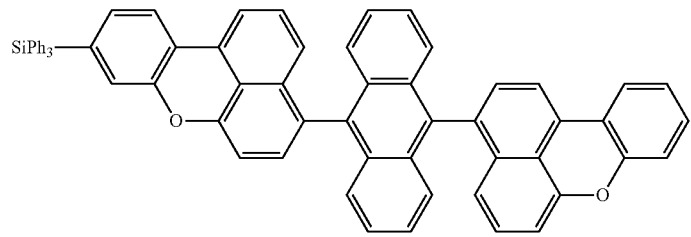
185

-continued
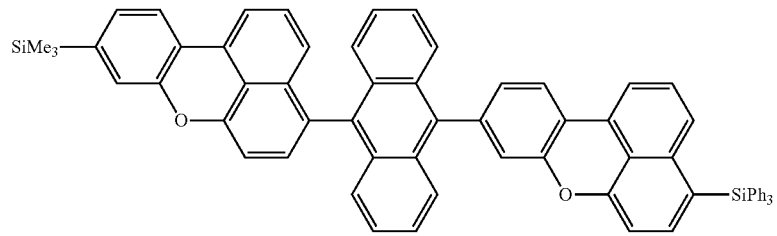
186
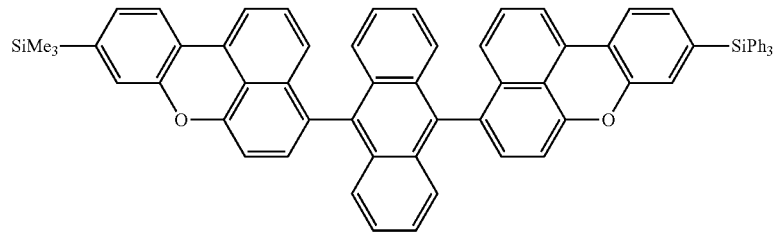
187
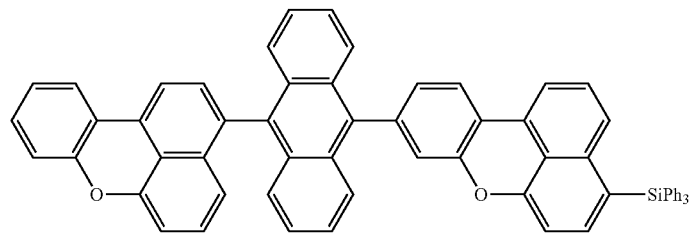
188
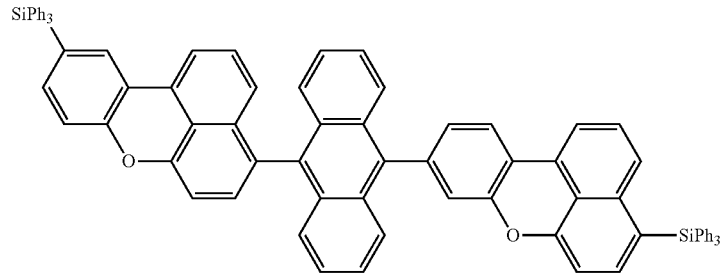
189
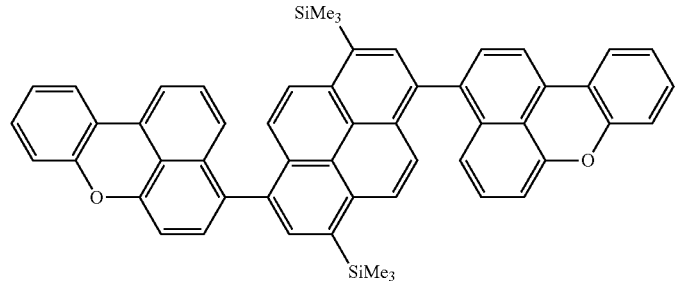
190
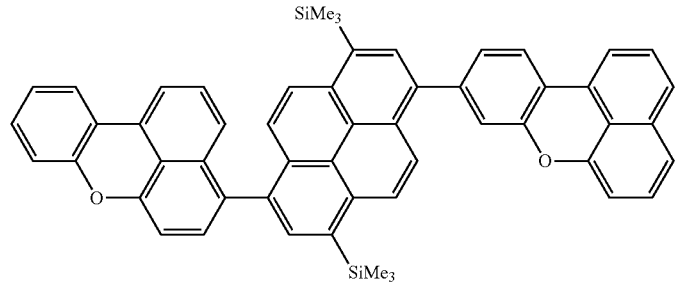
191

-continued
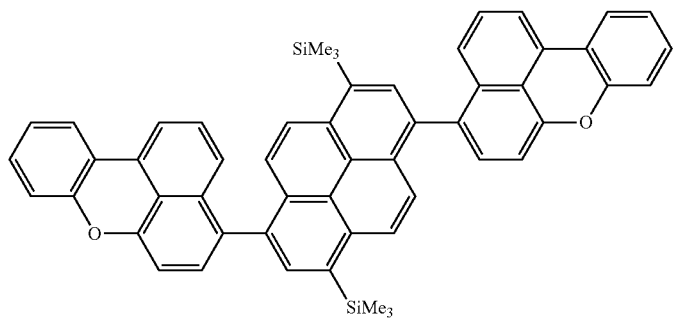
192
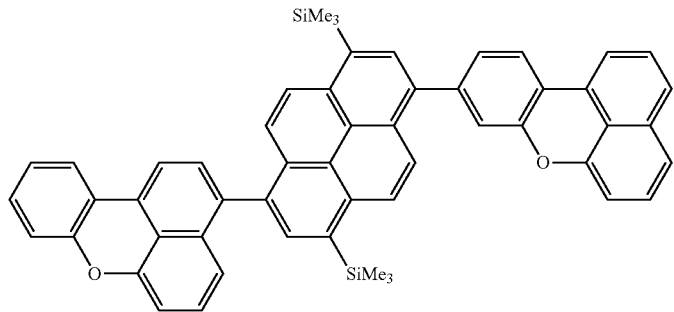
193
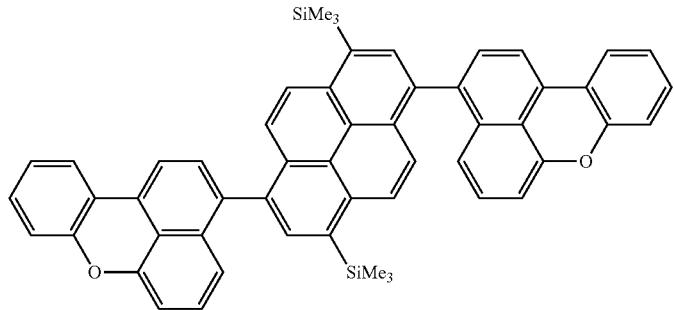
194
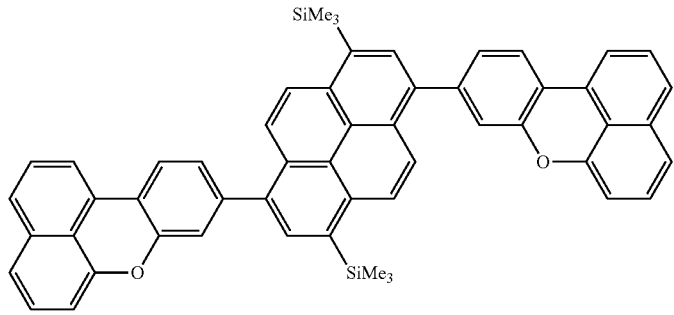
195
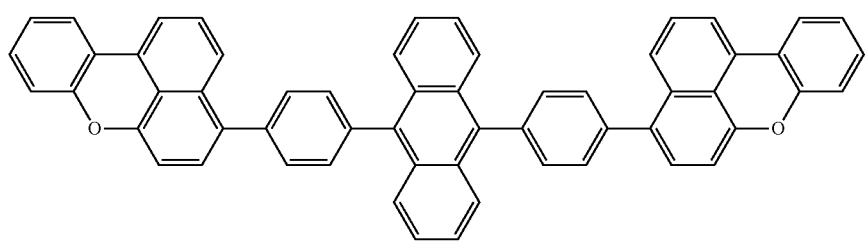
196

-continued
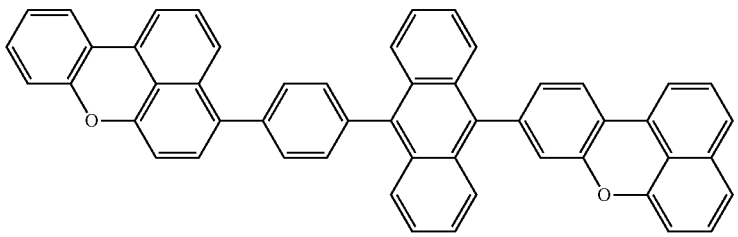
197
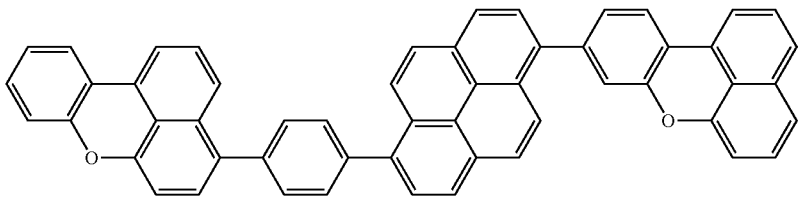
198
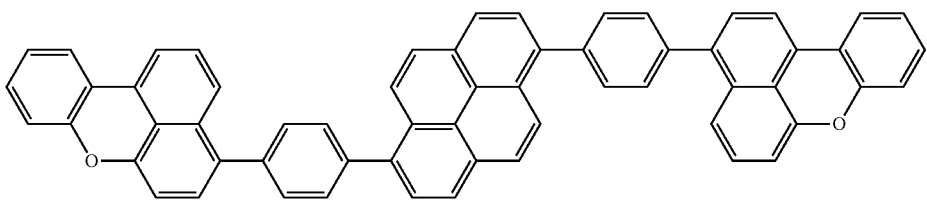
199
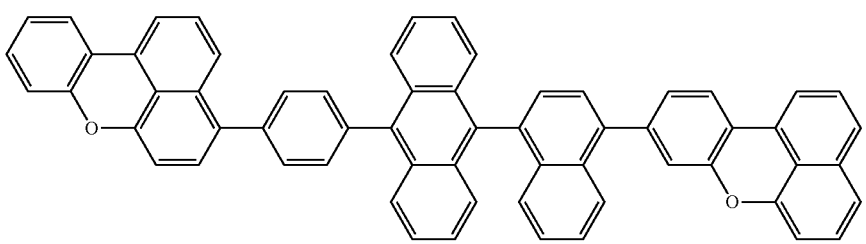
200
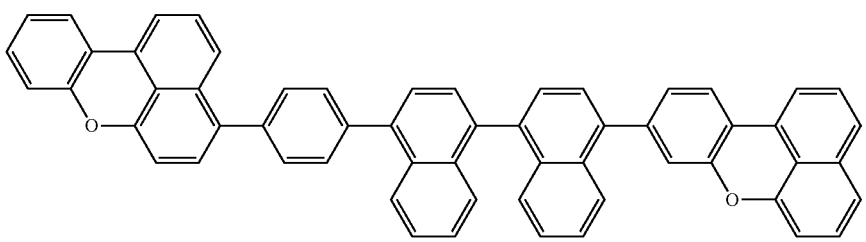
201
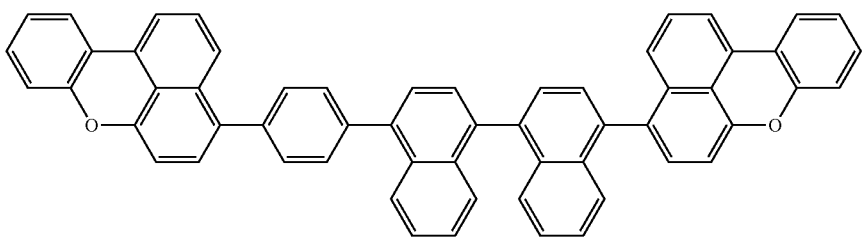
202
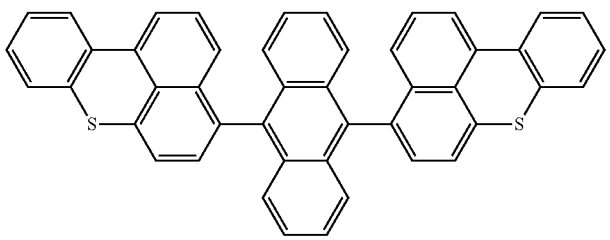
203

-continued
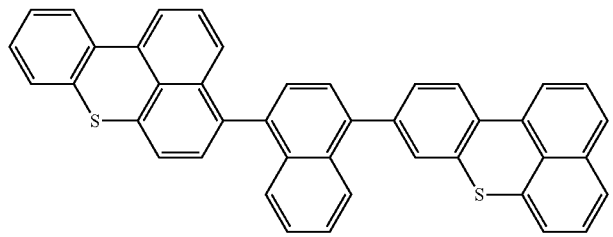
204
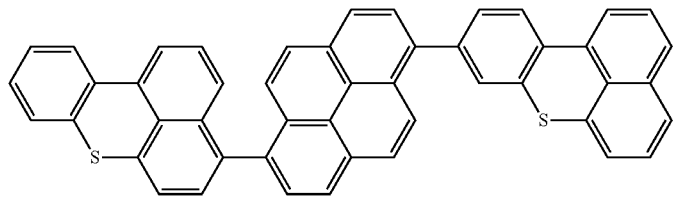
205
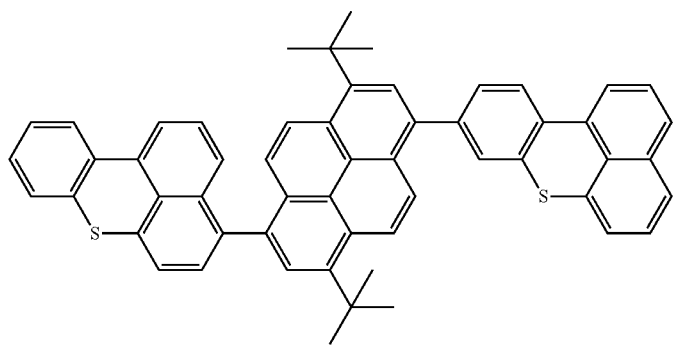
206
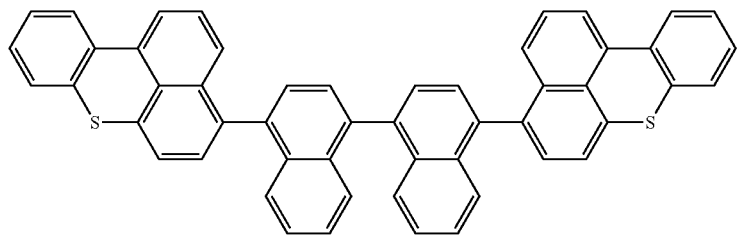
207
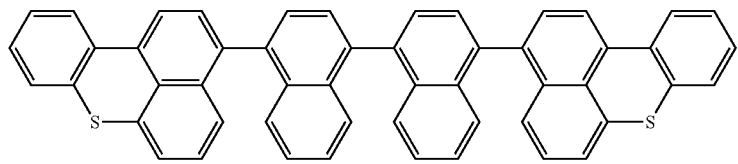
208
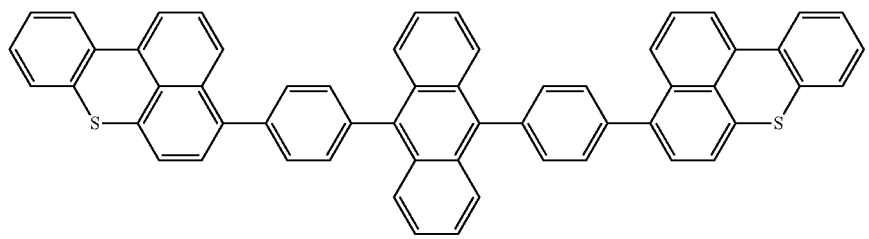
208'

209
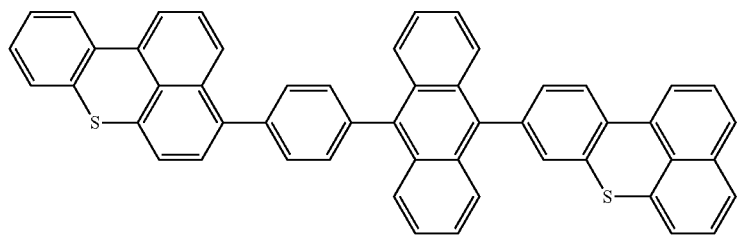
210
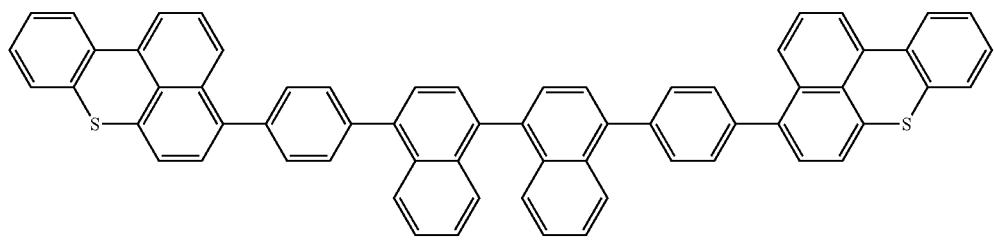
211
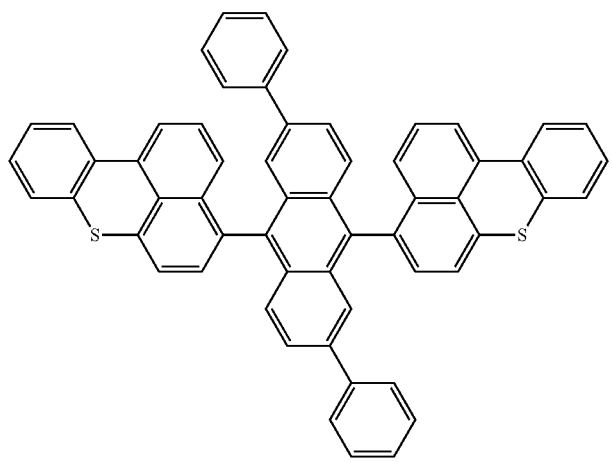
212
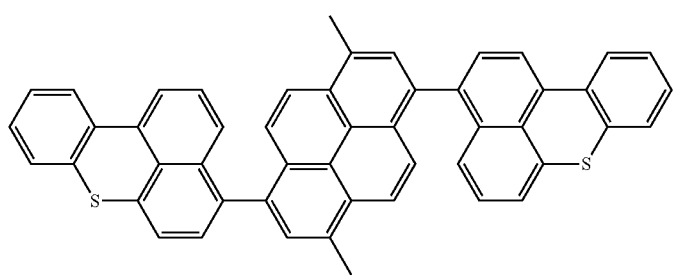
213
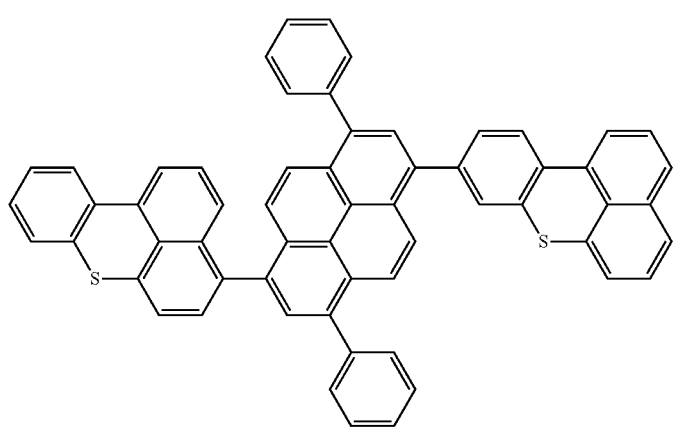

214
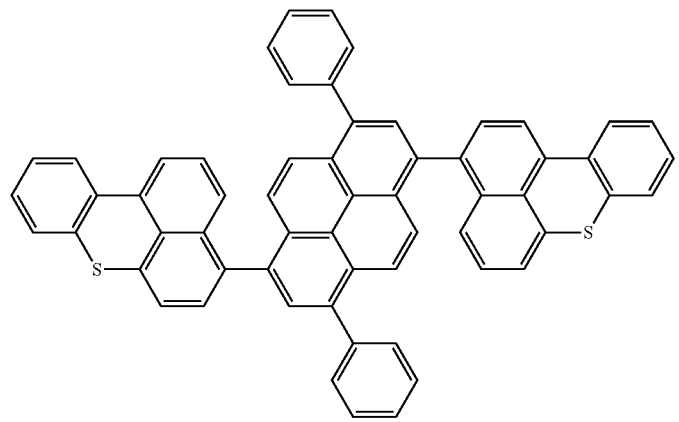
215
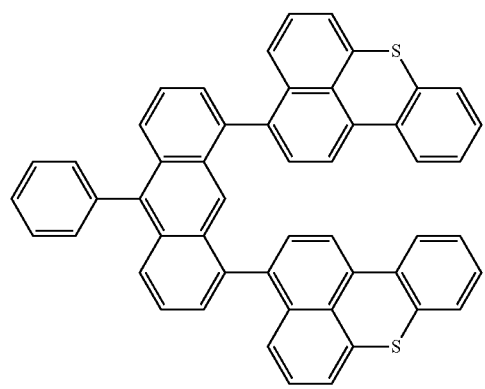
216
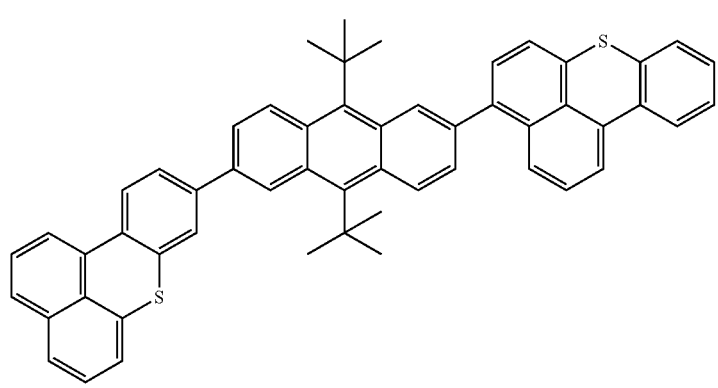
217
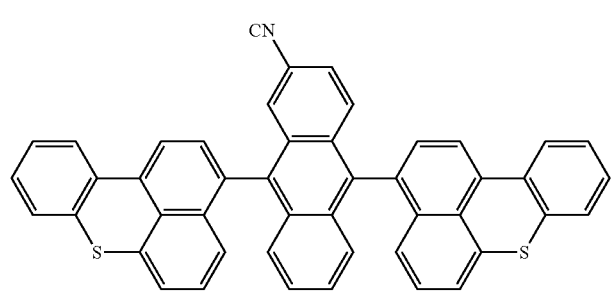

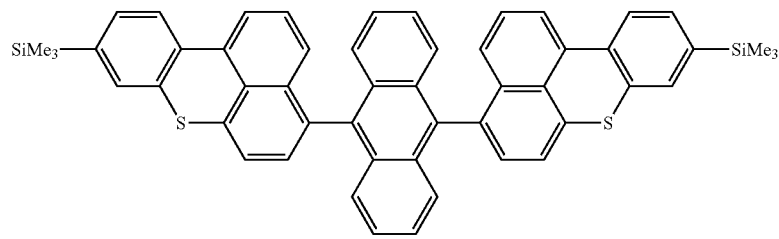

218

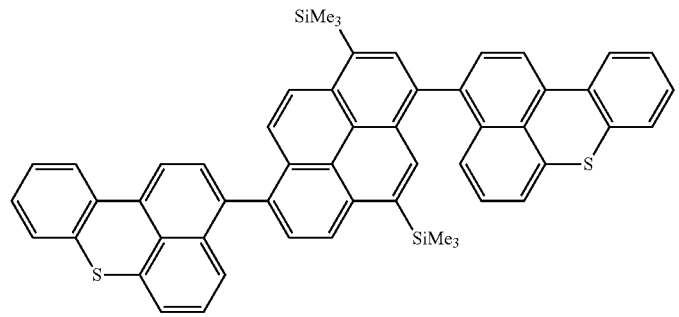

219

15. An organic light-emitting device comprising:
a first electrode;
a second electrode facing the first electrode; and
an organic layer between the first electrode and the second electrode, the organic layer including an emission layer, wherein the organic layer includes at least one condensed cyclic compound as claimed in claim 1.

16. The organic light-emitting device as claimed in claim 15, wherein the organic layer includes:
a hole transport region between the first electrode and the emission layer, the hole transport regin including at least one of a hole injection layer, a hole transport layer, a buffer layer, and an electron blocking layer, and
an electron transport region between the emission layer and the second electrode, the electron transport region including at least one selected from a hole blocking layer, an electron transport layer, and an electron injection layer.

17. The organic light-emitting device as claimed in claim 16, wherein the emission layer includes the condensed cyclic compound.

18. The organic light-emitting device as claimed in claim 17, wherein the emission layer further includes a dopant, and the condensed cyclic compound is a host.

19. The organic light-emitting device as claimed in claim 18, wherein the dopant is a fluorescent dopant.

20. The organic light-emitting device as claimed in claim 16, wherein the hole transport region includes at least one of a compound represented by Formula 201A below and a compound represented by Formula 202A below:

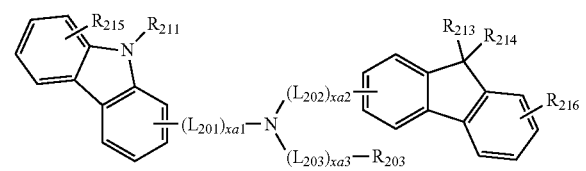

<Formula 201A>

-continued

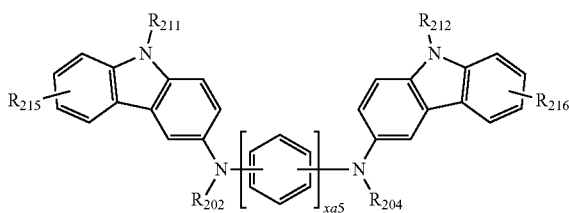

<Formula 202A> wherein Formulae 201A and 202A,
$L_{201}$ to $L_{203}$ are each independently selected from:
a phenylene group, a naphthylene group, a fluorenylene group, a spiro-fluorenylene group, a benzofluorenylene group, a dibenzofluorenylene group, a phenanthrenylene group, a anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and
a phenylene group, a naphthylene group, a fluorenylene group, a spiro-fluorenylene group, a benzofluorenylene group, a dibenzofluorenylene group, a phenanthrenylene group, a anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 are each independently 0 or 1;

$R_{203}$, $R_{211}$, and $R_{212}$ are each independently selected from:

a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ are each independently selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and $R_{215}$ and $R_{216}$ are each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group; and a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, a anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xa5 is 1 or 2.

* * * * *